United States Patent
Gollner et al.

(10) Patent No.: US 10,882,866 B1
(45) Date of Patent: Jan. 5, 2021

(54) SPIRO[3H-INDOLE-3,2'-PYRROLIDIN]-2(1H)-ONE COMPOUNDS AND DERIVATIVES AS MDM2-P53 INHIBITORS

(71) Applicant: Boehringer Ingelheim International GmbH, Ingelheim am Rhein (DE)

(72) Inventors: Andreas Gollner, Vienna (AT); Joachim Broeker, Moedling (AT); Nina Kerres, Vienna (AT); Christiane Kofink, Perchtoldsdorf (AT); Juergen Ramharter, Vienna (AT); Harald Weinstabl, Vienna (AT); Annika Gille, Ulm (DE); Stefan Goepper, Piberach an der Riss (DE); Manuel Henry, Schemmerhofen (DE); Guenther Huchler, Hochdorf (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/844,473

(22) Filed: Apr. 9, 2020

Related U.S. Application Data

(60) Division of application No. 16/003,232, filed on Jun. 8, 2018, which is a continuation of application No. 15/287,958, filed on Oct. 7, 2016, now Pat. No. 10,144,739.

(30) Foreign Application Priority Data

Oct. 9, 2015 (EP) ..................... 15189210

(51) Int. Cl.
| | |
|---|---|
| C07D 487/22 | (2006.01) |
| C07D 309/02 | (2006.01) |
| A61K 31/4162 | (2006.01) |
| A61K 31/437 | (2006.01) |
| A61K 31/4545 | (2006.01) |
| A61K 31/5377 | (2006.01) |
| A61P 35/00 | (2006.01) |
| C07D 471/22 | (2006.01) |
| C07D 209/02 | (2006.01) |
| A61K 45/06 | (2006.01) |

(52) U.S. Cl.
CPC ........ *C07D 487/22* (2013.01); *A61K 31/4162* (2013.01); *A61K 31/437* (2013.01); *A61K 31/4545* (2013.01); *A61K 31/5377* (2013.01); *A61K 45/06* (2013.01); *A61P 35/00* (2018.01); *C07D 209/02* (2013.01); *C07D 471/22* (2013.01)

(58) Field of Classification Search
CPC .............. C07D 487/22; C07D 209/02
USPC ............... 548/301.7, 300.7, 357.5
See application file for complete search history.

(56) References Cited

U.S. PATENT DOCUMENTS

| | | | |
|---|---|---|---|
| 8,119,623 B2 | 2/2012 | Burdack et al. | |
| 9,045,414 B2 | 6/2015 | Burdack et al. | |
| 10,138,251 B2 | 11/2018 | Gollner et al. | |
| 10,144,739 B2 * | 12/2018 | Gollner | A61K 31/4162 |
| 10,246,467 B2 | 4/2019 | Ramharter et al. | |
| 2010/0075949 A1 | 3/2010 | Burdack et al. | |
| 2011/0319378 A1 | 12/2011 | Bartberger et al. | |
| 2012/0071499 A1 | 3/2012 | Chu et al. | |
| 2012/0122839 A1 | 5/2012 | Burdack et al. | |
| 2015/0291611 A1 | 10/2015 | Gollner et al. | |

(Continued)

FOREIGN PATENT DOCUMENTS

| | | |
|---|---|---|
| CN | 102443004 A | 5/2012 |
| CN | 103910746 A | 7/2014 |

(Continued)

OTHER PUBLICATIONS

Kaur et al., "Synthesis and biological activity of 4-aryl-3-bezoyl-5-phenylspiro [pyrrolidine-2.3'-indolin]-2'-one derivatives as novel potent inhibitors of advanced glycation end product", European Journal of Chemistry, 2014, vol. 19, pp. 282-289.

(Continued)

*Primary Examiner* — Venkataraman Balasubramanian
(74) *Attorney, Agent, or Firm* — Philip I. Datlow

(57) ABSTRACT

The present invention encompasses intermediates for preparing compounds of formula (I)

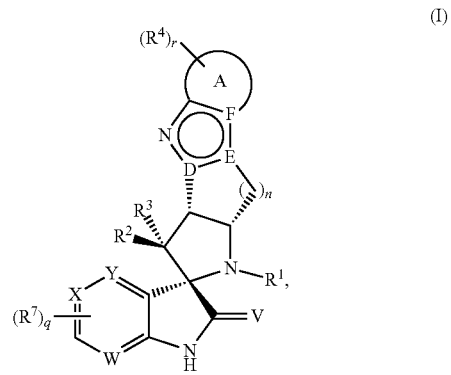

wherein the groups $R^1$ to $R^4$, $R^7$, A, D, E, F, V, W, X, Y, n, r and q are defined in claim 1, their use as inhibitors of MDM2-p53 interaction, pharmaceutical compositions which contain compounds of this kind, their use as medicaments, especially as agents for treatment and/or prevention of oncological diseases, and synthetic intermediates.

2 Claims, No Drawings

(56) References Cited

U.S. PATENT DOCUMENTS

| | | |
|---|---|---|
| 2016/0000764 A1 | 1/2016 | Weinstabl et al. |
| 2016/0052938 A1 | 2/2016 | Ramharter et al. |
| 2017/0174695 A1 | 6/2017 | Gollner et al. |
| 2017/0247394 A1 | 8/2017 | Ramharter et al. |
| 2018/0273541 A1 | 9/2018 | Gollner et al. |
| 2018/0291030 A1 | 10/2018 | Gollner et al. |

FOREIGN PATENT DOCUMENTS

| | | |
|---|---|---|
| JP | 2008531504 A | 8/2008 |
| JP | 2008531542 A | 8/2008 |
| JP | 2012502887 A | 2/2012 |
| JP | 2012162550 A | 8/2012 |
| JP | 2012524745 A | 10/2012 |
| JP | 2013530958 A | 8/2013 |
| WO | 9912904 A1 | 3/1999 |
| WO | 2006090261 A1 | 8/2006 |
| WO | 2006090646 A1 | 8/2006 |
| WO | 2006091646 A3 | 11/2006 |
| WO | 2010028862 A1 | 3/2010 |
| WO | 2010121995 A1 | 10/2010 |
| WO | 2012038307 A1 | 3/2012 |
| WO | 2012116989 A1 | 9/2012 |
| WO | 2015155332 A1 | 10/2015 |
| WO | 2016001376 A1 | 1/2016 |
| WO | 2016027195 A1 | 2/2016 |

OTHER PUBLICATIONS

Abstract in English for CN102443004, May 9, 2012.
Abstract in English for NPL: Li, B. et al., "Molecular Docking, QSAR and Molecular Dynamics Simulation on Spiro-oxindoles as MDM2 Inhibitors." Acta Chimica Sinica, 2013, vol. 71, No. 10, p. 1396.
Cecil Textbook of Medicine, edited by Bennet, J.C., 20th Edition, vol. 1, 1004-1010, 1996.
Chemical Abstracts Service, 2006, Accession No. 897585-13-6.
Chemical Abstracts Service, 2006, Accession No. 897585-15-8.
Chemical Abstracts Service, 2006, Accession No. 897585-17-0.
Chen, G. et al., "Spiro[pyrrolidine-2,3'-oxindole] derivatives synthesized by novel regionselective 1,3-dipolar cycloadditions." Molecular Diversity, 2011, vol. 16, No. 1, pp. 151-156.
Dandia, Reaction of Indole-2,3-Diones with 3-aminopropanol, Organic Preparations and Procedures, International, the New Journal for Organic Synthesis, 2003, vol. 35, No. 4, p. 433-438.
Dermer, Another Anniversary for the war on Cancer, Bio/Technology, 1994, vol. 12, p. 320-328.
Ding et al., Structure-Based Design of Spiro-oxindoles as Potent, Specific Small-Molecule Inhibitors of the MDM2-p53 Interaction, J. Med. Chem, 2006, 49, pp. 3432-3435.
European Search Report for EP 14175620.5 dated Aug. 8, 2014.
Freshney, Culture of Animal Cells, A Manual of Basic Technique, Liss, Inc., 1983, p. 4.

Gollner et al., "Discovery of Novel Spiro[3H-indole-3,2'-pyrrolidin]-2(1H)-one Compounds as Chemically Stable and Orally Active Inhibitors of the MDM2-p53 Interaction", J. Med Chem, 2016, 59, pp. 10147-10162.
Gollner et al., "Targeted Synthesis of Complex Spiro[3H-indole-3,2'- pyrrolidin]-2(1H)-ones by Intramolecular Cyclization of Azomethine Ylides: Highly Potent MDM2-p53 Inhibitors", Chem Med Chem, 2019, 14, pp. 88-93.
Golub, Molecular Classification of Cancer: Class Discovery and Class Prediction by Gene Expression Monitoring, Science, vol. 286, 1999, p. 531-537.
International Search Report and Written Opinion for corresponding application PCT/EP2016/074008, dated Nov. 3, 2016.
International Search Report and Written Opinion for PCT/EP2015/057839 dated May 15, 2015.
International Search Report and Written Opinion for PCT/EP2015/065134 dated Jul. 27, 2015.
International Search Report and Written Opinion for PCT/EP2015/069174 dated Sep. 22, 2015.
Kojima, Pharmacological activation of wild-type p53 in the therapy of leukemia, Exp. Hematol. 2016, p. 791-798.
Li, B. et al., "Molecular Docking, QSAR and Molecular Dynamics Simulation on Spiro-oxindoles as MDM2 Inhibitors." Acta Chimica Sinica, 2013, vol. 71, No. 10, pp. 1396-1403.
Li, Bo et al. "Molecular Docking, QSAR and Molecular Dynamics Simulation on Spiro-oxindoles as MDM2 Inhibitors" (2013) Shanghai Institute of Organic Chemistry, Chinese Academy of Sciences, vol. 71, 1396-1403.
Marx, M. et al., "Synthetic Design for Combinatorial Chemistry. Solution and Polymer-Supported Synthesis of Polycyclic Lactams by Intramolecular Cyclization of Azomethine Ylides." Journal of the American Chemical Society, 1997, vol. 119, No. 26, pp. 6153-6167.
Tisato, MDM2/X inhibitors under clinical evaluation: perpspectives for the mamagement of hematological malignancies and pediatric cancer, Journal of Hematology and Oncology, 2017, vol. 10, p. 1-17.
U.S. Appl. No. 15/287,958, filed Oct. 7, 2016, Andreas Gollner.
U.S. Appl. No. 12/560,051, filed Sep. 15, 2009, Christoph Burdack.
U.S. Appl. No. 13/351,914, filed Jan. 17, 2012, Christoph Burdack.
U.S. Appl. No. 14/683,173, filed Apr. 10, 2015, Andreas Gollner.
U.S. Appl. No. 14/790,032, filed Jul. 2, 2015, Harald Weinstabl.
U.S. Appl. No. 14/831,241 filed Aug. 20, 2015, Juergen Ramharter.
U.S. Appl. No. 15/503,754, filed Feb. 14, 2017, Juergen Ramharter.
U.S. Appl. No. 61/096,964, filed Sep. 15, 2008, Christoph Burdack.
U.S. Appl. No. 16/003,232, filed Jun. 8, 2018. Inventor: Andreas Gollner.
U.S. Appl. No. 16/005,316, filed Jun. 11, 2018. Inventor: Andreas Gollner.
Waite, Reductive Amination of Substituted Indole-2,3-diones, J. Chem. Soc, 1970. p. 550-552.
Zak, Krzysztof et al. Mdm2 and MdmX inhibitors for the treatment of cancer: a patent review (2011-present), (2013) Expert Opinion on Therapeutic Patents, 23:4, 425-448.
Kaur et al., "Synthesis and biological activity of 4-aryl-3-bezoyl-5-phenylspiro [pyrrolidine-2.3'-indolin]-2'-one derivatives as novel potent inhibitors of advanced glycation end product", European Journal of Chemistry, 2014, vol. 19, pp. 282-289.

\* cited by examiner

SPIRO[3H-INDOLE-3,2'-PYRROLIDIN]-2(1H)-ONE COMPOUNDS AND DERIVATIVES AS MDM2-P53 INHIBITORS

The present invention relates to new spiro[3H-indole-3,2'-pyrrolidin]-2(1H)-one compounds and derivatives of formula (I)

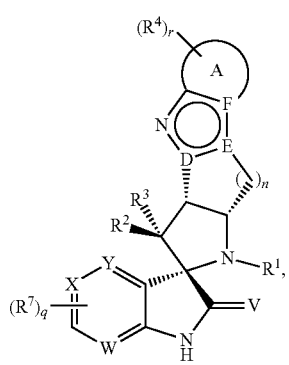

wherein the groups $R^1$ to $R^4$, $R^7$, A, D, E, F, V, W, X, Y, n, r and q have the meanings given in the claims and specification, their use as inhibitors of MDM2-p53 interaction, pharmaceutical compositions which contain compounds of this kind, their use as medicaments, especially as agents for treatment and/or prevention of oncological diseases, and synthetic intermediates.

BACKGROUND OF THE INVENTION

The tumor suppressor protein p53 is a sequence specific transcription factor and plays a central role in the regulation of several cellular processes, including cell cycle and growth arrest, apoptosis, DNA repair, senescence, angiogenesis, and innate immunity. The Mouse Double Minute 2 (MDM2) protein (or its human homolog also known as HDM2) acts to down-regulate p53 activity in an auto-regulatory manner, and under normal cellular conditions (absence of stress), the MDM2 protein serves to maintain p53 activity at low levels. MDM2 directly inhibits the transactivation function of p53, exports p53 out of the nucleus, and promotes proteasome-mediated degradation of p53 through its E3 ubiquitin ligase activity.

Deregulation of the MDM2/p53 balance by overexpression of MDM2 or by p53 mutation or loss leads to malignant transformation of normal cells. Presently p53 is known to play a key role in practically all types of human cancers, and the mutation or loss of the p53 gene can be identified in more than 50% of all human cancers worldwide. Analysis of 28 different types of human cancers in nearly 4,000 human tumor samples showed that MDM2 is amplified in 7% of human cancers and that MDM2 overexpression by amplification and p53 mutations are largely mutually exclusive (Momand et al., Nucleic Acid Res (1998) 26:3453-3459).

Because of the powerful tumor suppressor function of p53, reactivation of p53 has been long sought as a potentially novel cancer therapeutic strategy. In tumor harboring wild-type p53, MDM2 is the primary cellular inhibitor of p53 activity, and overexpression of MDM2 was found in many human tumors. Since MDM2 inhibits p53 through a direct protein-protein interaction, blocking this interaction using small molecules was pursued in several academic and industrial pharmaceutical laboratories in the last decade. A variety of non-peptide, drug-like small molecule as e.g. imidazole compounds (e.g. Nutlins or RG7112), benzodiazepinedione compounds, spirooxindole compounds (e.g. MI-219), substituted piperidines, pyrrolidinone compounds (e.g. PXN820-dl) and modifications thereof have been selected and designed in order to block MDM2/p53 interaction as a means to reactivate p53 in cells (Vassilev et al., Science (2004) 303:844-848; Grasberger et al., J Med Chem (2005) 48:909-912; Parks et al., Bioorg Med Chem Lett (2005) 15:765; Ding et al., J Am Soc (2005) 127:10130-10131; WO 2010/028862, U.S. Pat. No. 7,884,107, WO 2008/119741). A number of potent MDM2/p53 inhibitors have been evaluated in animal models of human cancer for their anti-tumor activity (Vassilev et al., Science (2004) 303:844-848; Tovar et al, Cancer Res (2013) 73 (8): 2587-2597; Ding et al, Journal of Medicinal Chemistry (2013) 56 (14): 5979-5983; Rew et al, Journal of Medicinal Chemistry (2012) 55: 4936-4954; Sun et al, Journal of Medicinal Chemistry (2014) 57 (4): 1454-1472).

In the pediatric preclinical testing program (PPTP) of the NCI, early evidence for high level anti-proliferative activity of RG7112, an inhibitor of the MDM2-p53 interaction, could be observed in vitro and in vivo. In particular, RG-7112 showed cytotoxic activity with lower median $IC_{50}$ values for p53 wild-type vs. p53 mutant cell lines (Carol et al., Pediatric Blood and Cancer (2013) 60(4):633-641). Moreover, RG-7112 induced tumor growth inhibition in solid tumor xenograft models and was particularly efficacious in in acute lymphoblastic leukemia (ALL) xenograft models with mixed-lineage leukemia (MLL) rearrangement, (Carol et al., Pediatric Blood and Cancer (2013) 60(4):633-641). Additionally, the antiproliferative and proapoptotic activity of RG7112 has been observed in human acute myeloid leukemia (AML) and human prostate tumor xenograft models harboring p53 wild-type (Tovar et al, Cancer Res (2013) 73 (8): 2587-2597).

Accordingly, small molecule inhibitors of the MDM2 protein interactions offer an important approach towards cancer therapy, either as a single agent, or in combination with a broad variety of anti-tumor therapies and thus, there is the need for further MDM2 inhibitors which can be useful in the treatment of cancer.

The following prior art documents disclose spiro oxindole compounds as inhibitors of MDM2-p53interaction:
WO 2007/104664; WO 2007/104714; WO 2008/141917; WO 2008/141975; WO 2009/077357; WO 2009/080488; WO 2010/084097; WO 2010/121995; WO 2011/067185; WO 2011/101297; WO 2011/134925; WO 2012/038307; WO 2012/022707; WO 2012/116989; WO 2006/091646; WO 2008/036168; WO 2011/060049; WO 2012/065022; WO 2012/155066; WO 2010/028862; WO 2011/153509, WO 2012/121361, WO 2015/155332, WO 2016/001376 and WO 2016/026937.

The aim of the present invention is to provide new compounds which can be used for the prevention and/or treatment of a disease and/or condition characterised by excessive or abnormal cell proliferation, especially a disease and/or condition wherein the inhibition of the interaction between MDM2 and p53 is of therapeutic benefit.

The compounds according to the invention are characterised by a powerful inhibitory effect on the interaction between MDM2 and p53 and in turn a high in vitro efficacy against tumour cells, e.g. osteosarcoma, ALL etc., which is mediated through the inhibition of the interaction between MDM2 and p53 and is the prerequisite for a corresponding efficacy in in vivo models and future patients. In addition to the inhibitory effect and cellular potency the compounds show good PK properties and selectivity against p53 mutant cell lines. Furthermore, they have good metabolic stability which is a pivotal requirement for an active pharmaceutical ingredient to reach its place of action and allow for a long-lasting efficacy. Finally, and in contrast to many compounds known in the prior art, the compounds have good chemical stability, i.e. they are for example less prone to epimerisation, a problem identified for many known representatives of spiro oxindoles in the prior art (see e.g. Zhao et al. *J. Am. Chem. Soc* 2013, 135, 7223-7234; Shu et al. Org. Process Res. Dev. 2013, 17, 247-256; WO 2012/065022). It is also emphasized that building up the scaffolds of compounds (I), i.e. the scaffolds of each subgroup (Ia), (Ib) and (Ic), is in itself unprecedented and needs highly sophisticated synthetic approaches to obtain these compounds of high structural complexity.

DETAILED DESCRIPTION OF THE INVENTION

It has now been found that, surprisingly, compounds of formula (I) wherein the groups $R^1$ to $R^4$, $R^7$, A, D, E, F, V, W, X, Y, n, r and q have the meanings given hereinafter act as inhibitors of the interaction of specific proteins which are involved in controlling cell proliferation. Thus, the compounds according to the invention may be used for example for the treatment of diseases connected with this protein-protein interaction and characterised by excessive or abnormal cell proliferation.

The present invention therefore relates to a compound of formula (I)

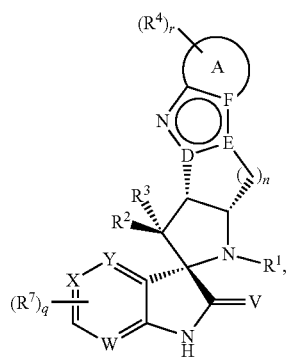

(I)

[A0]

$R^1$ is a group, optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{b1}$ is independently selected from among —$OR^{c1}$, —$NR^{c1}R^{c1}$, halogen, —CN, —C(O)$R^{c1}$, —C(O)O$R^{c1}$, —C(O)NR$^{c1}$R$^{c1}$, —S(O)$_2$R$^{c1}$, —S(O)$_2$NR$^{c1}$R$^{c1}$, —NHC(O)$R^{c1}$, —N(C$_{1-4}$alkyl)C(O)$R^{c1}$ and the bivalent substituent =O, while =O may only be a substituent in non-aromatic ring systems;

each $R^{c1}$ independently of one another denotes hydrogen or a group, optionally substituted by one or more, identical or different $R^{d1}$ and/or $R^{e1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{d1}$ is independently selected from among —$OR^{e1}$, —$NR^{e1}R^{e1}$, halogen, —CN, —C(O)$R^{e1}$, —C(O)O$R^{e1}$, —C(O)NR$^{e1}$R$^{e1}$, —S(O)$_2$R$^{e1}$, —S(O)$_2$NR$^{e1}$R$^{e1}$, —NHC(O)$R^{e1}$, —N(C$_{1-4}$alkyl)C(O)$R^{e1}$ and the bivalent substituent =O, while =O may only be a substituent in non-aromatic ring systems;

each $R^{e1}$ independently of one another denotes hydrogen or a group, optionally substituted by one or more, identical or different $R^{f1}$ and/or $R^{g1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{f1}$ is independently selected from among —$OR^{g1}$, —$NR^{g1}R^{g1}$, halogen, —CN, —C(O)$R^{g1}$, —C(O)O$R^{g1}$, —C(O)NR$^{g1}$R$^{g1}$, —S(O)$_2$R$^{g1}$, —S(O)$_2$NR$^{g1}$R$^{g1}$, —NHC(O)$R^{g1}$, —N(C$_{1-4}$alkyl)C(O)$R^{g1}$ and the bivalent substituent =O, while =O may only be a substituent in non-aromatic ring systems;

each $R^{g1}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

[B0]

$R^2$ and $R^3$, each independently, is selected from among hydrogen, $C_{6-10}$aryl, 5-10 membered heteroaryl and 3-10 membered heterocyclyl, wherein said $C_{6-10}$aryl, 5-10 membered heteroaryl and 3-10 membered heterocyclyl is optionally substituted by one or more, identical or different $R^{b2}$ and/or $R^{c2}$;

each $R^{b2}$ is independently selected from among —$OR^{c2}$, —$NR^{c2}R^{c2}$, halogen, —CN, —C(O)$R^{c2}$, —C(O)O$R^{c2}$, —C(O)NR$^{c2}$R$^{c2}$, —S(O)$_2$R$^{c2}$, —S(O)$_2$NR$^{c2}$R$^{c2}$, —NHC(O)$R^{c2}$, —N(C$_{1-4}$alkyl)C(O)$R^{c2}$ and the bivalent substituent =O, while =O may only be a substituent in non-aromatic ring systems;

each $R^{c2}$ independently of one another denotes hydrogen or a group, optionally substituted by one or more, identical or different $R^{d2}$ and/or $R^{e2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{d2}$ is independently selected from among —$OR^{e2}$, —$NR^{e2}R^{e2}$, halogen, —CN, —C(O)$R^{e2}$, —C(O)O$R^{e2}$, —C(O)NR$^{e2}$R$^{e2}$, —S(O)$_2$R$^{e2}$, —S(O)$_2$NR$^{e2}$R$^{e2}$, —NHC(O)$R^{e2}$, —N(C$_{1-4}$alkyl)C(O)$R^{e2}$ and the bivalent substituent =O, while =O may only be a substituent in non-aromatic ring systems;

each $R^{e2}$ independently of one another denotes hydrogen or a group selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

[C0]

A is selected from among phenyl and 5-6 membered heteroaryl if F is carbon or

A is 5-6 membered, nitrogen-containing heteroaryl if F is nitrogen;

each $R^4$ is independently selected from among $R^{a4}$ and $R^{b4}$;

each $R^{a4}$ independently of one another is a group, optionally substituted by one or more, identical or different $R^{b4}$ and/or $R^{c4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{b4}$ is independently selected from among —$OR^{c4}$, —$NR^{c4}R^{c4}$, halogen, —CN, —$C(O)R^{c4}$, —$C(O)OR^{c4}$, —$C(O)NR^{c4}R^{c4}$, —$C(O)NR^{g4}OR^{c4}$, —$S(O)_2R^{c4}$, —$S(O)_2NR^{c4}R^{c4}$, —$NHSO_2R^{c4}$, —$N(C_{1-4}alkyl)SO_2R^{c4}$, —$NHC(O)R^{c4}$, —$N(C_{1-4}alkyl)C(O)R^{c4}$ and the bivalent substituent =O, while =O may only be a substituent in non-aromatic ring systems;

each $R^{c4}$ independently of one another denotes hydrogen or a group, optionally substituted by one or more, identical or different $R^{d4}$ and/or $R^{e4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{d4}$ is independently selected from among —$OR^{e4}$, —$NR^{e4}R^{e4}$, halogen, —CN, —$C(O)R^{e4}$, —$C(O)OR^{e4}$, —$C(O)NR^{e4}R^{e4}$, —$C(O)NR^{g4}OR^{e4}$, —$S(O)_2R^{e4}$, —$S(O)_2NR^{e4}R^{e4}$, —$NHC(O)R^{e4}$, —$N(C_{1-4}alkyl)C(O)R^{e4}$ and the bivalent substituent =O, while =O may only be a substituent in non-aromatic ring systems;

each $R^{e4}$ independently of one another denotes hydrogen or a group, optionally substituted by one or more, identical or different $R^{f4}$ and/or $R^{g4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-6}$cycloalkenyl, $C_{6-10}$aryl, 5-10 membered heteroaryl and 3-10 membered heterocyclyl;

each $R^{f4}$ is independently selected from among —$OR^{g4}$, —$NR^{g4}R^{g4}$, halogen, —CN, —$C(O)R^{g4}$, —$C(O)OR^{g4}$, —$C(O)NR^{g4}R^{g4}$, —$C(O)NR^{g4}OR^{g4}$, —$S(O)_2R^{g4}$, —$S(O)_2NR^{g4}R^{g4}$, —$NHC(O)R^{g4}$, —$N(C_{1-4}alkyl)C(O)R^{g4}$ and the bivalent substituent =O, while =O may only be a substituent in non-aromatic ring systems;

each $R^{g4}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

r denotes the number 0, 1, 2 or 3;

[D0]

n denotes the number 1, 2 or 3;

[E0]

each $R^7$ is independently selected from among halogen, $C_{1-4}$alkyl, —CN, $C_{1-4}$haloalkyl, —$OC_{1-4}$alkyl and —$OC_{1-4}$haloalkyl;

q denotes the number 0, 1, 2 or 3;

[F0]

W, X and Y is each independently selected from —N= and —CH= with the proviso that the hydrogen in each —CH= may be replaced by a substituent $R^7$ if present and that a maximum of two of W, X and Y can be —N=;

[G0]

V is oxygen or sulfur;

[H0]

D is nitrogen, E is carbon and F is carbon; or

D is carbon, E is nitrogen and F is carbon; or

D is carbon, E is carbon and F is nitrogen;

or a salt thereof.

In one aspect the invention relates to a compound of formula (Ia)

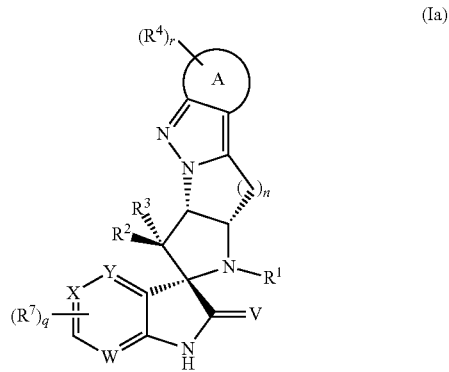

(Ia)

or a salt thereof.

In one aspect the invention relates to a compound of formula (Ib)

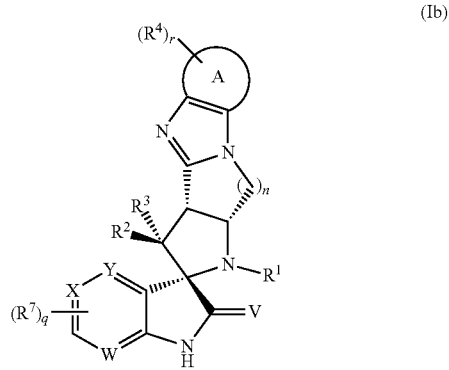

(Ib)

or a salt thereof.

In one aspect the invention relates to a compound of formula (Ic)

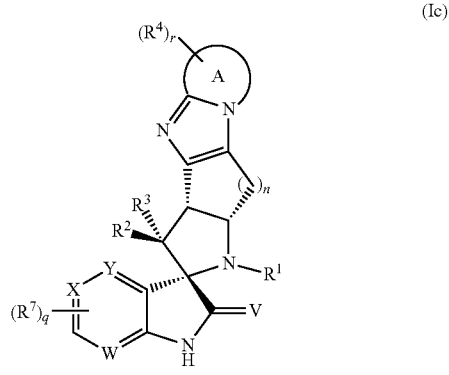

(Ic)

or a salt thereof.

In one aspect the invention relates to a compound of formula (Ia*)

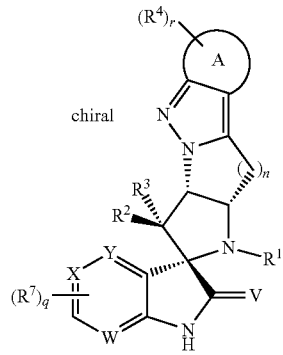

or a salt thereof.

In one aspect the invention relates to a compound of formula (Ib*)

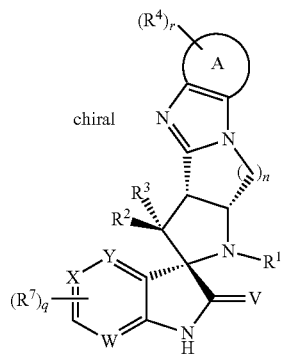

or a salt thereof.

In one aspect the invention relates to a compound of formula (Ic*)

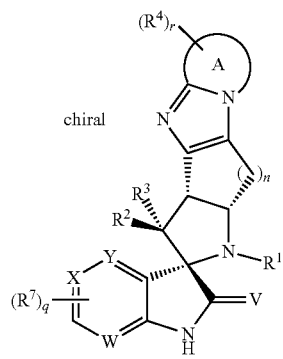

or a salt thereof.

It is to be understood that compounds (Ia), (Ib) and (Ic) each are a subset of compounds (I) and that whenever the term "compound(s) (I)" is used this also includes compound(s) (Ia), (Ib) and (Ic) unless stated otherwise.

It is to be understood that compounds (Ia*), (Ib*) and (Ic*) each are a subset of compounds (Ia), (Ib) and (Ic), respectively, and that whenever (Ia), (Ib) or (Ic) is used this also includes compound(s) (Ia*), (Ib*) and (Ic*), respectively, unless stated otherwise.

In another aspect [A1] the invention relates to a compound of formula (I), (Ia), (Ib), (Ic), (Ia*), (Ib*) or (Ic*), wherein $R^1$ is a group, optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{b1}$ is independently selected from among —$OR^{c1}$, —$NR^{c1}R^{c1}$, halogen, —CN, —$C(O)R^{c1}$, —$C(O)OR^{c1}$, —$C(O)NR^{c1}R^{c1}$, —$S(O)_2R^{c1}$, —$S(O)_2NR^{c1}R^{c1}$, —$NHC(O)R^{c1}$ and —$N(C_{1-4}alkyl)C(O)R^{c1}$;

each $R^{c1}$ independently of one another denotes hydrogen or a group, optionally substituted by one or more, identical or different $R^{d1}$ and/or $R^{e1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{d1}$ is independently selected from among —$OR^{e1}$, —$NR^{e1}R^{e1}$, halogen, —CN, —$C(O)R^{e1}$, —$C(O)OR^{e1}$, —$C(O)NR^{e1}R^{e1}$, —$S(O)_2R^{e1}$, —$S(O)_2NR^{e1}R^{e1}$, —$NHC(O)R^{e1}$ and —$N(C_{1-4}alkyl)C(O)R^{e1}$;

each $R^{e1}$ independently of one another denotes hydrogen or a group, optionally substituted by one or more, identical or different $R^{f1}$ and/or $R^{g1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{f1}$ is independently selected from among —$OR^{g1}$, —$NR^{g1}R^{g1}$, halogen, —CN, —$C(O)R^{g1}$, —$C(O)OR^{g1}$, —$C(O)NR^{g1}R^{g1}$, —$S(O)_2R^{g1}$, —$S(O)_2NR^{g1}R^{g1}$, —$NHC(O)R^{g1}$ and —$N(C_{1-4}alkyl)C(O)R^{g1}$;

each $R^{g1}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

or a salt thereof.

In another aspect [A2] the invention relates to a compound of formula (I), (Ia), (Ib), (Ic), (Ia*), (Ib*) or (Ic*), wherein $R^1$ is a group, optionally substituted by one or more, identical or different $R^{b1}$ and/or $R^{c1}$, selected from among $C_{1-6}$alkyl, $C_{2-6}$alkenyl, $C_{1-6}$haloalkyl and $C_{3-7}$cycloalkyl;

each $R^{b1}$ is independently selected from among —$OR^{c1}$, —$NR^{c1}R^{c1}$, halogen, —CN, —$C(O)R^{c1}$, —$C(O)OR^{c1}$, —$C(O)NR^{c1}R^{c1}$, —$S(O)_2R^{c1}$, —$S(O)_2NR^{c1}R^{c1}$, —$NHC(O)R^{c1}$ and —$N(C_{1-4}alkyl)C(O)R^{c1}$;

each $R^{c1}$ independently of one another denotes hydrogen or a group, optionally substituted by one or more, identical or different $R^{d1}$ and/or $R^{e1}$, selected from among $C_{1-6}$alkyl, $C_{3-7}$cycloalkyl, $C_{6-10}$aryl, 5-10 membered heteroaryl and 3-10 membered heterocyclyl;

each $R^{d1}$ is independently selected from among —$OR^{e1}$, —$NR^{e1}R^{e1}$, halogen, —CN, —$C(O)R^{e1}$, —$C(O)OR^{e1}$, —$C(O)NR^{e1}R^{e1}$, —$S(O)_2R^{e1}$, —$S(O)_2NR^{e1}R^{e1}$, —$NHC(O)R^{e1}$ and —$N(C_{1-4}alkyl)C(O)R^{e1}$;

each $R^{e1}$ independently of one another is selected from among hydrogen, $C_{1-6}$alkyl, $C_{1-6}$alkyl-O—$C_{1-6}$alkyl, $C_{3-7}$cycloalkyl, $C_{6-10}$aryl, 5-10 membered heteroaryl and 3-10 membered heterocyclyl;

or a salt thereof.

In another aspect [A3] the invention relates to a compound of formula (I), (Ia), (Ib), (Ic), (Ia*), (Ib*) or (Ic*), wherein R$^1$ is a group, optionally substituted by one or more, identical or different R$^{b1}$ and/or R$^{c1}$, selected from among C$_{1-6}$alkyl, C$_{2-6}$alkenyl, C$_{1-6}$haloalkyl and C$_{3-7}$cycloalkyl;

each R$^{b1}$ is independently selected from among —OR$^{c1}$, halogen and —S(O)$_2$R$^{c1}$;

each R$^{c1}$ independently of one another is a group, optionally substituted by one or more, identical or different R$^{d1}$ and/or R$^{e1}$, selected from among C$_{1-6}$alkyl, C$_{3-7}$cycloalkyl, C$_{6-10}$aryl and 3-10 membered heterocyclyl;

each R$^{d1}$ is independently selected from among —OR$^{e1}$, —CN and halogen;

each R$^{e1}$ independently of one another is C$_{1-6}$alkyl or C$_{1-6}$alkyl-O—C$_{1-6}$alkyl;

or a salt thereof.

In another aspect [A4] the invention relates to a compound of formula (I), (Ia), (Ib), (Ic), (Ia*), (Ib*) or (Ic*), wherein R$^1$ is a group, optionally substituted by one or more, identical or different R$^{b1}$ and/or R$^{c1}$, selected from among C$_{1-6}$alkyl, C$_{2-6}$alkenyl and C$_{1-6}$haloalkyl;

each R$^{b1}$ is independently selected from among —OR$^{c1}$ and —S(O)$_2$R$^{c1}$;

each R$^{c1}$ independently of one another is a group, optionally substituted by one or more, identical or different R$^{d1}$ and/or R$^{e1}$, selected from among C$_{1-6}$alkyl, C$_{3-7}$cycloalkyl and C$_{6-10}$aryl;

each R$^{d1}$ is independently selected from among —OR$^{e1}$, —CN and halogen;

each R$^{e1}$ independently of one another is C$_{1-6}$alkyl or C$_{1-6}$alkyl-O—C$_{1-6}$alkyl;

or a salt thereof.

In another aspect [A5] the invention relates to a compound of formula (I), (Ia), (Ib), (Ic), (Ia*), (Ib*) or (Ic*), wherein R$^1$ is a group, optionally substituted by one or more, identical or different R$^{b1}$ and/or R$^{c1}$, selected from among C$_{1-6}$alkyl, C$_{2-6}$alkenyl and C$_{1-6}$haloalkyl;

each R$^{b1}$ is independently selected from among —OR$^{c1}$ and —S(O)$_2$R$^{c1}$;

each R$^{c1}$ independently of one another is a group, optionally substituted by one or more, identical or different R$^{d1}$ and/or R$^{e1}$, selected from among C$_{1-6}$alkyl, C$_{3-7}$cycloalkyl and phenyl;

each R$^{d1}$ is independently selected from among —OR$^{e1}$, —CN and halogen;

each R$^{e1}$ independently of one another is C$_{1-6}$alkyl or C$_{1-6}$alkyl-O—C$_{1-6}$-alkyl;

or a salt thereof.

In another aspect [A6] the invention relates to a compound of formula (I), (Ia), (Ib), (Ic), (Ia*), (Ib*) or (Ic*), wherein R$^1$ is selected from among C$_{1-6}$alkyl, C$_{3-7}$cycloalkyl-C$_{1-6}$alkyl and C$_{2-6}$alkenyl;

or a salt thereof.

In another aspect [A7] the invention relates to a compound of formula (I), (Ia), (Ib), (Ic), (Ia*), (Ib*) or (Ic*), wherein R$^1$ is C$_{3-7}$cycloalkyl-C$_{1-6}$-alkyl;

or a salt thereof.

In another aspect [A8] the invention relates to a compound of formula (I), (Ia), (Ib), (Ic), (Ia*), (Ib*) or (Ic*), wherein R$^1$ is cyclopropylmethyl;

or a salt thereof.

In another aspect [B1] the invention relates to a compound of formula (I), (Ia), (Ib), (Ic), (Ia*), (Ib*) or (Ic*), wherein R$^2$ and R$^3$, each independently, is selected from among hydrogen, C$_{6-10}$aryl, 5-10 membered heteroaryl and 3-10 membered heterocyclyl, wherein said C$_{6-10}$aryl, 5-10 membered heteroaryl and 3-10 membered heterocyclyl is optionally substituted by one or more, identical or different R$^{b2}$ and/or R$^{c2}$;

each R$^{b2}$ is independently selected from among —OR$^{c2}$, —NR$^{c2}$R$^{c2}$, halogen, —CN, —C(O)R$^{c2}$, —C(O)OR$^{c2}$, —C(O)NR$^{c2}$R$^{c2}$, —S(O)$_2$R$^{c2}$, —S(O)$_2$NR$^{c2}$R$^{c2}$, —NHC(O)R$^{c2}$ and —N(C$_{1-4}$alkyl)C(O)R$^{c2}$;

each R$^{c2}$ independently of one another denotes hydrogen or a group, optionally substituted by one or more, identical or different R$^{d2}$ and/or R$^{e2}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, C$_{6-10}$aryl, 5-10 membered heteroaryl and 3-10 membered heterocyclyl;

each R$^{d2}$ is independently selected from among —OR$^{e2}$, —NR$^{e2}$R$^{e2}$, halogen, —CN, —C(O)R$^{e2}$, —C(O)OR$^{e2}$, —C(O)NR$^{e2}$R$^{e2}$, —S(O)$_2$R$^{e2}$, —S(O)$_2$NR$^{e2}$R$^{e2}$, —NHC(O)R$^{e2}$ and —N(C$_{1-4}$alkyl)C(O)R$^{e2}$;

each R$^{e2}$ independently of one another denotes hydrogen or a group selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, C$_{6-10}$aryl, 5-10 membered heteroaryl and 3-10 membered heterocyclyl;

or a salt thereof.

In another aspect [B2] the invention relates to a compound of formula (I), (Ia), (Ib), (Ic), (Ia*), (Ib*) or (Ic*), wherein one of R$^2$ and R$^3$ is hydrogen and the other is selected from among phenyl and 5-6 membered heteroaryl, wherein said phenyl and 5-6 membered heteroaryl is optionally substituted by one or more, identical or different R$^{b2}$ and/or R$^{c2}$;

each R$^{b2}$ is independently selected from among —OR$^{c2}$, —NR$^{c2}$R$^{c2}$, halogen, —CN, —C(O)R$^{c2}$, —C(O)OR$^{c2}$, —C(O)NR$^{c2}$R$^{c2}$, —S(O)$_2$R$^{c2}$, —S(O)$_2$NR$^{c2}$R$^{c2}$, —NHC(O)R$^{c2}$ and —N(C$_{1-4}$alkyl)C(O)R$^{c2}$;

each R$^{c2}$ independently of one another denotes hydrogen or a group selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, phenyl, 5-6 membered heteroaryl and 3-7 membered heterocyclyl;

or a salt thereof.

In another aspect [B3] the invention relates to a compound of formula (I), (Ia), (Ib), (Ic), (Ia*), (Ib*) or (Ic*), wherein one of R$^2$ and R$^3$ is hydrogen and the other is selected from among phenyl and 5-6 membered heteroaryl, wherein said phenyl and 5-6 membered heteroaryl is optionally substituted by one or more, identical or different substituents selected from among —OC$_{1-6}$alkyl, halogen, C$_{1-6}$alkyl and C$_{1-6}$haloalkyl;

or a salt thereof.

In another aspect [B4] the invention relates to a compound of formula (I), (Ia), (Ib), (Ic), (Ia*), (Ib*) or (Ic*), wherein one of R$^2$ and R$^3$ is hydrogen and the other is selected from among phenyl, thienyl and pyridyl, wherein said phenyl, thienyl and pyridyl is optionally substituted by one or more, identical or different substituents selected from among —OC$_{1-6}$alkyl, halogen, C$_{1-6}$alkyl and C$_{1-6}$haloalkyl;

or a salt thereof.

In another aspect [B5] the invention relates to a compound of formula (I), (Ia), (Ib), (Ic), (Ia*), (Ib*) or (Ic*), wherein one of $R^2$ and $R^3$ is hydrogen and the other is selected from among 3-chloro phenyl, 3-chloro-2-fluoro phenyl and 3-bromo 2-fluoro phenyl;
or a salt thereof.

In further aspects [B6], [B7], [B8], [B9], [B10] and [B11] the invention relates to a compound of formula (I), (Ia), (Ib), (Ic), (Ia*), (Ib*) or (Ic*) with structural aspects [B0], [B1], [B2] [B3], [B4] and [B5], wherein
$R^3$ is hydrogen;
or a salt thereof.

In further aspects [B12], [B13], [B14], [B15], [B16] and [B17] the invention relates to a compound of formula (I), (Ia), (Ib), (Ic), (Ia*), (Ib*) or (Ic*) with structural aspects [B0], [B1], [B2] [B3], [B4] and [B5], wherein
$R^2$ is hydrogen;
or a salt thereof.

In another aspect [C1] the invention relates to a compound of formula (I), (Ia), (Ib), (Ic), (Ia*), (Ib*) or (Ic*), wherein
A is selected from among phenyl and 5-6 membered heteroaryl if F is carbon or
A is 5-6 membered, nitrogen-containing heteroaryl if F is nitrogen;
each $R^4$ is independently selected from among $R^{a4}$ and $R^{b4}$;
  each $R^{a4}$ independently of one another is a group, optionally substituted by one or more, identical or different $R^{b4}$ and/or $R^{c4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
  each $R^{b4}$ is independently selected from among —$OR^{c4}$, —$NR^{c4}R^{c4}$, halogen, —CN, —$C(O)R^{c4}$, —$C(O)OR^{c4}$, —$C(O)NR^{c4}R^{c4}$, —$C(O)NR^{g4}OR^{c4}$, —$S(O)_2R^{c4}$, —$S(O)_2NR^{c4}R^{c4}$, —$NHSO_2R^{c4}$, —$N(C_{1-4}alkyl)SO_2R^{c4}$, —$NHC(O)R^{c4}$ and —$N(C_{1-4}alkyl)C(O)R^{c4}$;
  each $R^{c4}$ independently of one another denotes hydrogen or a group, optionally substituted by one or more, identical or different $R^{d4}$ and/or $R^{e4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
  each $R^{d4}$ is independently selected from among —$OR^{e4}$, —$NR^{e4}R^{e4}$, halogen, —CN, —$C(O)R^{e4}$, —$C(O)OR^{e4}$, —$C(O)NR^{e4}R^{e4}$, —$C(O)NR^{g4}OR^{e4}$, —$S(O)_2R^{e4}$, —$S(O)_2NR^{e4}R^{e4}$, —$NHC(O)R^{e4}$ and —$N(C_{1-4}alkyl)C(O)R^{e4}$;
  each $R^{e4}$ independently of one another denotes hydrogen or a group, optionally substituted by one or more, identical or different $R^{f4}$ and/or $R^{g4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
  each $R^{f4}$ is independently selected from among —$OR^{g4}$, —$NR^{g4}R^{g4}$, halogen, —CN, —$C(O)R^{g4}$, —$C(O)OR^{g4}$, —$C(O)NR^{g4}R^{g4}$, —$C(O)NR^{g4}OR^{g4}$, —$S(O)_2R^{g4}$, —$S(O)_2NR^{g4}R^{g4}$, —$NHC(O)R^{g4}$ and —$N(C_{1-4}alkyl)C(O)R^{g4}$;
  each $R^{g4}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
  r denotes the number 0, 1, 2 or 3;
or a salt thereof.

In another aspect [C2] the invention relates to a compound of formula (I), (Ia), (Ib), (Ia*) or (Ib*), wherein
A is phenyl and F is carbon;
each $R^4$ is independently selected from among $R^{a4}$ and $R^{b4}$;
  each $R^{a4}$ independently of one another is a group, optionally substituted by one or more, identical or different $R^{b4}$ and/or $R^{c4}$, selected from among $C_{1-6}$alkyl, $C_{1-6}$haloalkyl, $C_{3-7}$cycloalkyl and 3-10 membered heterocyclyl;
  each $R^{b4}$ is independently selected from among —$OR^{c4}$, —$NR^{c4}R^{c4}$, halogen, —$C(O)R^{c4}$, —$C(O)OR^{c4}$, —$C(O)NR^{c4}R^{c4}$, —$C(O)NR^{g4}OR^{c4}$, —$S(O)_2R^{c4}$ and —$NHC(O)R^4$;
  each $R^{c4}$ independently of one another denotes hydrogen or a group, optionally substituted by one or more, identical or different $R^{d4}$ and/or $R^{e4}$, selected from among $C_{1-6}$alkyl, $C_{1-6}$haloalkyl, $C_{3-7}$cycloalkyl and 3-10 membered heterocyclyl;
  each $R^{d4}$ is independently selected from among —$OR^{e4}$, $NR^{e4}R^{e4}$ and —$S(O)_2R^{e4}$;
  each $R^{e4}$ independently of one another denotes hydrogen or a group, optionally substituted by one or more, identical or different $R^{f4}$ and/or $R^{g4}$, selected from among $C_{1-6}$alkyl and 3-10 membered heterocyclyl;
  each $R^{f4}$ is —$OR^{g4}$;
  each $R^{g4}$ is independently selected from among hydrogen and $C_{1-6}$alkyl;
  r denotes the number 0, 1, 2 or 3;
or a salt thereof.

In another aspect [C3] the invention relates to a compound of formula (I), (Ia), (Ib), (Ic), (Ia*), (Ib*) or (Ic*), wherein
A is selected from among phenyl and 5-6 membered heteroaryl if F is carbon or
A is 5-6 membered, nitrogen-containing heteroaryl if F is nitrogen;
each $R^4$ is independently selected from among $R^{a4}$ and $R^{b4}$;
  each $R^{a4}$ independently of one another is a group, optionally substituted by one or more, identical or different $R^{b4}$ and/or $R^{c4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
  each $R^{b4}$ is independently selected from among —$OR^{c4}$, —$NR^{c4}R^{c4}$, halogen, —CN, —$C(O)R^{c4}$, —$C(O)OR^{c4}$, —$C(O)NR^{c4}R^{c4}$, —$C(O)NHOR^{c4}$, —$S(O)_2R^{c4}$, —$S(O)_2NR^{c4}R^{c4}$, —$NHSO_2R^{c4}$, —$N(C_{1-4}alkyl)SO_2R^{c4}$, —$NHC(O)R^{c4}$ and —$N(C_{1-4}alkyl)C(O)R^{c4}$;
  each $R^{c4}$ independently of one another is selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
  r denotes the number 0, 1, 2 or 3;
or a salt thereof.

In another aspect [C4] the invention relates to a compound of formula (I), (Ia), (Ib), (Ic), (Ia*), (Ib*) or (Ic*), wherein
A is selected from among phenyl and pyridyl if F is carbon or
A is pyridyl if F is nitrogen;
each $R^4$ is independently selected from among $R^{a4}$ and $R^{b4}$;
  each $R^{a4}$ independently of one another is $C_{1-6}$alkyl optionally substituted by one or more, identical or different $R^{b4}$;
  each $R^{b4}$ is independently selected from among —$OR^{c4}$, —$NR^{c4}R^{c4}$, halogen, —CN, —$C(O)R^{c4}$, —$C(O)OR^{c4}$, —C(O)NR$^{c4}$R$^{c4}$, —C(O)NR$^{g4}$OR$^{c4}$, —S(O)$_2$R$^{c4}$, —S(O)$_2$NR$^{c4}$R$^{c4}$, —NHSO$_2$R$^{c4}$, —N(C$_{1-4}$alkyl)SO$_2$R$^{c4}$, —NHC(O)R$^{c4}$ and —N(C$_{1-4}$alkyl)C(O)R$^{c4}$;

each R$^{c4}$ independently of one another is selected from among hydrogen and C$_{1-6}$alkyl;

r denotes the number 0, 1, 2 or 3;

or a salt thereof.

In another aspect [C5] the invention relates to a compound of formula (I), (Ia), (Ib), (Ic), (Ia*), (Ib*) or (Ic*), wherein A is selected from among phenyl and pyridyl if F is carbon or A is pyridyl if F is nitrogen;

each R$^4$ is independently selected from among R$^{a4}$ and R$^{b4}$;

each R$^{a4}$ independently of one another is C$_{1-6}$alkyl optionally substituted by one or more, identical or different R$^{b4}$;

each R$^{b4}$ is independently selected from among —OR$^{c4}$, halogen, —CN, —C(O)OR$^{c4}$, —C(O)NR$^{c4}$R$^{c4}$ and —S(O)$_2$R$^{c4}$;

each R$^{c4}$ independently of one another is selected from among hydrogen and C$_{1-6}$alkyl;

r denotes the number 0, 1, 2 or 3;

or a salt thereof.

In another aspect [C6] the invention relates to a compound of formula (I), (Ia), (Ib), (Ia*) or (Ib*), wherein A is phenyl and F is carbon;

each R$^4$ is independently selected from among R$^{a4}$ and R$^{b4}$;

each R$^{a4}$ independently of one another is C$_{1-6}$alkyl optionally substituted by one or more, identical or different R$^{b4}$;

each R$^{b4}$ is independently selected from among —OR$^{c4}$, halogen, —CN, —C(O)OR$^{c4}$, —C(O)NR$^{c4}$R$^{c4}$ and —S(O)$_2$R$^{c4}$;

each R$^{c4}$ independently of one another is selected from among hydrogen and C$_{1-6}$alkyl;

r denotes the number 0, 1, 2 or 3;

or a salt thereof.

In further aspects [C7], [C8], [C9], [C10], [C11], [C12] and [C13] the invention relates to a compound of formula (I), (Ia), (Ib), (Ic), (Ia*), (Ib*) or (Ic*) with structural aspects [C0], [C1], [C2], [C3], [C4], [C5] and [C6], wherein r denotes the number 1 or 2;

or a salt thereof.

In another aspect [C14] the invention relates to a compound of formula (I), (Ia), (Ib), (Ia*) or (Ib*), wherein A together with the r substituents R$^4$ is

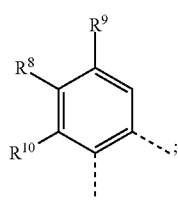

R$^8$ is selected from among hydrogen, C$_{1-6}$alkyl, —OC$_{1-6}$alkyl, halogen, —CN, —C(O)OH, —C(O)OC$_{1-6}$alkyl, —C(O)NH$_2$, —C(O)NHC$_{1-6}$alkyl, —C(O)N(C$_{1-6}$alkyl)$_2$ and —S(O)$_2$C$_{1-6}$alkyl;

R$^9$ is selected from among hydrogen, C$_{1-6}$alkyl, —OC$_{1-6}$alkyl, halogen, —CN, —C(O)OH, —C(O)OC$_{1-6}$alkyl, —C(O)NH$_2$, —C(O)NHC$_{1-6}$alkyl, —C(O)N(C$_{1-6}$alkyl)$_2$ and —S(O)$_2$C$_{1-6}$alkyl;

R$^{10}$ is selected from among hydrogen, C$_{1-6}$alkyl, —OC$_{1-6}$alkyl, halogen, —CN, —C(O)OH, —C(O)OC$_{1-6}$alkyl, —C(O)NH$_2$, —C(O)NHC$_{1-6}$alkyl, —C(O)N(C$_{1-6}$alkyl)$_2$ and —S(O)$_2$C$_{1-6}$alkyl;

with the proviso that at least one of R$^8$ to R$^{10}$ but not all of R$^8$ to R$^{10}$ is/are hydrogen;

or a salt thereof.

In another aspect [C15] the invention relates to a compound of formula (I), (Ia), (Ib), (Ia*) or (Ib*), wherein A together with the r substituents R$^4$ is

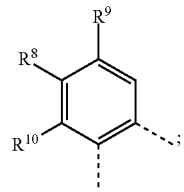

R$^8$ is —C(O)OH;

one of R$^9$ and R$^{10}$ is C$_{1-4}$alkyl and the other is hydrogen;

or a salt thereof.

In another aspect [D1] the invention relates to a compound of formula (I), (Ia), (Ib), (Ic), (Ia*), (Ib*) or (Ic*), wherein n denotes the number 1 or 2;

or a salt thereof.

In another aspect [D2] the invention relates to a compound of formula (I), (Ia), (Ib), (Ic), (Ia*), (Ib*) or (Ic*), wherein n is 1;

or a salt thereof.

In another aspect [D3] the invention relates to a compound of formula (I), (Ia), (Ib), (Ic), (Ia*), (Ib*) or (Ic*), wherein n is 2;

or a salt thereof.

In another aspect [E1] the invention relates to a compound of formula (I), (Ia), (Ib), (Ic), (Ia*), (Ib*) or (Ic*), wherein each R$^7$ independently is halogen or —CN and q is 1 or 2;

or a salt thereof.

In another aspect [E2] the invention relates to a compound of formula (I), (Ia), (Ib), (Ic), (Ia*), (Ib*) or (Ic*), wherein each R$^7$ independently is chlorine or fluorine and q is 1 or 2;

or a salt thereof.

In another aspect [F1] the invention relates to a compound of formula (I), (Ia), (Ib), (Ic), (Ia*), (Ib*) or (Ic*), wherein W, X and Y are —CH= with the proviso that the hydrogen in each —CH= may be replaced by a substituent R$^7$ if present;

or a salt thereof.

In another aspect [EF1] the invention relates to a compound of formula (I), (Ia), (Ib), (Ic), (Ia*), (Ib*) or (Ic*), wherein the 6-membered ring comprising W, X and Y together with the q substituents R$^7$ has a substructure selected from among (i) and (ii)

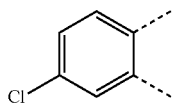

(i)

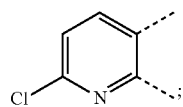

or a salt thereof.

In another aspect [G1] the invention relates to a compound of formula (I), (Ia), (Ib), (Ic), (Ia*), (Ib*) or (Ic*), wherein
V is oxygen;
or a salt thereof.

All the above-mentioned structural aspects A to A8, B1 to B17, C1 to C15, D1 to D3, E1 and E2, F1, G1 and E1 are preferred embodiments of the corresponding aspects A0, B0, C0, D0, E0, F0, EF0 and G0, respectively, wherein EF0 (EF) represents the combination of E0 (E) and F0 (F). The structural aspects A0 to A8, B0 to B17, C0 to C15, D0 to D3, E0 to E2, F0 and F1, EF0 and EF, and G0 and G1 relating to different molecular parts of the compounds (I), (Ia), (Ib), (Ic), (Ia*), (Ib*) and (Ic*) according to the invention may be permutated with one another as desired in combinations ABCDEFG, so as to obtain preferred compounds (I), (Ia), (Ib), (Ic), (Ia*), (Ib*) and (Ic*) (aspects E and F can be replaced by combination aspect EF). Each combination ABCDEFG represents and defines individual embodiments or generic subsets of compounds according to the invention.

Preferred embodiments of the invention with structure (Ia) are example compounds Ia-1 to Ia-57.

Preferred embodiments of the invention with structure (Ib) are example compounds Ib-1 to Ib-254.

Preferred embodiments of the invention with structure (Ic) are example compounds Ic-1 to Ic-38.

All synthetic intermediates generically defined as well es specifically disclosed herein and their salts are also part of the invention.

In a further aspect the invention also relates to synthetic intermediates of formula B-3 and their salts, which can be used as key intermediates in the synthesis of compounds of formula (Ia) and (Ia*):

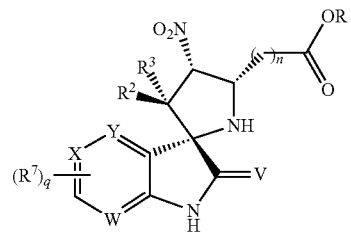

The definitions of groups $R^2$, $R^3$, $R^7$, V, W, X, Y, q and n in B-3 correspond to those as given for compound (I), (Ia), (Ib), (Ic), (Ia*), (Ib*) or (Ic*) above, i.e. [B0] for $R^2/R^3$, [D0] for n, [E0] for $R^7/q$, [F0] for W/X/Y and [G0] for V. R is a carboxyl protecting group, e.g. $C_{1-6}$alkyl or t-Bu.

Preferred intermediates B-3 are those which lead to preferred compounds (Ia) and (Ia*) according to the invention, i.e. preferred embodiments of B-3 have structural aspects selected from [B0] to [B17] for $R^2/R^3$, [D0] to [D3] for n, [E0] to [E2] for $R^7/q$, [F0] and [F1] for W/X/Y, [G0] and [G1] for V and [EF0] and [EF1] for $R^7/q$/W/X/Y altogether. These structural aspects (including definitions of R) may be permutated with one another as desired in combinations BDEFGR, so as to obtain preferred intermediates B-3 (aspects E and F can be replaced by combination aspect EF). Each combination BDEFGR represents and defines individual embodiments or generic subsets of intermediates B-3.

In a further aspect the invention also relates to the use of synthetic intermediates of formula B-3 or their salts (and the various embodiments and sub-groups as described and/or defined herein) in the synthesis of compounds (Ia) and (Ia*).

In a further aspect the invention also relates to synthetic intermediates of formula B-4 and their salts, which can be used as key intermediates in the synthesis of compounds of formula (Ia) and (Ia*):

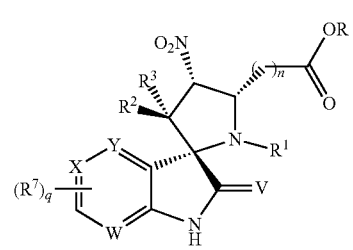

The definitions of groups $R^1$, $R^2$, $R^3$, $R^7$, V, W, X, Y, q and n in B-4 correspond to those as given for compound (I), (Ia), (Ib), (Ic), (Ia*), (Ib*) or (Ic*) above, i.e. [A0] for $R^1$, [B0] for $R^2/R$, [D0] for n, [E0] for R/q, [F0] for W/X/Y and [G0] for V. R is a carboxyl protecting group, e.g. $C_{1-6}$alkyl or t-Bu.

Preferred intermediates B-4 are those which lead to preferred compounds (Ia) and (Ia*) according to the invention, i.e. preferred embodiments of B-4 have structural aspects selected from [A0] to [A8] for $R^1$, [B0] to [B17] for $R^2/R^3$, [D0] to [D3] for n, [E0] to [E2] for $R^7/q$, [F0] and [F1] for W/X/Y, [G0] and [G1] for V and [EF0] and [EF1] for $R^7/q$/W/X/Y altogether. These structural aspects (including definitions of R) may be permutated with one another as desired in combinations ABDEFGR, so as to obtain preferred intermediates B-4 (aspects E and F can be replaced by combination aspect EF). Each combination ABDEFGR represents and defines individual embodiments or generic subsets of intermediates B-4.

In a further aspect the invention also relates to the use of synthetic intermediates of formula B-4 or their salts (and the various embodiments and sub-groups as described and/or defined herein) in the synthesis of compounds (Ia) and (Ia*).

In a further aspect the invention also relates to synthetic intermediates of formula B-7 and their salts, which can be used as key intermediates in the synthesis of compounds of formula (Ia) and (Ia*):

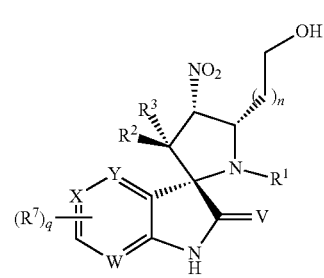

The definitions of groups $R^1$, $R^2$, R, $R^7$, V, W, X, Y, q and n in B-7 correspond to those as given for compound (I), (Ia), (Ib), (Ic), (Ia*), (Ib*) or (Ic*) above, i.e. [A0] for $R^1$, [B0] for $R^2$/R, [D0] for n, [E0] for R/q, [F0] for W/X/Y and [G0] for V.

Preferred intermediates B-7 are those which lead to preferred compounds (Ia) and (Ia*) according to the invention, i.e. preferred embodiments of B-7 have structural aspects selected from [A0] to [A8] for $R^1$, [B0] to [B17] for $R^2$/$R^3$, [D0] to [D3] for n, [E0] to [E2] for $R^7$/q, [F0] and [F1] for W/X/Y, [G0] and [G1] for V and [EF0] and [EF1] for $R^7$/q/W/X/Y altogether. These structural aspects may be permutated with one another as desired in combinations ABDEFG, so as to obtain preferred intermediates B-7 (aspects E and F can be replaced by combination aspect EF). Each combination ABDEFG represents and defines individual embodiments or generic subsets of intermediates B-7.

In a further aspect the invention also relates to the use of synthetic intermediates of formula B-7 or their salts (and the various embodiments and sub-groups as described and/or defined herein) in the synthesis of compounds (Ia) and (Ia*).

In a further aspect the invention also relates to synthetic intermediates of formula B-6 and their salts, which can be used as key intermediates in the synthesis of compounds of formula (Ia) and (Ia*):

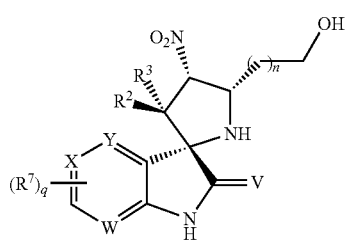

B-6

The definitions of groups $R^2$, $R^3$, $R^7$, V, W, X, Y, q and n in B-6 correspond to those as given for compound (I), (Ia), (Ib), (Ic), (Ia*), (Ib*) or (Ic*) above, i.e. [B0] for $R^2$/R, [D0] for n, [E0] for $R^7$/q, [F0] for W/X/Y and [G0] for V.

Preferred intermediates B-6 are those which lead to preferred compounds (Ia) and (Ia*) according to the invention, i.e. preferred embodiments of B-6 have structural aspects selected from [B0] to [B17] for $R^2$/R, [D0] to [D3] for n, [E0] to [E2] for $R^7$/q, [F0] and [F1] for W/X/Y, [G0] and [G1] for V and [EF0] and [EF1] for $R^7$/q/W/X/Y altogether. These structural aspects may be permutated with one another as desired in combinations BDEFG, so as to obtain preferred intermediates B-6 (aspects E and F can be replaced by combination aspect EF). Each combination BDEFG represents and defines individual embodiments or generic subsets of intermediates B-6.

In a further aspect the invention also relates to the use of synthetic intermediates of formula B-6 or their salts (and the various embodiments and sub-groups as described and/or defined herein) in the synthesis of compounds (Ia) and (Ia*).

In a further aspect the invention also relates to synthetic intermediates of formula B-8 and their salts, which can be used as key intermediates in the synthesis of compounds of formula (Ia) and (Ia*):

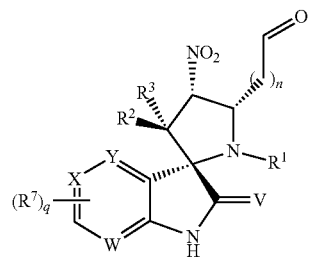

B-8

The definitions of groups $R^1$, $R^2$, R, $R^7$, V, W, X, Y, q and n in B-8 correspond to those as given for compound (I), (Ia), (Ib), (Ic), (Ia*), (Ib*) or (Ic*) above, i.e. [A0] for $R^1$, [B0] for $R^2$/$R^3$, [D0] for n, [E0] for $R^7$/q, [F0] for W/X/Y and [G0] for V.

Preferred intermediates B-8 are those which lead to preferred compounds (Ia) and (Ia*) according to the invention, i.e. preferred embodiments of B-8 have structural aspects selected from [A0] to [A8] for $R^1$, [B0] to [B17] for $R^2$/$R^3$, [D0] to [D3] for n, [E0] to [E2] for $R^7$/q, [F0] and [F1] for W/X/Y, [G0] and [G1] for V and [EF0] and [EF1] for $R^7$/q/W/X/Y altogether. These structural aspects may be permutated with one another as desired in combinations ABDEFG, so as to obtain preferred intermediates B-8 (aspects E and F can be replaced by combination aspect EF). Each combination ABDEFG represents and defines individual embodiments or generic subsets of intermediates B-8.

In a further aspect the invention also relates to the use of synthetic intermediates of formula B-8 or their salts (and the various embodiments and sub-groups as described and/or defined herein) in the synthesis of compounds (Ia) and (a*).

In a further aspect the invention also relates to synthetic intermediates of formula B-10 and their salts, which can be used as key intermediates in the synthesis of compounds of formula (Ia) and (Ia*):

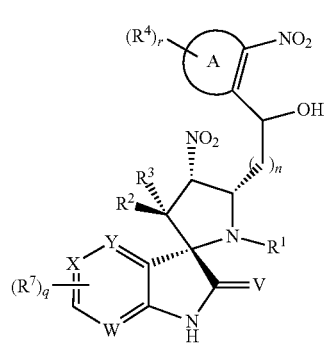

B-10

The definitions of groups $R^1$, $R^2$, $R^3$, $R^4$, $R^7$, A, V, W, X, Y, r, q and n in B-10 correspond to those as given for compound (I), (Ia), (Ib), (Ic), (Ia*), (Ib*) or (Ic*) above, i.e. [A0] for $R^1$, [B0] for $R^2$/$R^3$, [C0] for A/$R^4$/r, [D0] for n, [E0] for $R^7$/q, [F0] for W/X/Y and [G0] for V.

Preferred intermediates B-10 are those which lead to preferred compounds (Ia) and (Ia*) according to the invention, i.e. preferred embodiments of B-10 have structural aspects selected from [A0] to [A8] for $R^1$, [B0] to [B17] for $R^2$/$R^3$, [C0] to [C15] for A/$R^4$/r, [D0] to [D3] for n, [E0] to [E2] for $R^7$/q, [F0] and [F1] for W/X/Y, [G0] and [G1] for V and [EF0] and [EF1] for $R^7$/q/W/X/Y altogether. These structural aspects may be permutated with one another as desired in combinations ABCDEFG, so as to obtain preferred intermediates B-10 (aspects E and F can be replaced by combination aspect EF). Each combination ABCDEFG represents and defines individual embodiments or generic subsets of intermediates B-10.

In a further aspect the invention also relates to the use of synthetic intermediates of formula B-10 or their salts (and the various embodiments and sub-groups as described and/or defined herein) in the synthesis of compounds (Ia) and (Ia*).

In a further aspect the invention also relates to synthetic intermediates of formula B-11 and their salts, which can be used as key intermediates in the synthesis of compounds of formula (Ia) and (Ia*):

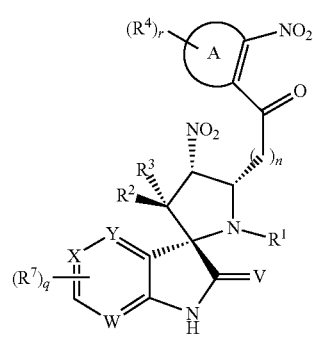

B-11

The definitions of groups $R^1$, $R^2$, $R^3$, $R^4$, $R^7$, A, V, W, X, Y, r, q and n in B-11 correspond to those as given for compound (I), (Ia), (Ib), (Ic), (Ia*), (Ib*) or (Ic*) above, i.e. [A0] for $R^1$, [B0] for $R^2/R^3$, [C0] for $A/R^4/r$, [D0] for n, [E0] for $R^7/q$, [F0] for W/X/Y and [G0] for V.

Preferred intermediates B-11 are those which lead to preferred compounds (Ia) and (Ia*) according to the invention, i.e. preferred embodiments of B-11 have structural aspects selected from [A0] to [A8] for $R^1$, [B0] to [B17] for $R^2/R^3$, [C0] to [C15] for $A/R^4/r$, [D0] to [D3] for n, [E0] to [E2] for $R^7/q$, [F0] and [F1] for W/X/Y, [G0] and [G1] for V and [EF0] and [EF1] for $R^7/q$/W/X/Y altogether. These structural aspects may be permutated with one another as desired in combinations ABCDEFG, so as to obtain preferred intermediates B-11 (aspects E and F can be replaced by combination aspect EF). Each combination ABCDEFG represents and defines individual embodiments or generic subsets of intermediates B-11.

In a further aspect the invention also relates to the use of synthetic intermediates of formula B-11 or their salts (and the various embodiments and sub-groups as described and/or defined herein) in the synthesis of compounds (Ia) and (Ia*).

In a further aspect the invention also relates to synthetic intermediates of formula B-12 and their salts, which can be used as key intermediates in the synthesis of compounds of formula (Ia) and (Ia*):

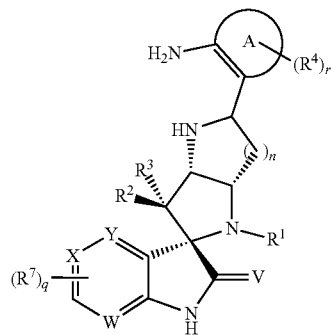

B-12

The definitions of groups $R^1$, $R^2$, $R^3$, $R^4$, $R^7$, A, V, W, X, Y, r, q and n in B-12 correspond to those as given for compound (I), (Ia), (Ib), (Ic), (Ia*), (Ib*) or (Ic*) above, i.e. [A0] for $R^1$, [B0] for $R^2/R^3$, [C0] for $A/R^4/r$, [D0] for n, [E0] for $R^7/q$, [F0] for W/X/Y and [G0] for V.

Preferred intermediates B-12 are those which lead to preferred compounds (Ia) and (Ia*) according to the invention, i.e. preferred embodiments of B-12 have structural aspects selected from [A0] to [A8] for $R^1$, [B0] to [B17] for $R^2/R^3$, [C0] to [C15] for $A/R^4/r$, [D0] to [D3] for n, [E0] to [E2] for $R^7/q$, [F0] and [F1] for W/X/Y, [G0] and [G1] for V and [EF0] and [EF1] for $R^7/q$/W/X/Y altogether. These structural aspects may be permutated with one another as desired in combinations ABCDEFG, so as to obtain preferred intermediates B-12 (aspects E and F can be replaced by combination aspect EF). Each combination ABCDEFG represents and defines individual embodiments or generic subsets of intermediates B-12.

In a further aspect the invention also relates to the use of synthetic intermediates of formula B-12 or their salts (and the various embodiments and sub-groups as described and/or defined herein) in the synthesis of compounds (Ia) and (Ia*).

In a further aspect the invention also relates to synthetic intermediates of formula B-16 and their salts, which can be used as key intermediates in the synthesis of compounds of formula (Ia) and (Ia*):

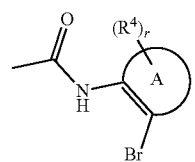

B-16

The definitions of group $R^4$, A and r in B-16 correspond to those as given for compound (I), (Ia), (Ib), (Ic), (Ia*), (Ib*) or (Ic*) above, i.e. [C0] for $A/R^4/r$.

Preferred intermediates B-16 are those which lead to preferred compounds (Ia) and (Ia*) according to the invention, i.e. preferred embodiments of B-16 have structural aspects selected from [C0] to [C15] for $A/R^4/r$ each defining individual embodiments or generic subsets of intermediates B-16. Preferred intermediates B-16 are selected from intermediates B-16a to B-16f (see table 15-2 below), including their salts.

In a further aspect the invention also relates to the use of synthetic intermediates of formula B-16 or their salts (and the various embodiments and sub-groups as described and/or defined herein) in the synthesis of compounds (Ia) and (Ia*).

In a further aspect the invention also relates to a method for synthesizing an intermediate of formula B-16

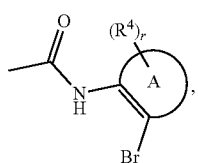
B-16 or a salt thereof,
comprising bromination of a compound of formula B-15

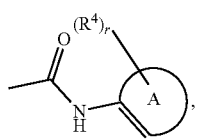
B-15 or a salt thereof, wherein
the reaction is performed in a solvent with a source of electrophilic bromine in the presence of a palladium catalyst and an acidic additive, and $R^4$, A and r is as hereinbefore defined.

STEP A

Embodiments/Conditions for STEP A

The solvent to be chosen can be an organic solvent, preferably chosen from the group consisting of a carboxylic acid, a carboxylic ester, an alkane and an aromatic solvent, or a mixture thereof. More preferably the solvent is chosen from the group consisting of AcOH, nBuOAc, iPrOAc, MCH, nHep, toluene and xylol (or a mixture thereof, e.g. nBuOAc/AcOH (9:1), iPrOAc/AcOH (9:1), toluene/AcOH (9:1)). Most preferred is AcOH.

The source of electrophilic bromine can, e.g., be selected from the group consisting of NBS, N-bromosaccharine and 1,3-dibromo-5,5-dimethylhydantoine. Preferably, NBS is chosen as source of electrophilic bromine.

Preferably, the palladium catalyst to be used can be a Pd(II) catalyst, e.g., a Pd(II) catalyst chosen from the group consisting of Pd(OAc)$_2$ and Pd(OC(O)CF$_3$)$_2$. The preferred Pd(II) catalyst is Pd(OAc)$_2$.

As far as the acidic additive is concerned this is preferentially an aromatic acid, preferably an aromatic sulfonic acid. Most preferred acidic additive is TsOH or a hydrate thereof.

The reaction can be performed at a temperature range of about 70° C. to about 100° C., preferably at about 60° C. to about 90° C. Most preferably, the temperature range is about 60° C. to about 80° C.

Preferred intermediates B-16 which may be synthesized by this method are selected from any one of intermediates B-16a to B-16f (see table 15-2 below), including their salts.

The advantage of the bromination step as described herein is its efficiency and high yield due to almost complete control of regiochemistry for the subsequent installation of the linker between substituted ring system A and the isatin (oxindole) scaffold which is also positively influenced by the anilide protecting group, the temperature range applied and the choice of AcOH as reaction solvent. In addition, the use of NBS is process friendly.

In a further aspect the invention also relates to synthetic intermediates of formula B-17 and their salts, which can be used as key intermediates in the synthesis of compounds of formula (Ia) and (Ia*):

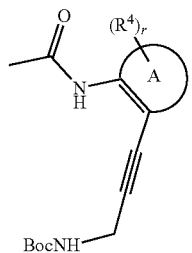
B-17

The definitions of group $R^4$, A and r in B-17 correspond to those as given for compound (I), (Ia), (Ib), (Ic), (Ia*), (Ib*) or (Ic*) above, i.e. [C0] for A/$R^4$/r.

Preferred intermediates B-17 are those which lead to preferred compounds (Ia) and (Ia*) according to the invention, i.e. preferred embodiments of B-17 have structural aspects selected from [C0] to [C15] for A/$R^4$/r each defining individual embodiments or generic subsets of intermediates B-17. Preferred intermediates B-17 are selected from intermediates B-17a to B-17f (see table 15-3 below), including their salts.

In a further aspect the invention also relates to the use of synthetic intermediates of formula B-17 or their salts (and the various embodiments and sub-groups as described and/or defined herein) in the synthesis of compounds (Ia) and (Ia*).

In a further aspect the invention also relates to a method for synthesizing an intermediate of formula B-17

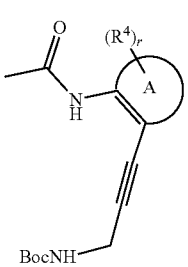
B-17 or a salt thereof,
comprising reacting a compound of formula B-16

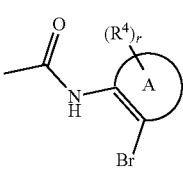
B-16 or a salt thereof,
with prop-2-ynyl-carbamic acid tert-butyl ester

[Structure: tert-butyl prop-2-ynylcarbamate]

wherein
the reaction is performed in a solvent in the presence of a palladium catalyst, a ligand, a base and, optionally, a copper co-catalyst, and $R^4$, A and r is as hereinbefore defined.

STEP B

Embodiments/Conditions for STEP B

The solvent to be chosen can be an organic solvent, preferably chosen from the group consisting of DMSO, DMF, ACN, THF, dioxane, NMP, iPrOAc, toluene, nBuOH, or a mixture thereof. Most preferred is DMSO.

Preferably, the palladium catalyst to be used is a Pd(II) or a Pd(0) catalyst, e.g., a palladium catalyst chosen from the group consisting of $Pd(OAc)_2$ and $Pd_2(dba)_3$. The preferred palladium catalyst is $Pd_2(dba)_3$.

The ligand to be used in the reaction is preferably an organophosphorous compound, e.g. a ligand selected from the group consisting of $[(tBu)_3PH]BF_4$, RuPhos and Xphos. The preferred ligand to be used is $[(tBu)_3PH]BF_4$.

The copper co-catalyst, if present, preferably is a copper salt, more preferably a Cu(I) salt, e.g. selected from the group consisting of CuI, CuCl and $Cu_2O$. The preferred copper co-catalyst is CuI.

The base to be used is preferably an organic base, more preferably an amine base, e.g. a secondary amine. Most preferred is the use of DIPA.

The reaction can be performed at a temperature range of about 20° C. to about 70° C., preferably at about 20° C. to about 40° C. Most preferably, the temperature range is about 20° C. to about 30° C.

Preferred intermediates B-17 which may be synthesized by this method are selected from any one of intermediates B-17a to B-17f (see table 15-3 below), including their salts.

In a further aspect the invention also relates to synthetic intermediates of formula B-18 and their salts, which can be used as key intermediates in the synthesis of compounds of formula (Ia) and (Ia*):

[Structure B-18]

The definitions of group $R^4$, A and r in B-18 correspond to those as given for compound (I), (Ia), (Ib), (Ic), (Ia*), (Ib*) or (Ic*) above, i.e. [C0] for A/$R^4$/r.

Preferred intermediates B-18 are those which lead to preferred compounds (Ia) and (Ia*) according to the invention, i.e. preferred embodiments of B-18 have structural aspects selected from [C0] to [C15] for A/$R^4$/r each defining individual embodiments or generic subsets of intermediates B-18. Preferred intermediates B-18 are selected from intermediates B-18a to B-18l (see tables 15-4 and 15-5 below), including their salts.

In a further aspect the invention also relates to the use of synthetic intermediates of formula B-18 or their salts (and the various embodiments and sub-groups as described and/or defined herein) in the synthesis of compounds (Ia) and (Ia*).

In a further aspect the invention also relates to a method for synthesizing an intermediate of formula B-18

[Structure B-18]

or a salt thereof,
comprising hydration and deprotection of a compound of formula B-17

[Structure B-17]

or a salt thereof, wherein
the hydration step is performed in the presence of a palladium catalyst in a solvent and the deprotection step is performed in the presence of an acid, and $R^4$, A and r is as hereinbefore defined.

STEP C

Embodiments/Conditions for STEP C

The solvent to be chosen can be an organic solvent, preferably a carboxylic acid. Most preferred is AcOH.

Preferably, the palladium catalyst to be used is a Pd(II) catalyst, e.g., a Pd(II) catalyst chosen from the group consisting of $Pd(OAc)_2$, $PdCl_2$ and $Pd(OC(O)CF_3)_2$. The preferred Pd(II) catalyst is $Pd(OAc)_2$.

The acid to be used in the deprotection step is preferably an aqueous inorganic acid, e.g. selected from the group consisting of aqueous HCl, HBr and $H_2SO_4$. Most preferred is aqueous HCl.

The hydration step can be performed at a temperature range of about 20° C. to about 80° C., preferably at a range of about 20° C. to about 50° C. Most preferred is a range of about 20° C. to about 30° C.

The deprotection step can be performed at a temperature range of about 20° C. to about 80° C.

Preferred intermediates B-18 which may be synthesized by this method are selected from any one of intermediates B-18a to B-18l (see table 15-4 and 15-5 below) and their salts.

The intermediate product obtained after the hydration step, i.e. B-18 still bearing the acetyl and Boc protecting group, is also part of the invention.

In a further aspect the invention also relates to synthetic intermediates of formula B-19 and their salts, which can be used as key intermediates in the synthesis of compounds of formula (Ia) and (Ia*):

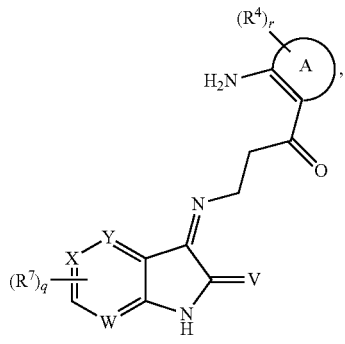

B-19

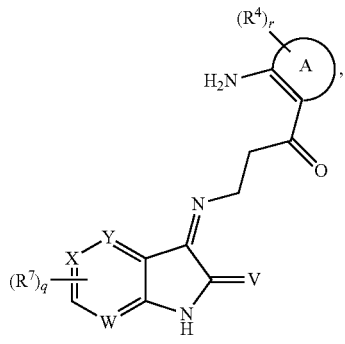

B-19

The definitions of groups $R^4$, $R^7$, A, V, W, X, Y, r and q in B-19 correspond to those as given for compound (I), (Ia), (Ib), (Ic), (a*), (Ib*) or (Ic*) above, i.e. [C0] for A/$R^4$/r, [E0] for $R^7$/q, [F0] for W/X/Y and [G0] for V.

Preferred intermediates B-19 are those which lead to preferred compounds (Ia) and (Ia*) according to the invention, i.e. preferred embodiments of B-19 have structural aspects selected from [C0] to [C15] for A/$R^4$/r, [E0] to [E2] for $R^7$/q, [F0] and [F1] for W/X/Y, [G0] and [G1] for V and [EF0] and [EF1] for $R^7$/q/W/X/Y altogether. These structural aspects may be permutated with one another as desired in combinations CEFG, so as to obtain preferred intermediates B-19 (aspects E and F can be replaced by combination aspect EF).

Each combination CEFG represents and defines individual embodiments or generic subsets of intermediates B-19. Preferred intermediates B-19 are selected from intermediates B-19a to B-19f (see table 15-6 below), including their salts.

In a further aspect the invention also relates to the use of synthetic intermediates of formula B-19 or their salts (and the various embodiments and sub-groups as described and/or defined herein) in the synthesis of compounds (Ia) and (a*).

In a further aspect the invention also relates to a method for synthesizing an intermediate of formula B-19 or a salt thereof,
comprising reacting a compound of formula B-18

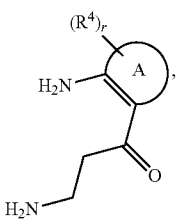

B-18 or a salt thereof,
with a compound of formula S-1

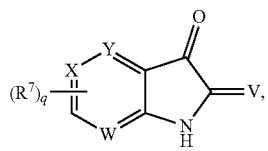

S-1 or a salt thereof,
wherein the reaction is performed in a solvent in the presence of an acid and a base, and $R^4$, $R^7$, A, V, W, X, Y, r and q is as hereinbefore defined.

STEP D

Embodiments/Conditions for STEP D

The solvent to be chosen can be an organic solvent, preferably chosen from the group consisting of MeOH, DMF, ACN, NMP and THF, or a mixture thereof. Most preferred is a mixture of MeOH and DMF.

The acid to be used is preferably an organic acid, more preferably a carboxylic acid. Most preferred is the use of AcOH.

The base to be used is preferably an organic base, more preferably an amine base, e.g. a tertiary amine. The tertiary amine is preferably selected from the group consisting of TEA, DIPEA and N-ethyl-dicyclohexyl amine. Most preferred is the use of TEA.

The reaction can be performed at a temperature range of about −10° C. to about 50° C., preferably at about 10° C. to about 20° C.

Preferred intermediates B-19 which may be synthesized by this method are selected from any one of intermediates B-19a to B-19l (see table 15-6 below) including their salts.

In a further aspect the invention also relates to synthetic intermediates of formula B-20 and their salts, which can be used as key intermediates in the synthesis of compounds of formula (Ia) and (Ia*):

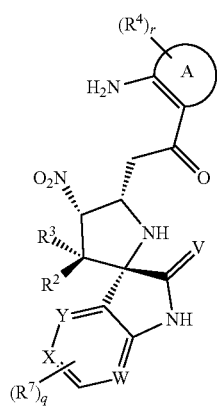

B-20

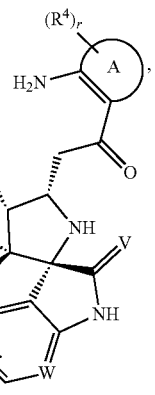

B-20 or a salt thereof,
comprising reacting a compound of formula B-2

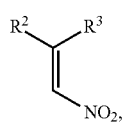

B-2 or a salt thereof,
with a compound of formula B-19

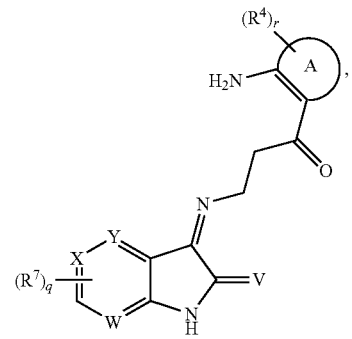

B-19 or a salt thereof, wherein
the reaction is performed in a solvent in the presence of a base, and $R^2$, $R^3$, $R^4$, $R^7$, A, V, W, X, Y, r and q is as hereinbefore defined.

The definitions of groups $R^2$, $R^3$, $R^4$, $R^7$, A, V, W, X, Y, r and q in B-20 correspond to those as given for compound (I), (Ia), (Ib), (Ic), (Ia*), (Ib*) or (Ic*) above, i.e. [B0] for $R^2/R^3$, [C0] for A/$R^4$/r, [E0] for $R^7$/q, [F0] for W/X/Y and [G0] for V.

Preferred intermediates B-20 are those which lead to preferred compounds (Ia) and (Ia*) according to the invention, i.e. preferred embodiments of B-20 have structural aspects selected from [B0] to [B17] for $R^2/R^3$, [C0] to [C15] for A/$R^4$/r, [E0] to [E2] for $R^7$/q, [F0] and [F1] for W/X/Y, [G0] and [G1] for V and [EF0] and [EF1] for $R^7$/q/W/X/Y altogether. These structural aspects may be permutated with one another as desired in combinations BCEFG, so as to obtain preferred intermediates B-20 (aspects E and F can be replaced by combination aspect EF). Each combination BCEFG represents and defines individual embodiments or generic subsets of intermediates B-20. Preferred intermediates B-20 are selected from intermediates B-20a to B-20f (see table 15-7 below), including their salts.

In a further aspect the invention also relates to the use of synthetic intermediates of formula B-20 or their salts (and the various embodiments and sub-groups as described and/or defined herein) in the synthesis of compounds (Ia) and (a*).

In a further aspect the invention also relates to a method for synthesizing an intermediate of formula B-20

STEP E

Embodiments/Conditions for STEP E

The solvent to be chosen is an organic solvent or a mixture of an organic solvent and water. Preferably, the organic solvent is selected from the group consisting of MeTHF, dioxane, DCM, ACN, toluene, 2-methyl-2-butanol and iPrOH, or a mixture thereof, or a mixture of the organic solvent(s) with water. Most preferred is a mixture of toluene and water.

The base to be used is preferably an organic base, more preferably an amine base. The amine base is preferably selected from the group consisting of N-methylpyrrolidine, N-ethylpyrrolidine, N-methylpiperidine, 1-(2-hydroxyethyl)-pyrrolidine, 3-quinuclidinol and DABCO. Most preferred is the use of N-methylpyrrolidine.

The reaction can be performed at a temperature range of about 35° C. to about 110° C., preferably at about 40° C. to about 85° C.

Preferred intermediates B-20 which may be synthesized by this method are selected from any one of intermediates B-20a to B-20f (see table 15-7 below) including their salts.

In a further aspect the invention also relates to a method for chiral separation of a mixture comprising both enantiomers of an intermediate of formula B-20

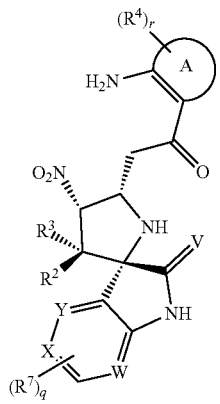

B-20 comprising precipitating a salt of one enantiomer formed with a chiral acid.

Embodiments/conditions for chiral separation:

The chiral acid to be used is, e.g., preferably selected from among (+)-Di-O,O'-dibenzoyl-D-tartaric acid, (−)-Di-O,O'-dibenzoyl-L-tartaric acid, (+)-Di-O,O'-p-toluoyl-D-tartaric acid, (−)-Di-O,O'-p-toluoyl-L-tartaric acid, (1 S)-(+)-camphor-10-sulfonic acid, (1R)-(−)-camphor-10-sulfonic acid, (R)-(−)-mandelic acid, (S)-(+)-mandelic acid, L-pyroglutamic acid, D-pyroglutamic acid L-(+)-tartaric acid and D-(−)-tartaric acid. Most preferred is (1R)-(−)- and (1 S)-(+)-camphor-10-sulfonic acid. The salt of the enantiomer is precipitated from a solution or suspension of compounds B-20 in an appropriate solvent, preferably ACN. Without wishing to be bound by theory, it is assumed that the formation of labile acetonitrile solvates of the precipitating camphor-10-sulfonic acid salt may be responsible for the resolution of racemic mixtures of the most preferred compounds. The salt precipitates selectively, i.e. one enantiomer precipitates as a salt of the chiral acid whereas the other enantiomer remains/is substantially dissolved under the conditions applied. The free enantiomer can be recovered from the salt by ion exchange. The method described hereinbefore can also be applied for the enrichment of one enantiomer in relation to the other if complete separation can not be achieved or the steps can be repeated several times to achieve complete separation. Separation means that the respective enantiomer/salt is obtained in a form that is substantially free of the other enantiomer. Preferably, the chiral acid is used in sub-stoichiometric amounts in relation to the enantiomer being separated, i.e. preferably in a range of 0.5-0.9 eq. (about 0.6 eq. being most preferred). The total concentration of racemate in the solution/suspension before separation is preferably in a range of 50-150 g/L, about 100 g/L being most preferred.

Preferred chiral intermediates B-20 which may be separated from their enantiomer by this method are selected from any one of intermediates B-20g to B-20l (see table 15-7 below) including their salts.

In a further aspect the invention also relates to synthetic intermediates of formula B-21 and their salts, which can be used as key intermediates in the synthesis of compounds of formula (Ia) and (Ia*):

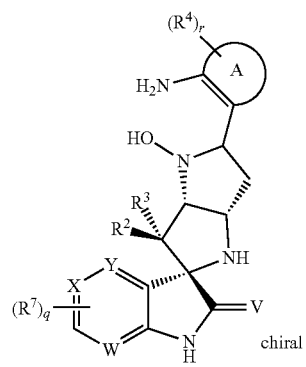

B-21

The definitions of groups $R^2$, $R^3$, $R^4$, $R^7$, A, V, W, X, Y, r and q in B-21 correspond to those as given for compound (I), (Ia), (Ib), (Ic), (Ia*), (Ib*) or (Ic*) above, i.e. [B0] for $R^2/R^3$, [C0] for A/$R^4$/r, [E0] for $R^7$/q, [F0] for W/X/Y and [G0] for V.

Preferred intermediates B-21 are those which lead to preferred compounds (Ia) and (Ia*) according to the invention, i.e. preferred embodiments of B-21 have structural aspects selected from [B0] to [B17] for $R^2/R^3$, [C0] to [C15] for A/$R^4$/r, [E0] to [E2] for $R^7$/q, [F0] and [F1] for W/X/Y, [G0] and [G1] for V and [EF0] and [EF1] for $R^7$/q/W/X/Y altogether. These structural aspects may be permutated with one another as desired in combinations BCEFG, so as to obtain preferred intermediates B-21 (aspects E and F can be replaced by combination aspect EF). Each combination BCEFG represents and defines individual embodiments or generic subsets of intermediates B-21. Preferred intermediates B-21 are selected from intermediates B-21a to B-21f (see table 15-8 below), including their salts.

In a further aspect the invention also relates to the use of synthetic intermediates of formula B-21 or their salts (and the various embodiments and sub-groups as described and/or defined herein) in the synthesis of compounds (Ia) and (Ia*).

In a further aspect the invention also relates to a method for synthesizing an intermediate of formula B-21

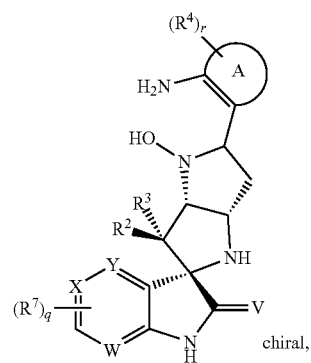

or a salt thereof,
comprising hydrogenating a compound of formula B-20,

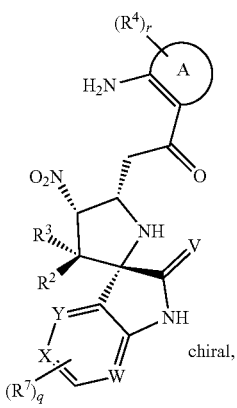

or a salt thereof, wherein
the reaction is performed in a solvent in the presence of a Pt catalyst, and $R^2$, $R^3$, $R^4$, $R^7$, A, V, W, X, Y, r and q is as hereinbefore defined.

Embodiments/Conditions for this Step:

The solvent to be chosen can be an organic solvent. Preferably, the organic solvent is selected from the group consisting of MeTHF, THF, MeOH, nBuOAc and iPrOAc, or a mixture thereof. Most preferred is MeTHF.

Preferably, the Pt catalyst to be used is Pt/C.

The reaction can be performed at a temperature range of about 20° C. to about 100° C., preferably at about 20° C. to about 30° C.

The $H_2$-pressure applied for hydrogenation is preferably in the range of about 20 bar to about 70 bar. Most preferred the $H_2$-pressure is in the range of about 60 bar to about 70 bar Preferred intermediates B-21 which may be synthesized by this method are selected from any one of intermediates B-21a to B-21f (see table 15-8 below) including their salts.

In a further aspect the invention also relates to synthetic intermediates of formula B-22 and their salts, which can be used as key intermediates in the synthesis of compounds of formula (Ia) and (Ia*):

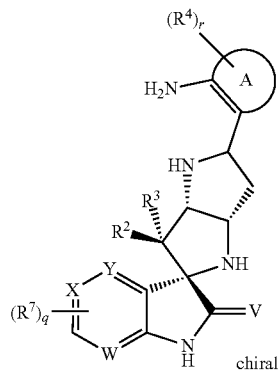

The definitions of groups $R^2$, $R^3$, $R^4$, $R^7$, A, V, W, X, Y, r and q in B-22 correspond to those as given for compound (I), (Ia), (Ib), (Ic), (Ia*), (Ib*) or (Ic*) above, i.e. [B0] for $R^2/R^3$, [C0] for $A/R^4/r$, [E0] for $R^7/q$, [F0] for W/X/Y and [G0] for V.

Preferred intermediates B-22 are those which lead to preferred compounds (Ia) and (Ia*) according to the invention, i.e. preferred embodiments of B-22 have structural aspects selected from [B0] to [B17] for $R^2/R^3$, [C0] to [C15] for $A/R^4/r$, [E0] to [E2] for $R^7/q$, [F0] and [F1] for W/X/Y, [G0] and [G1] for V and [EF0] and [EF1] for $R^7/q/W/X/Y$ altogether.

These structural aspects may be permutated with one another as desired in combinations BCEFG, so as to obtain preferred intermediates B-22 (aspects E and F can be replaced by combination aspect EF). Each combination BCEFG represents and defines individual embodiments or generic subsets of intermediates B-22. Preferred intermediates B-22 are selected from intermediates B-22a to B-22f (see table 15-8 below), including their salts.

In a further aspect the invention also relates to the use of synthetic intermediates of formula B-22 or their salts (and the various embodiments and sub-groups as described and/or defined herein) in the synthesis of compounds (Ia) and (Ia*).

In a further aspect the invention also relates to a method for synthesizing an intermediate of formula B-22

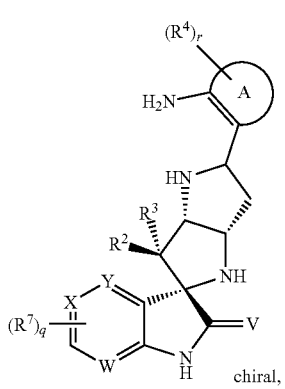

or a salt thereof, comprising hydrogenating a compound of formula B-21,

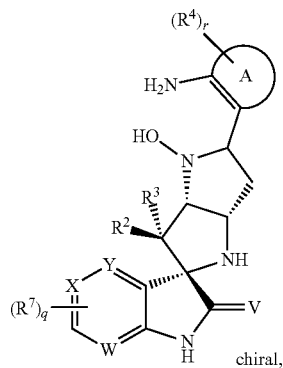

B-21 or a salt thereof, wherein

The reaction is performed in a solvent in the presence of a Pt catalyst and a V catalyst, and $R^2$, $R^3$, $R^4$, $R^7$, A, V, W, X, Y, r and q is as hereinbefore defined.

Embodiments/Conditions for this Step

The solvent to be chosen can be an organic solvent. Preferably, the organic solvent is selected from the group consisting of MeTHF, THF, MeOH, nBuOAc and iPrOAc, or a mixture thereof. Most preferred is MeTHF.

Preferably, the Pt catalyst to be used is Pt/C.

Preferably, the V catalyst to be used is a V(IV) catalyst. Most preferred is VO(acac)$_2$.

The reaction can be performed at a temperature range of about 20° C. to about 60° C., preferably at about 20° C. to about 30° C.

The H$_2$-pressure applied for hydrogenation is preferably in the range of about 3 to about 70 bar. Most preferred the H$_2$-pressure is in the range of about 60 bar to about 70 bar.

Preferred intermediates B-22 which may be synthesized by this method are selected from any one of intermediates B-22a to B-22f (see table 15-8 below) including their salts.

In a further aspect the invention also relates to a method for chiral separation of a mixture comprising both enantiomers of an intermediate of formula B-22

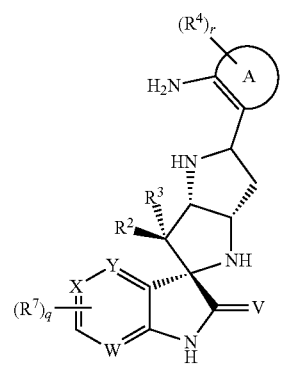

B-22 comprising precipitating a salt of one enantiomer formed with a chiral acid.

Embodiments/Conditions for Chiral Separation

The chiral acid to be used is, e.g., preferably selected from among (+)-Di-O,O'-dibenzoyl-D-tartaric acid, (−)-Di-O,O'-dibenzoyl-L-tartaric acid, (+)-Di-O,O'-p-toluoyl-D-tartaric acid, (−)-Di-O,O'-p-toluoyl-L-tartaric acid, (1 S)-(+)-camphor-10-sulfonic acid, (1R)-(−)-camphor-10-sulfonic acid, (R)-(−)-mandelic acid, (S)-(+)-mandelic acid, L-pyroglutamic acid, D-pyroglutamic acid, L-(+)-tartaric acid, D-(−)-tartaric acid, L-(+)-lactic acid and L-(+)-lactic acid. Most preferred is (+)-Di-O,O'-p-toluoyl-D-tartaric acid and (−)-Di-O,O'-p-toluoyl-L-tartaric acid. The salt of the enantiomer is precipitated from a solution or suspension of compounds B-22 in an appropriate solvent, preferably ACN. The salt precipitates selectively, i.e. one enantiomer precipitates as a salt of the chiral acid whereas the other enantiomer remains/is substantially dissolved under the conditions applied. The free enantiomer can be recovered from the salt by ion exchange. The method described hereinbefore can also be applied for the enrichment of one enantiomer in relation to the other if complete separation can not be achieved or the steps can be repeated several times to achieve complete separation. Separation means that the respective enantiomer/salt is obtained in a form that is substantially free of the other enantiomer. Preferably, the chiral acid is used in sub-stoichiometric amounts in relation to the enantiomer being separated, i.e. preferably in a range of 0.5-1 eq. (1 eq. being most preferred). The total concentration of racemate in the solution/suspension before separation is preferably in a range of 50-150 g/L, about 100 g/L being most preferred.

Preferred chiral intermediates B-22 which may be separated from their enantiomer by this method are selected from any one of intermediates B-22a to B-22f (see table 15-7 below) including their salts.

In a further aspect the invention also relates to synthetic intermediates of formula B-23 and their salts, which can be used as key intermediates in the synthesis of compounds of formula (Ia) and (Ia*):

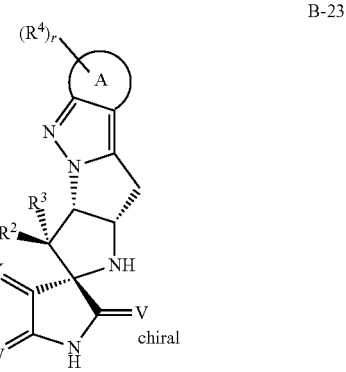

B-23

The definitions of groups $R^2$, $R^3$, $R^4$, $R^7$, A, V, W, X, Y, r and q in B-23 correspond to those as given for compound (I), (Ia), (Ib), (Ic), (Ia*), (Ib*) or (Ic*) above, i.e. [B0] for $R^2/R^3$, [C0] for A/$R^4$/r, [E0] for $R^7$/q, [F0] for W/X/Y and [G0] for V.

Preferred intermediates B-23 are those which lead to preferred compounds (Ia) and (Ia*) according to the invention, i.e. preferred embodiments of B-23 have structural aspects selected from [B0] to [B17] for $R^2/R^3$, [C0] to [C15] for A/$R^4$/r, [E0] to [E2] for $R^7$/q, [F0] and [F1] for W/X/Y, [G0] and [G1] for V and [EF0] and [EF1] for $R^7$/q/W/X/Y altogether. These structural aspects may be permutated with one another as desired in combinations BCEFG, so as to obtain preferred intermediates B-23 (aspects E and F can be replaced by combination aspect EF). Each combination BCEFG represents and defines individual embodiments or generic subsets of intermediates B-23. Preferred intermediates B-23 are selected from intermediates B-23a to B-23f (see table 15-9 below), including their salts.

In a further aspect the invention also relates to the use of synthetic intermediates of formula B-23 or their salts (and the various embodiments and sub-groups as described and/or defined herein) in the synthesis of compounds (Ia) and (Ia*).

In a further aspect the invention also relates to a method for synthesizing an intermediate of formula B-23

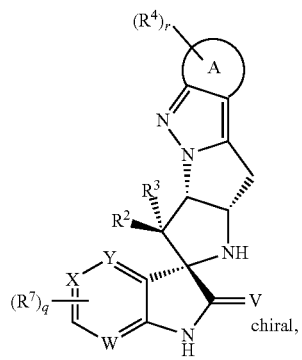

B-23 or a salt thereof,
comprising oxidation of a compound of formula B-22,

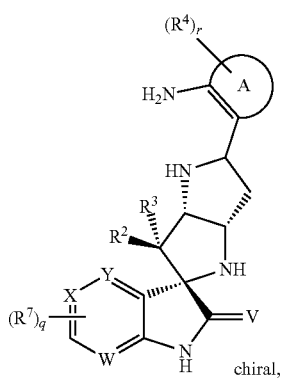

B-22 or a salt thereof, wherein
the reaction is performed in a solvent in the presence of a catalyst and an oxidizing agent, and $R^2$, $R^3$, $R^4$, $R^7$, A, V, W, X, Y, r and q is as hereinbefore defined.

Embodiments/Conditions for this Step

The solvent to be chosen is an organic solvent or a mixture of an organic solvent and water. Preferably, the organic solvent is selected from the group consisting of DCM and toluene, or a mixture thereof, or a mixture of the organic solvent(s) with water. Most preferred is a mixture of DCM and water.

The catalyst to be used can be a Mo-, V- or W-catalyst. Preferably, the catalyst is selected from the group consisting of $(NH_4)_2MoO_4$, $Na_2MoO_4$, $VO(acac)_2$, $MoO_2(acac)_2$, $Na_2WO_4*2H_2O$. Most preferred is $Na_2WO_4*2H_2O$.

As far as the oxidizing agent is concerned $H_2O_2$ is preferably used, in particular $H_2O_2$ in water.

The reaction can be performed at a temperature range of about 0° C. to about 50° C., preferably at about 35° C. to about 40° C.

Preferred intermediates B-23 which may be synthesized by this method are selected from any one of intermediates B-23a to B-23f (see table 15-9 below) including their salts.

Synthetic steps B-20+B-21, B-21+B-22 and B-22+B-23 can also be performed with racemic intermediate B-20, B-21 and B-22, respectively (if chiral separation of B-20 is not performed). Racemic B-21, B-22 and B-23 and the corresponding reaction steps with the racemic intermediates are also part of the invention.

In a further aspect the invention also relates to a method for synthesizing an intermediate of formula B-18 comprising STEP A as hereinbefore described (VARIANT 1). In a further aspect the invention also relates to a method for synthesizing an intermediate of formula B-18 comprising STEP A and STEP B as hereinbefore described (VARIANT 2). In a further aspect the invention also relates to a method for synthesizing an intermediate of formula B-18 comprising STEP A and STEP B and STEP C as hereinbefore described (VARIANT 3). Syntheses according to VARIANTS 1 to 3 are advantageous over alternative approaches that may be considered and allow for an improved overall synthetic efficiency and througput, lower costs and reduced solvents and waste.

In a further aspect the invention also relates to a method for synthesizing an intermediate of formula B-20 comprising STEP D as hereinbefore described (VARIANT 4). In a further aspect the invention also relates to a method for synthesizing an intermediate of formula B-20 comprising STEP D and STEP E as hereinbefore described (VARIANT 5). In a further aspect the invention also relates to a method for synthesizing an intermediate of formula B-20 comprising STEP A and STEP B and STEP C and STEP D and STEP E as hereinbefore described (VARIANT 6).

In a further aspect the invention also relates to a method for synthesizing a compound of formula (Ia) and (Ia*) comprising a variant selected from VARIANT 1 to 6.

All STEPS as referred to hereinbefore include all embodiments/conditions of how the STEPS can be performed as disclosed hereinbefore.

In a further aspect the invention also relates to synthetic intermediates of formula A-12 and their salts, which can be used as key intermediates in the synthesis of compounds of formula (Ib) and (Ib*):

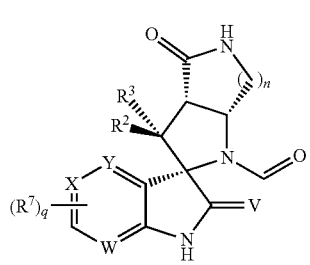

A-12

The definitions of groups $R^2$, $R^3$, $R^7$, V, W, X, Y, n and q in A-12 correspond to those as given for compound (I), (Ia), (Ib), (Ic), (Ia*), (Ib*) or (Ic*) above, i.e. [B0] for $R^2/R^3$, [D0] for n, [E0] for $R^7/q$, [F0] for W/X/Y and [G0] for V.

Preferred intermediates A-12 are those which lead to preferred compounds (Ib) and (Ib*) according to the invention, i.e. preferred embodiments of A-12 have structural aspects selected from [B0] to [B17] for $R^2/R^3$, [D0] to [D3] for n, [E0] to [E2] for $R^7/q$, [F0] and [F1] for W/X/Y, [G0] and [G1] for V and [EF0] and [EF1] for $R^7/q/W/X/Y$ altogether. These structural aspects may be permutated with one another as desired in combinations BDEFG, so as to obtain preferred intermediates A-12 (aspects E and F can be replaced by combination aspect EF). Each combination BDEFG represents and defines individual embodiments or generic subsets of intermediates A-12.

In a further aspect the invention also relates to the use of synthetic intermediates of formula A-12 or their salts (and the various embodiments and sub-groups as described and/or defined herein) in the synthesis of compounds (Ib) and (Ib*).

In a further aspect the invention also relates to synthetic intermediates of formula A-13 and their salts, which can be used as key intermediates in the synthesis of compounds of formula (Ib) and (Ib*):

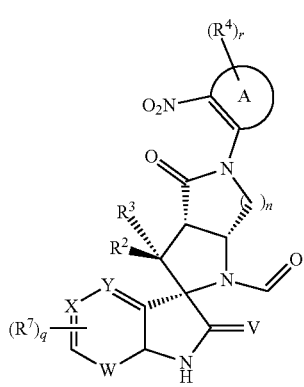

A-13

The definitions of groups $R^2$, $R^3$, $R^4$, $R^7$, A, V, W, X, Y, n, q and r in A-13 correspond to those as given for compound (I), (a), (Ib), (Ic), (Ia*), (Ib*) or (c*) above, i.e. [B0] for $R^2/R^3$, [C0] for $A/R^4/r$, [D0] for n, [E0] for $R^7/q$, [F0] for W/X/Y and [G0] for V.

Preferred intermediates A-13 are those which lead to preferred compounds (Ib) and (Ib*) according to the invention, i.e. preferred embodiments of A-13 have structural aspects selected from [B0] to [B17] for $R^2/R^3$, [C0] to [C15] for $A/R^4/r$, [D0] to [D3] for n, [E0] to [E2] for $R^7/q$, [F0] and [F1] for W/X/Y, [G0] and [G1] for V and [EF0] and [EF1] for $R^7/q/W/X/Y$ altogether. These structural aspects may be permutated with one another as desired in combinations BCDEFG, so as to obtain preferred intermediates A-13 (aspects E and F can be replaced by combination aspect EF). Each combination BCDEFG represents and defines individual embodiments or generic subsets of intermediates A-13.

In a further aspect the invention also relates to the use of synthetic intermediates of formula A-13 or their salts (and the various embodiments and sub-groups as described and/or defined herein) in the synthesis of compounds (Ib) and (Ib*).

In a further aspect the invention also relates to synthetic intermediates of formula A-14 and their salts, which can be used as key intermediates in the synthesis of compounds of formula (Ib) and (Ib*):

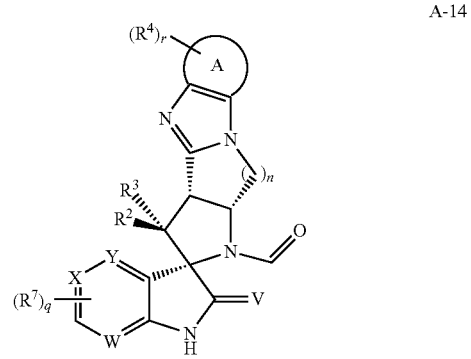

A-14

The definitions of groups $R^2$, $R^3$, $R^4$, $R^7$, A, V, W, X, Y, n, q and r in A-15 correspond to those as given for compound (I), (a), (Ib), (Ic), (Ia*), (Ib*) or (c*) above, i.e. [B0] for $R^2/R^3$, [C0] for $A/R^4/r$, [D0] for n, [E0] for $R^7/q$, [F0] for W/X/Y and [G0] for V.

Preferred intermediates A-14 are those which lead to preferred compounds (Ib) and (Ib*) according to the invention, i.e. preferred embodiments of A-14 have structural aspects selected from [B0] to [B17] for $R^2/R^3$, [C0] to [C15] for $A/R^4/r$, [D0] to [D3] for n, [E0] to [E2] for $R^7/q$, [F0] and [F1] for W/X/Y, [G0] and [G1] for V and [EF0] and [EF1] for $R^7/q/W/X/Y$ altogether. These structural aspects may be permutated with one another as desired in combinations BCDEFG, so as to obtain preferred intermediates A-14 (aspects E and F can be replaced by combination aspect EF). Each combination BCDEFG represents and defines individual embodiments or generic subsets of intermediates A-14.

In a further aspect the invention also relates to the use of synthetic intermediates of formula A-14 or their salts (and the various embodiments and sub-groups as described and/or defined herein) in the synthesis of compounds (Ib) and (Ib*).

In a further aspect the invention also relates to synthetic intermediates of formula A-15 and their salts, which can be used as key intermediates in the synthesis of compounds of formula (Ib) and (Ib*):

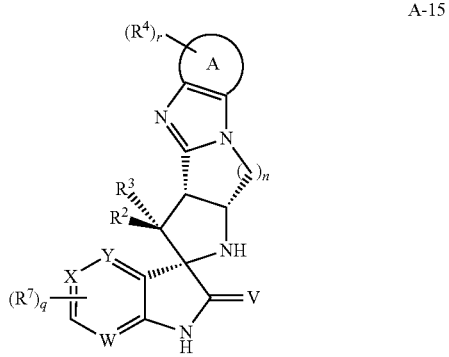

A-15

The definitions of groups $R^2$, $R^3$, $R^4$, $R^7$, A, V, W, X, Y, n, q and r in A-15 correspond to those as given for compound (I), (a), (Ib), (Ic), (Ia*), (Ib*) or (c*) above, i.e. [B0] for $R^2/R^3$, [C0] for $A/R^4/r$, [D0] for n, [E0] for $R^7/q$, [F0] for W/X/Y and [G0] for V.

Preferred intermediates A-15 are those which lead to preferred compounds (Ib) and (Ib*) according to the invention, i.e. preferred embodiments of A-15 have structural aspects selected from [B0] to [B17] for $R^2/R^3$, [C0] to [C15] for $A/R^4/r$, [D0] to [D3] for n, [E0] to [E2] for $R^7/q$, [F0] and [F1] for W/X/Y, [G0] and [G1] for V and [EF0] and [EF1] for $R^7/q/W/X/Y$ altogether. These structural aspects may be permutated with one another as desired in combinations BCDEFG, so as to obtain preferred intermediates A-15 (aspects E and F can be replaced by combination aspect EF). Each combination BCDEFG represents and defines individual embodiments or generic subsets of intermediates A-15.

In a further aspect the invention also relates to the use of synthetic intermediates of formula A-15 or their salts (and the various embodiments and sub-groups as described and/or defined herein) in the synthesis of compounds (Ib) and (b*).

In a further aspect the invention also relates to synthetic intermediates of formula A-17 and their salts, which can be used as key intermediates in the synthesis of compounds of formula (Ib) and (Ib*):

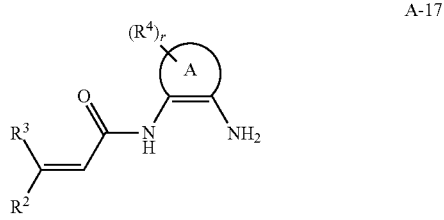

A-17

The definitions of groups $R^2$, R, $R^4$, A and r in A-17 correspond to those as given for compound (I), (Ia), (Ib), (Ic), (Ia*), (Ib*) or (c*) above, i.e. [B0] for $R^2/R^3$ and [C0] for $A/R^4/r$.

Preferred intermediates A-17 are those which lead to preferred compounds (Ib) and (Ib*) according to the invention, i.e. preferred embodiments of A-17 have structural aspects selected from [B0] to [B17] for $R^2/R^3$ and [C0] to [C15] for $A/R^4/r$. These structural aspects may be permutated with one another as desired in combinations BC, so as to obtain preferred intermediates A-17. Each combination BC represents and defines individual embodiments or generic subsets of intermediates A-17.

In a further aspect the invention also relates to the use of synthetic intermediates of formula A-17 or their salts (and the various embodiments and sub-groups as described and/or defined herein) in the synthesis of compounds (Ib) and (b*).

In a further aspect the invention also relates to synthetic intermediates of formula A-18 and their salts, which can be used as key intermediates in the synthesis of compounds of formula (Ib) and (Ib*):

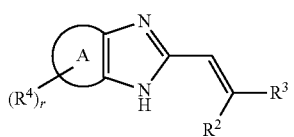

A-18

The definitions of groups $R^2$, $R^3$, $R^4$, A and r in A-18 correspond to those as given for compound (I), (Ia), (Ib), (Ic), (Ia*), (Ib*) or (c*) above, i.e. [B0] for $R^2/R^3$ and [C0] for $A/R^4/r$.

Preferred intermediates A-18 are those which lead to preferred compounds (Ib) and (Ib*) according to the invention, i.e. preferred embodiments of A-18 have structural aspects selected from [B0] to [B17] for $R^2/R^3$ and [C0] to [C15] for $A/R^4/r$. These structural aspects may be permutated with one another as desired in combinations BC, so as to obtain preferred intermediates A-18. Each combination BC represents and defines individual embodiments or generic subsets of intermediates A-18.

In a further aspect the invention also relates to the use of synthetic intermediates of formula A-18 or their salts (and the various embodiments and sub-groups as described and/or defined herein) in the synthesis of compounds (Ib) and (Ib*).

In a further aspect the invention also relates to synthetic intermediates of formula A-20 and their salts, which can be used as key intermediates in the synthesis of compounds of formula (Ib) and (Ib*):

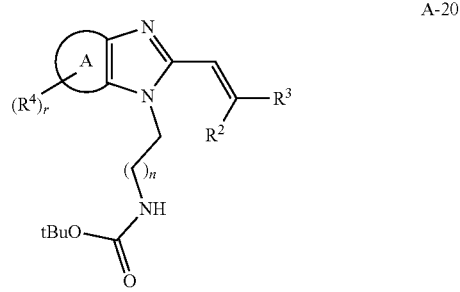

A-20

The definitions of groups $R^2$, $R^3$, $R^4$, A, n and r in A-20 correspond to those as given for compound (I), (Ia), (Ib), (Ic), (Ia*), (Ib*) or (c*) above, i.e. [B0] for $R^2/R^3$, [C0] for $A/R^4/r$ and [D0] for n.

Preferred intermediates A-20 are those which lead to preferred compounds (Ib) and (Ib*) according to the invention, i.e. preferred embodiments of A-20 have structural aspects selected from [B0] to [B17] for $R^2/R^3$, [C0] to [C15] for $A/R^4/r$ and [D0] to [D3] for n. These structural aspects may be permutated with one another as desired in combinations BCD, so as to obtain preferred intermediates A-20. Each combination BCD represents and defines individual embodiments or generic subsets of intermediates A-20.

In a further aspect the invention also relates to the use of synthetic intermediates of formula A-20 or their salts (and the various embodiments and sub-groups as described and/or defined herein) in the synthesis of compounds (Ib) and (b*).

In a further aspect the invention also relates to synthetic intermediates of formula A-21 and their salts, which can be used as key intermediates in the synthesis of compounds of formula (Ib) and (Ib*):

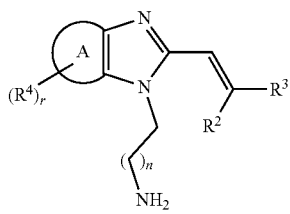
A-21

The definitions of groups $R^2$, R, $R^4$, A, n and r in A-21 correspond to those as given for compound (I), (Ia), (Ib), (Ic), (Ia*), (Ib*) or (c*) above, i.e. [B0] for $R^2$/R, [C0] for A/$R^4$/r and [D0] for n.

Preferred intermediates A-21 are those which lead to preferred compounds (Ib) and (Ib*) according to the invention, i.e. preferred embodiments of A-21 have structural aspects selected from [B0] to [B17] for $R^2/R^3$, [C0] to [C15] for A/$R^4$/r and [D0] to [D3] for n. These structural aspects may be permutated with one another as desired in combinations BCD, so as to obtain preferred intermediates A-21. Each combination BCD represents and defines individual embodiments or generic subsets of intermediates A-21.

In a further aspect the invention also relates to the use of synthetic intermediates of formula A-21 or their salts (and the various embodiments and sub-groups as described and/or defined herein) in the synthesis of compounds (Ib) and (b*).

The present invention further relates to hydrates, solvates, polymorphs, metabolites, derivatives, isomers and prodrugs of a compound of formula (I), (Ia), (Ib), (Ic), (Ia*), (Ib*) or (Ic*).

Compounds of formula (I), (Ia), (Ib), (Ic), (Ia*), (Ib*) or (Ic*) which e.g. bear ester groups are potential prodrugs the ester being cleaved under physiological conditions.

The present invention further relates to a pharmaceutically acceptable salt of a compound of formula (I), (Ia), (Ib), (Ic), (Ia*), (Ib*) or (c*).

The present invention further relates to a co-crystal, preferably a pharmaceutically acceptable co-crystal, of a compound of formula (I), (a), (Ib), (Ic), (Ia*), (Ib*) or (c*).

In one aspect compounds (I), (a), (Ib), (Ic), (Ia*), (Ib*) or (c*) according to the invention are in amorphous form.

The present invention further relates to a pharmaceutically acceptable salt of a compound of formula (I), (Ia), (Ib), (Ic), (Ia*), (Ib*) or (Ic*) with inorganic or organic acids or bases.

The present invention is directed to compounds of formula (I), (Ia), (Ib), (Ic), (Ia*), (Ib*) or (Ic*) which are useful in the prevention and/or treatment of a disease and/or condition wherein the inhibition of the interaction between MDM2 and p53 is of therapeutic benefit, including but not limited to the treatment and/or prevention of cancer.

In another aspect the invention relates to a compound of formula (I), (Ia), (Ib), (Ic), (Ia*), (Ib*) or (Ic*)—or a pharmaceutically acceptable salt thereof—for use as a medicament.

In another aspect the invention relates to a compound of formula (I), (Ia), (Ib), (Ic), (Ia*), (Ib*) or (Ic*)—or a pharmaceutically acceptable salt thereof—for use in a method for treatment of the human or animal body.

In another aspect the invention relates to a compound of formula (I), (Ia), (Ib), (Ic), (Ia*), (Ib*) or (Ic*)—or a pharmaceutically acceptable salt thereof—for use in the treatment and/or prevention of a disease and/or condition wherein the inhibition of the interaction between MDM2 and p53 is of therapeutic benefit.

In another aspect the invention relates to a compound of formula (I), (Ia), (Ib), (Ic), (Ia*), (Ib*) or (Ic*)—or a pharmaceutically acceptable salt thereof—for use in the treatment and/or prevention of cancer, infections, inflammations or autoimmune diseases.

In another aspect the invention relates to a compound of formula (I), (Ia), (Ib), (Ic), (Ia*), (Ib*) or (Ic*)—or a pharmaceutically acceptable salt thereof—for use in a method for treatment and/or prevention of cancer, infections, inflammations or autoimmune diseases in the human and animal body.

In another aspect the invention relates to the use of a compound of formula (I), (Ia), (Ib), (Ic), (Ia*), (Ib*) or (Ic*)—or a pharmaceutically acceptable salt thereof—for preparing a pharmaceutical composition for the treatment and/or prevention of cancer, infections, inflammations or autoimmune diseases.

In another aspect the invention relates to a compound of formula (I), (Ia), (Ib), (Ic), (Ia*), (Ib*) or (Ic*)—or a pharmaceutically acceptable salt thereof—for use in the treatment and/or prevention of cancer.

In another aspect the invention relates to the use of a compound of formula (I), (Ia), (Ib), (Ic), (Ia*), (Ib*) or (Ic*)—or a pharmaceutically acceptable salt thereof—for preparing a pharmaceutical composition for the treatment and/or prevention of cancer.

In another aspect the invention relates to a compound of formula (I), (Ia), (Ib), (Ic), (Ia*), (Ib*) or (Ic*)—or a pharmaceutically acceptable salt thereof—for use in a method for treatment and/or prevention of cancer in the human or animal body.

In another aspect the invention relates to a compound of formula (I), (Ia), (Ib), (Ic), (Ia*), (Ib*) or (Ic*)—or a pharmaceutically acceptable salt thereof—for use in the treatment and/or prevention of acute myeloid leukaemia (AML), prostate cancer or lung cancer, wherein the cancer cells have functional p53, preferably wherein the cancer cells are p53 wild-type.

In another aspect the invention relates to a compound of formula (I), (Ia), (Ib), (Ic), (Ia*), (Ib*) or (Ic*)—or a pharmaceutically acceptable salt thereof—for use in the treatment and/or prevention of acute myeloid leukaemia (AML), prostate cancer or lung cancer, wherein the cancer cells preferably have functional p53, more preferably wherein the cancer cells are p53 wild-type.

In another aspect the invention relates to the use of a compound of formula (I), (Ia), (Ib), (Ic), (Ia*), (Ib*) or (Ic*)—or a pharmaceutically acceptable salt thereof—for preparing a pharmaceutical composition for the treatment and/or prevention of acute myeloid leukaemia (AML), prostate cancer or lung cancer, wherein the cancer cells have functional p53, preferably wherein the cancer cells are p53 wild-type.

In another aspect the invention relates to the use of a compound of formula (I), (Ia), (Ib), (Ic), (Ia*), (Ib*) or (Ic*)—or a pharmaceutically acceptable salt thereof—for preparing a pharmaceutical composition for the treatment and/or prevention of acute myeloid leukaemia (AML), prostate cancer or lung cancer, wherein the cancer cells preferably have functional p53, more preferably wherein the cancer cells are p53 wild-type.

In another aspect the invention relates to a method for the treatment and/or prevention of a disease and/or condition wherein the inhibition of the interaction between MDM2 and p53 is of therapeutic benefit comprising administering a therapeutically effective amount of a compound of formula (I), (Ia), (Ib), (Ic), (Ia*), (Ib*) or (Ic*)—or a pharmaceutically acceptable salt thereof—to a human being.

In another aspect the invention relates to a method for the treatment and/or prevention of cancer comprising administering a therapeutically effective amount of a compound of formula (I), (Ia), (Ib), (Ic), (Ia*), (Ib*) or (Ic*)—or a pharmaceutically acceptable salt thereof—to a human being.

In another aspect the invention relates to a pharmaceutical composition comprising at least one compound of formula (I), (Ia), (Ib), (Ic), (Ia*), (Ib*) or (Ic*)—or a pharmaceutically acceptable salt thereof—and a pharmaceutically acceptable carrier.

In another aspect the invention relates to a pharmaceutical preparation comprising a compound of formula (I), (Ia), (Ib), (Ic), (Ia*), (Ib*) or (Ic*)—or a pharmaceutically acceptable salt thereof—and at least one other cytostatic and/or cytotoxic active substance.

In another aspect the invention relates to a compound of formula (I), (Ia), (Ib), (Ic), (Ia*), (Ib*) or (Ic*)—or a pharmaceutically acceptable salt thereof—for use in the treatment and/or prevention of cancer, infections, inflammations or autoimmune diseases wherein said compound is administered before, after or together with at least one other cytostatic or cytotoxic active substance.

In another aspect the invention relates to the use of a compound of formula (I), (Ia), (Ib), (Ic), (Ia*), (Ib*) or (Ic*)—or a pharmaceutically acceptable salt thereof—for preparing a medicament for the treatment and/or prevention of cancer, infections, inflammations or autoimmune diseases wherein said compound is administered before, after or together with at least one other cytostatic or cytotoxic active substance.

In another aspect the invention relates to a cytostatic or cytotoxic active substance prepared for being administered before, after or together with a compound of formula (I), (Ia), (Ib), (Ic), (Ia*), (Ib*) or (Ic*)—or a pharmaceutically acceptable salt thereof—for use in the treatment and/or prevention of cancer, infections, inflammations or autoimmune diseases.

In another aspect the invention relates to a method for the treatment and/or prevention of cancer, infections, inflammations or autoimmune diseases comprising administering to a patient in need thereof a therapeutically effective amount of a compound of formula (I), (Ia), (Ib), (Ic), (Ia*), (Ib*) or (Ic*)—or a pharmaceutically acceptable salt thereof—before, after or together with at least one other cytostatic or cytotoxic active substance.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a natural number (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroalkyl, heteroaryl, heteroarylalkyl, heterocyclyl, heterocycylalkyl) relates to the total number of atoms of all the ring members or chain members or the total of all the ring and chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

Further examples of alkyl are methyl (Me; $-CH_3$), ethyl (Et; $-CH_2CH_3$), 1-propyl (n-propyl; n-Pr; $-CH_2CH_2CH_3$), 2-propyl (i-Pr; iso-propyl; $-CH(CH_3)_2$), 1-butyl (n-butyl; n-Bu; $-CH_2CH_2CH_2CH_3$), 2-methyl-1-propyl (iso-butyl; i-Bu; $-CH_2CH(CH_3)_2$), 2-butyl (sec-butyl; sec-Bu; $-CH(CH_3)CH_2CH_3$), 2-methyl-2-propyl (tert-butyl; t-Bu; $-C(CH_3)_3$), 1-pentyl (n-pentyl; $-CH_2CH_2CH_2CH_2CH_3$), 2-pentyl ($-CH(CH_3)CH_2CH_2CH_3$), 3-pentyl ($-CH(CH_2CH_3)_2$), 3-methyl-1-butyl (iso-pentyl; $-CH_2CH_2CH(CH_3)_2$), 2-methyl-2-butyl ($-C(CH_3)_2CH_2CH_3$), 3-methyl-2-butyl ($-CH(CH_3)CH(CH_3)_2$), 2,2-dimethyl-1-propyl (neo-pentyl; $-CH_2C(CH_3)_3$), 2-methyl-1-butyl ($-CH_2CH(CH_3)CH_2CH_3$), 1-hexyl (n-hexyl; $-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$), 2,3-dimethyl-1-butyl ($-CH_2CH(CH_3)CH(CH_3)CH_3$), 2,2-dimethyl-1-butyl ($-CH_2C(CH_3)_2CH_2CH_3$), 3,3-dimethyl-1-butyl ($-CH_2CH_2C(CH_3)_3$), 2-methyl-1-pentyl ($-CH_2CH(CH_3)CH_2CH_2CH_3$), 3-methyl-1-pentyl ($-CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —CH$_3$ and —CH$_2$—, —CH$_2$CH$_3$ and —CH$_2$CH$_2$— or >CHCH$_3$ etc.

The term "$C_{1-4}$alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CH(CH(CH$_3$))$_2$)—and —C(CH$_3$)(CH$_2$CH$_3$)—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group such as for example in HO—$C_{x-y}$alkyleneamino or H$_2$N—$C_{x-y}$alkyleneoxy.

Unlike alkyl, alkenyl consists of at least two carbon atoms, wherein at least two adjacent carbon atoms are joined together by a C=C double bond and a carbon atom can only be part of one C=C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C=C double bond and a carbon atom can only be part of one C=C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or H$_2$N—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x\text{-}y}$alkynyleneamino or $H_2N$—$C_{x\text{-}y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHFCH_2F$ and —CHFCHF— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x\text{-}y}$cycloalkylamino, $C_{x\text{-}y}$cycloalkyloxy or $C_{x\text{-}y}$cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:

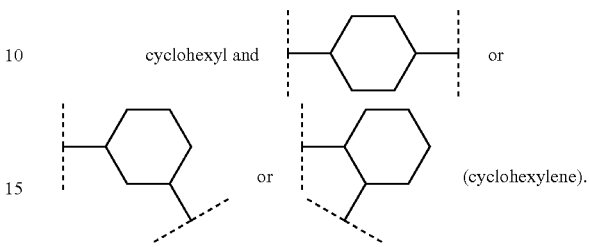

cyclohexyl and ... or ... or ... (cyclohexylene).

The above definition for cycloalkylene also applies if cycloalkylene is part of another (combined) group as for example in HO—$C_{x\text{-}y}$cycloalkyleneamino or $H_2N$—$C_{x\text{-}y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C=C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x\text{-}y}$cycloalkenylamino, $C_{x\text{-}y}$cycloalkenyloxy or $C_{x\text{-}y}$cycloalkenylalkyl.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners.

Formally, the second valency is obtained by removing a hydrogen atom from a cycloalkenyl. Corresponding groups are for example:

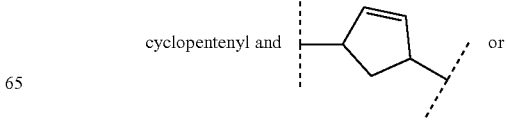

cyclopentenyl and ... or

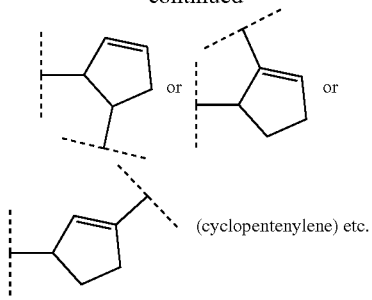

(cyclopentenylene) etc.

The above definition for cycloalkenylene also applies if cycloalkenylene is part of another (combined) group as for example in HO—C$_{x-y}$cycloalkenyleneamino or H$_2$N—C$_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example: phenyl and or or (o, m, p-phenylene),

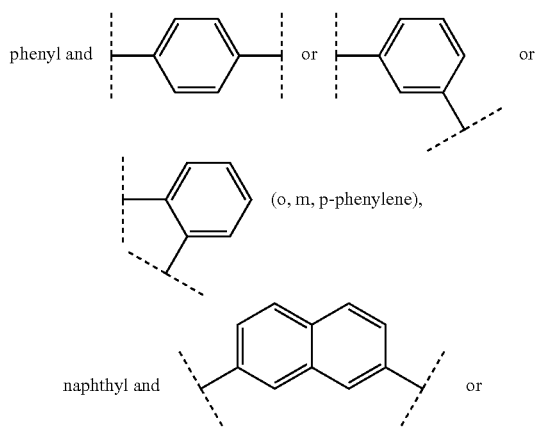

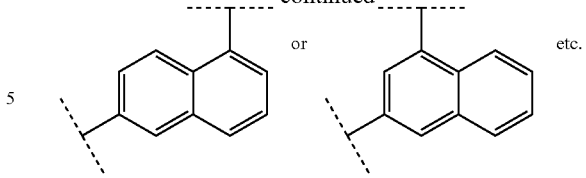

The above definition for arylene also applies if arylene is part of another (combined) group as for example in HO-aryleneamino or H$_2$N-aryleneoxy.

Heterocyclyl denotes ring systems, which are derived from the previously defined cycloalkyl, cycloalkenyl and aryl by replacing one or more of the groups —CH$_2$— independently of one another in the hydrocarbon rings by the groups —O—, —S— or —NH— or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulphoxide —SO—, sulphone —SO$_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the sub-groups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2.8-diaza-spiro[4,5]decyl etc.

Further examples are the structures illustrated below, which may be attached via each hydrogen-carrying atom (exchanged for hydrogen):
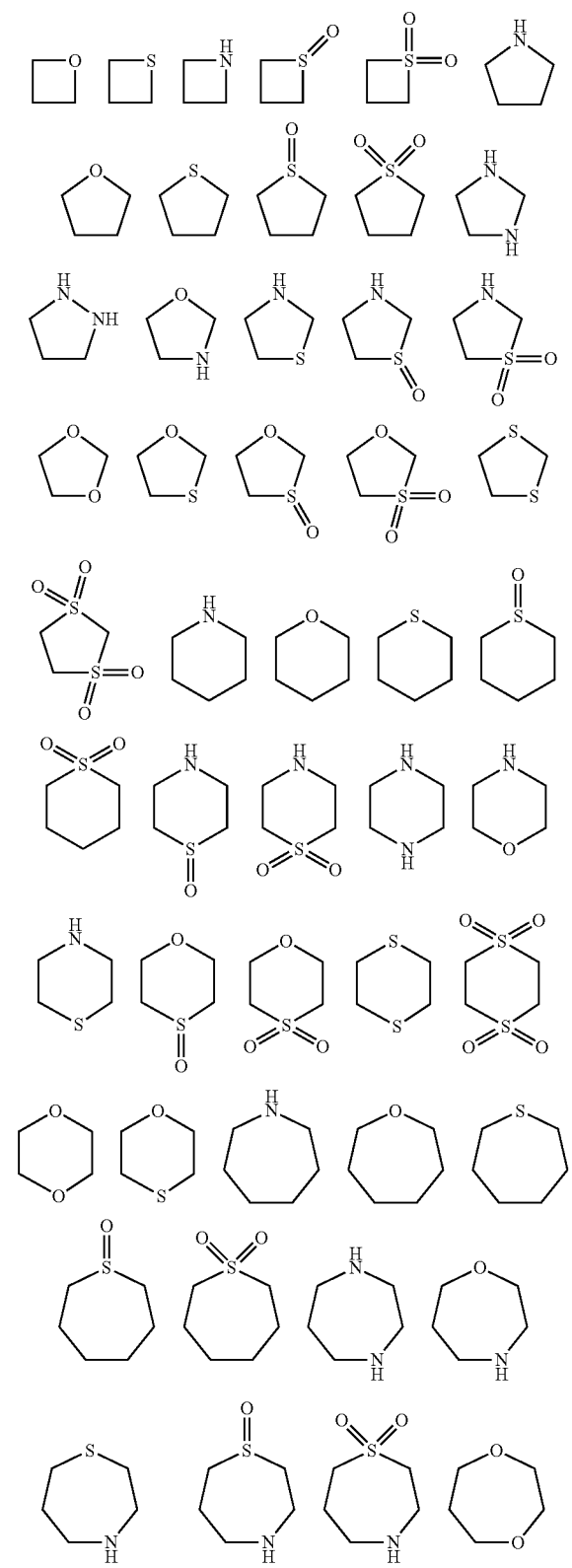
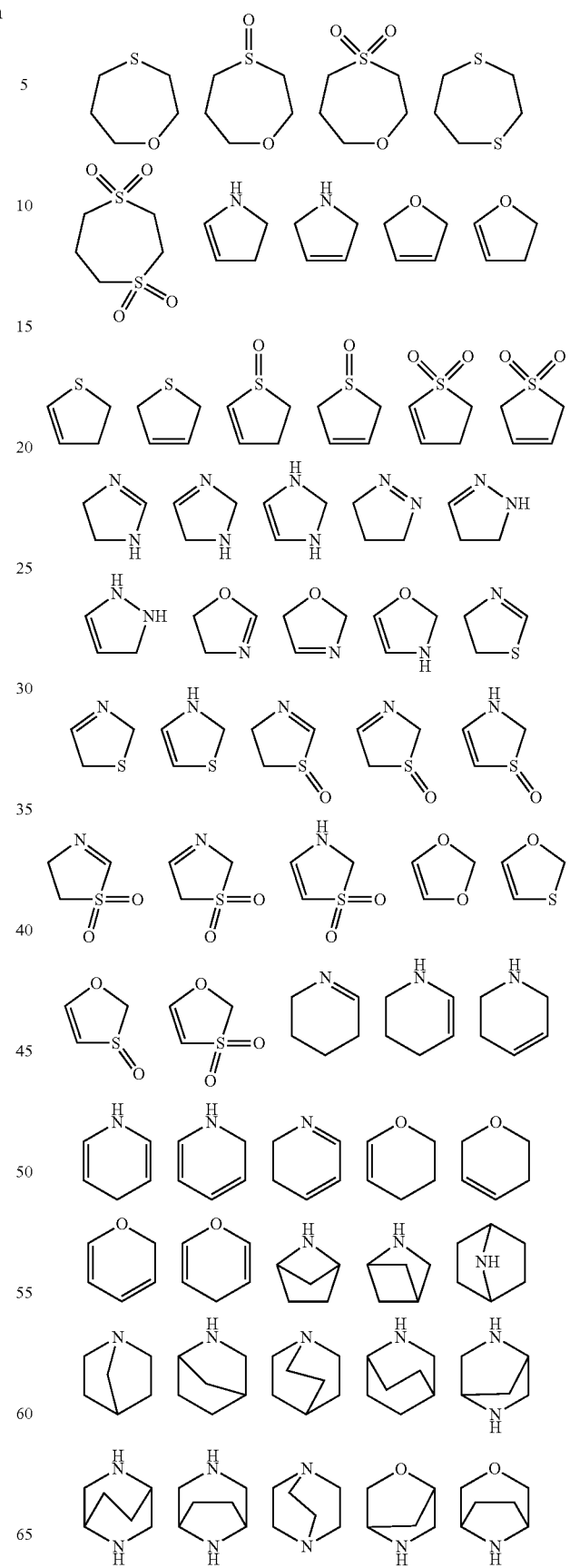

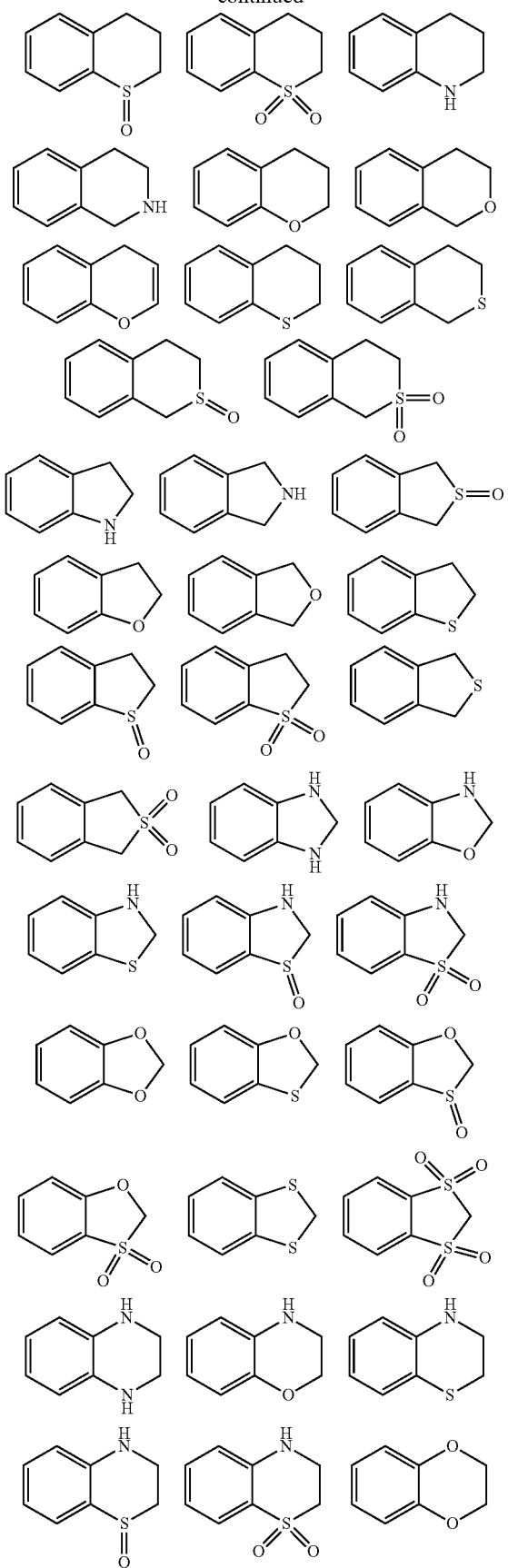

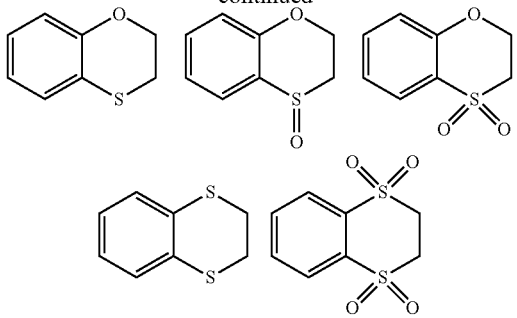

Preferably, heterocyclyls are 4 to 8 membered, monocyclic and have one or two heteroatoms independently selected from oxygen, nitrogen and sulfur Preferred heterocyclyls are: piperazinyl, piperidinyl, morpholinyl, pyrrolidinyl, azetidinyl, tetrahydropyranyl, tetrahydrofuranyl.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

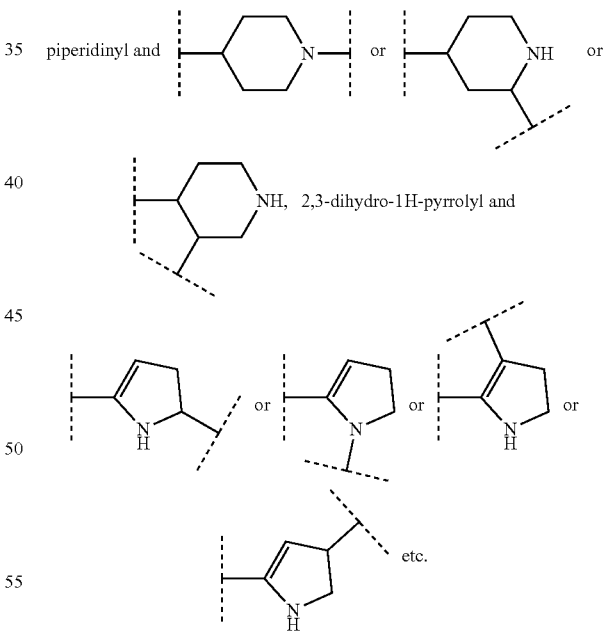

The above definition of heterocyclylene also applies if heterocyclylene is part of another (combined) group as for example in HO-heterocyclyleneamino or $H_2N$-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

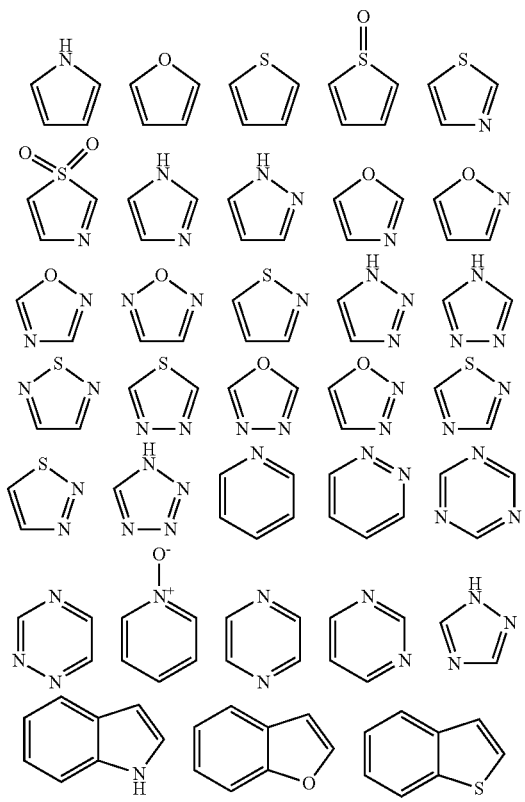

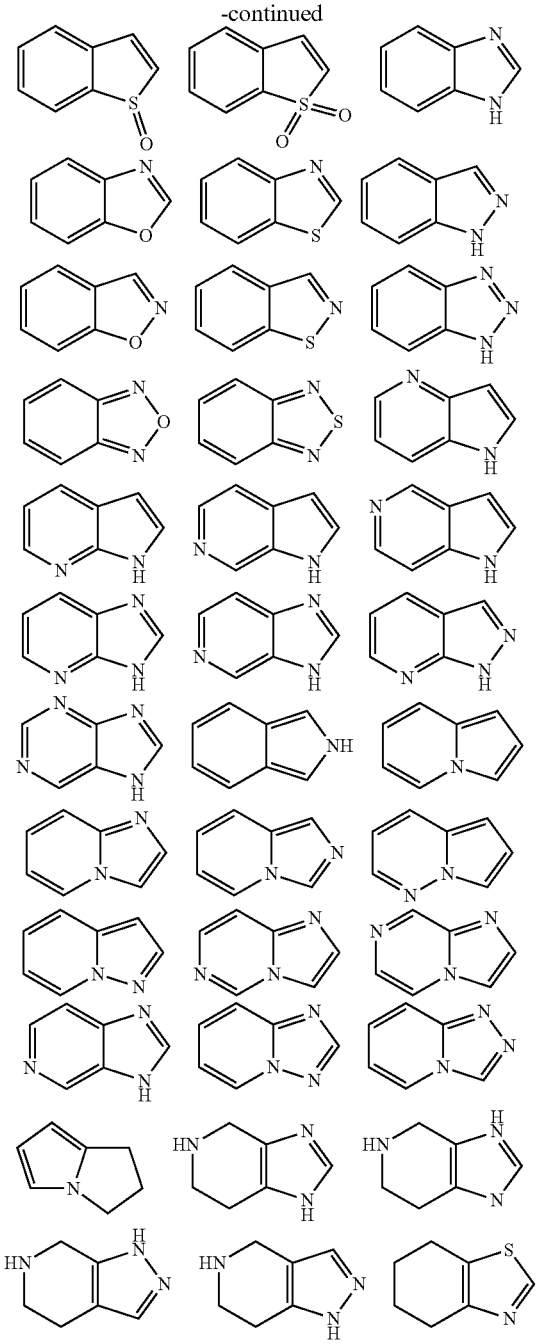

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl.

Corresponding groups are for example:

pyrrolyl and 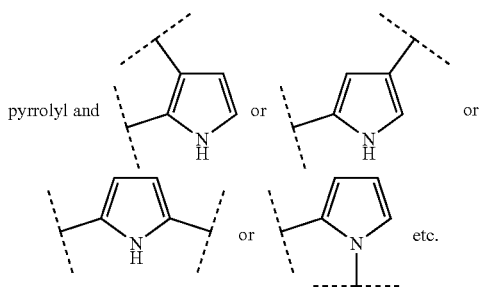 etc.

The above definition of heteroarylene also applies if heteroarylene is part of another (combined) group as for example in HO-heteroaryleneamino or H$_2$N-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents on carbon atoms, wherein the bivalent substituent =O may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH$_2$— or sulphur atoms (=O only) of a ring system.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from ammonia, L-arginine, betaine, benethamine, benzathine, calcium hydroxide, choline, deanol, diethanolamine (2,2'-iminobis (ethanol)), diethylamine, 2-(diethylamino)-ethanol, 2-(dimethylamino)-ethanol, 2-aminoethanol, ethylenediamine, N-ethyl-glucamine, hydrabamine, 1H-imidazole, lysine (L-lysine), proline (L-proline), magnesium hydroxide, 4-(2-hydroxyethyl)-morpholine, morpholine, piperazine, potassium hydroxide, 1-(2-hydroxyethyl)-pyrrolidine, 1-(2-hydroxyethyl)-pyrrolidone, sodium hydroxide, triethanolamine (2,2',2''-nitrilotris(ethanol), tromethamine, zinc hydroxide, acetic acid, 2,2-dichloro acetic acid, adipic acid, alginic acid, ascorbic acid (L), L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid (capric acid), dodecylsulfuric acid, ethane-1,2-disulfonic acid, ethanesulfonic acid, 2-hydroxyethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxoglutaric acid, glycerophosphoric acid, glycine, glycolic acid, hexanoic acid (caproic acid), hippuric acid, hydrobromic acid, hydrochloric acid, isobutyric acid, DL-lactic acid, lactobionic acid, lauric acid, maleic acid, (−)-L-malic acid, malonic acid, DL-mandelic acid, methanesulfonic acid, naphthalene-1,5-disulfonic acid, naphthalene-2-sulfonic acid, 1-hydroxy-2-naphthoic acid, nicotinic acid, nitric acid, octanoic acid (caprylic acid), oleic acid, orotic acid, oxalic acid, palmitic acid, pamoic acid (embonic acid), phosphoric acid, propionic acid, (−)-L-pyroglutamic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid and undecylenic acid.

The salts include acetates, ascorbates, benzenesulfonates, benzoates, besylates, bicarbonates, bitartrates, bromides/hydrobromides, Ca-edetates/edetates, camsylates, carbonates, camphorsulfonate, chlorides/hydrochlorides, chlorotheophyllinate, citrates, edisylates, ethane disulfonates, estolates esylates, fumarates, gluceptates, gluconates, glucuronate, glutamates, glycolates, glycollylarsnilates, hexylresorcinates, hippurate, hydrabamines, hydroxymaleates, hydroxynaphthoates, iodides, isethionates, isothionates, lactates, lactobionates, laurylsulfates, malates, maleates, mandelates, methanesulfonates, mesylates, methylbromides, methylnitrates, methylsulfates, mucates, naphthoate, napsylates, nitrates, octadecanoates, oleates, oxalates, pamoates, pantothenates, phenylacetates, phosphates/diphosphates, polygalacturonates, propionates, salicylates, stearates subacetates, succinates, sulfamides, sulfates, sulfosalicylates, tannates, tartrates, teoclates, toluenesulfonates, triethiodides, trifluoroacetates, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

The present invention also includes the co-crystals of any compound according to the invention, i.e. those crystalline forms composed of at least two components (one being the compound according to the invention, the other being co-crystal formers) forming a unique crystalline structure without, in contrast to the crystalline salts, proton transfer from one component to the other. Potential co-crystal formers are acids and bases as listed above for salts/salt formers.

In a representation such as for example

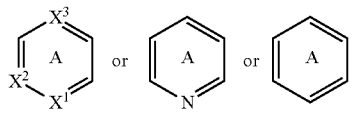

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

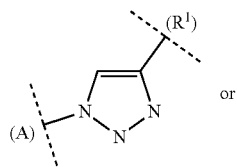

$(R^2)$—C(O)NH— or $(R^2)$—NHC(O)—;

Groups or substituents are frequently selected from among a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

The term "about" when used to specify a temperature or a temperature range usually means the temperature given ±5° C., when used to specify a pressure or a pressure range the pressure given ±0.5 bar. In all other cases "about" includes the range ±5% around the specific value given.

| List of abbreviations | |
|---|---|
| Ac | acetyl |
| acac | acetylacetonate |
| AcCN | acetonitrile |
| aq. | aquatic, aqueous |
| ATP | adenosine triphosphate |
| Bn | benzyl |
| Boc | tert-butyloxycarbonyl |
| Bu | butyl |
| c | concentration |
| d | day(s) |
| dba | dibenzylideneacetone |
| TLC | thin layer chromatography |
| DABCO | 1,4-diazabicyclo[2.2.2]octan |
| Davephos | 2-dimethylamino-2'-dicyclohexylaminophosphinobiphenyl |
| DBA | dibenzylideneacetone |
| DCM | dichloromethane |
| DEA | diethylamine |
| DEAD | diethyl azodicarboxylate |
| DIPA | N,N-diisopropylamine |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1.1'-bis(diphenylphosphino)ferrocene |
| EDTA | ethylenediaminetetraacetic acid |
| EGTA | ethyleneglycoltetraacetic acid |
| eq | equivalent(s) |
| ESI | electron spray ionization |
| Et | ethyl |
| $Et_2O$ | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| IBX | 2-iodoxy benzoic acid |
| i | iso |
| conc. | concentrated |
| LC | liquid chromatography |
| LiHMDS | lithium bis(trimethylsilyl)amide |
| sln. | solution |
| MCH | methyl cyclohexane |
| Me | methyl |
| MeOH | methanol |
| min | minutes |
| MPLC | medium pressure liquid chromatography |
| MS | mass spectrometry |
| MTBE | methyl tert-butyl ether |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| Py | pyridine |
| rac | racemic |
| red. | reduction |
| Rf ($R_f$) | retention factor |
| RP | reversed phase |
| rt | ambient temperature |
| SFC | supercritical fluid chromatography |
| $S_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethylamine |
| temp. | temperature |
| tert | tertiary |
| Tf | triflate |
| TFA | trifluoroacetic acid |
| THF | tetrahydrofuran |

| List of abbreviations | |
|---|---|
| TMS | trimethylsilyl |
| $t_{Ret.}$ | retention time (HPLC) |
| TRIS | tris(hydroxymethyl)-aminomethane |
| TsOH | p-toluenesulphonic acid |
| UV | ultraviolet |

Features and advantages of the present invention will become apparent from the following detailed examples which illustrate the principles of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein). If a compound is to be represented both by a structural formula and by its nomenclature, in the event of a conflict the structural formula is decisive.

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.

Chromatography

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out on Agilent or Gilson systems with columns made by Waters (names: SunFire™ Prep C18, OBD™ 10 μm, 50×150 mm or SunFire™ Prep C18 OBD™ 5 μm, 30×50 mm or XBridge™ Prep C18, OBD™ 10 μm, 50×150 mm or XBridge™ Prep C18, OBD™ 5 μm, 30×150 mm or XBridge™ Prep C18, OBD™ 5 μm, 30×50 mm) and YMC (names: Actus-Triart Prep C18, 5 μm, 30×50 mm).

Different gradients of $H_2O$/acetonitrile are used to elute the compounds, while for Agilent systems 5% acidic modifier (20 mL HCOOH to 1 L $H_2O$/acetonitrile (1/1)) is added to the water (acidic conditions). For Gilson systems the water is added 0.1% HCOOH.

For the chromatography under basic conditions for Agilent systems $H_2O$/acetonitrile gradients are used as well, while the water is made alkaline by addition of 5% basic modifier (50 g $NH_4HCO_3$+50 mL $NH_3$ (25% in $H_2O$) to 1 L with $H_2O$). For Gilson systems the water is made alkaline as follows: 5 mL $NH_4HCO_3$ solution (158 g in 1 L $H_2O$) and 2 mL $NH_3$ (28% in $H_2O$) are replenished to 1 L with $H_2O$.

The supercritical fluid chromatography (SFC) of the intermediates and example compounds according to the invention is carried out on a JASCO SFC-system with the following columns: Chiralcel OJ (250×20 mm, 5 μm), Chiralpak AD (250×20 mm, 5 μm), Chiralpak AS (250×20 mm, 5 μm), Chiralpak IC (250×20 mm, 5 μm), Chiralpak IA (250×20 mm, 5 μm), Chiralcel OJ (250×20 mm, 5 μm), Chiralcel OD (250×20 mm, 5 μm), Phenomenex Lux C2 (250×20 mm, 5 μm).

The analytical HPLC (reaction control) of intermediate and final compounds is carried out using columns made by Waters (names: XBridge™ C18, 2.5 μm, 2.1×20 mm or XBridge™ C18, 2.5 μm, 2.1×30 mm or Aquity UPLC BEH C18, 1.7 μm, 2.1×50 mm) and YMC (names: Triart C18, 3.0 μm, 2.0×30 mm) and Phenomenex (names: Luna C18, 5.0 μm, 2.0×30 mm). The analytical equipment is also equipped with a mass detector in each case.

HPLC-Mass Spectroscopy/UV-Spectrometry

The retention times/MS-ESI+ for characterizing the example compounds according to the invention are produced using an HPLC-MS apparatus (high performance liquid chromatography with mass detector). Compounds that elute at the injection peak are given the retention time $t_{Ret.}$=0.00.

HPLC-Methods:

| Method A | |
|---|---|
| HPLC | Agilent 1100 Series |
| MS | Agilent LC/MSD SL |
| column | Waters, Xbridge ™ C18, 2.5 μm, 2.1 × 20 mm, Part.No. 186003201 |
| solvent | A: 20 mM $NH_4HCO_3$/$NH_3$ pH 9 |
| | B: acetonitrile (HPLC grade) |
| detection | MS: positive and negative |
| | mass range: 120-900 m/z |
| | fragmentor: 120 |
| | gain EMV: 1 |
| | threshold: 150 |
| | stepsize: 0.2 |
| | UV: 315 nm |
| | bandwidth: 170 nm |
| | reference: off |
| | range: 230-400 nm |
| | range step: 1.00 nm |
| | peakwidth: <0.01 min |
| | slit: 1 nm |
| injection | 5 μL |
| flow | 1.00 mL/min |
| column temperature | 60° C. |
| gradient | 0.00 min 10% B |
| | 0.00-1.50 min 10% → 95% B |
| | 1.50-2.00 min 95% B |
| | 2.00-2.10 min 95% → 10% B |

| Method B | |
|---|---|
| HPLC | Agilent 1200 Series |
| MS | Agilent 6130 Quadropole LC/MS |
| column | Waters, Xbridge ™ C18, 2.5 μm, 2.1 × 30 mm |
| solvent | A: 20 mM $NH_4HCO_3$/$NH_3$ in water; pH 9.3 |
| | B: acetonitrile (HPLC grade) |
| detection | MS: |
| | polarity: positive |
| | ionizator: MM-ES + APCI |
| | mass range: 150-750 m/z |
| | fragmentor values: |
| | mass    fragmentor |
| | 150    70 |
| | 750    110 |
| | gain EMV: 1.00 |
| | threshold: 150 |
| | stepsize: 0.2 |
| | UV: |
| | 254 nm: reference off |
| | 214 nm: reference off |
| | range: 190-400 nm |
| | range step: 2.00 nm |
| | threshold: 1.00 mAU |
| | peakwidth: 0.0025 min (0.05 s) |
| | slit: 4 nm |

| | |
|---|---|
| injection | 0.5 μL |
| flow | 1.400 mL/min |
| column temperature | 45° C. |
| gradient | 0.00-1.00 min 15% -> 95% B |
| | 1.00-1.30 min 95% B |

Method C

| | |
|---|---|
| HPLC | Agilent 1200 Series |
| MS | Agilent 6130 Quadropole LC/MS |
| column | YMC, Triart C18, 3.0 μm, 2.0 × 30 mm, 12 nm |
| solvent | A: water + 0.1% HCOOH |
| | B: acetonitrile + 0.1% HCOOH (HPLC grade) |
| detection | MS: |
| | polarity: positive |
| | mass range: 150-750 m/z |
| | fragmentor values: |
| | mass      fragmentor |
| | 150          70 |
| | 750          110 |
| | gain EMV: 1.00 |
| | threshold: 150 |
| | stepsize: 0.20 |
| | UV: |
| | 254 nm: reference off |
| | 214 nm: reference off |
| | range: 190-400 nm |
| | range step: 4.00 nm |
| | threshold: 1.00 mAU |
| | peakwidth: 0.005 min (0.1 s) |
| | slit: 4 nm |
| injection | 0.5 μL |
| flow | 1.400 mL/min |
| column temperature | 45° C. |
| gradient | 0.0-1.00 min 15% → 100% B |
| | 1.00-1.13 min 100% B |

Method D

| | |
|---|---|
| HPLC | Agilent 1200 Series |
| MS | Agilent 6130 Quadropole LC/MS |
| column | Waters, Xbridge ™ C18, 2.5 μm, 2.1 × 30 mm |
| solvent | A: 20 mM NH$_4$HCO$_3$/NH$_3$ in water; pH 9.3 |
| | B: acetonitrile (HPLC grade) |
| detection | MS: |
| | polarity: positive + negative |
| | ionization: MM-ES |
| | mass range: 150-750 m/z |
| | fragmentor values: |
| | mass      fragmentor |
| | 150          70 |
| | 750          110 |
| | gain EMV: 1.00 |
| | threshold: 150 |
| | stepsize: 0.2 |
| | UV: |
| | 254 nm: reference off |
| | 214 nm: reference off |
| | range: 190-400 nm |
| | range step: 2.00 nm |
| | threshold: 1.00 mAU |
| | peakwidth: 0.0025 min (0.05 s) |
| | slit: 4 nm |
| injection | 0.5 μL |
| flow | 1.400 mL/min |
| column temperature | 45° C. |
| gradient | 0.00 -1.00 min 15% → 95% B |
| | 1.00-1.30 min 95% B |

Method E

| | |
|---|---|
| HPLC | Agilent 1200 Series: |
| MS | Agilent 6130 Quadropole LC/MS |
| column | Waters, Xbridge ™ C18, 2.5 μm, 2.1 × 30 mm |
| | Column XP; Part.No. 186006028 |
| solvent | A: 20 mM NH$_4$HCO$_3$/NH$_3$ in water; pH 9.3 |
| | B: acetonitrile (HPLC grade) |
| detection | MS: |
| | polarity: positive + negative |
| | ionizator: API-ES |
| | mass range: 150-750 m/z |
| | fragmentor values: |
| | mass      fragmentor |
| | 150          70 |
| | 750          110 |
| | gain EMV: 1.00 |
| | threshold: 150 |
| | stepsize: 0.2 |
| | UV: |
| | 254 nm: reference off |
| | 214 nm: reference off |
| | range: 190-400 nm |
| | range step: 2.00 nm |
| | threshold: 1.00 mAU |
| | peakwidth: 0.0025 min (0.05 s) |
| | slit: 4 nm |
| injection | 0.5 μL |
| flow | 1.400 mL/min |
| column temperature | 45° C. |
| gradient | 0.00-1.00 min 15% → 95% B |
| | 1.00-1.30 min 95% B |

Method F

| | |
|---|---|
| HPLC | Agilent 1200 Series |
| MS | Agilent 6130 Quadropole LC/MS |
| column | YMC, Triart C18, 3.0 μm, 2.0 ×30 mm, 12 nm |
| solvent | A: water + 0.1% HCOOH |
| | B: acetonitrile + 0.1% HCOOH (HPLC grade) |
| detection | MS: |
| | polarity: positive + negative |
| | mass range: 150-750 m/z |
| | fragmentor values: |
| | mass      fragmentor |
| | 150          70 |
| | 750          110 |
| | gain EMV: 1.00 |
| | threshold: 150 |
| | stepsize: 0.20 |
| | UV: |
| | 254 nm: reference off |
| | 214 nm: reference off |
| | range: 190-400 nm |
| | range step: 4.00 nm |
| | threshold: 1.00 mAU |
| | peakwidth: 0.0063 min (0.13 s) |
| | slit: 4 nm |
| injection | 0.5 μL |
| flow | 1.400 mL/min |
| column temperature | 45° C. |
| gradient | 0.00-1.00 min 15% → 100% B |
| | 1.00-1.13 min 100% B |

Method G

| | |
|---|---|
| HPLC | Agilent 1200 Series |
| MS | Agilent 6130 Quadropole LC/MS |
| column | YMC, Triart C18, 3.0 μm, 2.0 × 30 mm, 12 nm |
| solvent | A: water +0.1% HCOOH |
| | B: acetonitrile + 0.1% HCOOH (HPLC grade) |
| detection | MS: |
| | polarity: positive + negative |
| | mass range: 150-750 m/z |
| | fragmentor values: |
| | Mass      Fragmentor |
| | 150          70 |
| | 750          110 |
| | gain EMV: 1.00 |
| | threshold: 150 |
| | stepsize: 0.20 |
| | UV: |
| | 254 nm: reference off |
| | 230 nm: reference off |
| | 214 nm: reference off |
| | range: 190-400 nm |
| | range step: 4.00 nm |
| | threshold: 1.00 mAU |

-continued

| | |
|---|---|
| | peakwidth: 0.005 min (0.1 s) |
| | slit: 4 nm |
| injection | 0.5 μL |
| flow | 1.400 mL/min |
| column temperature | 45° C. |
| gradient | 0.00-1.00 min 15% → 100% B |
| | 1.00-1.13 min 100% B |

Method H

| | |
|---|---|
| HPLC | Agilent 1200 Series |
| MS | Agilent 6130 Quadropole LC/MS |
| column | YMC, Triart C18, 3.0 μm, 2.0 × 30 mm, 12 nm |
| solvent | A: water + 0.1% HCOOH |
| | B: acetonitrile + 0.1% HCOOH (HPLC grade) |
| detection | MS: |
| | polarity: positive + negative |
| | mass range: 200-800 m/z |
| | fragmentor : 70 |
| | gain: 1.00 |
| | threshold: 150 |
| | stepsize: 0.20 |
| | UV: |
| | 254 nm: reference off |
| | 230 nm: reference off |
| | range: 190-400 nm |
| | range step: 2.00 nm |
| | peakwidth: >0.01 min (0.2 s) |
| | slit: 4 nm |
| injection | 1.0 μL |
| flow | 1.000 mL/min |
| column temperature | 45° C |
| gradient | 0.00-0.10 min 5% B |
| | 0.10-1.85 min 5% B → 95.0% B |
| | 1.85-1.90 min 95%B |
| | 1.95-1.92 min 95% B → 5.0% B |

Method I

| | |
|---|---|
| HPLC | Agilent 1200 Series |
| MS | Agilent 6130 Quadropole LC/MS |
| column | YMC, Triart C18, 3.0 μm, 2.0 × 30 mm, 12 nm |
| solvent | A: water + 0.1% HCOOH |
| | B: acetonitrile + 0.1% HCOOH (HPLC grade) |
| detection | MS: |
| | polarity: positive + negative |
| | mass range: 200-800 m/z |
| | fragmentor: 70 |
| | gain: 1.00 |
| | threshold: 150 |
| | stepsize: 0.20 |
| | UV: |
| | 254 nm: reference off |
| | 230 nm: reference off |
| | range: 190-400 nm |
| | range step: 2.00 nm |
| | peakwidth: >0.01 min (0.2 s) |
| | slit: 4 nm |
| injection | 1.0 μL |
| flow | 1.000 mL/min |
| column temperature . | 45° C |
| gradient | 0.00-0.10 min 15% B |
| | 0.10-1.55 min 15% B → 95.0% B |
| | 1.55-1.90 min 95% B |
| | 1.95-1.92 min 95% B → 15.0% B |

Method J

| | |
|---|---|
| HPLC | Agilent 1260 Series |
| MS | Agilent 6130 Quadropole LC/MS |
| column | YMC, Triart C18, 3.0 μm, 2.0 × 30 mm, 12 nm |
| solvent | A: water + 0.1% HCOOH |
| | B: acetonitrile (HPLC grade) |
| detection | MS: |
| | polarity: positive + negative |
| | mass range: 100-800 m/z |
| | fragmentor: 70 |
| | gain: 1.00 |
| | threshold: 100 |
| | stepsize: 0.15 |
| | UV: |
| | 254 nm: reference off |

-continued

| | |
|---|---|
| | 230 nm: reference off |
| | range: 190-400 nm |
| | range step: 4.00 nm |
| | peakwidth: >0.013 min (0.25 s) |
| | slit: 4 nm |
| injection | 0.5 μL |
| flow | 1.400 mL/min |
| column temperature | 45° C. |
| gradient | 0.00-1.00 min 5% → 100% B |
| | 1.00-1.37 min 100% B |
| | 1.37-1.40 min 100% → 5% B |

Method K

| | |
|---|---|
| HPLC | Agilent 1260 Series |
| MS | Agilent 6130 Quadropole LC/MS |
| column | Waters, Xbridge ™ C18, 2.5 μm, 2.1 × 30 mm |
| solvent | A: 5 mM NH4HCO3/19 mM NH3 in water |
| | B: acetonitrile (HPLC grade) |
| detection | MS: |
| | polarity: positive + negative |
| | mass range: 100-800 m/z |
| | fragmentor: 70 |
| | gain: 1.00 |
| | threshold: 100 |
| | stepsize: 0.15 |
| | UV: |
| | 254 nm: reference off |
| | 230 nm: reference off |
| | range: 190-400 nm |
| | range step: 4.00 nm |
| | peakwidth: >0.013 min (0.25 s) |
| | slit: 4 nm |
| injection | 0.5 μL |
| flow | 1.400 mL/min |
| column temperature | 45° C. |
| gradient | 0.00-0.01 min 5% B |
| | 0.01-1.00 min 5% → 100% B |
| | 1.00-1.37 min 100% B |
| | 1.37-1.40 min 100% → 5% B |

Method L

| | |
|---|---|
| HPLC/MS | Waters UPLC-micromass Triple quad |
| column | Aquity UPLC BEH C18, 1.7 μM, 2.1 × 50 mm |
| solvent | A: water + 0.1% HCOOH |
| | B: acetonitrile (HPLC grade) + 0.1% HCOOH |
| detection | MS: |
| | ES/APCI positive and negative mode |
| | mass range: 100-1000 m/z |
| | capillary voltage: 3500 V |
| | cone voltage: 30-50 V |
| | disolvation gas: 600 L/h |
| | disolvation temp: 300° C. |
| | UV: |
| | bandwidth: 190 nm |
| | range: 210-400 nm |
| | resolution: 1.20 nm |
| | sample rate: 5 |
| injection | 0.5 μL |
| flow | 0.400 mL/min |
| column temperature | 40° C. |
| gradient | 0.00-1.80 min 0% B |
| | 1.80-3.80 min 0% → 75% B |
| | 3.80-4.50 min 75% → 95% B |
| | 4.50-6.00 min 95% B |
| | 6.00-6.01 min 95% → 0% B |

Method M

| | |
|---|---|
| HPLC/MS | Agilent 1200, 6120MS |
| column | Luna C18(2) 5 μm, 30 × 2.0 mm |
| solvent | A: water + 0.037% TFA |
| | B: acetonitrile + 0.018% TFA |
| detection | MS: positive and negative mode |
| | mass range: 100-1000 m/z |
| | fragmentor: 70 |
| | gain EMV: 1 |
| | threshold: 150 |
| | stepsize: 0.1 |
| | UV: 220/254 nm |
| | bandwidth: 200 nm |

-continued

| | |
|---|---|
| | reference: off |
| | range: 200-400 nm |
| | range step: 0.4 nm |
| | Peakwidth: >0.05 min |
| | Slit: 4 nm |
| injection | 0.5 µL |
| flow | 1.0 mL/min |
| column temperature | 50° C. |
| gradient | 0.00-0.30 min 0% B |
| | 0.30-1.40 min 0% → 60% B |
| | 1.40-1.55 min 60% B |
| | 1.55-1.56 min 60% → 0% B |
| | 1.56-2.00 min 0% B |

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known prior art compounds or methods described herein. Substances described in the literature are prepared according to the published methods of synthesis.

Compounds (Ia)

General Reaction Scheme and Summary of the Synthesis Route

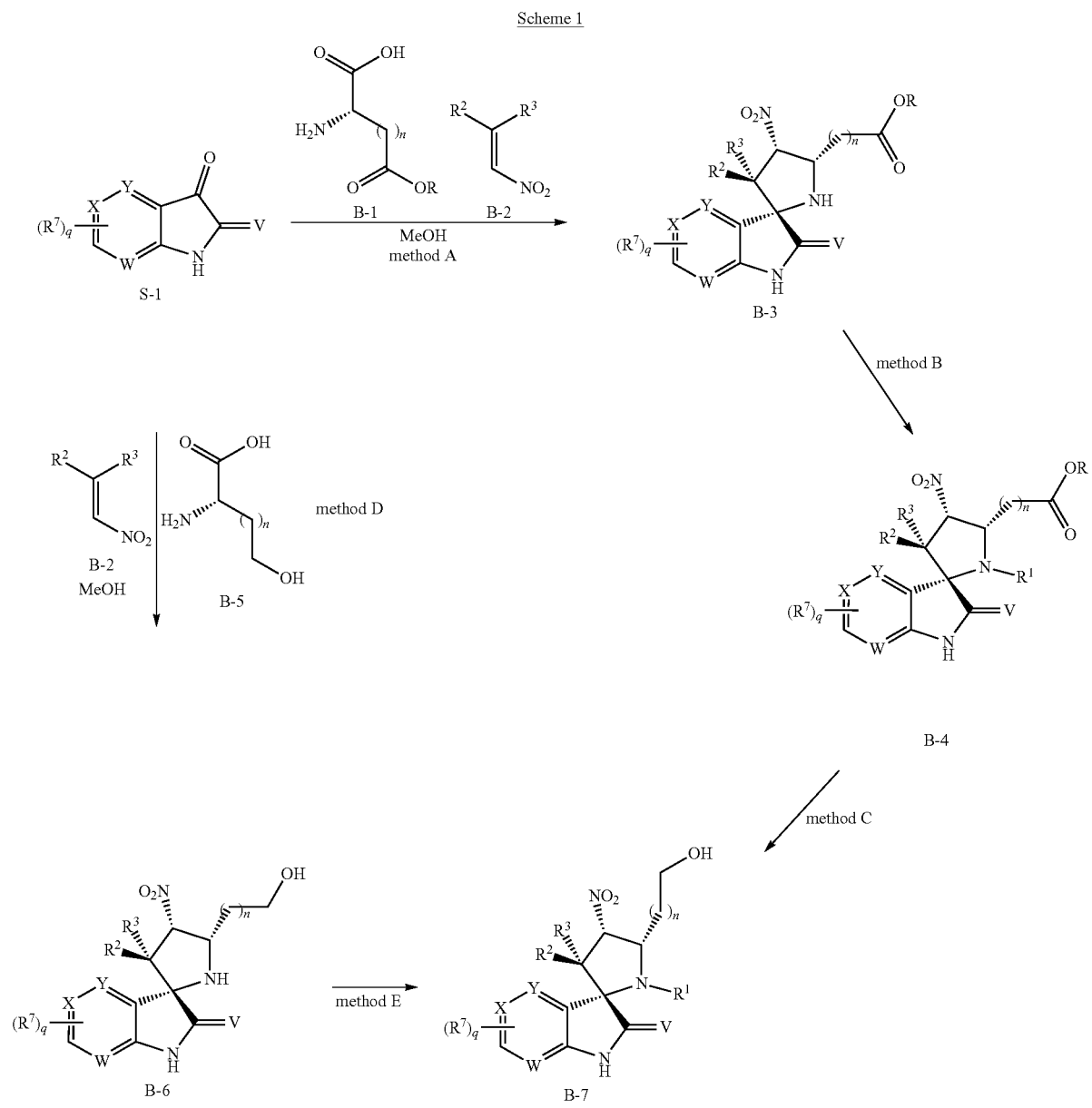

R = e.g. alkyl

Scheme 2
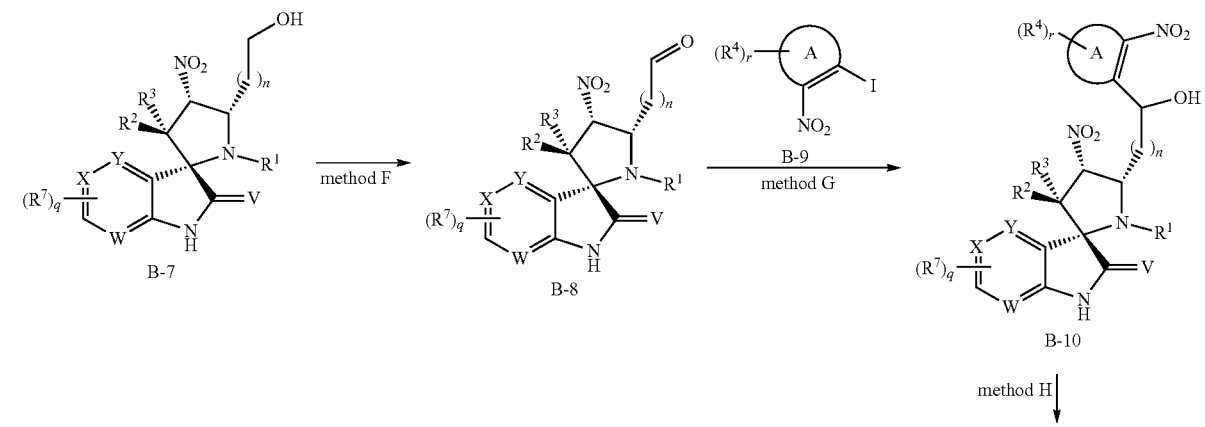
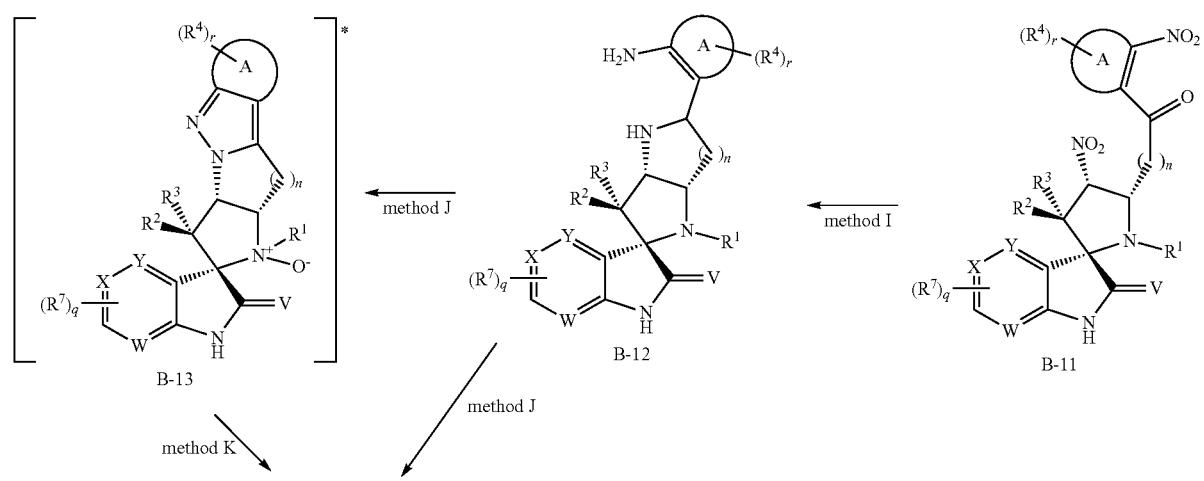
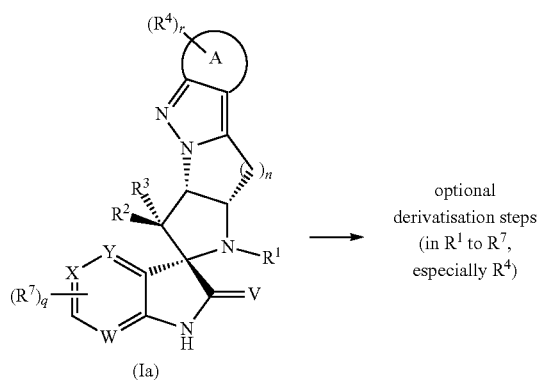
(Ia)
optional derivatisation steps (in $R^1$ to $R^7$, especially $R^4$)
* The location of overoxidation/N-oxid formaton is not entirely clear. B-13 as depicted in scheme 2 seems to be probable.

Scheme 3
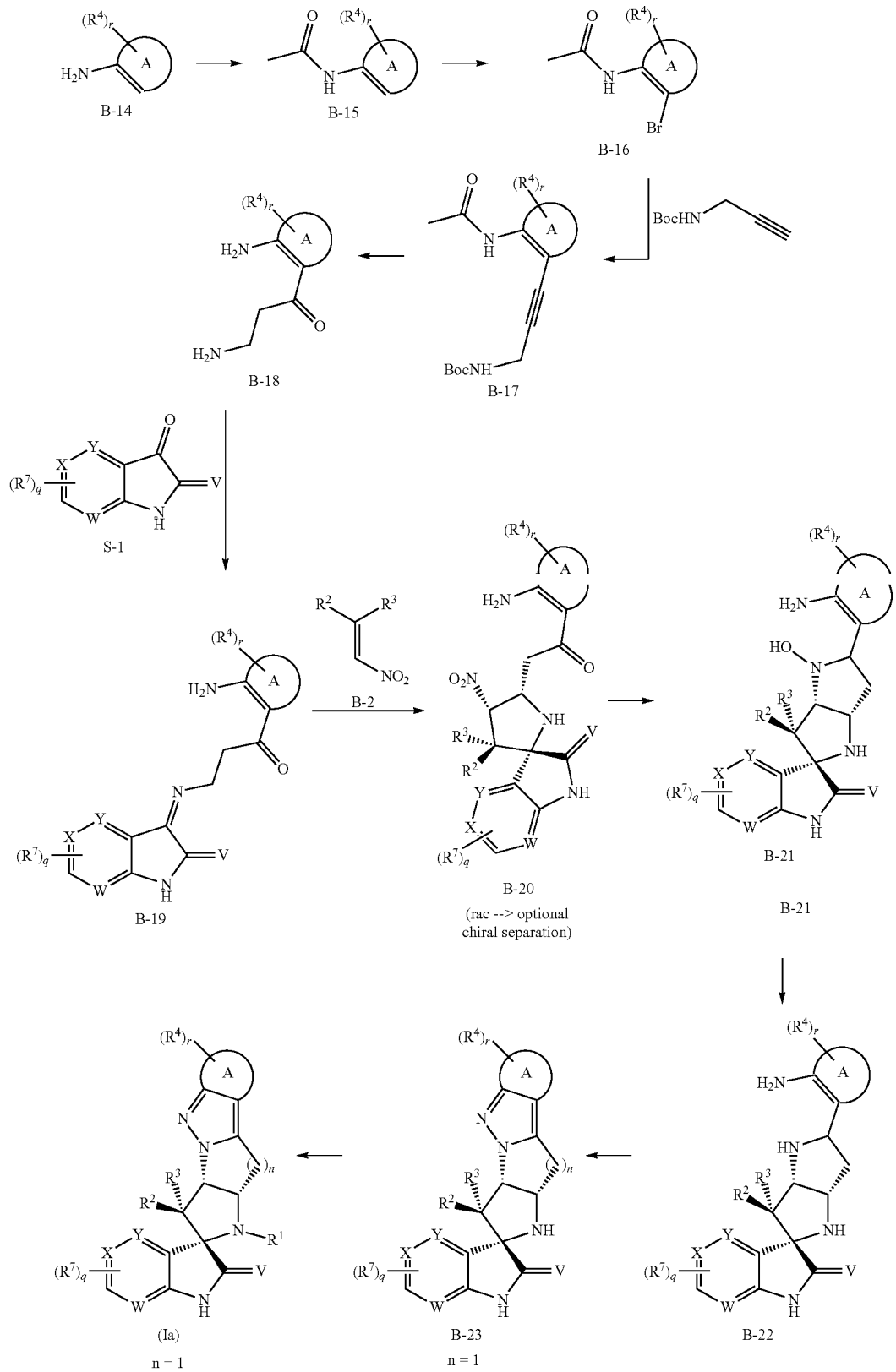

Novel compounds of structure (Ia) can be prepared stepwise starting with a synthesis route depicted in scheme 1 from isatin derivatives S-1 via a decarboxylative 1,3 dipolar cycloaddition with an amino acid B-1 (method A) or B-5 (method D) and a nitro ethene B-2 to build up spiro systems B-3 and B-6 as a racemic mixture potentially along with other regio- and/or diastereoisomers of B-3 and B-6. The enantiomers of B-3 and B-6 can be separated at this stage by chiral SFC or alternatively the racemic mixture can be separated at any later stage of the synthesis. Also all other means known for separation of enantiomers can be applied here or after any later synthetic step herein described, e.g. crystallisation, chiral resolution, chiral HPLC etc. (see also *Enantiomers, racemates, and resolutions*, Jean Jacques, André Collet, Samuel H Wilen John Wiley and Sons, N Y, 1981).

B-3 and B-6 can be reacted with aldehydes or ketones in a reductive amination reaction to give B-4 (method B) and B-7 (method E). Alternatively, an alkylation, addition, acylation or sulfonylation reaction can be performed with B-3 and B-6 to obtain intermediates B-4 and B-7.

Intermediate B-4 can be reduced with DIBAL or another reducing reagent and will then also yield intermediates B-7 (method C).

The hydoxy group of intermediate B-7 is oxidized, e.g. with DESS-MARTIN periodinan, IBX or an alternative oxidizing reagent, to the corresponding carbonyl compound B-8 (method F, scheme 2) which can be further reacted with nucleophiles, especially organometallic reagents like GRIGNARD or organo-zinc reagents (obtainable from B-9 via a metal-halogen exchange reaction) to intermediate B-10 as a mixture of two diastereomers (method G).

The diastereoisomers of intermediates B-10 are not separated and used as mixtures for further reactions.

Intermediates B-10 can be oxidized to the ketone intermediates B-11 by using DESS-MARTIN periodinan, IBX or other oxidation methods (method H).

Reduction of both nitro groups of intermediates B-11 and subsequent reductive cyclization is triggered by treatment of intermediates B-11 with hydrogen under RANEY-Ni catalysis, or with alternative reducing agents, and gives intermediates B-12 as a mixture of two diastereoisomers (method I). The diastereomers of intermediates B-12 are not separated and used as the mixture for further reactions.

An oxidative cyclization of intermediates B-12 by treatment with OXONE© (potassium peroxymonosulfate) in a mixture of water and DCM, or by treatment with alternative oxidizing agents gives compounds (Ia) according to the invention (method J). If overoxidation occurs when treated with OXONE© a subsequent reduction of the crude mixture containing overoxidation product B-13 with bis(pinacolato) diborone or other reducing can be performed to yield compounds (Ia).

Compounds (Ia) which are initially obtained from B-12 or B-13 can be derivatized in optional derivatization steps not explicitly depicted in the schemes in all residues, especially in $R^4$, if they carry functional groups, that can be further modified such as e.g. halogen atoms, amino and hydroxy groups (including cyclic amines), carboxylic acid or ester functions, nitrils etc. to further compounds (Ia) by well-established organic chemical transformations such as metal-catalyzed cross coupling reactions, acylation, amidation, addition, reduction or (reductive) alkylation or cleavage of protecting groups. These additional steps are not depicted in the general schemes. Likewise, it is also possible to include these additional steps in the synthetic routes depicted in the general schemes, i.e. to carry out derivatization reactions with intermediate compounds. In addition, it may also be possible that building blocks bearing protecting groups are used, i.e. further steps for deprotection are necessary.

Alternatively, compounds (Ia) can also be prepared with the following reaction sequence:

Starting from anilines or amino heteroaryls B-14 the amino function can be acetylated with acetic anhydride or other standard acetylation methods to give intermediates B-15. Intermediates B-15 are brominated with NBS, TsOH and $Pd(OAc)_2$ to yield bromo intermediates B-16. SONOGASHIRA coupling with Boc-prop-2-ynyl-amine under Pd and Cu catalysis gives intermediates B-17 which can by hydratized in acidic conditions under $Pd(OAc)_2$ catalysis followed by global deprotection under acidic conditions (HCl) to yield amines B-18. Modifications of intermediates thus obtained, e.g. esterification of free carboxyl groups (if one of $R^4$=COOH) with $SOCl_2$ and MeOH or a alternative esterification method, gives additional intermediates B-18. Imine formation of intermediates B-18 with isatins S-1 gives imine intermediates B-19 which can then react in a 1,3 dipolar cycloaddition with nitro ethenes B-2 to yield racemic intermediates B-20 along with other regio- and stereoisomers. The enantiomers of B-20 can be separated at this stage by chiral SFC or alternatively the racemic mixture can be separated at any later stage of the synthesis, e.g. when intermediate B-22 is reached. Also all other means known for separation of enantiomers can be applied here or after any later synthetic step herein described, e.g. crystallisation, chiral resolution, chiral HPLC etc. (see also *Enantiomers, racemates, and resolutions*, Jean Jacques, André Collet, Samuel H Wilen John Wiley and Sons, N Y, 1981). Reduction and cyclisation of intermediate B-20 with $H_2$ under Pt/C catalysis gives intermediates B-21 which can be reduced subsequently by addition of $VO(acac)_2$ to the reaction mixture and continued stirring under $H_2$ pressure to yield intermediates B-22. An oxidative cyclization of intermediates B-22 with $Na_2WO_4$ dihydrate and $H_2O_2$, or by treatment with alternative oxidizing agents gives intermediates B-23 that can be converted to compounds (Ia) by reactions with aldehydes or ketones in a reductive amination reaction. Alternatively, an alkylation, addition, acylation or sulfonylation reaction can be performed with B-23 to obtain additional compounds (Ia).

Compounds (Ia) have been tested for their activity to affect MDM2-p53 interaction in their racemic form or alternatively as the enantiopure form (in particular (Ia*)). Each of the two enantiomers of a racemic mixture may have activity against MDM2 although with a different binding mode. Enantiopure compounds are marked with the label "Chiral". Compounds listed in any table below that are labeled "Chiral" (both intermediates as well as compounds (Ib) according to the invention) can be separated by chiral SFC chromatography from their enantiomer or are synthesized from enantiopure starting material which is separated by chiral SFC.

EXAMPLE

A
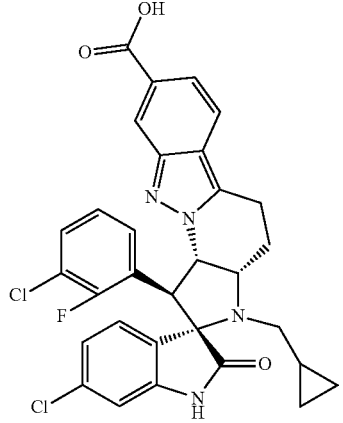

B
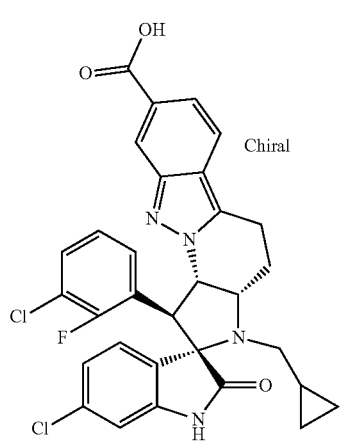
Chiral

C
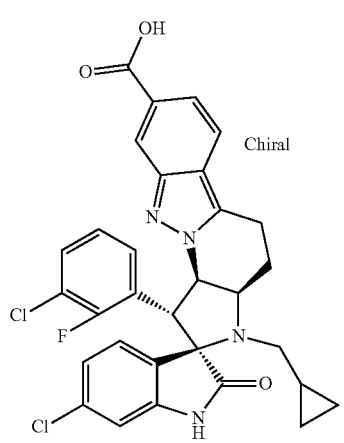
Chiral

Structure A defines the racemic mixture of compounds with structure B and C, i.e. structure A encompasses two structures (compounds B and C), whereas structures B and C, respectively, are enantiopure and only define one specific compound. Thus, formulae (Ia) and (Ia*)

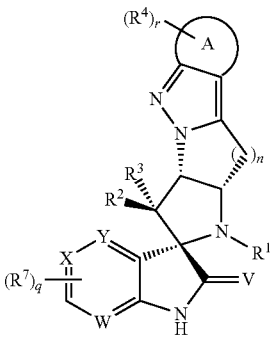
(Ia)

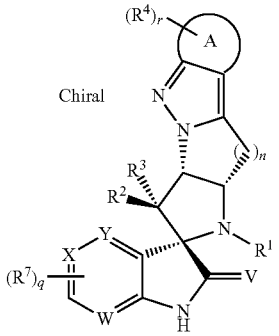
(Ia*)
Chiral with a set of specific definitions for groups $R^1$ to $R^4$, $R^7$, V, W, X, Y, n, r and q represent the racemic mixture of two enantiomers (→(Ia); structure A above is one specific example of such a racemic mixture) or a single enantiomer (→(Ia*); structure B above is one specific enantiomer), unless there are additional stereocenters present in one or more of the substituents. The same definition applies to synthetic intermediates.

Synthesis of Intermediates B-6

Experimental Procedure for the Synthesis of B-6a (Method D)

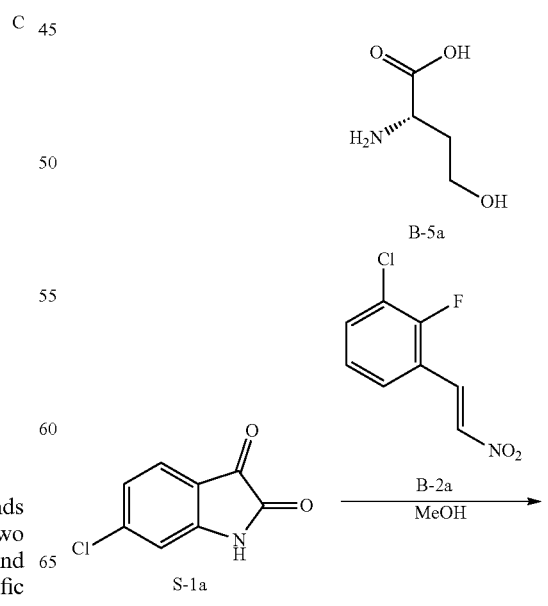

-continued

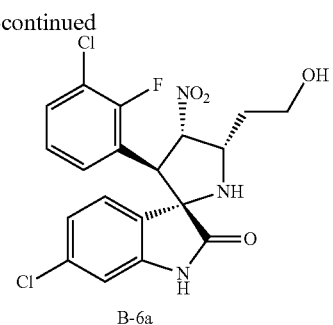
B-6a

6-Chloroisatin S-1a (31.5 g, 174 mmol), 1-(3-chloro-2-fluoro-phenyl)-2-nitroethene B-2a (35 g, 174 mmol) and L-homoserine B-5a (20.7 g, 174 mmol) are refluxed in MeOH for 4 h. The reaction mixture is concentrated in vacuo and purified by crystallization or chromatography if necessary.

The following intermediates B-6 (table 1) are available in an analogous manner starting from different annulated 1H-pyrrole-2,3-diones S-1, amino acids B-5 and nitroethenes B-2.

TABLE 1

| # | structure | $t_{ret}$ [min] | $[M + H]^+$ | HPLC method |
|---|-----------|-----------------|-------------|-------------|
| B-6a | 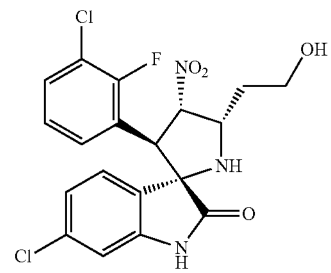 | 1.21 | 440 | A |
| B-6b | Chiral | 1.21 | 440 | A |
| B-6c | 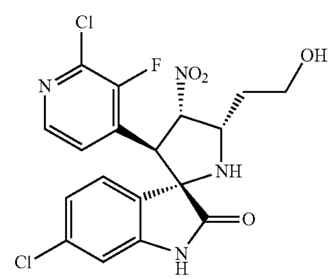 [SMILES: O=C1Nc2cc(Cl)ccc2[C@]12N[C@@H](CCO)[C@@H]([N+](=O)[O-])[C@@H]2c1ccnc(Cl)c1F] | 1.09 | 441 | A |
| B-6d | Chiral | 1.09 | 441 | A |

TABLE 1-continued

| # | structure | t_ret [min] | [M + H]+ | HPLC method |
|---|---|---|---|---|
| B-6e | 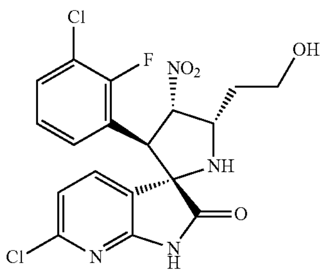 [SMILES: O=C1Nc2nc(Cl)ccc2[C@]12N[C@@H](CCO)[C@@H]([N+](=O)[O-])[C@@H]2c1cccc(Cl)c1F] | 1.13 | 441 | A |
| B-6f | Chiral | 1.13 | 441 | A |
| B-6g | 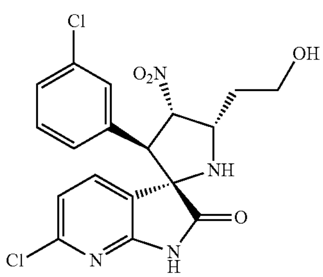 [SMILES: O=C1Nc2nc(Cl)ccc2[C@]12N[C@@H](CCO)[C@@H]([N+](=O)[O-])[C@@H]2c1cccc(Cl)c1] | 1.17 | 422 | A |
| B-6h | Chiral | 1.17 | 422 | A |
| B-6i | 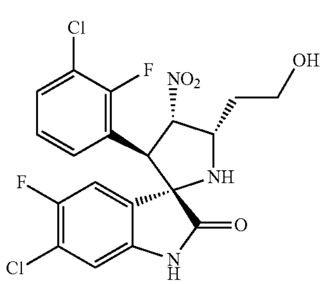 [SMILES: O=C1Nc2cc(Cl)c(F)cc2[C@]12N[C@@H](CCO)[C@@H]([N+](=O)[O-])[C@@H]2c1cccc(Cl)c1F] | 1.25 | 458 | A |

TABLE 1-continued

| # | structure | $t_{ret}$ [min] | [M + H]$^+$ | HPLC method |
|---|---|---|---|---|
| B-6j | 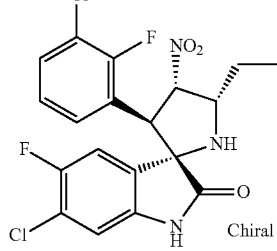 | 1.25 | 458 | A |

(structure shown with Chiral designation)

Synthesis of Intermediates B-7

Experimental Procedure for the Synthesis of B-7a (Method E)

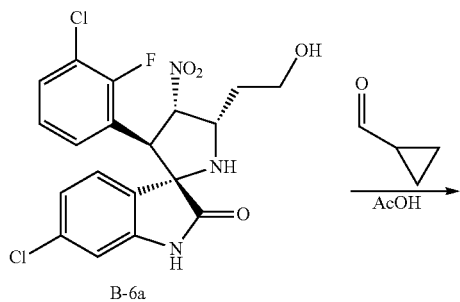

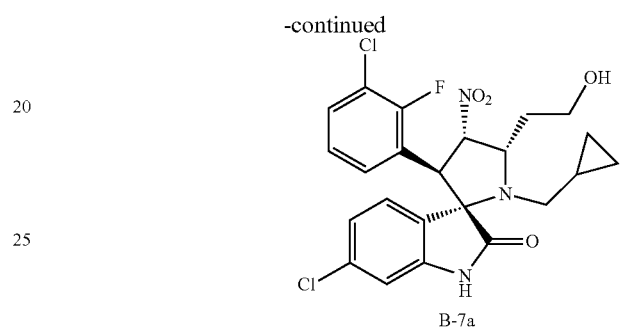

To a solution of cyclopropanecarbaldehyde (1.7 mL, 22.7 mmol) in AcOH (19.5 mL) is added intermediate B-6a (1.60 g, 3.8 mmol) and the reaction mixture is stirred for 15 min. Sodium triacetoxyborohydride (1.34 g, 6.3 mmol) is added and the reaction mixture is stirred overnight. Water is added to the reaction mixture and it is extracted with EtOAc. The combined organic layer is dried (MgSO$_4$), filtered, concentrated in vacuo and the crude product B-7a is purified by chromatography if necessary.

The following intermediates B-7 (table 2) are available in an analogous manner starting from different intermediates B-6 and aldehydes.

TABLE 2

| # | structure | $t_{ret}$ [min] | [M + H]$^+$ | HPLC method |
|---|---|---|---|---|
| B-7a | 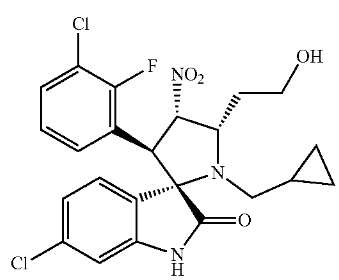 | 1.37 | 494 | A |

TABLE 2-continued
| # | structure | $t_{ret}$ [min] | $[M + H]^+$ | HPLC method |
|---|---|---|---|---|
| B-7b | 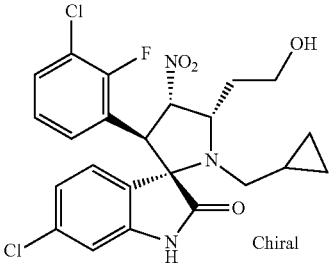 | 1.37 | 494 | A |
| B-7c | 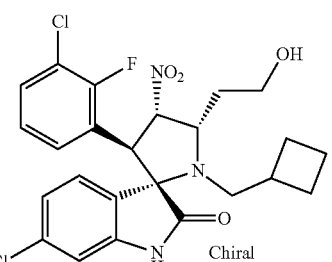 | 1.44 | 508 | A |
| B-7d | 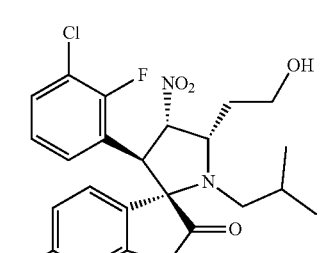 | 1.43 | 496 | A |
| B-7e | 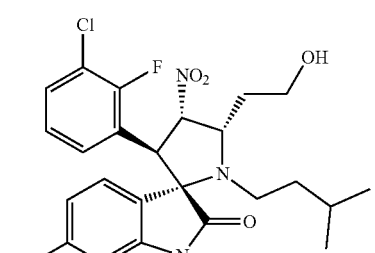 | 1.47 | 510 | A |
| B-7f | 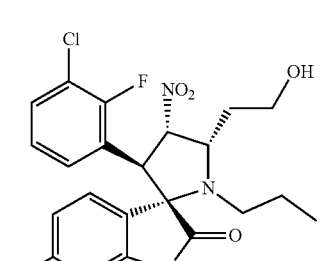 | 1.37 | 482 | A |

TABLE 2-continued
| # | structure | $t_{ret}$ [min] | [M + H]$^+$ | HPLC method |
|---|---|---|---|---|
| B-7g | 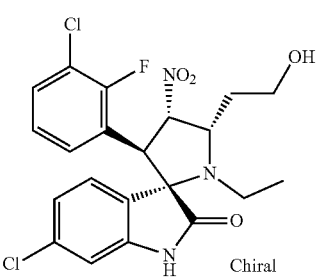 | 1.32 | 468 | A |
| B-7h | 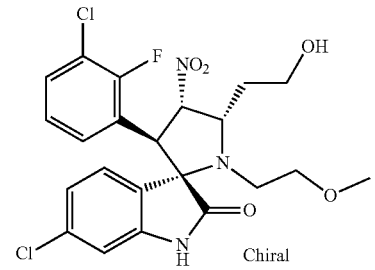 | 1.28 | 498 | A |
| B-7i | 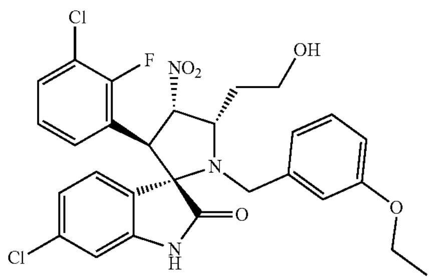 [SMILES: CCOc1cccc(CN2[C@@H](CCO)[C@@H]([N+](=O)[O-])[C@H](c3cccc(Cl)c3F)[C@]23C(=O)Nc2cc(Cl)ccc23)c1] | 1.47 | 574 | A |
| B-7j | 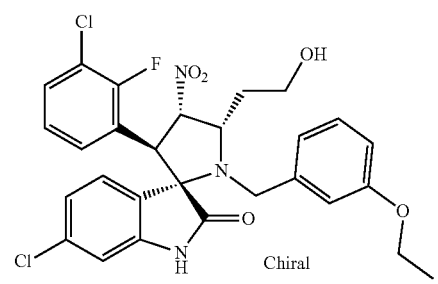 | 1.45 | 574 | A |
| B-7k | 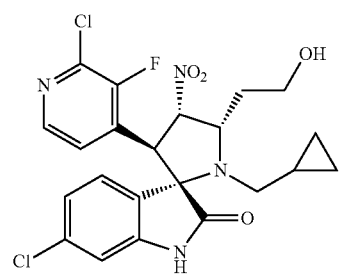 [SMILES: O=C1Nc2cc(Cl)ccc2[C@@]12[C@@H](c1ccnc(Cl)c1F)[C@H]([N+](=O)[O-])[C@H](CCO)N2CC1CC1] | 495 | 1.29 | A |

TABLE 2-continued
| # | structure | $t_{ret}$ [min] | $[M + H]^+$ | HPLC method |
|---|---|---|---|---|
| B-7l | 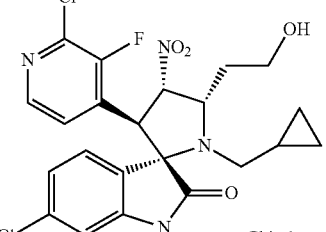 | 1.29 | 495 | A |
| B-7m | 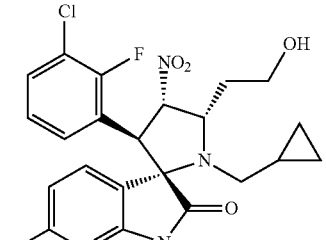 | 1.29 | 495 | A |
| B-7n | 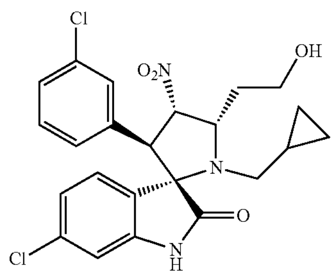 [SMILES: O=C1Nc2cc(Cl)ccc2[C@@]12[C@@H](c1cccc(Cl)c1)[C@H]([N+](=O)[O-])[C@H](CCO)N2CC1CC1] | 1.37 | 476 | A |
| B-7o | 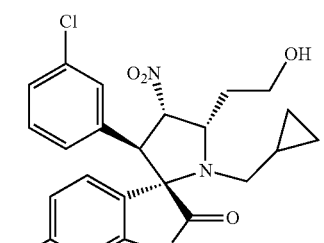 | 1.37 | 476 | A |
| B-7p | 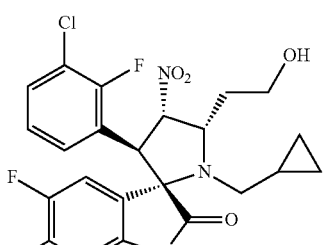 | 1.38 | 512 | A |

TABLE 2-continued

| # | structure | $t_{ret}$ [min] | $[M + H]^+$ | HPLC method |
|---|---|---|---|---|
| B-7q | 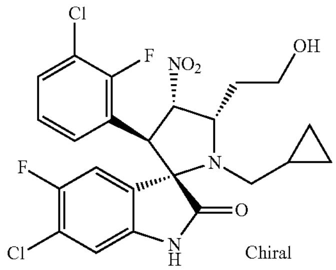 | 1.38 | 512 | A |
| B-7r | 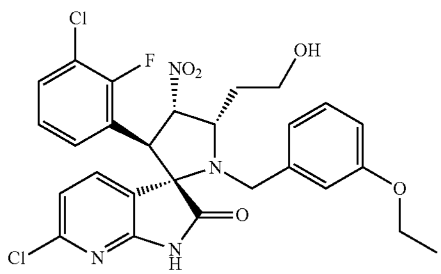 [SMILES: CCOc1cccc(CN2[C@@H](CCO)[C@@H]([N+](=O)[O-])[C@H](c3cccc(Cl)c3F)[C@]23C(=O)Nc2nc(Cl)ccc23)c1] | 0.80 | 575 | E |
| B-7s | 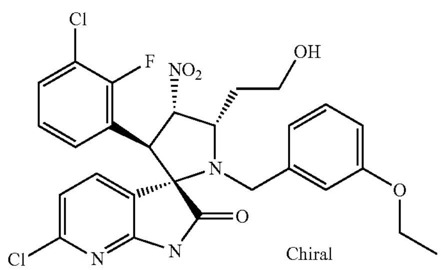 [SMILES: CCOc1cccc(CN2[C@@H](CCO)[C@@H]([N+](=O)[O-])[C@H](c3cccc(Cl)c3F)[C@]23C(=O)Nc2nc(Cl)ccc23)c1 ; "Chiral"] | 0.80 | 575 | E |

Synthesis of Intermediates B-3

Experimental Procedure for the Synthesis of B-3a (Method A)

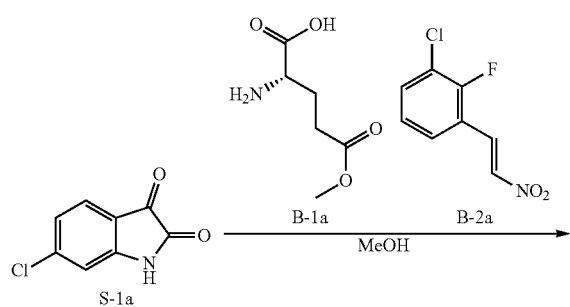

6-Chloroisatin S-1a (5 g, 27.0 mmol), 1-(3-chloro-2-fluoro-phenyl)-2-nitroethene B-2a (5.5 g, 27.0 mmol) and amino acid B-1a (4.4 g, 27.0 mmol) are refluxed in MeOH for 4 h. The reaction mixture is concentrated in vacuo and purified by crystallization or chromatography if necessary.

The following intermediates B-3 (table 3) are available in an analogous manner starting from different annulated 1H-pyrrole-2,3-diones S-1, amino acids B-1 and nitroethenes B-2.

TABLE 3

| # | structure | $t_{ret}$ [min] | $[M + H]^+$ | HPLC method |
|---|---|---|---|---|
| B-3a | 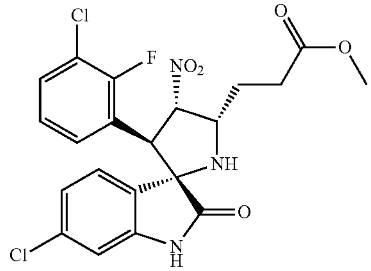 [SMILES: COC(=O)CC[C@@H]1N[C@@]2(C(=O)Nc3cc(Cl)ccc32)[C@@H](c2cccc(Cl)c2F)[C@@H]1[N+](=O)[O-]] | 1.42 | 482 | A |
| B-3b | Chiral | 1.42 | 482 | A |

Synthesis of Intermediates B-4

Experimental Procedure for the Synthesis of B-4a (Method B)

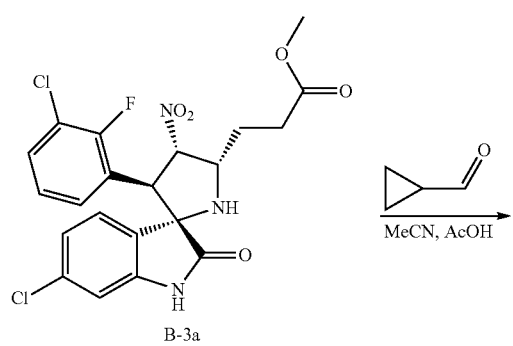

B-3a

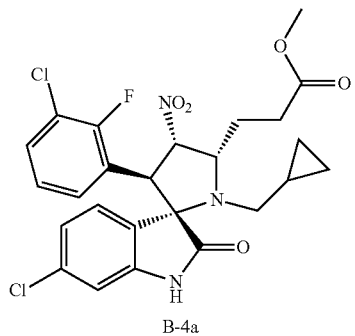

B-4a

To a solution of cyclopropanecarbaldehyde (0.64 g, 8.9 mmol) in AcOH (0.5 mL) is added intermediate B-3a (2.68 g, 4.4 mmol) and the reaction mixture is stirred for 15 min. Sodium triacetoxyborohydride (2.8 g, 13.3 mmol) is added and the reaction mixture is stirred overnight. Water is added to the reaction mixture and it is extracted with EtOAc. The combined organic layer is dried ($MgSO_4$), filtered, concentrated in vacuo and the crude product B-4a is purified by chromatography if necessary.

The following intermediates B-4 (table 4) are available in an analogous manner starting from different intermediates B-3 and different aldehydes.

TABLE 4

| # | structure | $t_{ret}$ [min] | $[M + H]^+$ | HPLC method |
|---|---|---|---|---|
| B-4a | 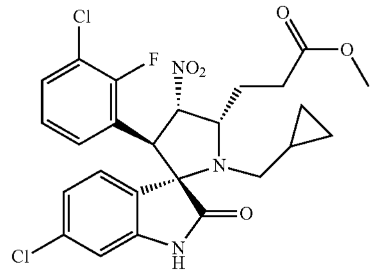 [SMILES: COC(=O)CC[C@H]1[C@@H]([N+](=O)[O-])[C@H](c2cccc(Cl)c2F)[C@]2(C(=O)Nc3cc(Cl)ccc32)N1CC1CC1] | 1.52 | 536 | A |
| B-4b |  Chiral | 1.52 | 536 | A |

Synthesis of Additional Intermediates B-7

Experimental Procedure for the Synthesis of B-7t (Method C)

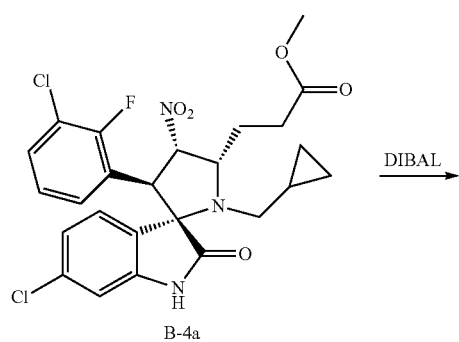 →DIBAL→ 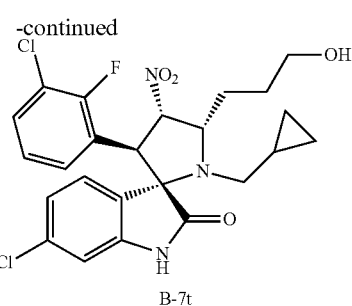

B-4a

B-7t

To a solution of B-4a (2.38 g, 4.0 mmol) in DCM is added DIBAL (18.0 mL, 18 mmol, 1.0 M in DCM) slowly at 0° C. and the reaction mixture is stirred for 1 h. To the reaction mixture is added water and saturated aqueous potassium sodium tartrate solution and the mixture is stirred overnight at rt. The phases are separated and the aqueous phase is extracted with DCM. The combined organic layer is dried ($MgSO_4$), filtered, concentrated in vacuo and the crude product B-7t is purified by chromatography if necessary.

The following intermediates B-7 (table 5) are available in an analogous manner starting from different intermediates B-4.

TABLE 5

| # | structure | $t_{ret}$ [min] | $[M + H]^+$ | HPLC method |
|---|---|---|---|---|
| B-7t | 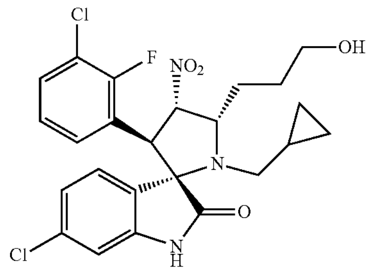 [SMILES: O=C1Nc2cc(Cl)ccc2[C@@]12[C@@H](c1cccc(Cl)c1F)[C@H]([N+](=O)[O-])[C@H](CCCO)N2CC1CC1] | 1.52 | 508 | A |
| B-7u | 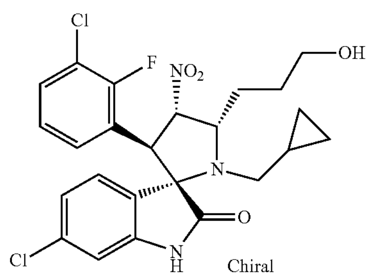 | 1.52 | 508 | A |

Synthesis of Intermediates B-8

Experimental Procedure for the Synthesis of B-8b (Method F)

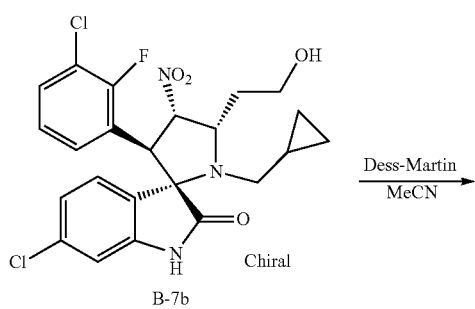

B-7b

Dess-Martin / MeCN →

-continued

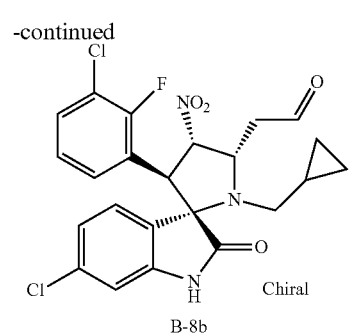

B-8b

To a solution of intermediate B-7b (1 g, 2.02 mmol) in ACN (20 mL) is added NaHCO₃ (0.34 g, 4.05 mmol) and stirred for 5 min before DESS-MARTIN periodinan (1.72 g, 4.05 mmol) is added portionwise to the mixture. The reaction mixture is stirred for additional 30 min before it is diluted with H₂O, saturated NaHCO₃ and EtOAc. The reaction mixture is extracted with EtOAc. The combined organic layer is dried (MgSO₄), filtered, concentrated in vacuo and the crude product B-8b is purified by chromatography if necessary.

The following intermediates B-8 (table 6) are available in an analogous manner starting from different intermediates B-7.

TABLE 6

| # | structure | $t_{ret}$ [min] | [M + H]⁺ | HPLC method |
|---|---|---|---|---|
| B-8a | 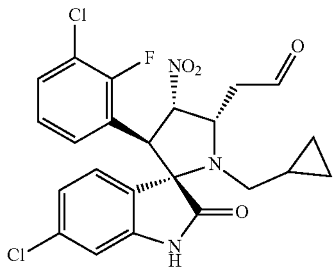 [SMILES: O=CC[C@H]1[C@@H]([N+](=O)[O-])[C@H](c2cccc(Cl)c2F)[C@]2(C(=O)Nc3cc(Cl)ccc32)N1CC1CC1] | 1.45 | 492 | A |
| B-8b | 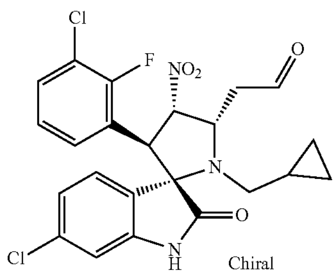 | 1.46 | 492 | A |
| B-8c | 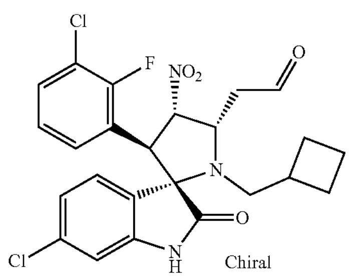 | 1.48 | 506 | A |
| B-8d | 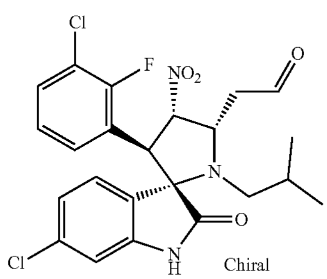 | 1.50 | 494 | A |
| B-8e | 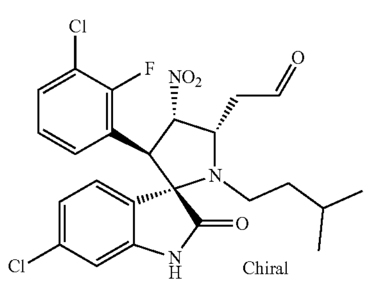 | 1.55 | 506 | A |

TABLE 6-continued
| # | structure | $t_{ret}$ [min] | $[M + H]^+$ | HPLC method |
|---|---|---|---|---|
| B-8f | 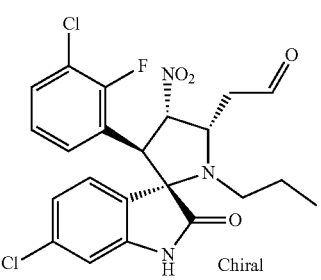 | 1.46 | 480 | A |
| B-8g | 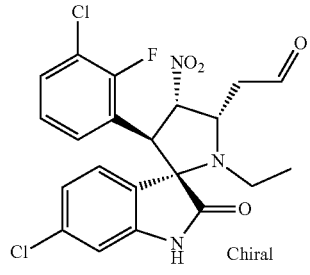 | 1.39 | 464 | A |
| B-8h | 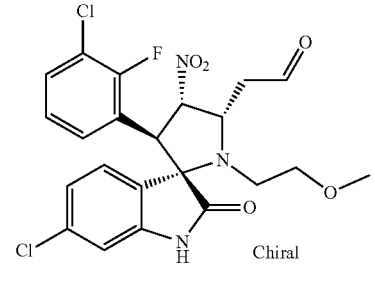 | 1.35 | 494 | A |
| B-8i | 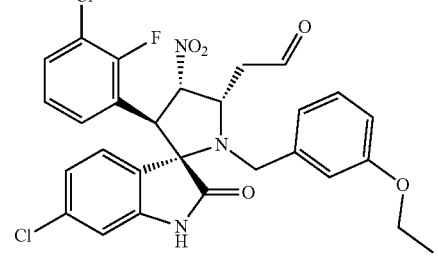 | 0.91 | 572 | B |
| B-8j | 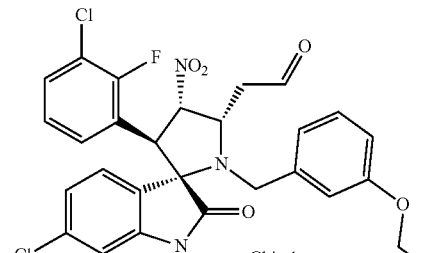 | 1.53 | 572 | A |

TABLE 6-continued

| # | structure | $t_{ret}$ [min] | $[M + H]^+$ | HPLC method |
|---|---|---|---|---|
| B-8k | 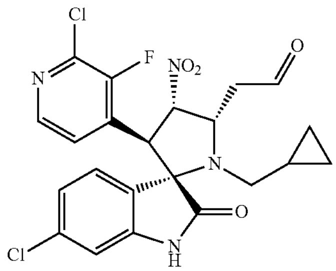 [SMILES: O=CC[C@H]1[C@@H]([N+](=O)[O-])[C@H](c2ccnc(Cl)c2F)[C@]2(C(=O)Nc3cc(Cl)ccc32)N1CC1CC1] | 1.37 | 493 | A |
| B-8l | 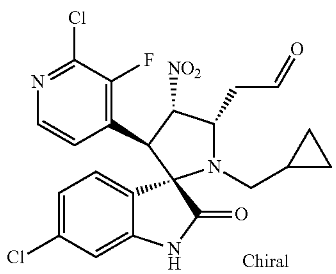 | 1.37 | 493 | A |
| B-8m | 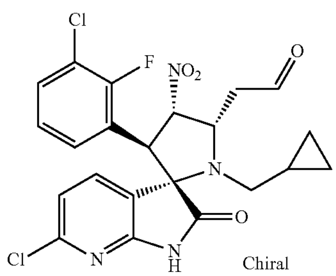 | 1.34 | 493 | A |
| B-8n | 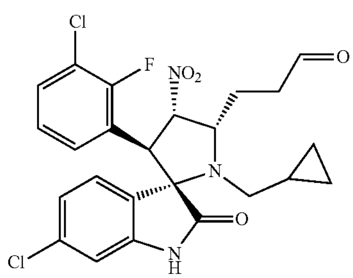 [SMILES: O=CCC[C@H]1[C@@H]([N+](=O)[O-])[C@H](c2cccc(Cl)c2F)[C@]2(C(=O)Nc3cc(Cl)ccc32)N1CC1CC1] | 1.42 | 506 | A |
| B-8o | 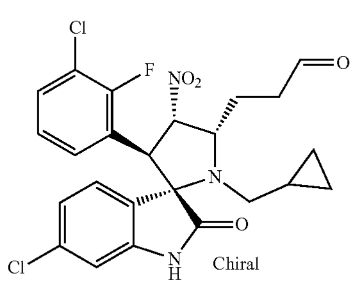 | 1.42 | 506 | A |

TABLE 6-continued

| # | structure | $t_{ret}$ [min] | $[M + H]^+$ | HPLC method |
|---|---|---|---|---|
| B-8p | 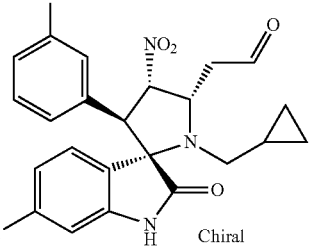 | 1.46 | 474 | A |
| B-8q | 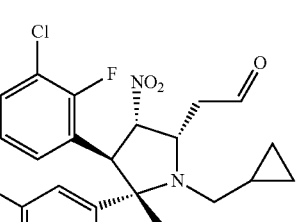 | 0.84 | 510 | B |
| B-8r | 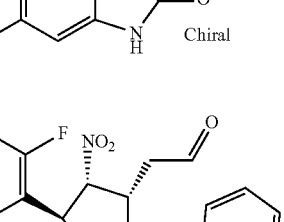 | n.a. | n.a. | n.a. |

Synthesis of Intermediates B-10

Experimental Procedure for the Synthesis of B-10a (Method G)

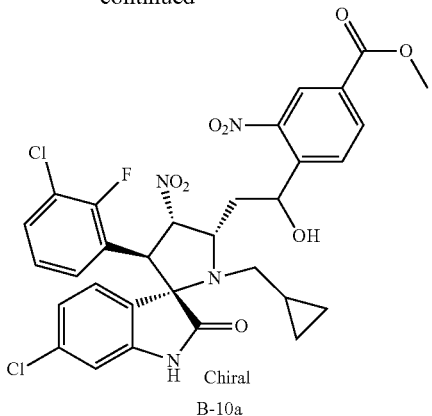

A solution of 4-iodo-3-nitro-benzoic acid methyl ester B-9a (2.60 g, 8.48 mmol) in THF (17 mL) is cooled to −50° C. and phenylmagnesium chloride (4.05 mL, 8.09 mmol, 2 M) is added dropwise and the reaction mixture is stirred for additional 30 min at −50° C. A solution of intermediate B-8b (1.90 g, 3.85 mmol) in THF (7.7 mL) is added to the reaction mixture dropwise at −50° C. and the reaction mixture is stirred for additional 15 min at the same temperature. The reaction mixture is slowly warmed to rt and stirred for additional 2 h before saturated aqueous KHSO₄ solution and EtOAc is added. The reaction mixture is extracted with EtOAc. The combined organic layer is dried (MgSO₄), filtered, concentrated in vacuo and the crude product B-10a is purified by chromatography. B-10a is obtained as a mixture of two diastereomers which is used for the next step without separation.
The following intermediates B-10 (table 7) are available in an analogous manner starting from different intermediates B-8 and different iodides B-9.
TABLE 7
| # | structure | $t_{ret}$ [min] | $[M + H]^+$ | HPLC method |
|---|-----------|-----------------|-------------|-------------|
| B-10a | 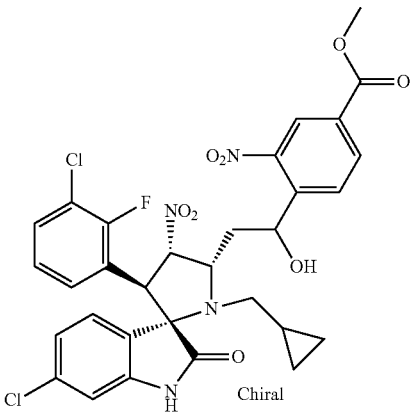 | 1.58 | 673 | A |
| B-10b | 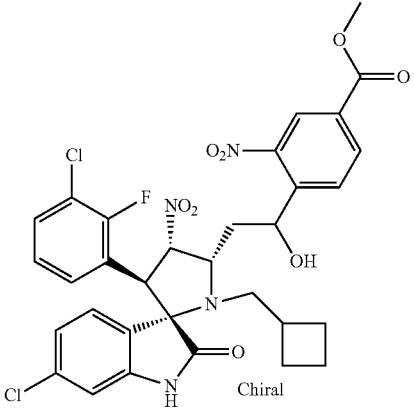 | 1.63 | 687 | A |
| B-10c | 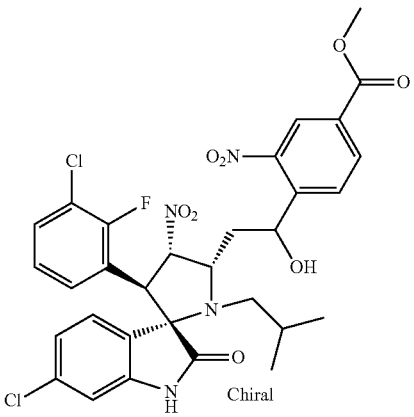 | 1.61 | 675 | A |

TABLE 7-continued
| # | structure | $t_{ret}$ [min] | [M + H]$^+$ | HPLC method |
|---|---|---|---|---|
| B-10d | 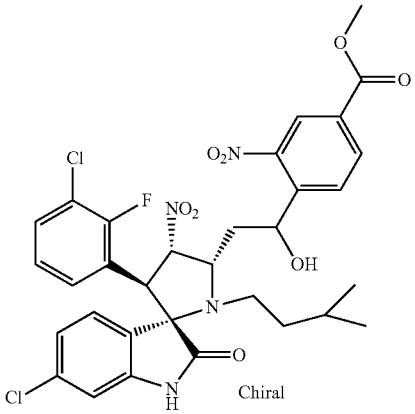 | 1.62 | 687 | A |
| B-10e | 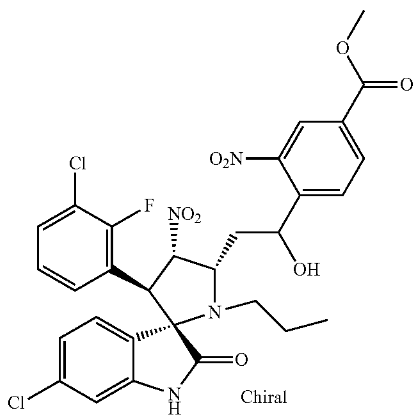 | 1.57 | 659 | A |
| B-10f | 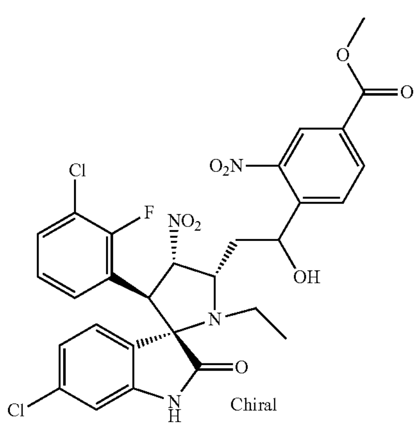 | 1.53 | 647 | A |

TABLE 7-continued
| # | structure | $t_{ret}$ [min] | [M + H]⁺ | HPLC method |
|---|---|---|---|---|
| B-10g | 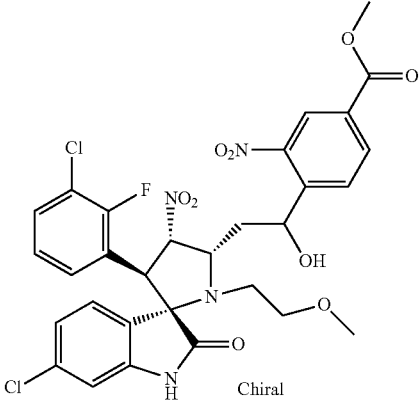 | 1.49 | 675 | A |
| B-10h | 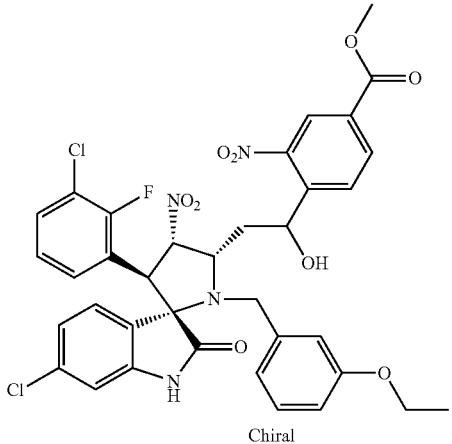 | 1.63 | 753 | A |
| B-10i | 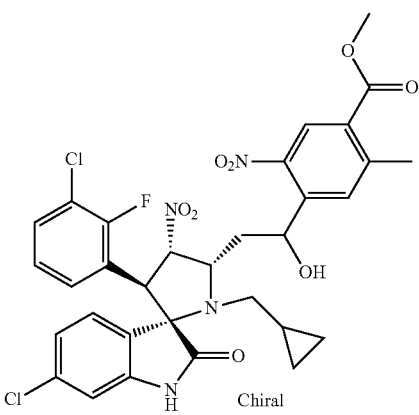 | 1.61 | 687 | A |

TABLE 7-continued
| # | structure | $t_{ret}$ [min] | $[M + H]^+$ | HPLC method |
|---|---|---|---|---|
| B-10j | 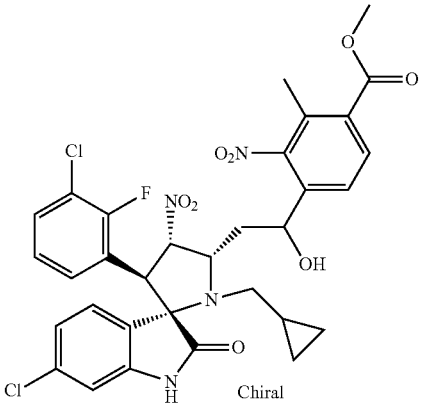 | 1.62 | 687 | A |
| B-10k | 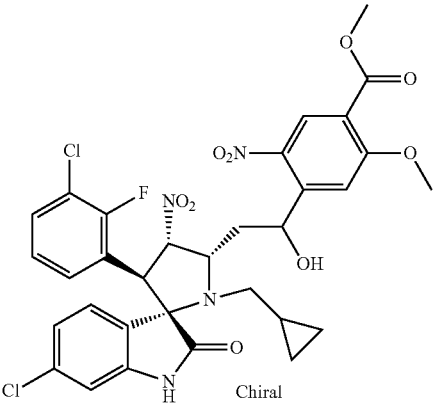 | 1.52 | 703 | A |
| B-10l | 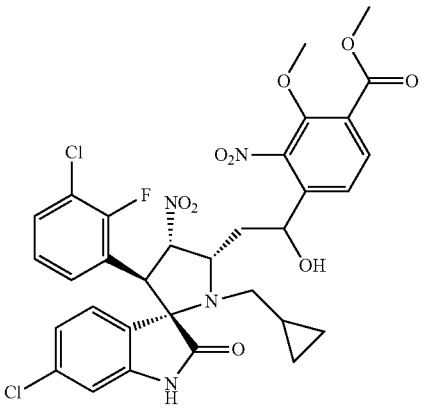 [SMILES: COC(=O)c1ccc(C(O)C[C@H]2[C@@H]([N+](=O)[O-])[C@H](c3cccc(Cl)c3F)[C@]3(C(=O)Nc4cc(Cl)ccc43)N2CC2CC2)c([N+](=O)[O-])c1OC] | 1.58 | 709 | A |

TABLE 7-continued

| # | structure | $t_{ret}$ [min] | $[M + H]^+$ | HPLC method |
|---|---|---|---|---|
| B-10m | 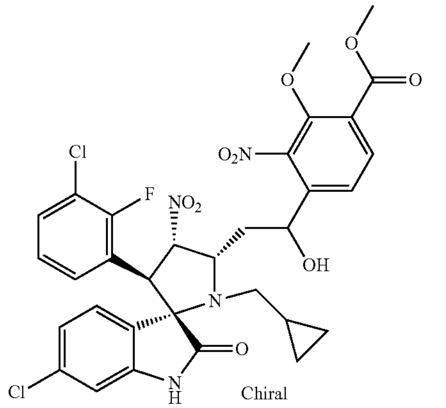 | 1.58 | 709 | A |
| B-10n | 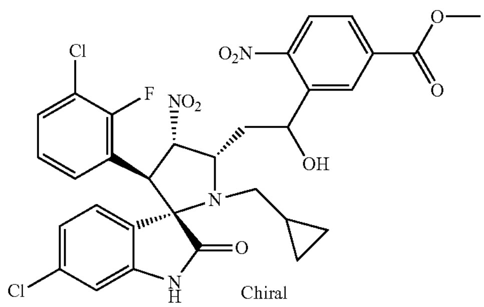 | 1.54 | 673 | A |
| B-10o | 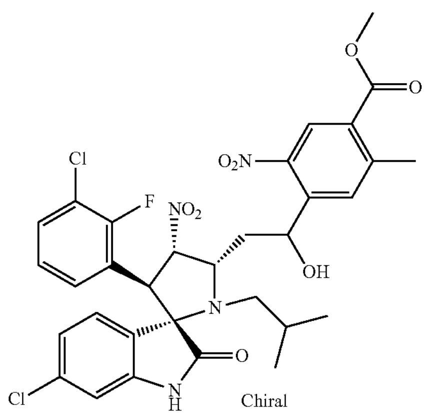 | 1.66 | 698 | A |
| B-10p | 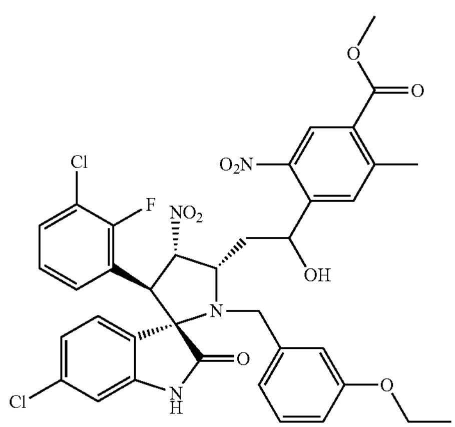 | 1.62 | 767 | A |

TABLE 7-continued

| # | structure | $t_{ret}$ [min] | [M + H]$^+$ | HPLC method |
|---|---|---|---|---|
| B-10q | 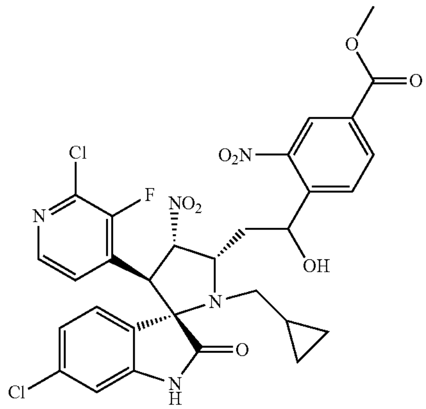 [SMILES: COC(=O)c1ccc(C(O)C[C@H]2[C@@H]([N+](=O)[O-])[C@H](c3ccnc(Cl)c3F)[C@]3(C(=O)Nc4cc(Cl)ccc43)N2CC2CC2)c([N+](=O)[O-])c1] | 1.51 | 674 | A |
| B-10r | 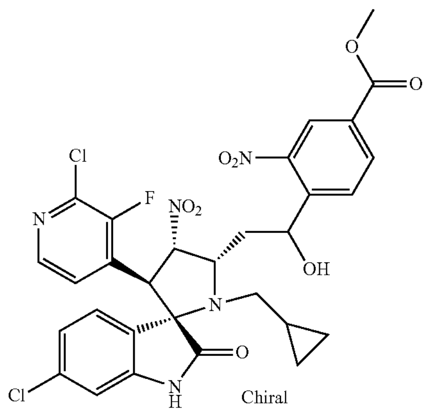 | 1.51 | 674 | A |
| B-10s | 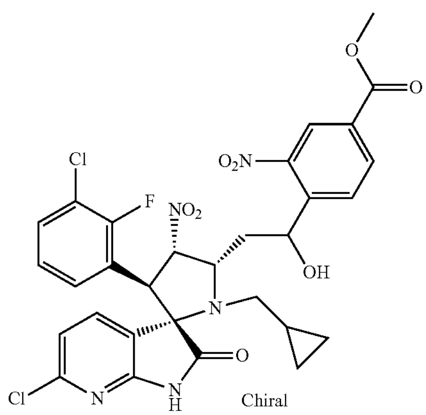 | 1.48 | 674 | A |
| B-10t | 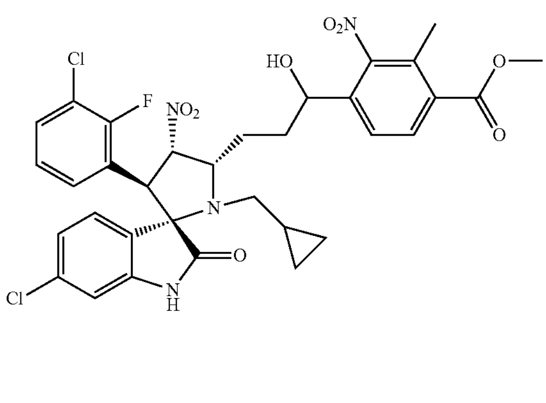 [SMILES: COC(=O)c1ccc(C(O)CC[C@H]2[C@@H]([N+](=O)[O-])[C@H](c3cccc(Cl)c3F)[C@]3(C(=O)Nc4cc(Cl)ccc43)N2CC2CC2)c([N+](=O)[O-])c1C] | n.a. | n.a. | — |

TABLE 7-continued

| # | structure | $t_{ret}$ [min] | $[M + H]^+$ | HPLC method |
|---|---|---|---|---|
| B-10u | 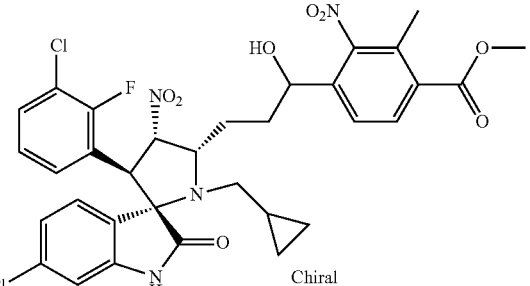 | n.a. | n.a. | — |

Synthesis of Intermediates B-9

Experimental Procedure for the Synthesis of B-9b

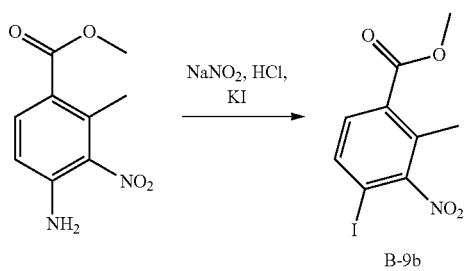

To a solution of 4-amino-2-methyl-3-nitro-benzoic acid methyl ester (2.4 g, 11.0 mmol) in HCl (25 mL) at 0° C. is slowly added sodium nitrite and the mixture is stirred for 30 min at the same temperature. Potassium iodide (5.7 g, 34.0 mmol) is added portionwise at 0° C. and the mixture is stirred at rt for 1 h. To the reaction mixture is added water and Et$_2$O. The phases are separated and the aqueous phase is extracted with Et$_2$O. The combined organic layer is dried (MgSO$_4$), filtered, concentrated in vacuo and the crude product B-9b is purified by chromatography if necessary.

Experimental Procedure for the Synthesis of B-9c

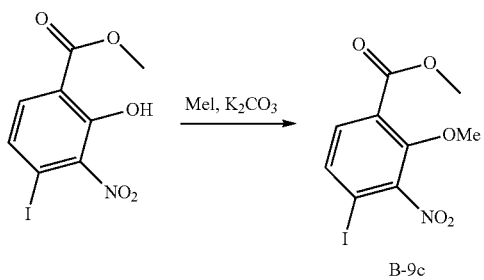 [SMILES: COC(=O)c1ccc(I)c([N+](=O)[O-])c1O ; COC(=O)c1ccc(I)c([N+](=O)[O-])c1OC]

To a solution of 2-hydroxy-4-iodo-3-nitro-benzoic acid methyl ester (1.0 g, 3.1 mmol) is added potassium carbonate (1.3 g, 9.3 mmol) and methyl iodide (0.4 mL, 6.2 mmol) at rt. The reaction mixture is stirred at rt for 4 h. Water is added to the mixture and the formed solid is filtered and dried to yield intermediate B-9c.

TABLE 8

| # | structure | $t_{ret}$ [min] | $[M + H]^+$ | HPLC method |
|---|---|---|---|---|
| B-9b | 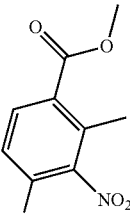 | 1.25 | n.a. | A |
| B-9c | 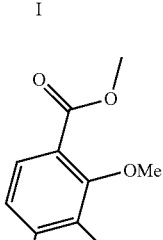 | 1.19 | 338 | A |

Synthesis of Intermediates B-11

Experimental Procedure for the Synthesis of B-11a

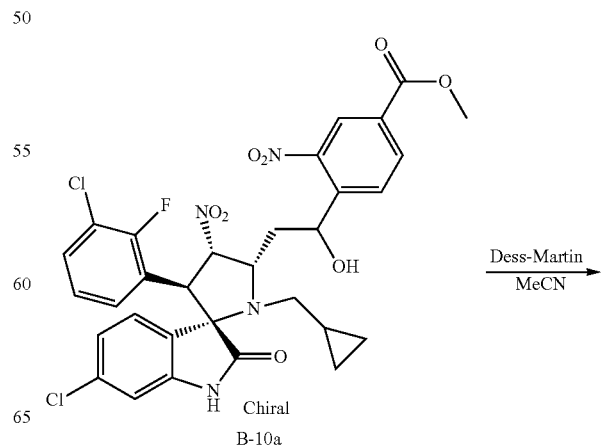

B-10a

-continued

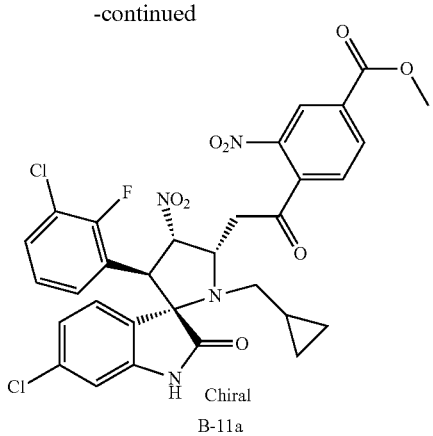

B-11a

To a solution of intermediate B-10a (1 g, 1.49 mmol) in THF (10 mL) is added NaHCO₃ (0.34 g, 1.49 mmol) and stirred for 5 min before DESS-MARTIN periodinan (1.26 g, 2.97 mmol) is added portionwise to the mixture. The reaction mixture is stirred for additional 2 h at rt before it is diluted with H₂O, saturated NaHCO₃ and EtOAc. The reaction mixture is extracted with EtOAc. The combined organic layer is dried (MgSO₄), filtered, concentrated in vacuo and the crude product B-11a is purified by chromatography if necessary.

The following intermediates B-11 (table 9) are available in an analogous manner starting from different intermediates B-10.

TABLE 9

| # | structure | $t_{ret}$ [min] | $[M + H]^+$ | HPLC method |
|---|---|---|---|---|
| B-11a | 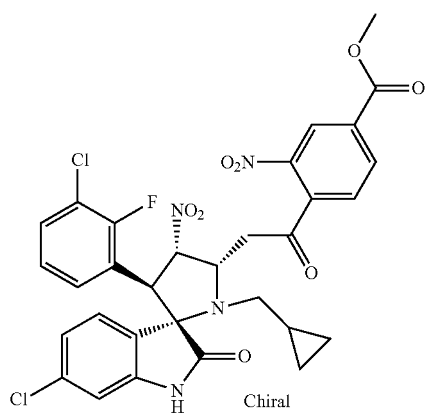 | 1.57 | 671 | A |
| B-11b | 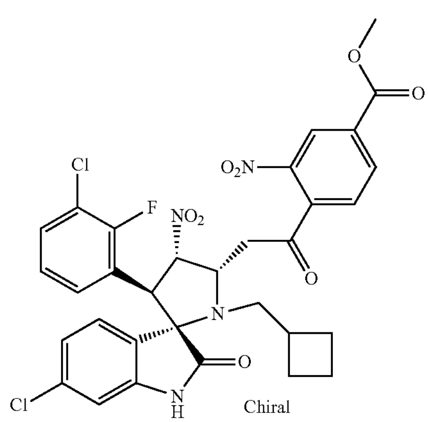 | 1.66 | 685 | A |

TABLE 9-continued
| # | structure | $t_{ret}$ [min] | $[M + H]^+$ | HPLC method |
|---|---|---|---|---|
| B-11c | 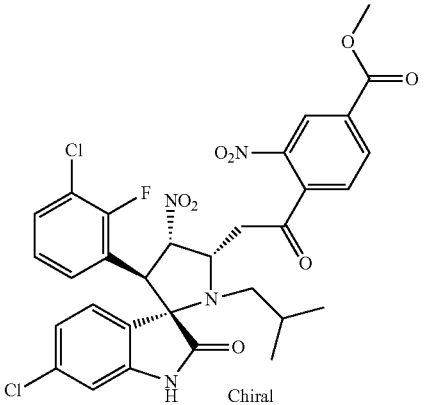 | 1.64 | 673 | A |
| B-11d | 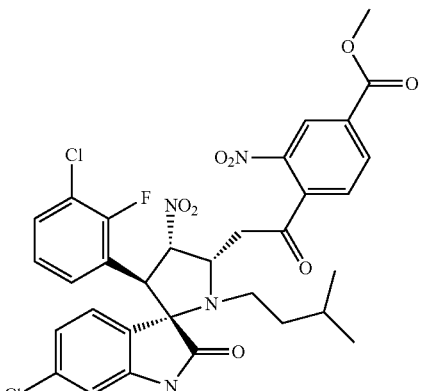 | 1.65 | 687 | A |
| B-11e | 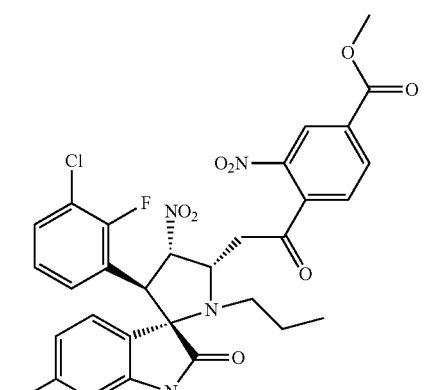 | 1.60 | 659 | A |

TABLE 9-continued
| # | structure | $t_{ret}$ [min] | [M + H]$^+$ | HPLC method |
|---|---|---|---|---|
| B-11f | 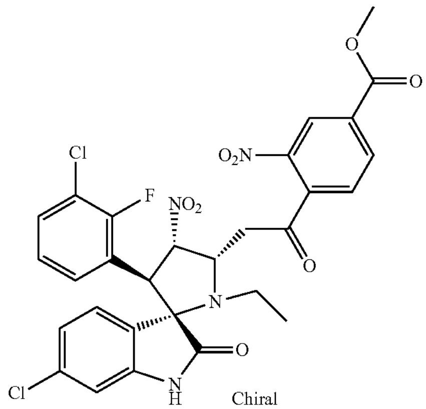 | 1.56 | 645 | A |
| B-11g | 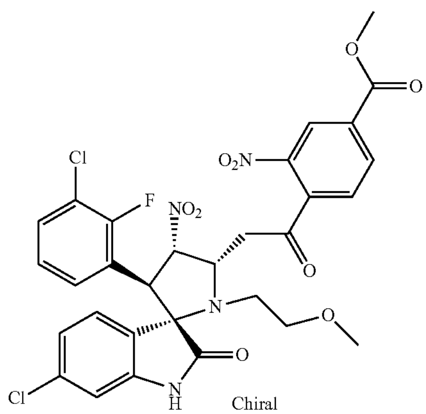 | 1.50 | 675 | A |
| B-11h | 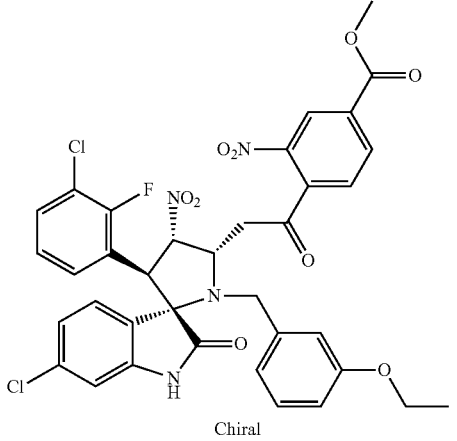 | 1.63 | 751 | A |

TABLE 9-continued
| # | structure | $t_{ret}$ [min] | [M + H]$^+$ | HPLC method |
|---|---|---|---|---|
| B-11i | 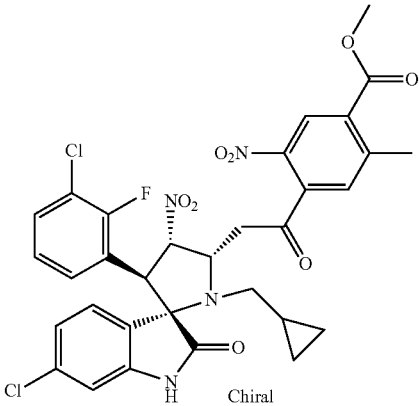 | 1.63 | 685 | A |
| B-11j | 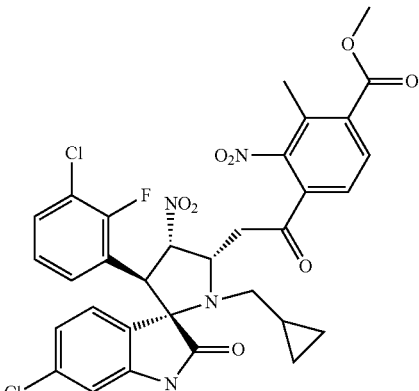 | 1.62 | 685 | A |
| B-11k | 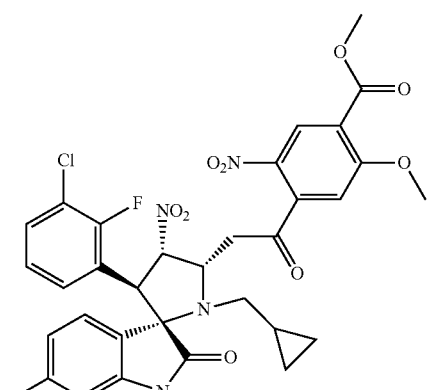 | 1.57 | 701 | A |

TABLE 9-continued

| # | structure | $t_{ret}$ [min] | [M + H]$^+$ | HPLC method |
|---|---|---|---|---|
| B-11l | 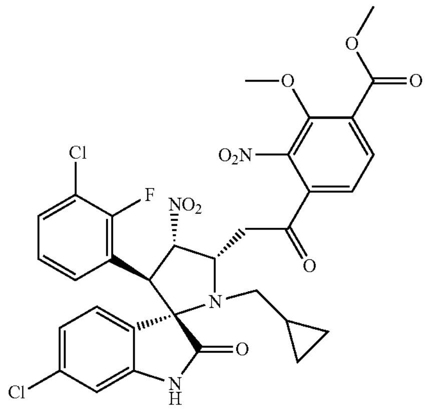 | 1.54 | 701 | A |
| B-11m | 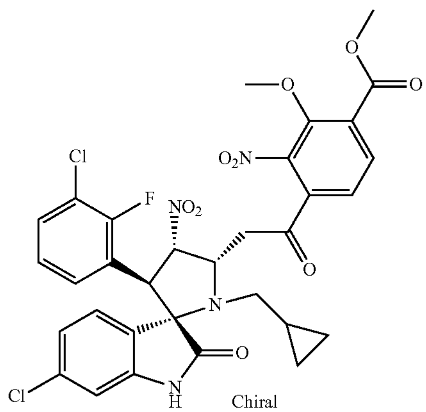 | 1.54 | 701 | A |
| B-11n | 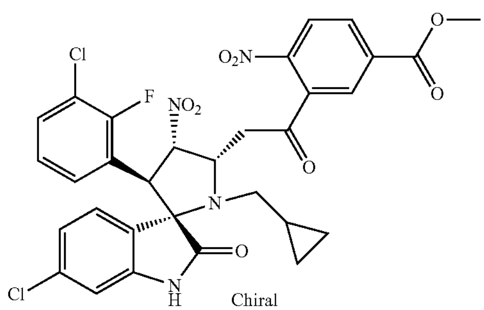 | 1.56 | 671 | A |
| B-11o | 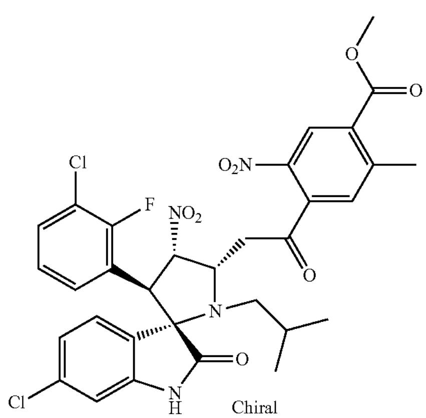 | 1.70 | 687 | A |

TABLE 9-continued
| # | structure | $t_{ret}$ [min] | $[M + H]^+$ | HPLC method |
|---|---|---|---|---|
| B-11p | 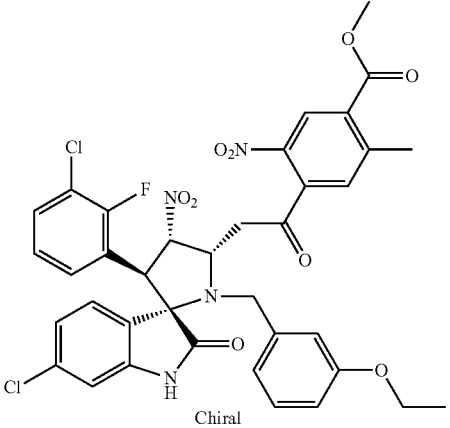 | 1.65 | 765 | A |
| B-11q | 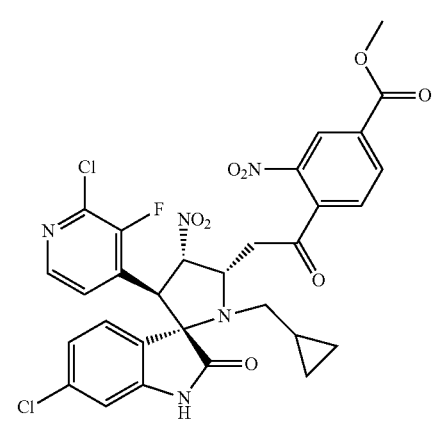 | 1.55 | 672 | A |
| B-11r | 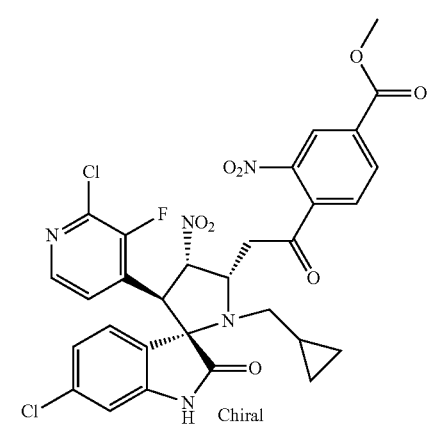 | 1.55 | 672 | A |

TABLE 9-continued
| # | structure | $t_{ret}$ [min] | $[M + H]^+$ | HPLC method |
|---|-----------|-----------------|-------------|-------------|
| B-11s | 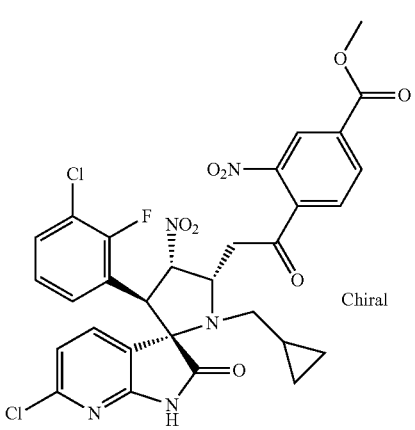 Chiral | 0.89 | 672 | J |
| B-11t | 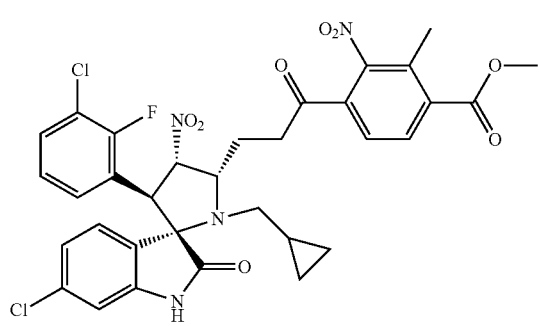 | 0.98 | 699 | E |
| B-11u | 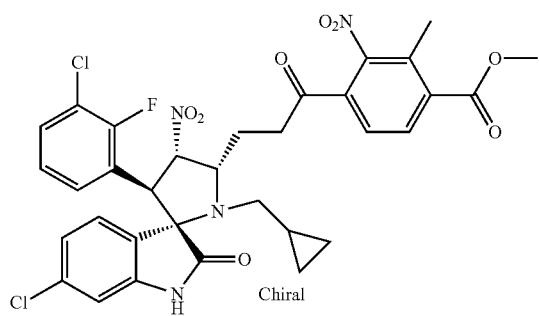 Chiral | 0.98 | 699 | E |

Synthesis of Intermediates B-12

Experimental Procedure for the Synthesis of B-12a (Method I)

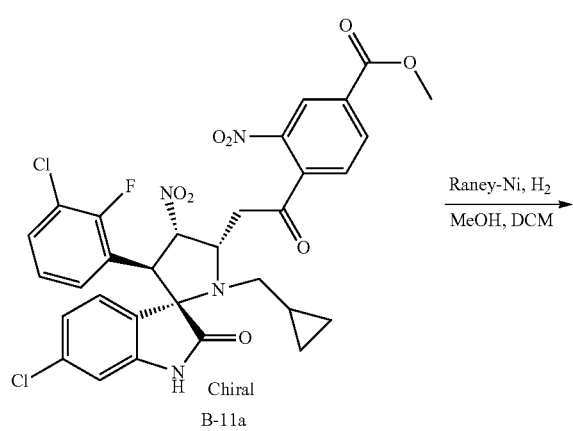

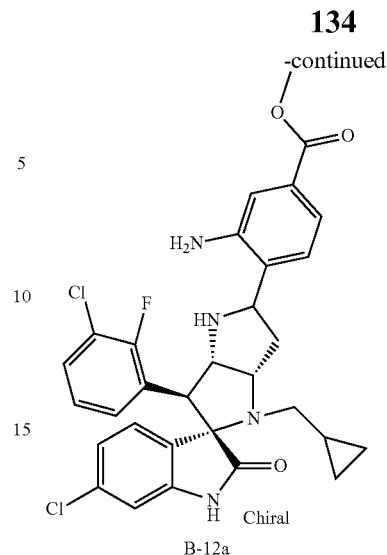

B-12a

To a solution of intermediate B-11a (1.10 g, 1.60 mmol) in MeOH (6 mL) and DCM (9 mL) in an autoclave is added a catalytic amount of RANEY nickel and the reaction mixture is stirred for 24 h under an atmosphere of hydrogen (8 bar). Additional RANEY nickel is added and the reaction mixture is stirred for additional 24 h under an atmosphere of hydrogen (8 bar). The reaction mixture is filtered (Celite©) and the solvents are removed in vacuo. The residue is dissolved in EtOAc and saturated aqueous $NaHCO_3$ solution is added. The reaction mixture is extracted with EtOAc. The combined organic layer is dried ($MgSO_4$), filtered, concentrated in vacuo and the crude product B-12a is purified by chromatography if necessary. Intermediate B-12a is obtained as a mixture of two diastereomers which is used for the next step without further separation.

The following intermediates B-12 (table 10) are available in an analogous manner starting from different intermediates B-11.

TABLE 10

| # | structure | $t_{ret}$ [min] | $[M + H]^+$ | HPLC method |
|---|---|---|---|---|
| B-12a | 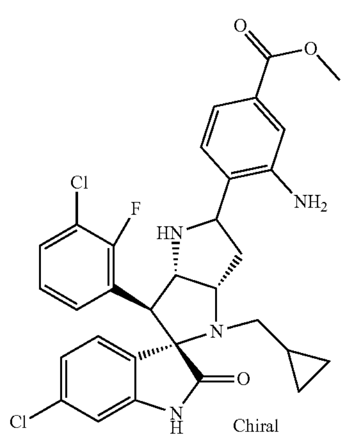 | 1.52 | 595 | A |

TABLE 10-continued
| # | structure | t_ret [min] | [M + H]+ | HPLC method |
|---|---|---|---|---|
| B-12b | 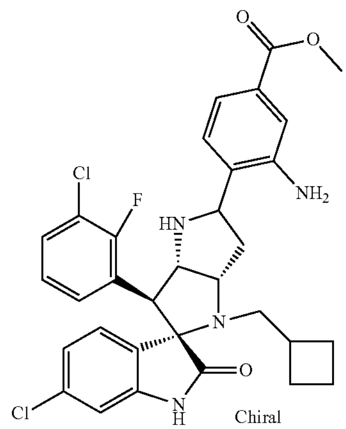 | 1.59 | 609 | A |
| B-12c | 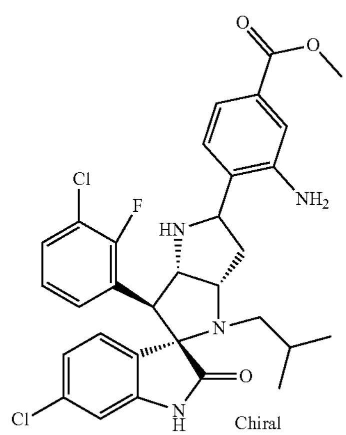 | 1.58 | 597 | A |
| B-12d | 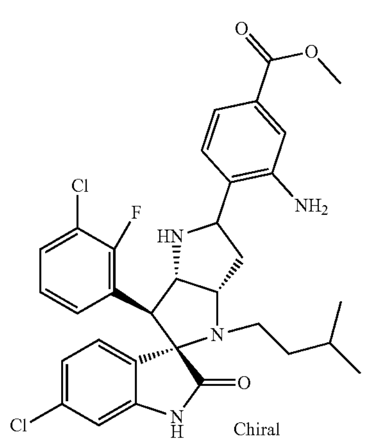 | 1.62 | 611 | A |

TABLE 10-continued
| # | structure | $t_{ret}$ [min] | $[M + H]^+$ | HPLC method |
|---|---|---|---|---|
| B-12e | 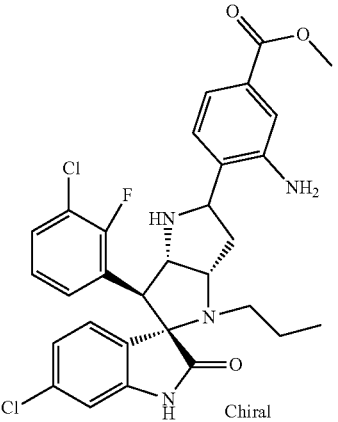 | 1.53 | 583 | A |
| B-12f | 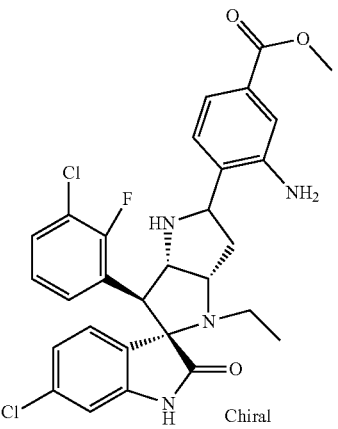 | 1.48 | 568 | A |
| B-12g | 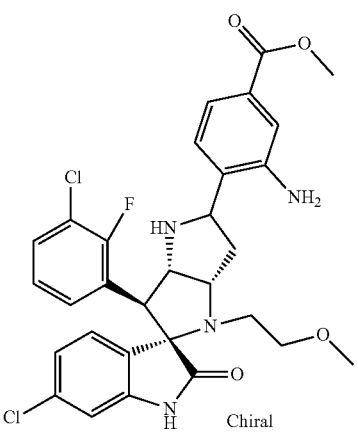 | 1.40 | 599 | A |

TABLE 10-continued
| # | structure | $t_{ret}$ [min] | $[M + H]^+$ | HPLC method |
|---|---|---|---|---|
| B-12h | 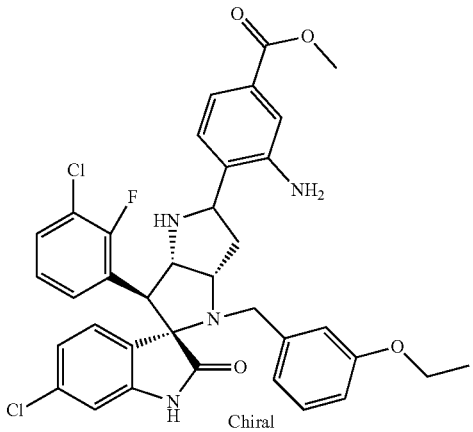 | 1.56 | 675 | A |
| B-12i | 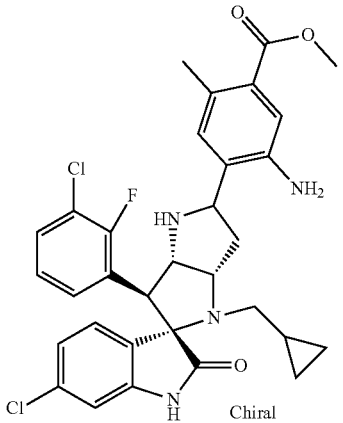 | 1.55 | 609 | A |
| B-12j | 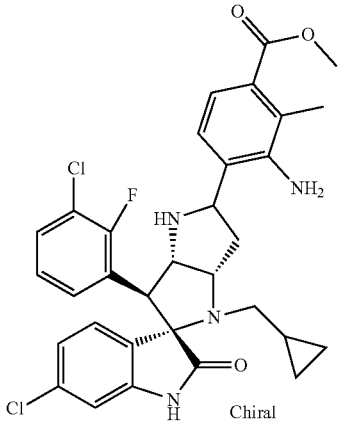 | 1.58 | 609 | A |

TABLE 10-continued
| # | structure | $t_{ret}$ [min] | [M + H]$^+$ | HPLC method |
|---|---|---|---|---|
| B-12k | 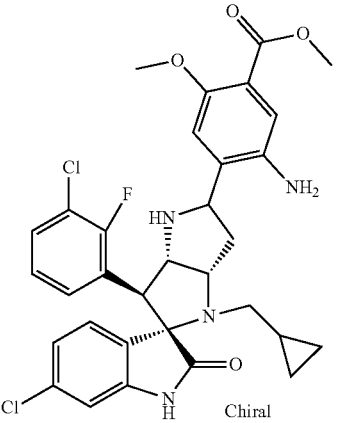 | 1.42 | 625 | A |
| B-12l | 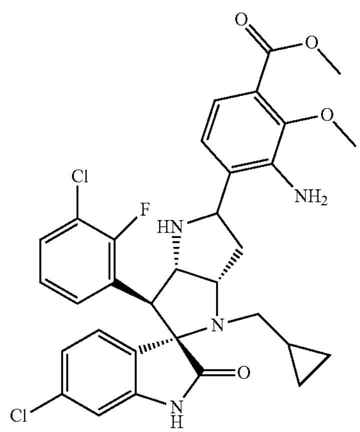 | 1.55 | 625 | A |
| B-12m | 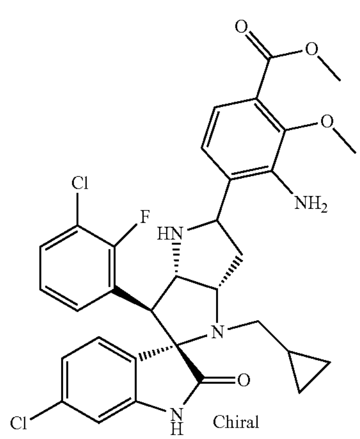 | 1.55 | 625 | A |

TABLE 10-continued
| # | structure | $t_{ret}$ [min] | $[M + H]^+$ | HPLC method |
|---|---|---|---|---|
| B-12n | 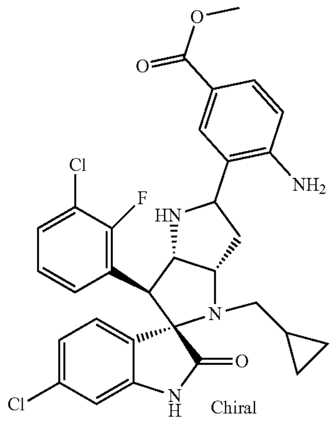 | 1.50 | 595 | A |
| B-12o | 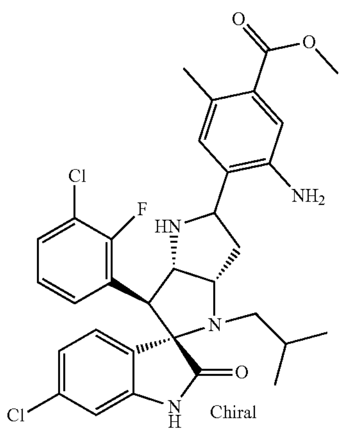 | 1.63 | 611 | A |
| B-12p | 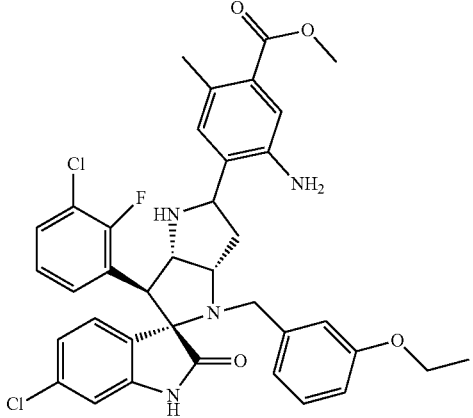 | 1.61 | 689 | A |

TABLE 10-continued
| # | structure | t_ret [min] | [M + H]+ | HPLC method |
|---|---|---|---|---|
| B-12q | 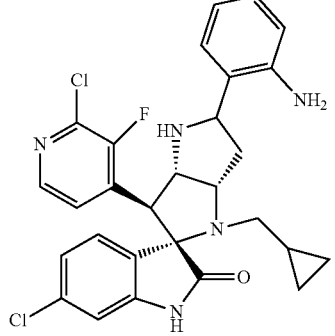 | 1.48 | 596 | A |
| B-12r | 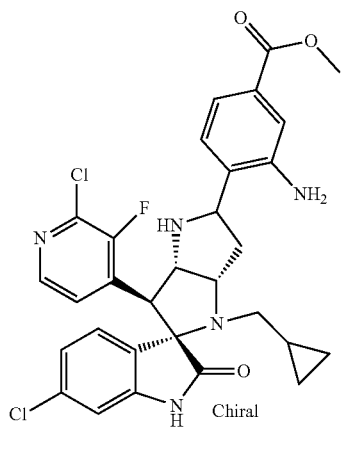 | 1.48 | 596 | A |
| B-12s | 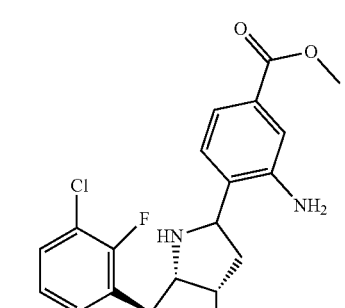 | 1.44 | 596 | A |

TABLE 10-continued

| # | structure | $t_{ret}$ [min] | $[M + H]^+$ | HPLC method |
|---|---|---|---|---|
| B-12t | 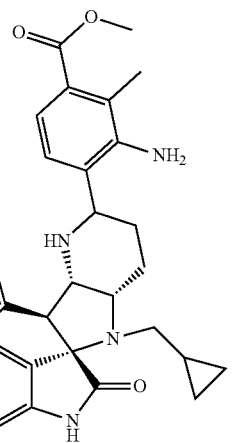 | 1.61 | 623 | A |
| B-12u | 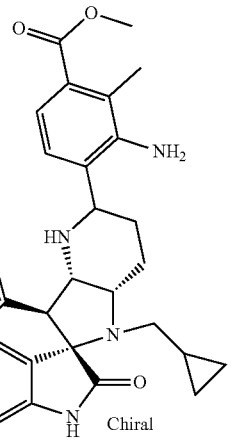 | 1.61 | 623 | A |

Synthesis of Compounds (Ia) According to the Invention

Experimental Procedure for the Synthesis of Ia-1 (Method J)

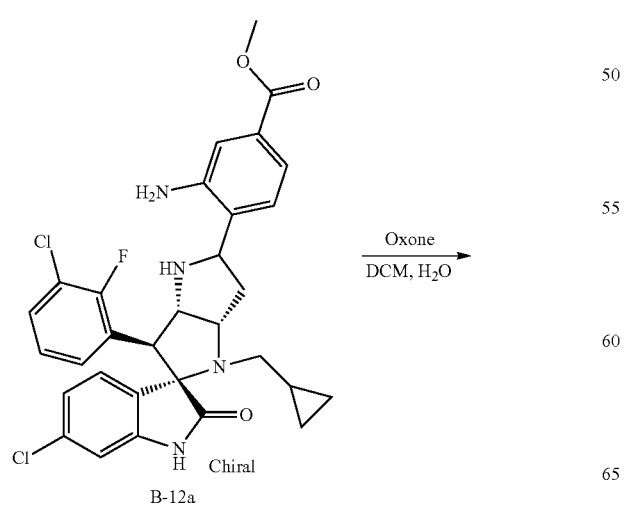

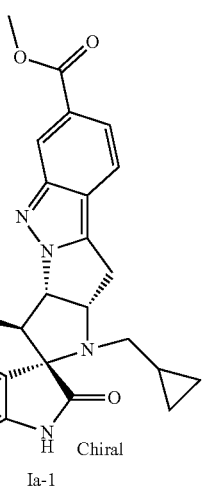

To a solution of intermediate B-12a (329 mg, 0.65 mmol) in DCM (7 mL) is added a solution of Oxone© (793 mg, 1.29 mmol) in H$_2$O (7 mL) at 0° C. dropwise. The biphasic reaction mixture is stirred vigorously for 20 min at 0° C. and for additional 2 h at rt. The reaction mixture is diluted with H$_2$O and is extracted with DCM. The combined organic layer is dried (MgSO₄), filtered, concentrated in vacuo and the crude product is purified by chromatography which gives compound Ia-1.

The following compounds (Ia) (table 11) are available in an analogous manner starting from different intermediates B-12.

TABLE 11

| # | structure | t_ret [min] | [M + H]⁺ | HPLC method |
|---|-----------|-------------|----------|-------------|
| Ia-1 | 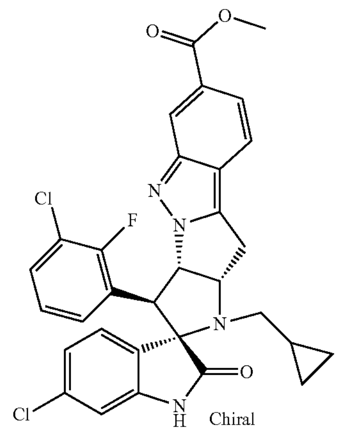 | 1.60 | 591 | A |
| Ia-2 | 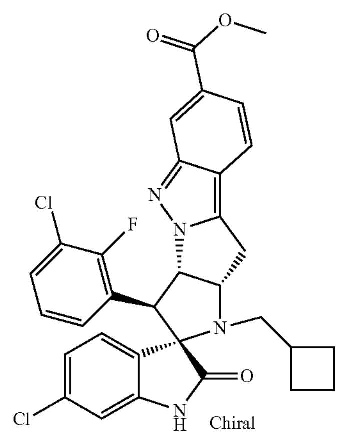 | 1.67 | 605 | A |
| Ia-3 | 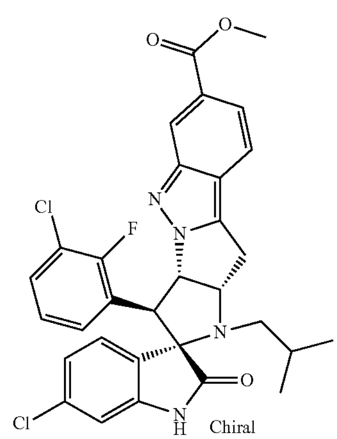 | 1.64 | 593 | A |

TABLE 11-continued
| # | structure | $t_{ret}$ [min] | [M + H]$^+$ | HPLC method |
|---|---|---|---|---|
| Ia-4 | 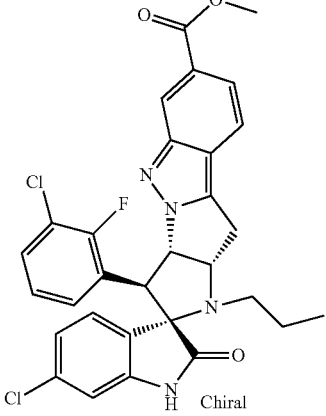 | 1.59 | 579 | A |
| Ia-5 | 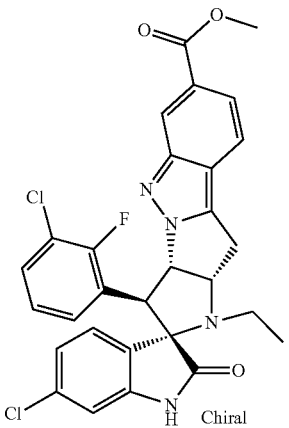 | 1.54 | 565 | A |
| Ia-6 | 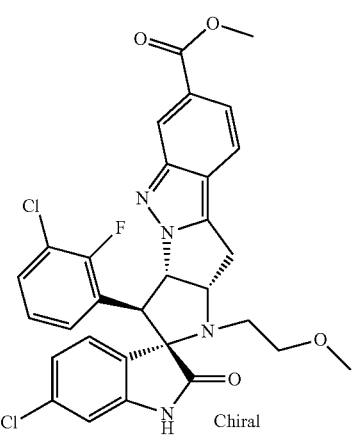 | 1.49 | 595 | A |

TABLE 11-continued
| # | structure | $t_{ret}$ [min] | [M + H]$^+$ | HPLC method |
|---|-----------|-----------------|-------------|-------------|
| Ia-7 | 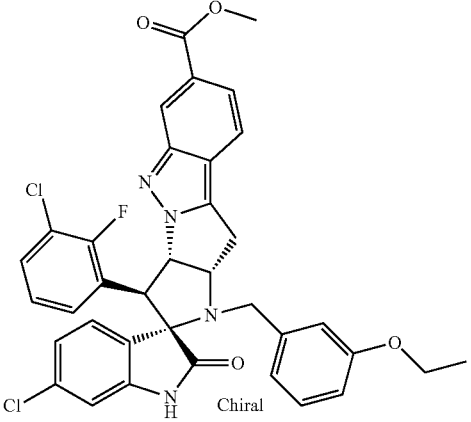 | 1.59 | 671 | A |
| Ia-8 | 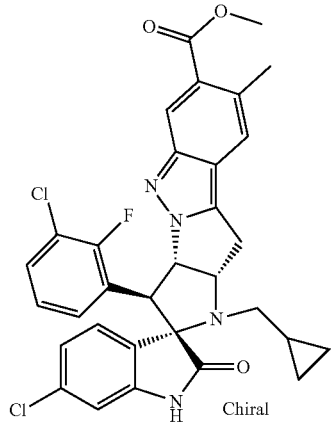 | 1.64 | 605 | A |
| Ia-9 | 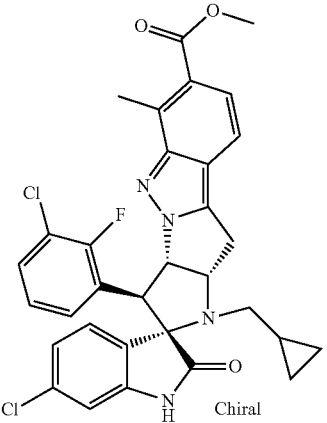 | 1.63 | 605 | A |

TABLE 11-continued
| # | structure | $t_{ret}$ [min] | [M + H]$^+$ | HPLC method |
|---|---|---|---|---|
| Ia-10 | 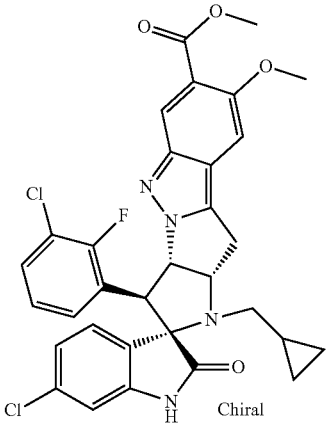 | 1.50 | 621 | A |
| Ia-11 | 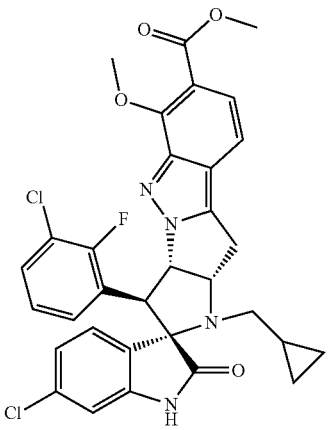 [SMILES: COC(=O)c1ccc2c3n(nc2c1OC)[C@@H]1[C@H](C3)N(CC2CC2)[C@@]2(C(=O)Nc3cc(Cl)ccc32)[C@H]1c1cccc(Cl)c1F] | 1.58 | 621 | A |
| Ia-12 | 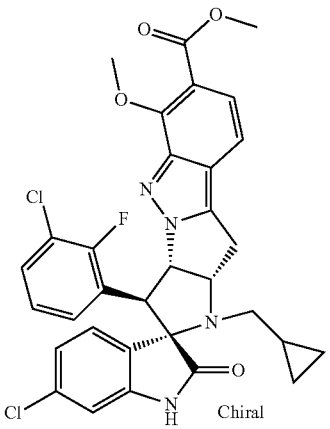 | 1.58 | 621 | A |

TABLE 11-continued

| # | structure | $t_{ret}$ [min] | [M + H]⁺ | HPLC method |
|---|---|---|---|---|
| Ia-13 | 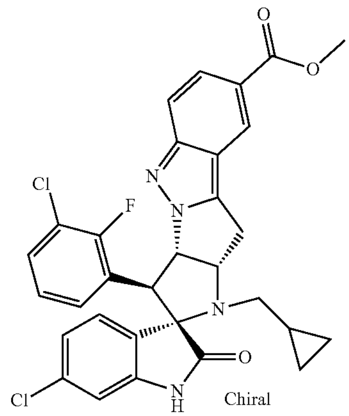 | 1.59 | 591 | A |
| Ia-14 | 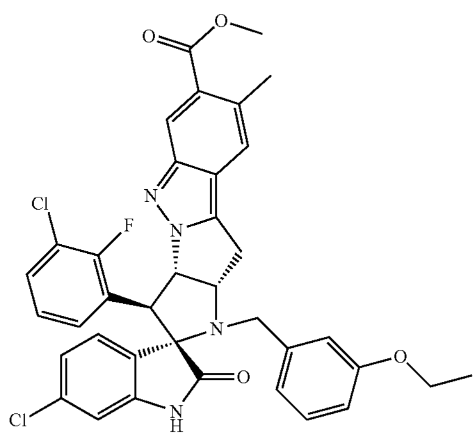 | 1.69 | 685 | A |
| Ia-15 | 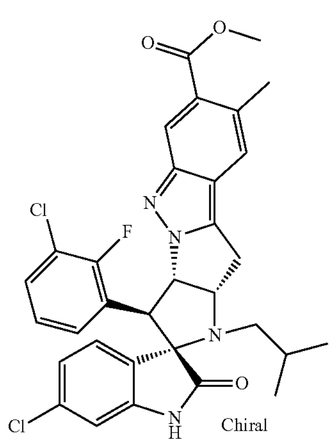 | 1.67 | 607 | A |

TABLE 11-continued
| # | structure | $t_{ret}$ [min] | [M + H]$^+$ | HPLC method |
|---|---|---|---|---|
| Ia-16 | 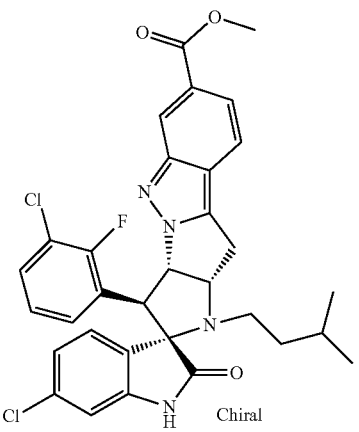 | 1.66 | 607 | A |
| Ia-17 | 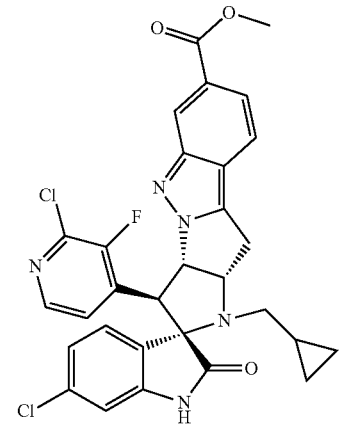 [SMILES: COC(=O)c1ccc2c3n(nc2c1)[C@@H]1[C@H](C3)N(CC2CC2)[C@@]2(C(=O)Nc3cc(Cl)ccc32)[C@H]1c1ccnc(Cl)c1F] | 1.48 | 592 | A |
| Ia-18 | 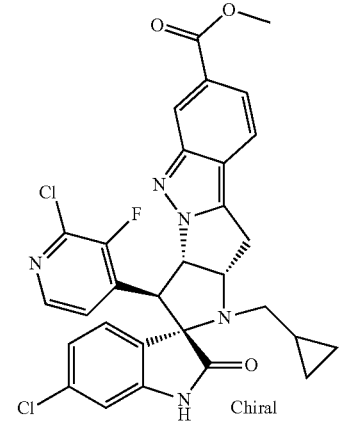 | 1.48 | 592 | A |

TABLE 11-continued

| # | structure | $t_{ret}$ [min] | $[M + H]^+$ | HPLC method |
|---|---|---|---|---|
| Ia-19 | 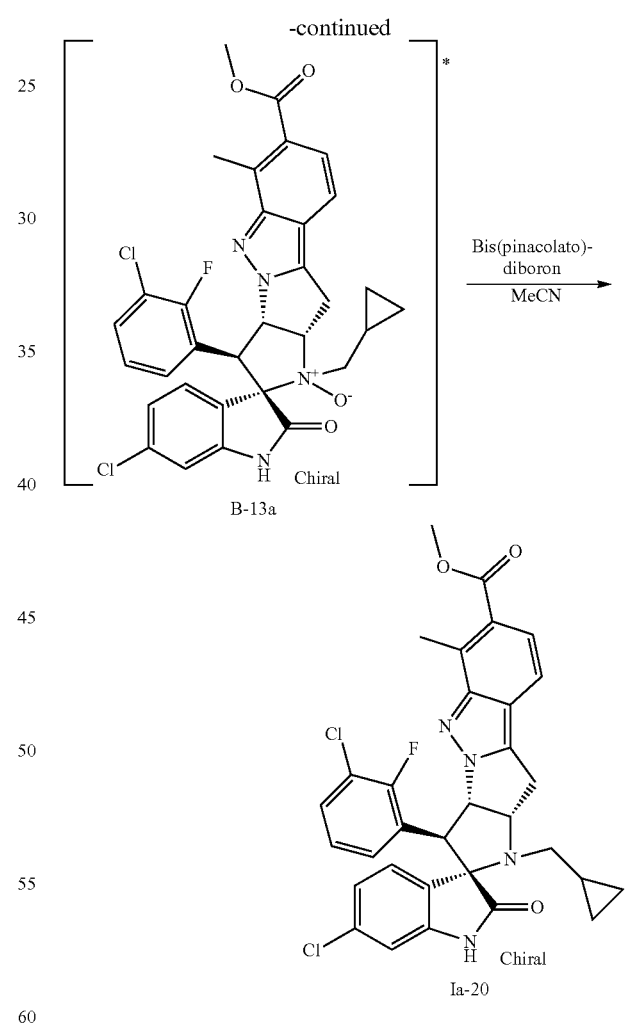 | 1.48 | 592 | A |

Synthesis of Additional Compounds (Ia) According to the Invention

Experimental Procedure for the Synthesis of Ia-20 (Method J+Method K)

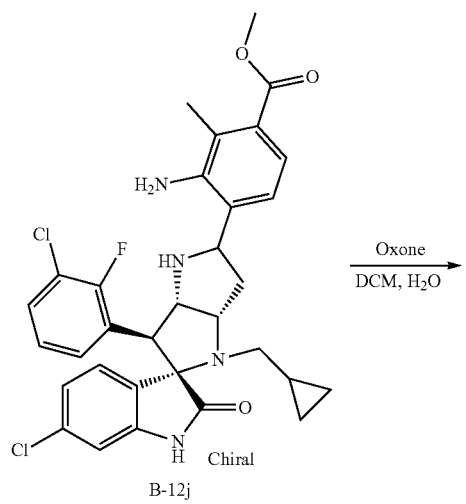

\* The location of overoxidation/N-oxid formation is not entirely clear. B-13a as depicted seems to be probable.

To a solution of intermediate B-12j (417 mg, 0.68 mmol) in DCM (10 mL) is added a solution of Oxone© (841 mg, 1.37 mmol) in H₂O (7 mL) at 0° C. dropwise. The biphasic reaction mixture is stirred vigorously for 20 min at 0° C. and for additional 6 h at rt. The reaction mixture is diluted with H₂O and extracted with DCM. The combined organic layer is dried (MgSO₄), filtered, concentrated in vacuo which gives a crude mixture of Ia-20 and an oxidized form B-13a (M+H=621). This mixture is dissolved in MeCN (4.2 mL) and bis(pinacolato)diborone (326 mg, 1.28 mmol) is added. The reaction mixture is heated under microwave irradiation to 100° C. for 30 min. The reaction mixture is diluted with H₂O and extracted with DCM. The combined organic layer is dried (MgSO₄), filtered, concentrated in vacuo and the crude product is purified by chromatography which gives compound Ia-20.

The following overoxidized compounds B-13 (table 12) are available in an analogous manner starting from different intermediates B-12 and can be reduced to additional compounds (Ia) (table 13).

TABLE 12

| # | structure | $t_{ret}$ [min] | [M + H]⁺ | HPLC method |
|---|---|---|---|---|
| B-13a | 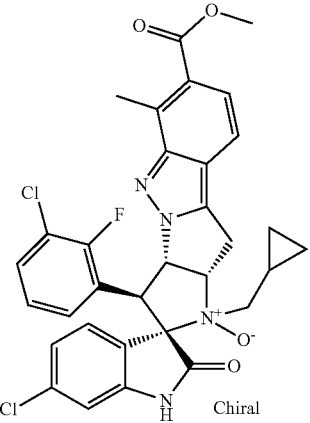 | 0.96 | 621 | C |
| B-13b | 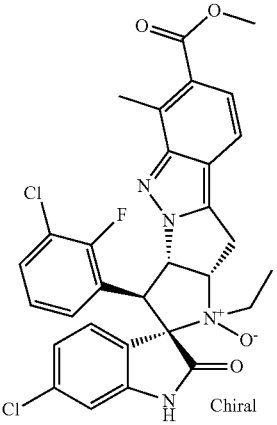 | 0.89 | 565 | C |
| B-13c | 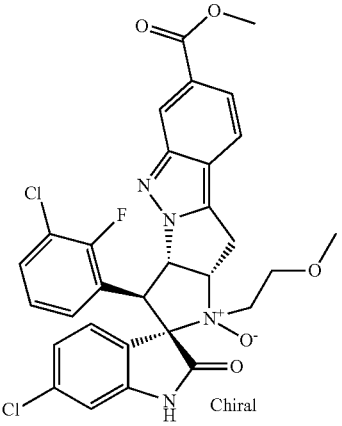 | 0.94 | 611 | C |

TABLE 12-continued
| # | structure | $t_{ret}$ [min] | [M + H]$^+$ | HPLC method |
|---|---|---|---|---|
| B-13d | 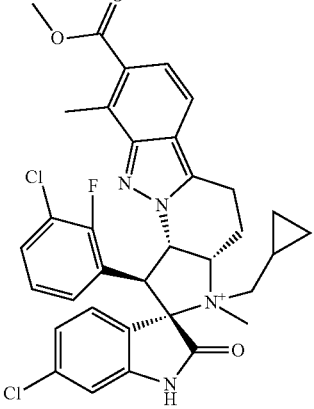 | 0.95 | 635 | E |
| B-13e | 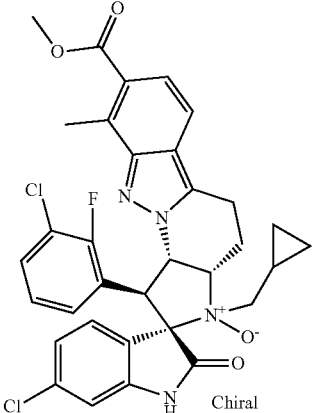 | 0.95 | 635 | E |
TABLE 13
| # | structure | $t_{ret}$ [min] | [M + H]$^+$ | HPLC method |
|---|---|---|---|---|
| Ia-20 | 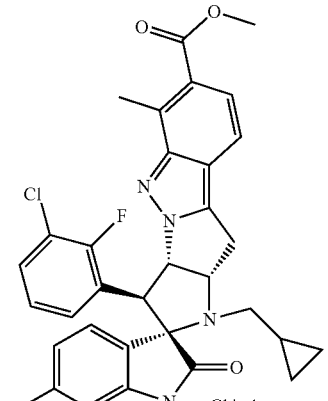 | 1.66 | 605 | A |

TABLE 13-continued
| # | structure | $t_{ret}$ [min] | $[M + H]^+$ | HPLC method |
|---|---|---|---|---|
| Ia-21 | 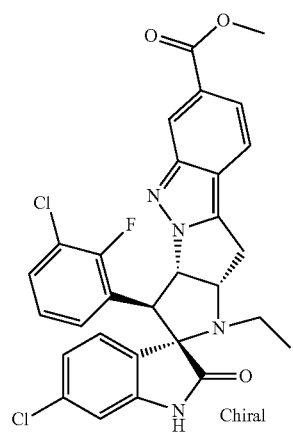 | 1.54 | 565 | A |
| Ia-22 | 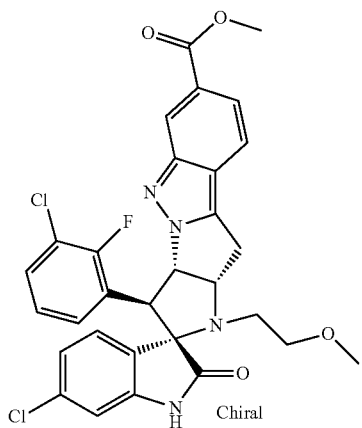 | 1.46 | 595 | A |

TABLE 13-continued

| # | structure | $t_{ret}$ [min] | $[M + H]^+$ | HPLC method |
|---|---|---|---|---|
| Ia-23 | 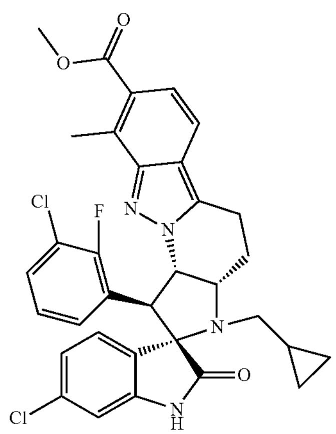 [SMILES: COC(=O)c1ccc2c3n(nc2c1C)[C@@H]1[C@H](CC3)N(CC2CC2)[C@@]2(C(=O)Nc3cc(Cl)ccc32)[C@H]1c1cccc(Cl)c1F] | 1.01 | 619 | E |
| Ia-24 | 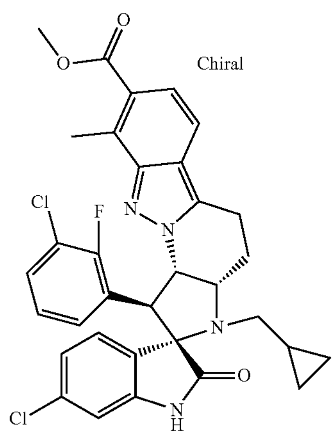 [SMILES: COC(=O)c1ccc2c3n(nc2c1C)[C@@H]1[C@H](CC3)N(CC2CC2)[C@@]2(C(=O)Nc3cc(Cl)ccc32)[C@H]1c1cccc(Cl)c1F ; "Chiral"] | 1.01 | 619 | E |

Synthesis of Further Compounds (Ia) Via Ester Saponification

Experimental Procedure for the Synthesis of Ia-25

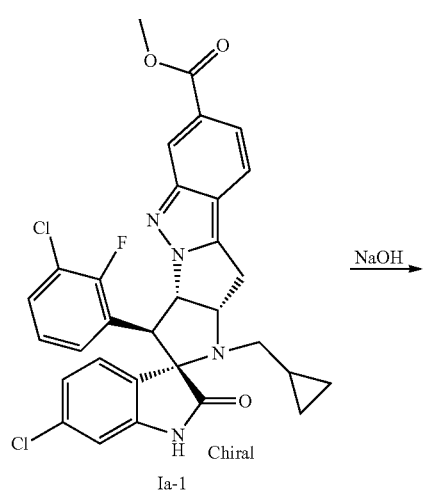

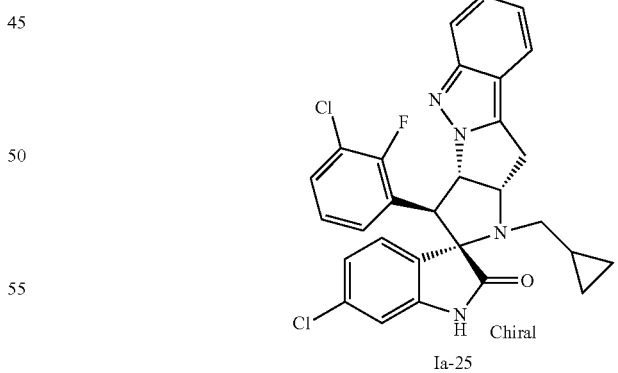

Ia-1 (405 mg, 0.69 mmol) is dissolved in THF (30 mL) and aq. NaOH solution (2 mL, 8 M) is added. The reaction mixture is stirred at 70° C. for 8 h. After acidification with 2 M aq. HCl and extraction with EtOAc the organic phase is dried with MgSO₄. Purification with reversed phase HPLC leads to pure Ia-25.

The following compounds (Ia) (table 14) are available in an analogous manner starting from initially obtained compounds (Ia).
TABLE 14
| # | structure | $t_{ret}$ [min] | $[M + H]^+$ | HPLC method |
|---|---|---|---|---|
| Ia-25 | 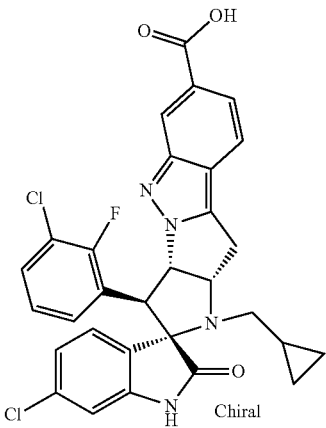 | 1.04 | 577 | A |
| Ia-26 | 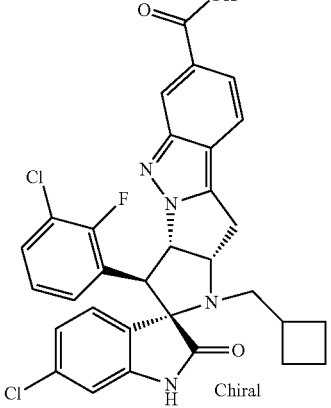 | 1.10 | 591 | A |
| Ia-27 | 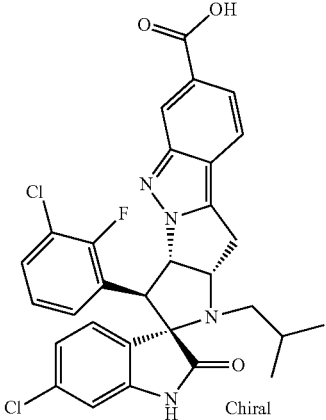 | 1.09 | 579 | A |

TABLE 14-continued
| # | structure | $t_{ret}$ [min] | [M + H]⁺ | HPLC method |
|---|---|---|---|---|
| Ia-28 | 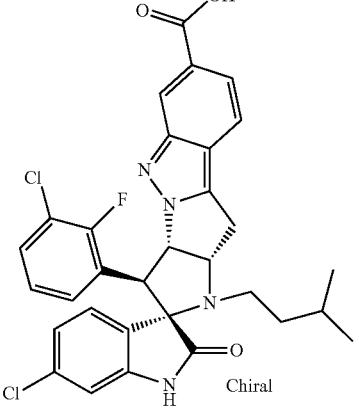 | 1.14 | 593 | A |
| Ia-29 | 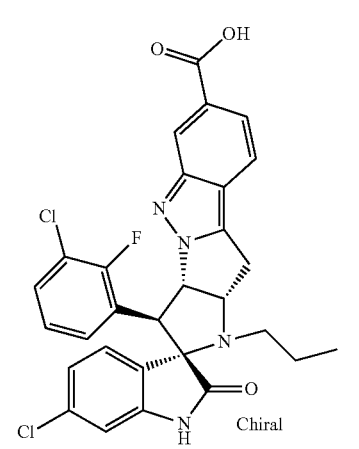 | 1.06 | 565 | A |
| Ia-30 | 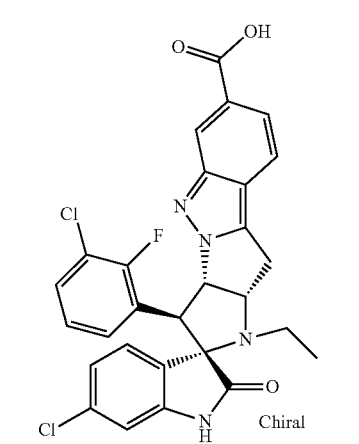 | 1.00 | 551 | A |

TABLE 14-continued
| # | structure | $t_{ret}$ [min] | [M + H]$^+$ | HPLC method |
|---|---|---|---|---|
| Ia-31 | 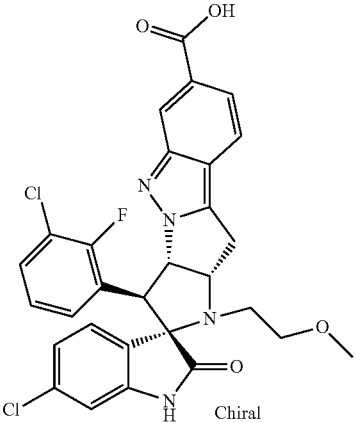 | 0.95 | 581 | A |
| Ia-32 | 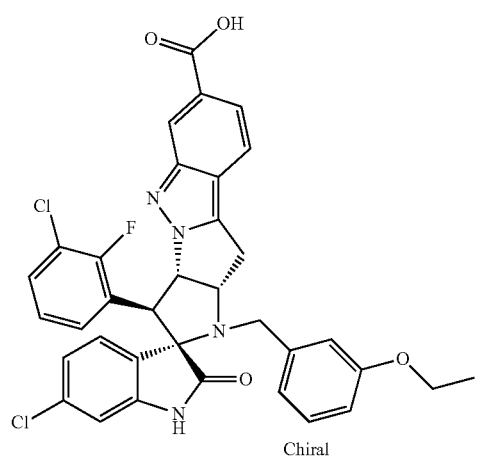 | 1.11 | 657 | A |
| Ia-33 | 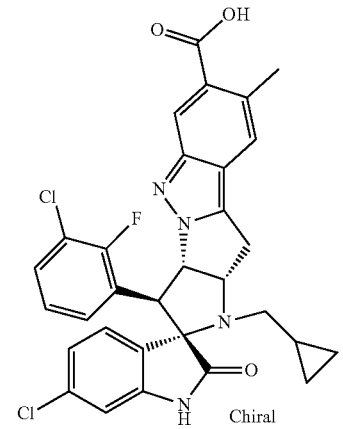 | 1.07 | 591 | A |

TABLE 14-continued
| # | structure | t_ret [min] | [M + H]+ | HPLC method |
|---|---|---|---|---|
| Ia-34 | 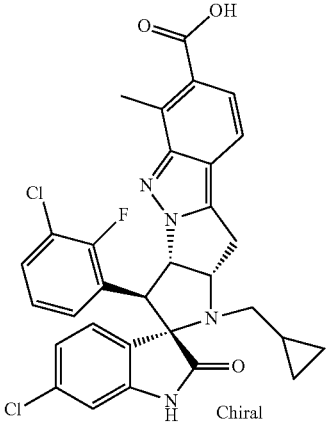 | 1.03 | 591 | A |
| Ia-35 | 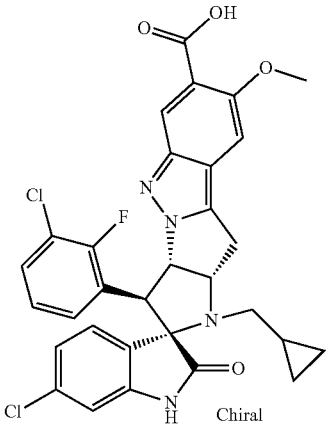 | 1.04 | 607 | A |
| Ia-36 | 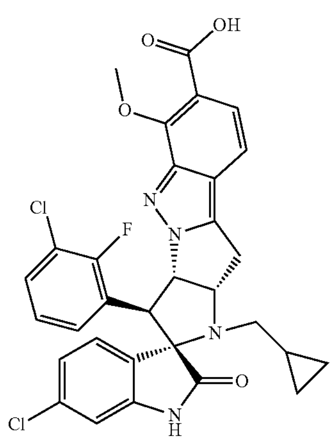 [SMILES: COc1c(C(=O)O)ccc2c3n(nc12)[C@@H]1[C@H](C3)N(CC2CC2)[C@@]2(C(=O)Nc3cc(Cl)ccc32)[C@H]1c1cccc(Cl)c1F] | 1.04 | 607 | A |

TABLE 14-continued
| # | structure | $t_{ret}$ [min] | [M + H]$^+$ | HPLC method |
|---|---|---|---|---|
| Ia-37 | 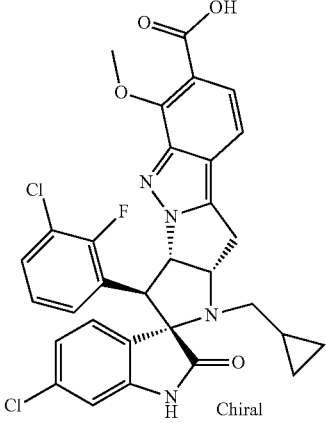 | 1.04 | 607 | A |
| Ia-38 | 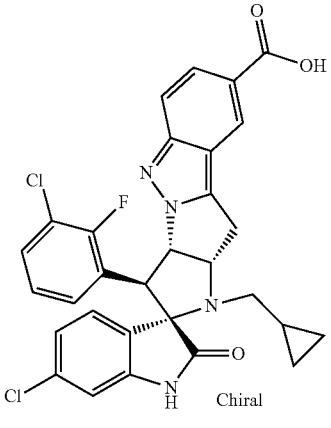 | 1.01 | 577 | A |
| Ia-39 | 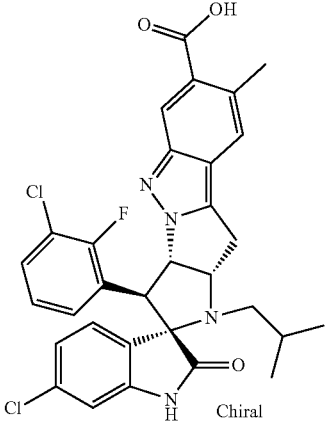 | 1.09 | 593 | A |

TABLE 14-continued
| # | structure | $t_{ret}$ [min] | [M + H]⁺ | HPLC method |
|---|---|---|---|---|
| Ia-40 | 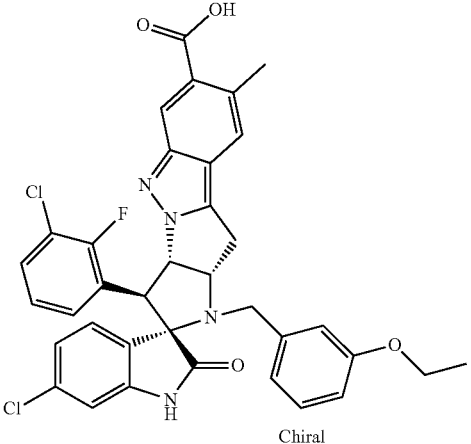 Chiral | 1.13 | 671 | A |
| Ia-41 | 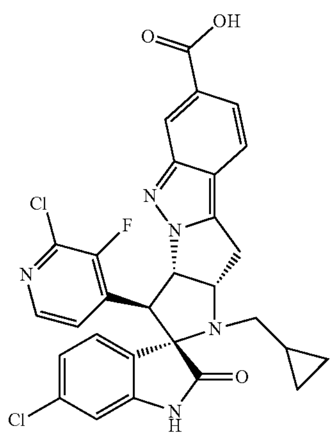 | 1.02 | 578 | A |
| Ia-42 |  Chiral | 1.02 | 578 | A |

TABLE 14-continued
| # | structure | $t_{ret}$ [min] | [M + H]$^+$ | HPLC method |
|---|---|---|---|---|
| Ia-43 | 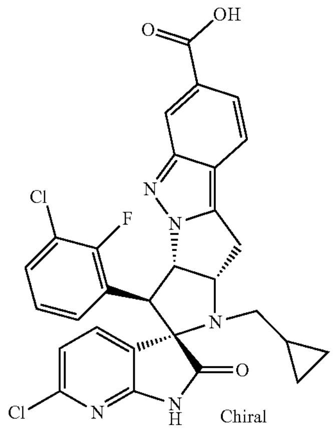 | 1.02 | 578 | A |
| Ia-44 | 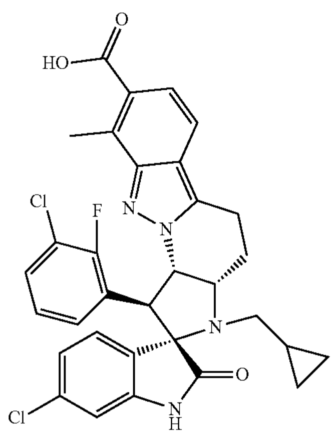 [SMILES: Cc1c(C(=O)O)ccc2c3n(nc12)[C@@H]1[C@H](CC3)N(CC2CC2)[C@@]2(C(=O)Nc3cc(Cl)ccc32)[C@H]1c1cccc(Cl)c1F] | 1.07 | 605 | A |
| Ia-45 | 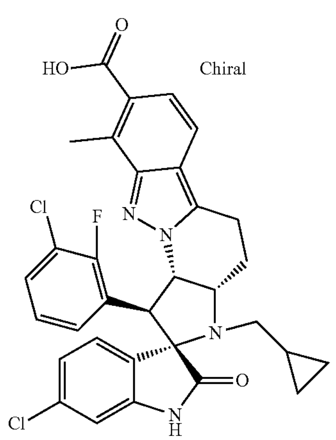 [SMILES: Cc1c(C(=O)O)ccc2c3n(nc12)[C@@H]1[C@H](CC3)N(CC2CC2)[C@@]2(C(=O)Nc3cc(Cl)ccc32)[C@H]1c1cccc(Cl)c1F ; "Chiral"] | 1.07 | 605 | A |

Synthesis of Further Compounds (Ia) Via Amidation

Experimental Procedure for the Synthesis of Ia-46

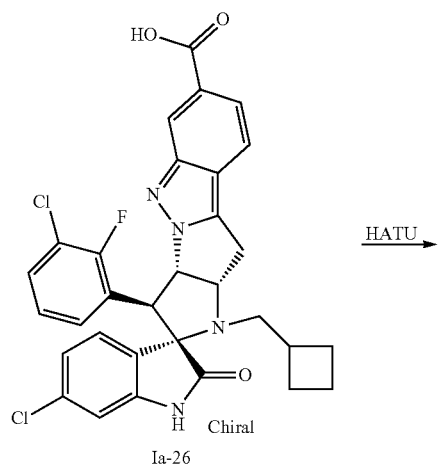

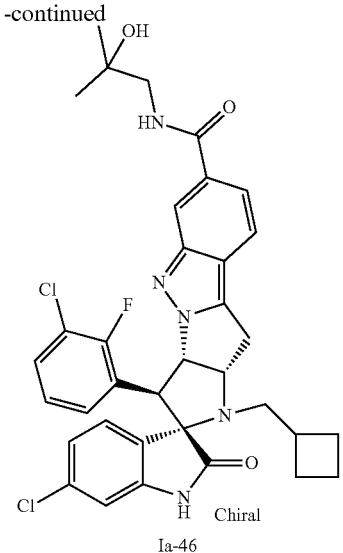

Ia-26 (10 mg, 0.02 mmol) is dissolved in anhydrous THF (1 mL) and HATU (8 mg, 0.02 mmol) is added at rt. After addition of DIPEA (3.4 mg, 0.03 mmol) the reaction mixture is allowed to stir at rt for 15 min. 1-Amino-2-methylpropan-2-ol (2 M in THF, 1.5 mg, 0.02 mmol) is added and the reaction is allowed to stir for additional 60 min. The crude reaction mixture is submitted to reversed phase column chromatography yielding pure Ia-46.

The following compounds (Ia) (Table 15) are available in an analogous manner starting from initially obtained compounds (Ia).

TABLE 15

| # | structure | $t_{ret}$ [min] | $[M + H]^+$ | HPLC method |
|---|---|---|---|---|
| Ia-46 | 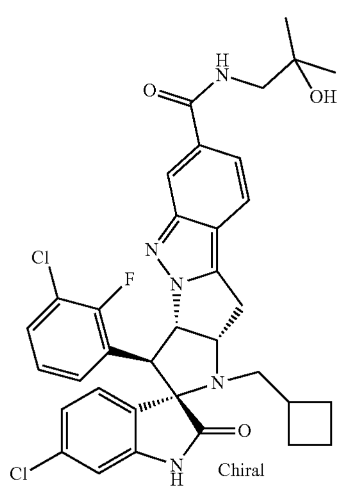 | 1.43 | 662 | A |

TABLE 15-continued
| # | structure | t_ret [min] | [M + H]+ | HPLC method |
|---|---|---|---|---|
| Ia-47 | 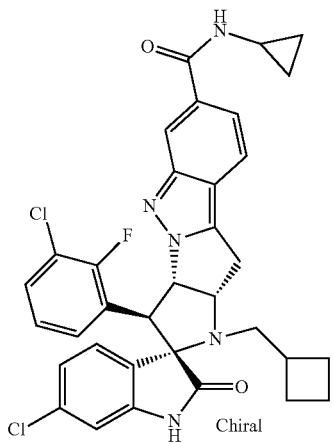 | 1.49 | 630 | A |
| Ia-48 | 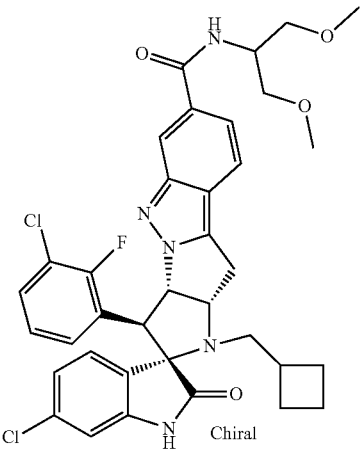 | 1.51 | 692 | A |
| Ia-49 | 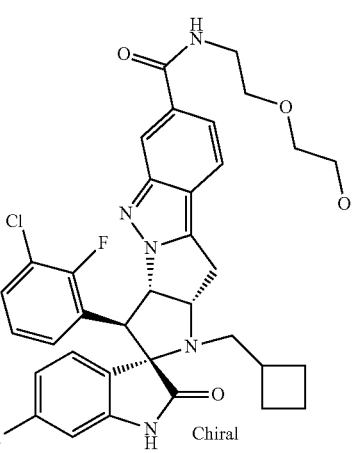 | 1.46 | 692 | A |

TABLE 15-continued
| # | structure | $t_{ret}$ [min] | [M + H]$^+$ | HPLC method |
|---|---|---|---|---|
| Ia-50 | 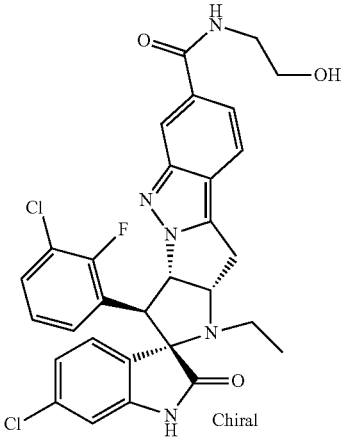 | 1.22 | 594 | A |
| Ia-51 | 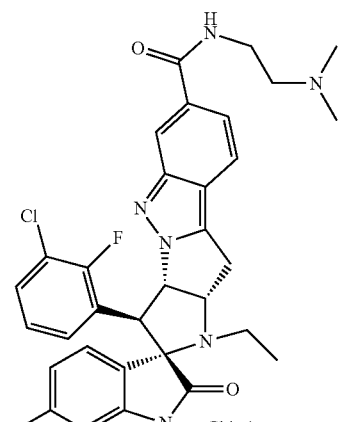 | 1.35 | 621 | A |
| Ia-52 | 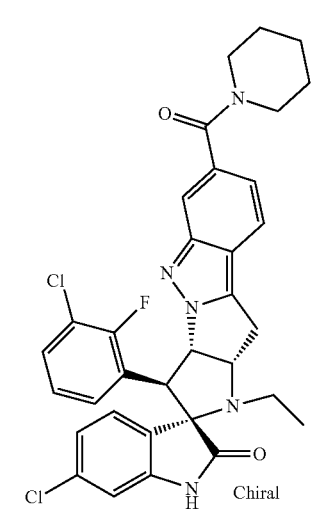 | 1.50 | 618 | A |

TABLE 15-continued
| # | structure | $t_{ret}$ [min] | [M + H]$^+$ | HPLC method |
|---|---|---|---|---|
| Ia-53 | 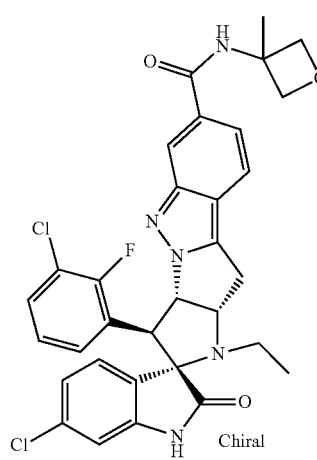 | 1.33 | 620 | A |
| Ia-54 | 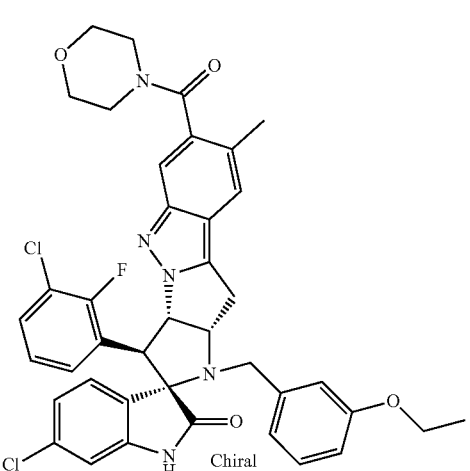 | 1.52 | 740 | A |
| Ia-55 | 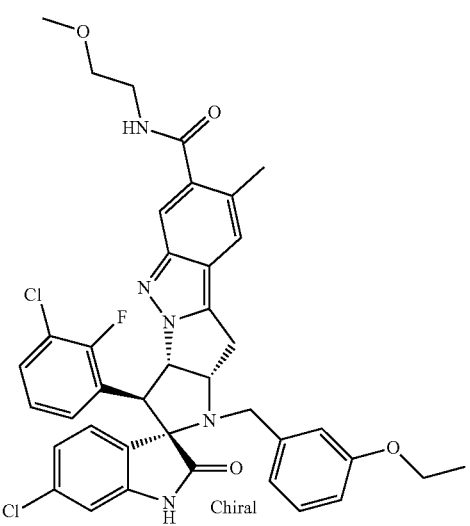 | 1.51 | 728 | A |

TABLE 15-continued

| # | structure | $t_{ret}$ [min] | $[M + H]^+$ | HPLC method |
|---|---|---|---|---|
| Ia-56 | 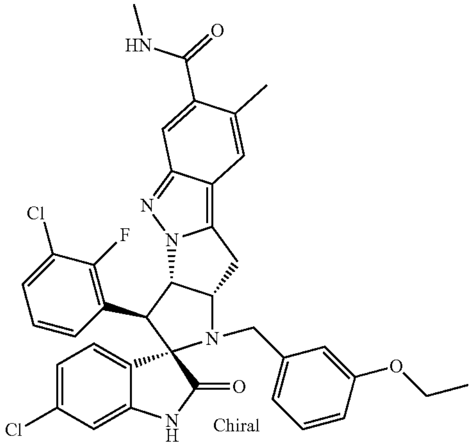 | 1.49 | 684 | A |
| Ia-57 | 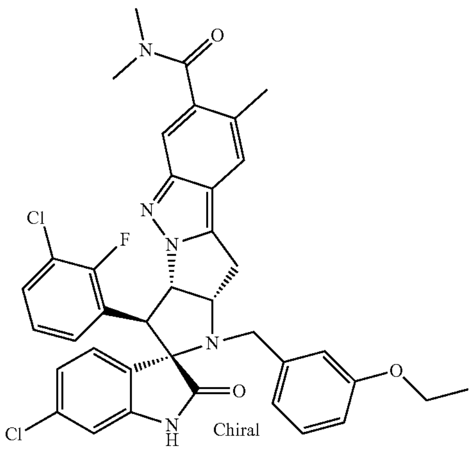 | 1.54 | 698 | A |

Synthesis of Starting Material S-1

Experimental Procedure for the Synthesis of S-1b

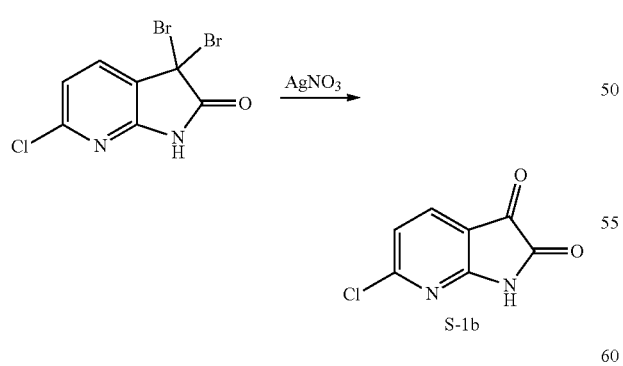

3,3-Dibromo-6-chloro-1,3-dihydro-pyrrolo[2,3-b]pyridin-2-one (7.6 g, 23.3 mmol) is suspended in acetonitrile (500 mL) and water (25 mL). AgNO$_3$ (8.9 g, 52.7 mmol) is added and the reaction mixture is stirred at rt for 1 h. Acetonitrile is removed under reduced pressure and EtOAc is added. The phases are separated and the organic layer is dried with MgSO$_4$. Removal of the solvents gives pure 6-chloro-1H-pyrrolo[2,3-b]pyridine-2,3-dione S-1b.

Synthesis of Intermediates B-15

Experimental Procedure for the Synthesis of B-15a

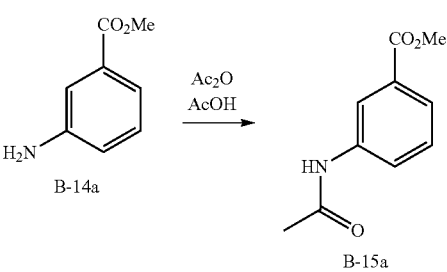

To a solution of B-14a (1 eq.) in toluene is added Ac$_2$O (1.05 eq.) dropwise at reflux and the mixture is stirred at reflux for several minutes. The product B-15a can be crystallized out of the mixture by cooling down and further dilution.

The following intermediates B-15 (table 15-1) are available in an analogous manner starting from different anilines B-14.

TABLE 15-1

| # | structure | [M + H]+ |
|---|---|---|
| B-15a | (3-acetamido methyl benzoate) | 194 |
| B-15b | (methyl 3-acetamido-2-methylbenzoate) | 208 |
| B-15c | (methyl 5-acetamido-2-methoxybenzoate) | 224 |
| B-15d | (methyl 3-acetamido-2-methoxybenzoate) | 224 |
| B-15e | (methyl 4-acetamidobenzoate) | 194 |
| B-15f | (methyl 5-acetamido-2-methylbenzoate) | 208 |

Synthesis of Intermediates B-16

Experimental Procedure for the Synthesis of B-16a

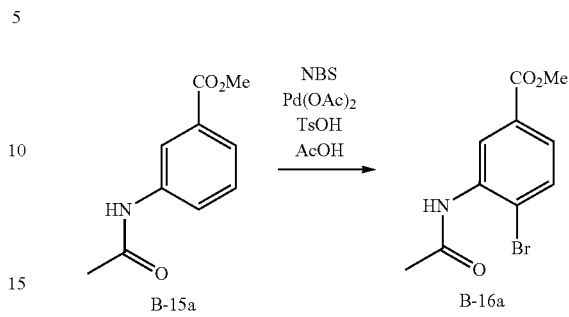

To a solution of B-15a (1 eq.) in AcOH are added TsOH monohydrate (0.5 eq.) and Pd(OAc)$_2$ (0.03 eq.). The mixture is heated up to 75-80° C. and NBS (1.1 eq.) is added in portions. After stirring at 75-80° C. for a few minutes, the solution is cooled down and water is added. The product B-16a can be isolated by filtration.

The following intermediates B-16 (table 15-2) are available in an analogous manner starting from different acetamides B-15.

TABLE 15-2

| # | structure | [M + H]+ |
|---|---|---|
| B-16a | (methyl 3-acetamido-4-bromobenzoate) | 273 |
| B-16b | (methyl 3-acetamido-4-bromo-2-methylbenzoate) | 287 |
| B-16c | (methyl 5-acetamido-4-bromo-2-methoxybenzoate) | 303 |
| B16-d | (methyl 3-acetamido-4-bromo-2-methoxybenzoate) | 303 |

TABLE 15-2-continued

| # | structure | [M + H]⁺ |
|---|---|---|
| B-16e | 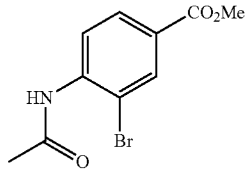 | 273 |
| B-16f | 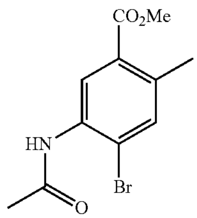 [SMILES: COC(=O)c1cc(NC(C)=O)c(Br)cc1C] | 287 |

Synthesis of Intermediates B-17

Experimental Procedure for the Synthesis of B-17a

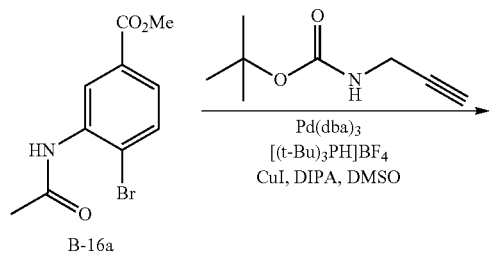

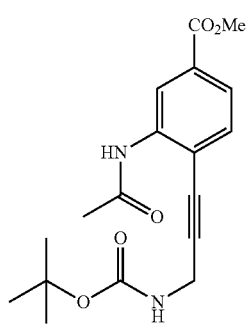

B-17a

To a suspension of B-16a (1 eq.) in DMSO are added Boc-prop-2-ynyl-amine (1.3 eq.), CuI (0.02 eq.), $Pd_2(dba)_3$ (0.01 eq.), $[(tBu)_3P]BF_4$ (0.04 eq.) and DIPA (5 eq.). The mixture is stirred at room temperature for 3 days. After cooling down the suspension and adding water the product B-17a can be isolated by filtration.

The following intermediates B-17 (table 15-3) are available in an analogous manner starting from different bromo acetamides B-16.

TABLE 15-3

| # | structure | [M + H]⁺ |
|---|---|---|
| B-17a | 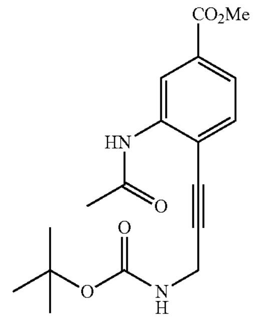 [SMILES: COC(=O)c1ccc(C#CCNC(=O)OC(C)(C)C)c(NC(C)=O)c1] | 347 |
| B-17b | 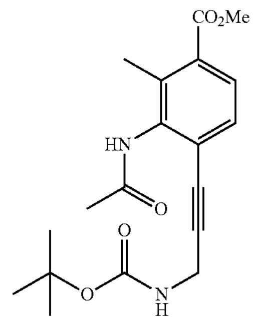 [SMILES: COC(=O)c1ccc(C#CCNC(=O)OC(C)(C)C)c(NC(C)=O)c1C] | 361 |
| B-17c | 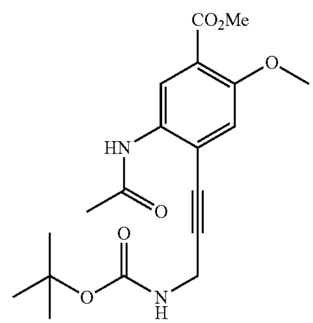 [SMILES: COC(=O)c1cc(NC(C)=O)c(C#CCNC(=O)OC(C)(C)C)cc1OC] | 377 |
| B-17d | 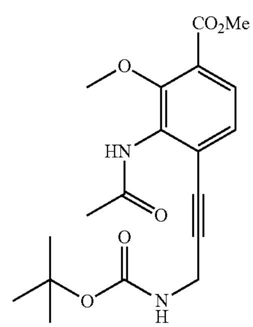 [SMILES: COC(=O)c1ccc(C#CCNC(=O)OC(C)(C)C)c(NC(C)=O)c1OC] | 377 |
| B-17e | 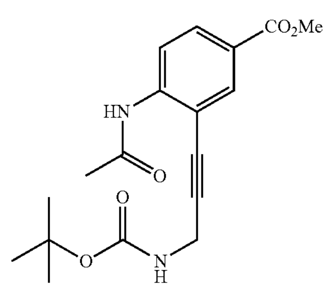 [SMILES: COC(=O)c1ccc(NC(C)=O)c(C#CCNC(=O)OC(C)(C)C)c1] | 347 |

TABLE 15-3-continued

| # | structure | [M + H]⁺ |
|---|---|---|
| B-17f | 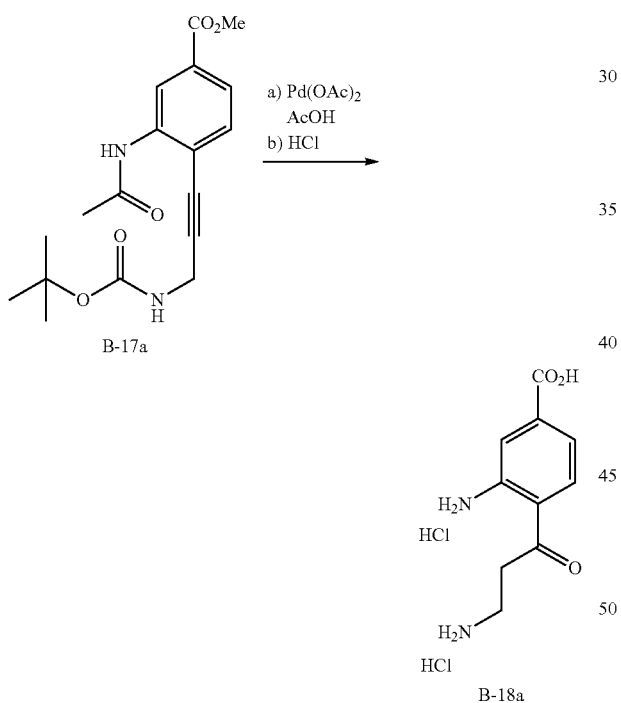 | 361 |

Synthesis of Intermediates B-18

Experimental Procedure for the Synthesis of B-18a

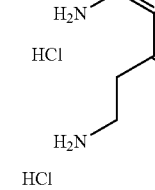

To a solution of B-17a (1 eq.) in AcOH is added Pd(OAc)$_2$ (0.02 eq.) and the mixture is stirred at room temperature until complete consumption of B-17a. Subsequently, water and conc. HCl are added. After the cleavage of the Boc group (decreasing CO2 formation), the mixture is heated up to 70° C. and stirred at this temperature for 3 days. The product B-18a can be crystallized from the reaction mixture by cooling down.

The following intermediates B-18 (table 15-4) are available in an analogous manner starting from different phenyl alkynyls B-17.

TABLE 15-4

| # | structure | [M + H]⁺ |
|---|---|---|
| B-18a | 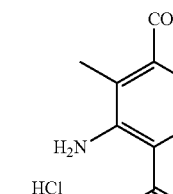 | 209 |
| B-18b | 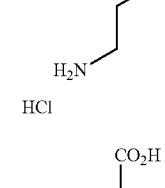 | 223 |
| B-18c | 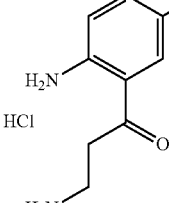 | 239 |
| B-18d | 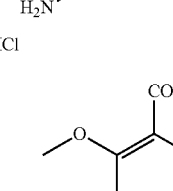 | 239 |
| B-18e | 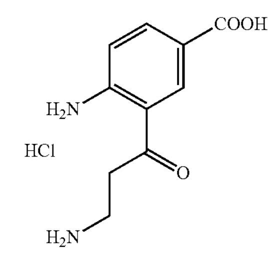 | 209 |

TABLE 15-4-continued

| # | structure | [M + H]+ |
|---|-----------|----------|
| B-18f | (structure) | 223 |

Experimental Procedure for the Synthesis of B-18q

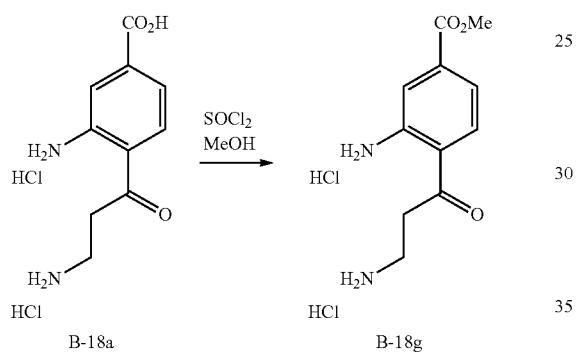

To a suspension of B-18a (1 eq.) in MeOH is added SOCl$_2$ (3 eq.) dropwise at 60° C. and the mixture is stirred overnight at this temperature. After cooling down to room temperature the mixture is filtrated over an activated carbon filter and the solvents are afterwards removed under reduced pressure. The product B-18g can be purified by crystallization.

The following benzoic acid ester intermediates B-18 (table 15-5) are available in an analogous manner starting from different benzoic acids B-18 initially obtained.

TABLE 15-5

| # | structure | [M + H]+ |
|---|-----------|----------|
| B-18g | (structure) | 223 |
| B-18h | (structure) | 237 |
| B-18i | (structure) | 253 |
| B-18j | (structure) | 253 |
| B-18k | (structure) | 223 |
| B-18l | (structure) | 237 |

Synthesis of Intermediates B-19

Experimental Procedure for the Synthesis of B-19a

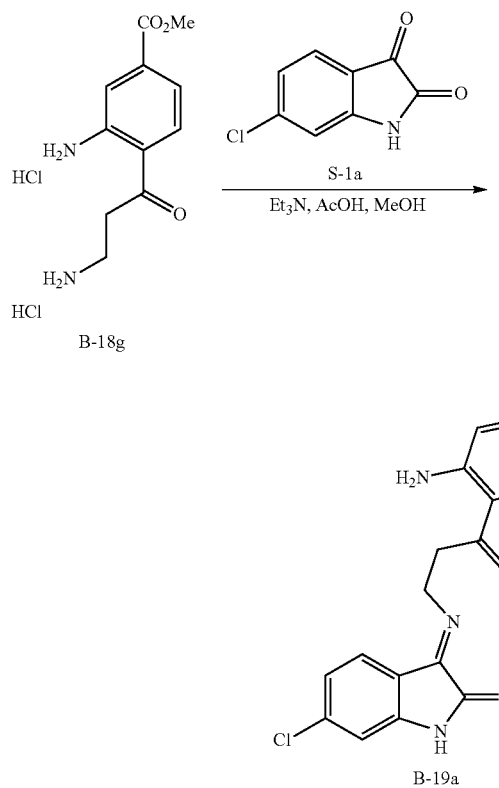

To a suspension of B-18g (1 eq.) in MeOH is added 6-chloroisatin S-1a (1.1 eq.), AcOH (2.4 eq.) and TEA (2 eq.). After 3 days of stirring at room temperature the product B-19a can be filtrated.

The following imine intermediates B-19 (table 15-6) are available in an analogous manner starting from different benzoic acid esters B-18.

TABLE 15-6

| # | structure | [M + H]$^+$ |
|---|-----------|-------------|
| B-19a | 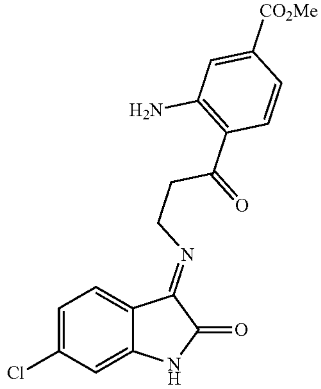 [SMILES: COC(=O)c1ccc(C(=O)CC/N=C2/C(=O)Nc3cc(Cl)ccc32)c(N)c1] | 387 |
| B-19b | 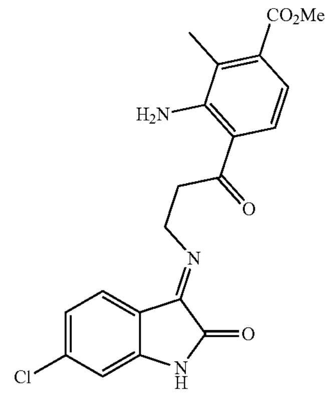 [SMILES: COC(=O)c1ccc(C(=O)CC/N=C2/C(=O)Nc3cc(Cl)ccc32)c(N)c1C] | 400 |
| B-19c | 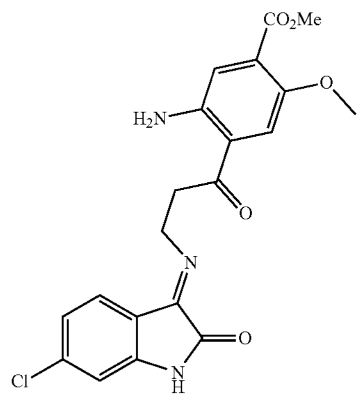 [SMILES: COC(=O)c1cc(N)c(C(=O)CC/N=C2/C(=O)Nc3cc(Cl)ccc32)cc1OC] | 416 |
| B-19d | 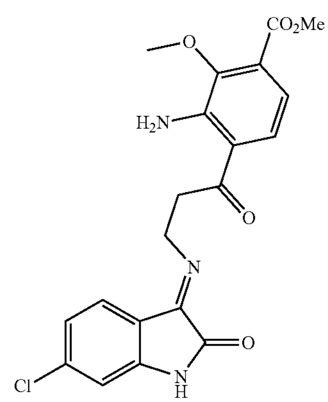 [SMILES: COC(=O)c1ccc(C(=O)CC/N=C2/C(=O)Nc3cc(Cl)ccc32)c(N)c1OC] | 416 |
| B-19e | 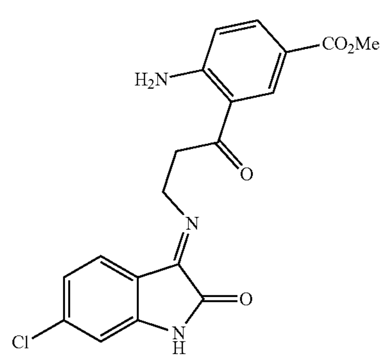 [SMILES: COC(=O)c1ccc(N)c(C(=O)CC/N=C2/C(=O)Nc3cc(Cl)ccc32)c1] | 387 |

TABLE 15-6-continued

| # | structure | [M + H]+ |
|---|---|---|
| B-19f | 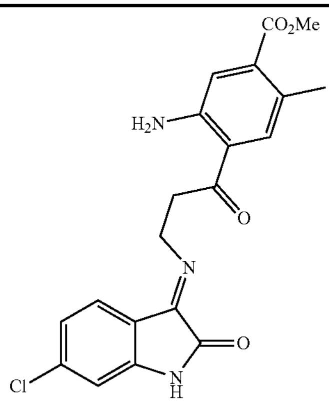 | 400 |

Synthesis of Intermediates B-20

Experimental Procedure for the Synthesis of B-20a

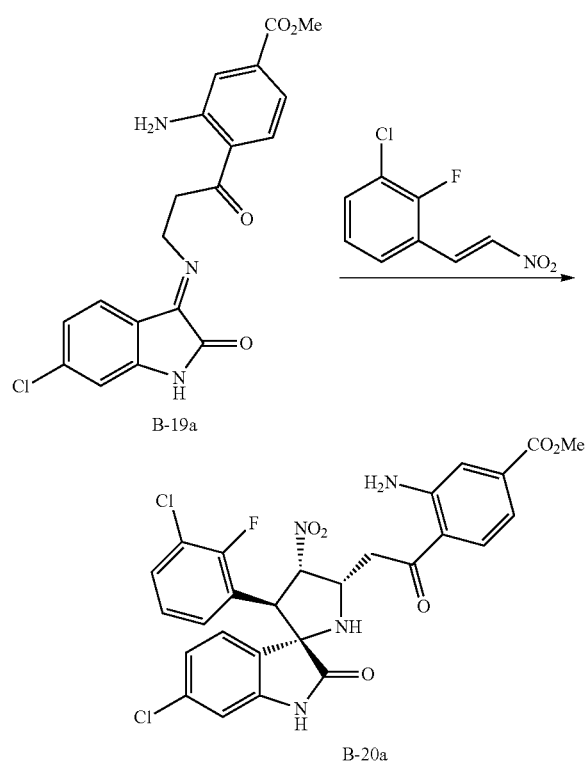

B-19a

1-Chloro-2-fluoro-3-(E)-2-nitro-vinyl)-benzene (1.1 eq.) is suspended in toluene and water and heated up. Subsequently, the imine B-19a (1 eq.) and 1-methylpyrrolidine (4 eq.) are added. The mixture is stirred under reflux. The reaction is quenched at 0° C. by the addition of AcOH. The organic phase is washed with water and saline and is then added dropwise to nHep. The product B-20a can be purified by crystallization.

If a chiral separation of the enantiomers of the racemic mixture of intermediate B-20a is desired then a crystallization with chiral acids like e.g. (S,S)-(+)-2,3-dibenzoyl-D-tartaric acid, (S,S)-(+)-2,3-p-toluyl-D-tartaric acid, (1S)-(+) camphor-10-sulfonic acid, (1R)-(−)camphor-10-sulfonic acid, (R)-(−)-mandelic acid, L-pyroglutamic acid or (S,S)-D-(−)-tartaric acid can be considered. The use of (1R)-(−) camphor-10-sulfonic acid is preferred.

The following intermediates B-20 (table 15-7) are available in an analogous manner starting from different imines B-19.

TABLE 15-7

| # | structure | [M + H]+ |
|---|---|---|
| B-20a | 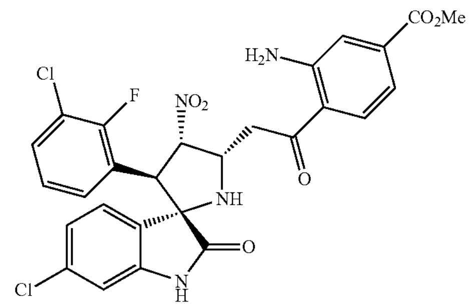 [SMILES: COC(=O)c1ccc(C(=O)C[C@@H]2N[C@@]3(C(=O)Nc4cc(Cl)ccc43)[C@@H](c3cccc(Cl)c3F)[C@@H]2[N+](=O)[O-])c(N)c1] | 587 |
| B-20b | 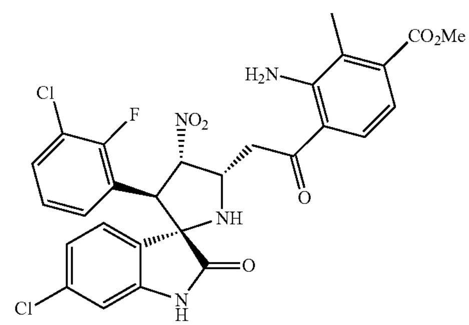 [SMILES: COC(=O)c1ccc(C(=O)C[C@@H]2N[C@@]3(C(=O)Nc4cc(Cl)ccc43)[C@@H](c3cccc(Cl)c3F)[C@@H]2[N+](=O)[O-])c(N)c1C] | 601 |
| B-20c | 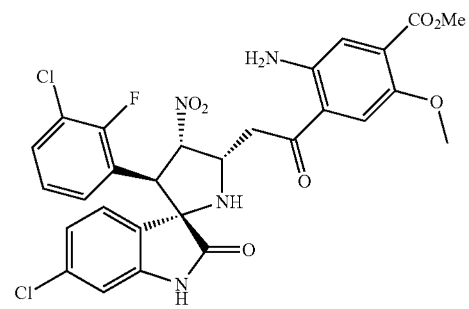 [SMILES: COC(=O)c1cc(N)c(C(=O)C[C@@H]2N[C@@]3(C(=O)Nc4cc(Cl)ccc43)[C@@H](c3cccc(Cl)c3F)[C@@H]2[N+](=O)[O-])cc1OC] | 617 |
| B-20d | 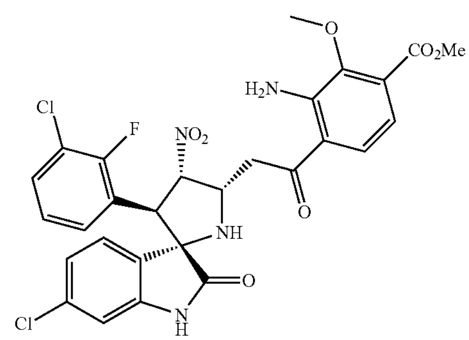 [SMILES: COC(=O)c1ccc(C(=O)C[C@@H]2N[C@@]3(C(=O)Nc4cc(Cl)ccc43)[C@@H](c3cccc(Cl)c3F)[C@@H]2[N+](=O)[O-])c(N)c1OC] | 617 |

TABLE 15-7-continued

| # | structure | [M + H]⁺ |
|---|---|---|
| B-20e | 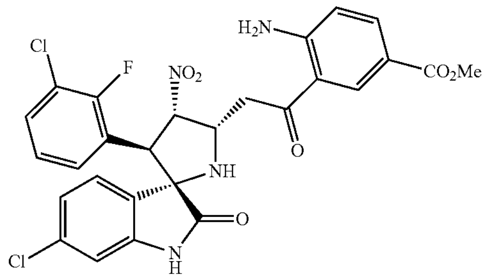 [SMILES: COC(=O)c1ccc(N)c(C(=O)C[C@@H]2N[C@@]3(C(=O)Nc4cc(Cl)ccc43)[C@@H](c3cccc(Cl)c3F)[C@@H]2[N+](=O)[O-])c1] | 587 |
| B-20f | 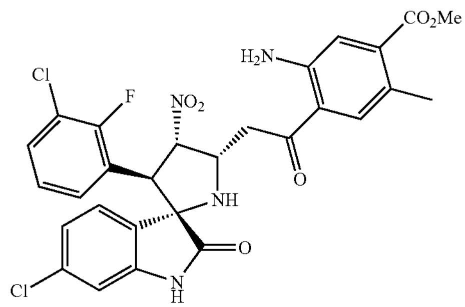 [SMILES: COC(=O)c1cc(N)c(C(=O)C[C@@H]2N[C@@]3(C(=O)Nc4cc(Cl)ccc43)[C@@H](c3cccc(Cl)c3F)[C@@H]2[N+](=O)[O-])cc1C] | 601 |
| B-20g | 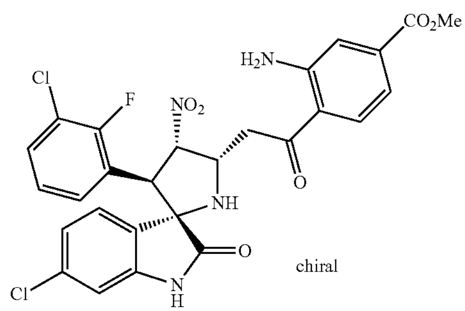 | 587 |
| B-20h | 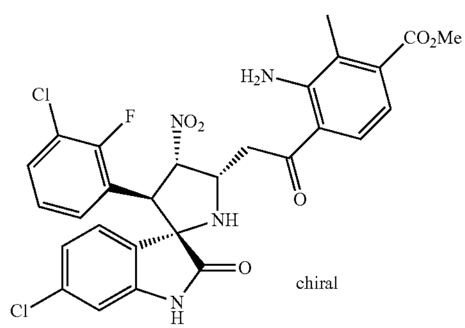 | 601 |
| B-20i | 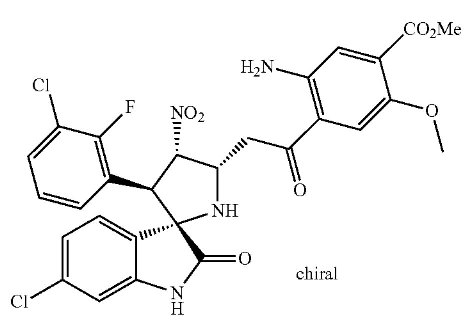 | 617 |
| B-20j | | 617 |
| B-20k | | 587 |
| B-20l | | 601 |

Synthesis of Intermediates B-22

Experimental Procedure for the Synthesis of B-22a

B-20g →(Pt/C, H₂, MeTHF)

-continued

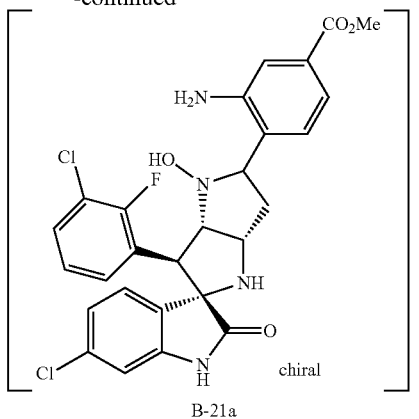

B-21a

VO(acac)$_2$
H$_2$

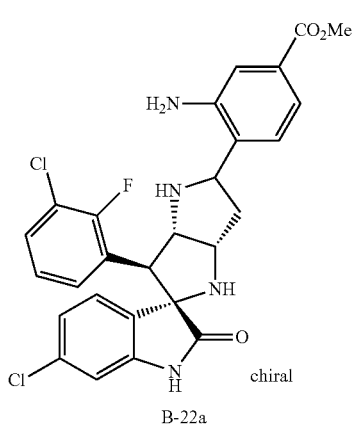

B-22a

To a solution of B-20g (1 eq.) in MeTHF is added water and Pt/C (15 wt %). The mixture is hydrogenated for 3 days at 30° C. under 70 bar H$_2$ pressure. After complete conversion to B-21a, VO(acac)$_2$ (0.11 eq.) is added and the mixture is further hydrogenated at 30° C. at 70 bar for 2 days. The catalysts are filtered out and the solvent is removed under reduced pressure. The product B-22a is dissolved in toluene and by adding 2 M H$_2$SO$_4$ (1.11 eq.) the sulfate of B-22a can be precipitated.

The reaction sequence B-20→B-21→B-22 is also possible with racemic B-20 (if there is no chiral separation of B-20). In this case chiral separation can also be performed on the stage of B-22 by a crystallization with chiral acids like e.g. (S,S)-(+)-2,3-dibenzoyl-D-tartaric acid, (S,S)-(+)-2,3-p-toluyl-D-tartaric acid, (1S)-(+)camphor-10-sulfonic acid, (R)-(−)-mandelic acid, L-pyroglutamic acid, (S,S)-D-(−)-tartaric acid, (S)-(−)-L-malic acid or L-(+)-lactic acid ((S,S)-(+)-2,3-p-toluyl-D-tartaric acid is preferred).

The following intermediates B-21 and B-22 (table 15-8) are available in an analogous manner starting from different intermediates B-20.

TABLE 15-8

| # | structure | [M + H]$^+$ |
|---|---|---|
| B-21a | 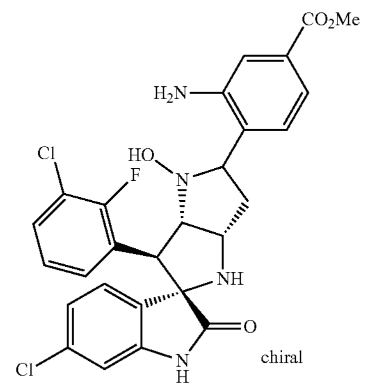 | 557 |
| B-21b | 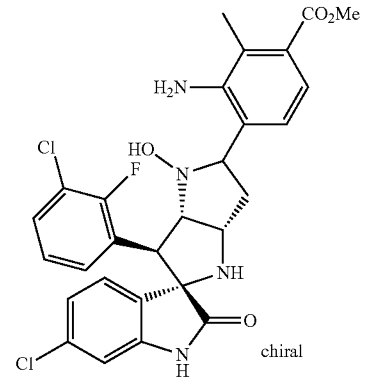 | 571 |
| B-21c | 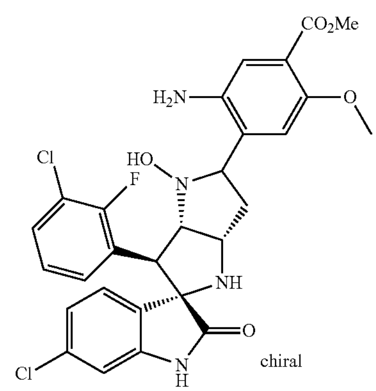 | 587 |
| B-21d | 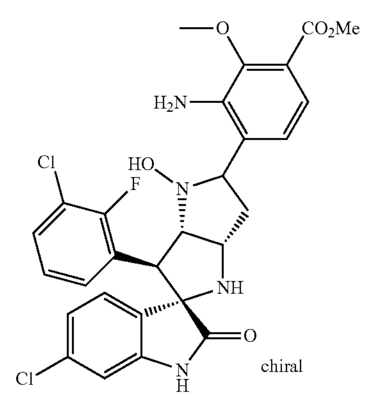 | 587 |

TABLE 15-8-continued

| # | structure | [M + H]+ |
|---|---|---|
| B-21e | 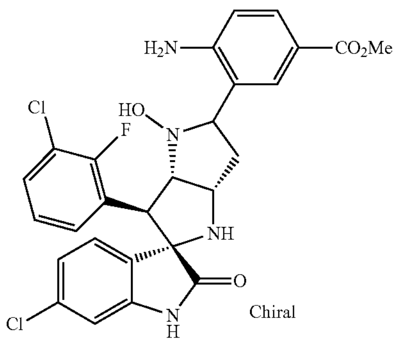 | 557 |
| B-21f | 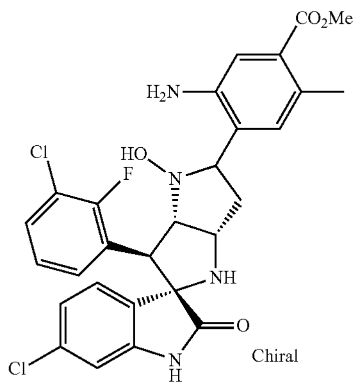 | 571 |
| B-22a | 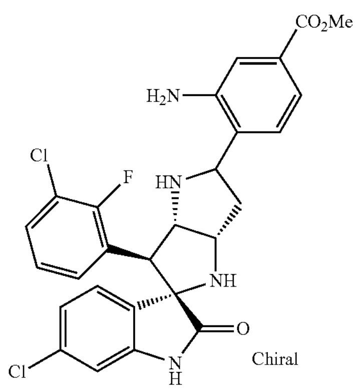 | 541 |
| B-22b | 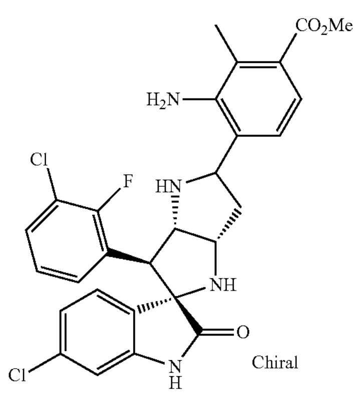 | 555 |

TABLE 15-8-continued

| # | structure | [M + H]+ |
|---|---|---|
| B-22c | 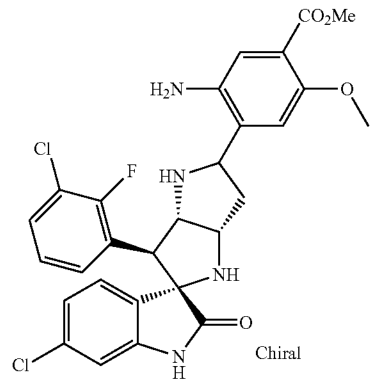 | 571 |
| B-22d | 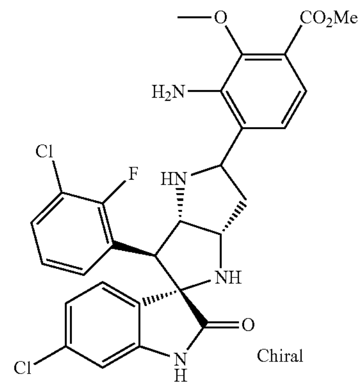 | 571 |
| B-22e | 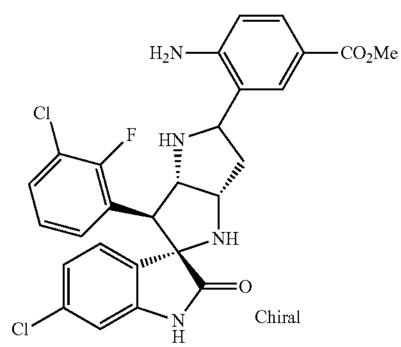 | 541 |
| B-22f | 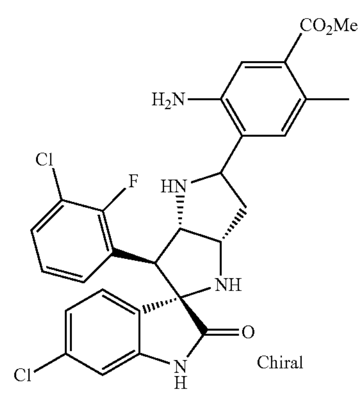 | 555 |

Synthesis of Intermediates B-23

Experimental Procedure for the Synthesis of B-23a

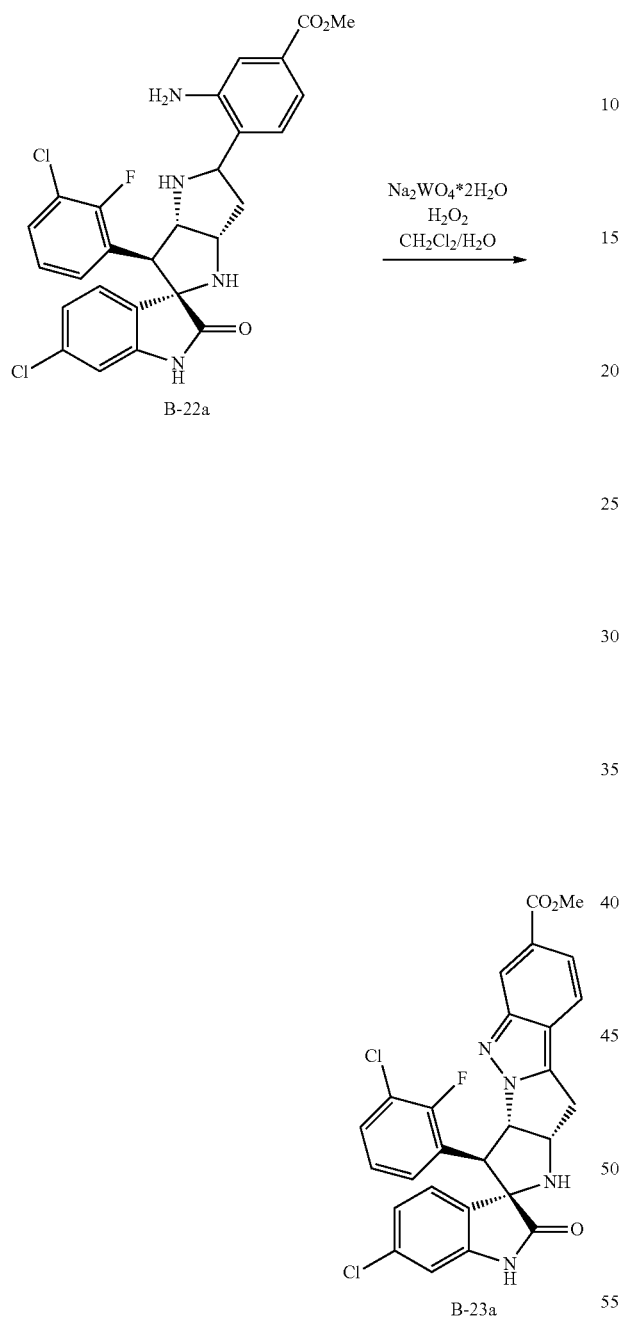

To a suspension of B-22a (1 eq.) in CH$_2$Cl$_2$ and water (4:1) is added Na$_2$WO$_4$ dihydrate (0.01 eq.) and H$_2$O$_2$ solution (30% in water, 2.5 eq.) and the mixture is stirred under reflux for 2 h. Then a solution of K$_2$CO$_3$ (2 eq.) in water is added and the CH$_2$Cl$_2$ is removed under reduced pressure. The solid product B-23a can be purified by slurrying in an appropriate solvent.

The following intermediates B-23 (table 15-10) are available in an analogous manner starting from different intermediates B-22.

TABLE 15-9

| # | structure | [M + H]$^+$ |
|---|---|---|
| B-23a | 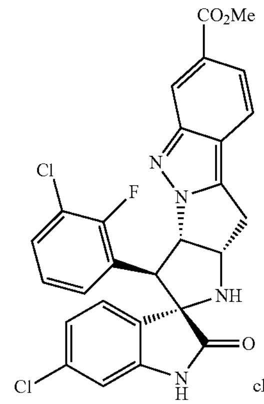 | 537 |
| B-23b | 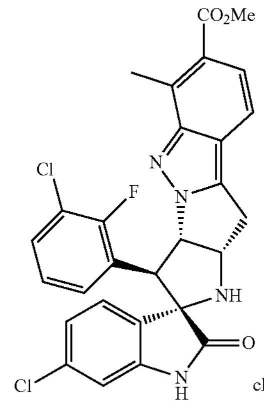 | 551 |
| B-23c | 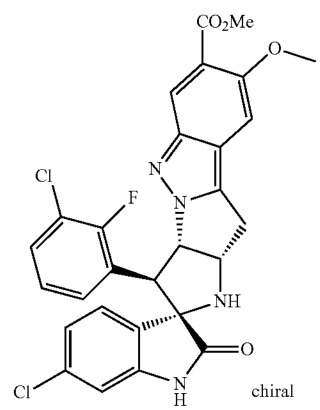 | 567 |
| B-23d | 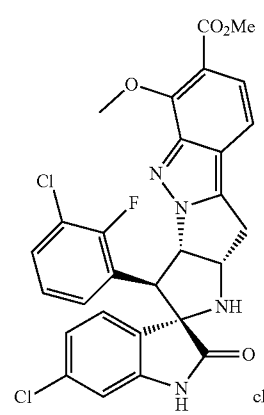 | 567 |

TABLE 15-9-continued
| # | structure | [M + H]+ |
|---|---|---|
| B-23e | 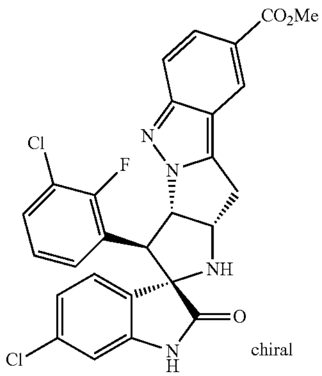 | 537 |
| B-23f | | 551 |
Compounds (Ib)
General Reaction Scheme and Summary of the Synthesis Route
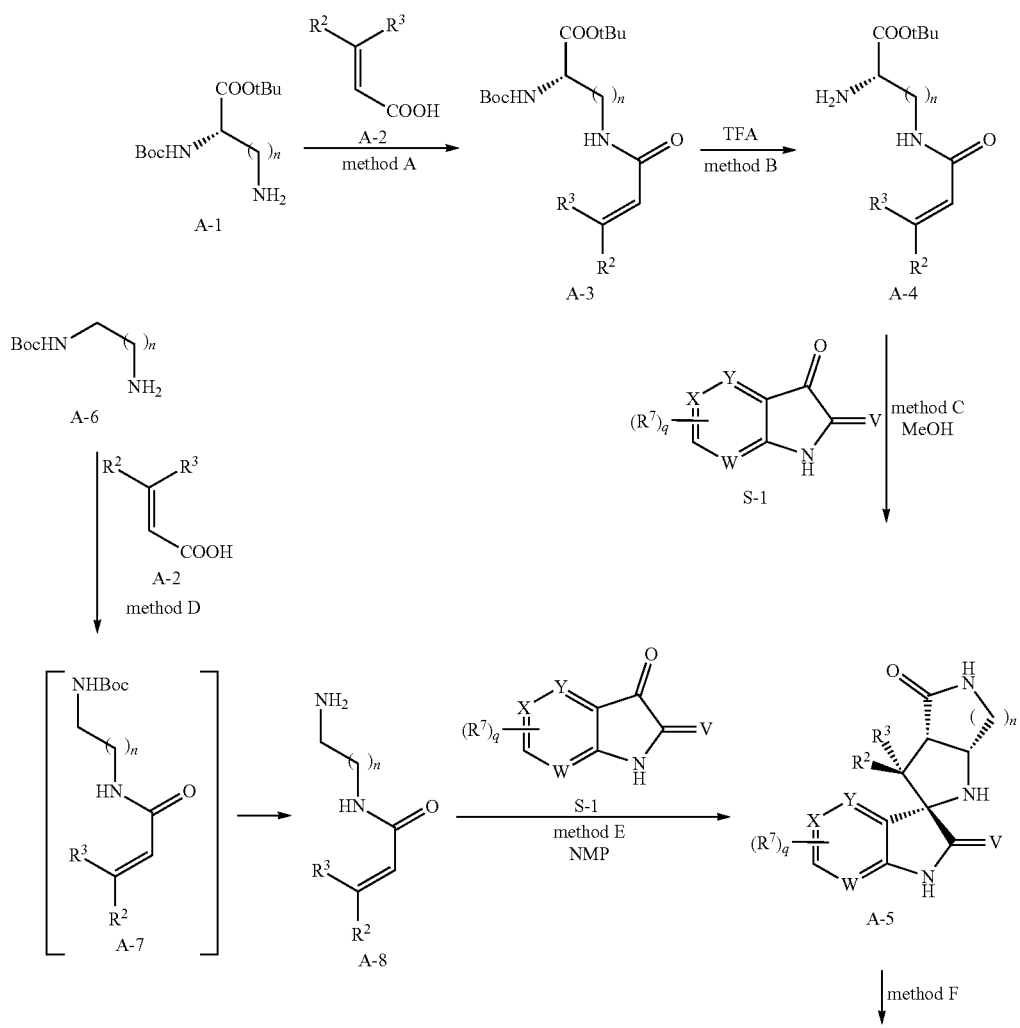

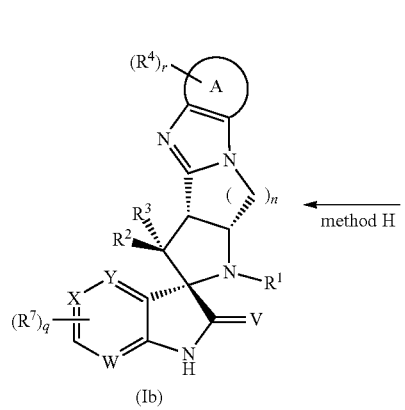

(Ib)

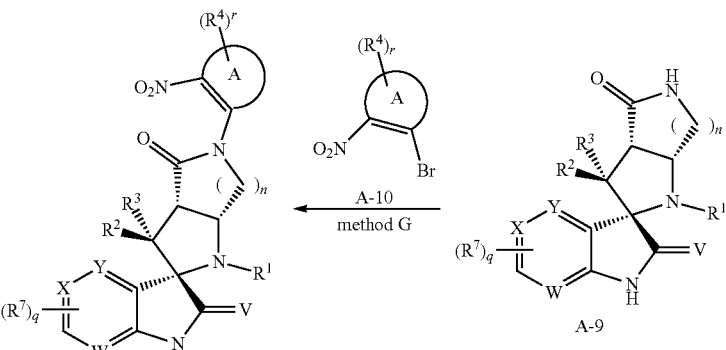

A-11 ← method G ← A-9

Novel compounds of structure (Ib) can be prepared stepwise by a synthesis route starting from protected amino acids A-1 (scheme 3). First, an acylation reaction using acrylic acid derivatives A-2 yields compounds of structure A-3 (method A). Acrylic acids which are not directly available can be obtained e.g. by WITTIG reaction (D-1, D-2, not depicted in scheme 3). Treatment of intermediates A-3 under acidic conditions, preferentially with trifluoro acetic acid, forms free unsaturated amino acid derivatives A-4 (method B). A decarboxylative 1,3-dipolar cycloaddition of A-4 and isatin derivatives S-1 yields cycloadducts A-5 as a mixture of diastereo isomers and builds up the spiro system (method C). The diastereomers can be separated, e.g. by HPLC or SFC. The obtainable racemic mixture can be resolved by chiral SFC separation or at any later stage in the synthesis. Also all other means known for separation of enantiomers can be applied here or after any later synthetic step herein described, e.g. crystallisation, chiral resolution, chiral HPLC etc. (see also *Enantiomers, racemates, and resolutions*, Jean Jacques, André Collet, Samuel H Wilen John Wiley and Sons, N Y, 1981).

Alternatively cycloadduct A-5 can be prepared by a 1,3-dipolar cycloaddition of amine A-8 and isatin derivatives S-1 as a mixture of diastereo isomers (method E). Intermediates A-8 can be prepared in one pot from amines A-6 by an acylation reaction using acrylic acid derivatives A-2 and subsequent cleavage of the Boc-protecting group by addition of HCl (method D).

Intermediates A-5 can be reacted with aldehydes or ketones in a reductive amination reaction to give intermediates A-9 (introduction of $R^1$, method F). Alternatively, an alkylation, addition, acylation or sulfonylation reaction can be performed with A-5 to additional intermediates of formula A-9. Subjecting intermediates A-9 to metal-catalyzed cross coupling reactions (e.g. BUCHWALD amidation) with substituted nitro (hetero)aryl halides A-10 gives intermediates A-11 (method G). A reductive cyclization of intermediates A-11 by treatment with iron powder in acetic acid, or alternative reducing agents gives compounds (Ib).

Compounds (Ib) which are initially obtained can be derivatized in optional derivatization steps not explicitly depicted in the schemes in all residues, especially in $R^4$, if they carry functional groups, that can be further modified such as e.g. halogen atoms, amino and hydroxy groups (including cyclic amines), carboxylic acid or ester functions, nitrils etc. to further compounds (Ia) by well-established organic chemical transformations such as metal-catalyzed cross coupling reactions, acylation, amidation, addition, reduction or (reductive) alkylation or cleavage of protecting groups. These additional steps are not depicted in the general schemes. Likewise, it is also possible to include these additional steps in the synthetic routes depicted in the general schemes, i.e. to carry out derivatization reactions with intermediate compounds. In addition, it may also be possible that building blocks bearing protecting groups are used, i.e. further steps for deprotection are necessary.

Scheme 4

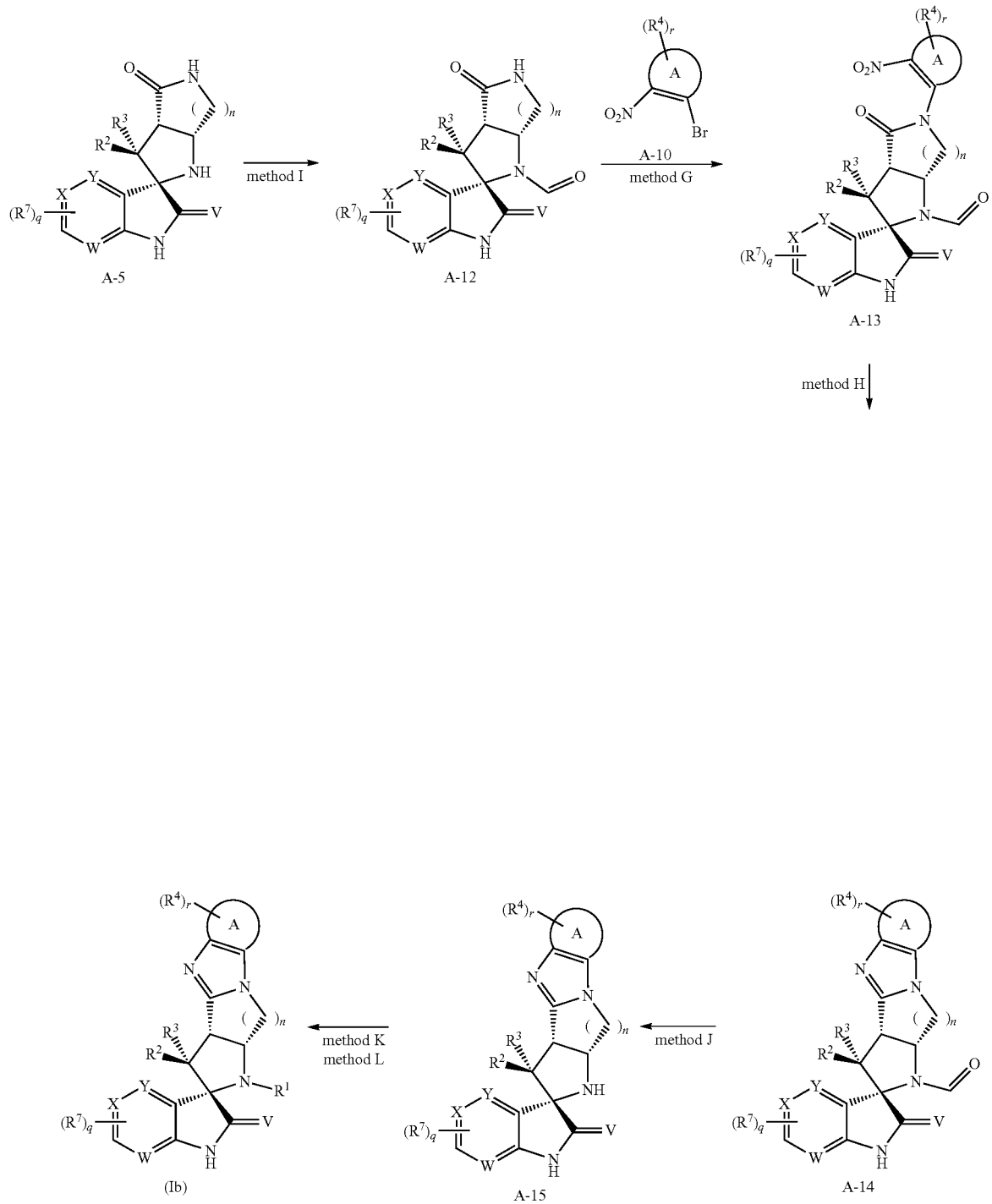

Alternatively, novel compounds of structure (Ib) can be prepared stepwise by a synthesis route starting from intermediates A-5 (scheme 4). Intermediates A-5 are treated with acetic anhydride in formic acid to generate intermediates A-12 (method I). Subjecting intermediates A-12 to metal-catalyzed cross coupling reactions (e.g. BUCHWALD amidation) with substituted nitro (hetero)aryl halides A-10 gives intermediates A-13 (method G). A reductive cyclization of intermediates A-13 by treatment with iron powder in acetic acid, or alternative reducing agents, gives intermediates A-14. Deformylation mediated by hydrochloric acid in MeOH gives intermediates A-15 (method J). Intermediates A-15 can be reacted with aldehydes or ketones in a reductive amination reaction to give compounds (Ib) (introduction of $R^1$, methods K and L). Alternatively, an alkylation, addition, acylation or sulfonylation reaction can be performed with A-15 to additional compounds of formula (Ib).

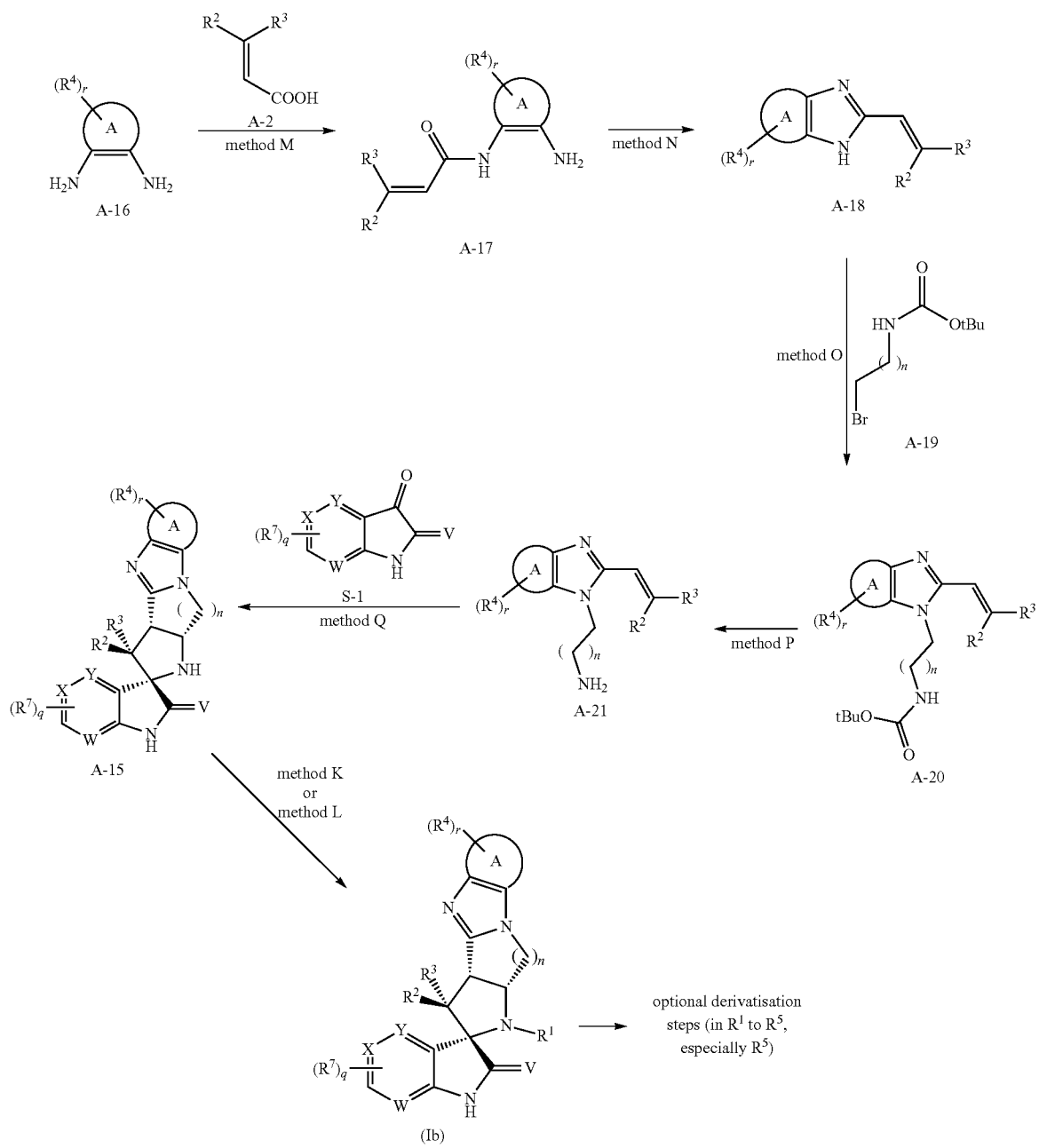

Alternatively, novel compounds of structure (Ib) can be prepared stepwise by a synthesis route starting from diamino (hetero)aryls A-16 (scheme 5). First, an acylation reaction using acrylic acid derivatives A-2 yields compounds of structure A-17 (method M). Acrylic acids which are not directly available can be obtained e.g. by WITTIG reaction (D-1, D-2, not depicted in scheme 5). Treatment of intermediates A-17 with hydrochloric acid gives condensed imidazole (e.g. benzimidazole) intermediates A-18 (method N). Alkylation of intermediate A-18 with bromides A-19, or alternative alkylating agents, gives intermediates A-20 (method O). Treatment of intermediates A-20 under acidic conditions, preferentially with trifluoro acetic acid, forms free unsaturated amine derivatives A-21 (method P). A 1,3-dipolar cycloaddition of A-21 and isatin derivatives S-1 yields cycloadducts A-15 as a mixture of diastereo isomers and builds up the spiro system (method Q). Intermediates A-15, as described above, can be reacted with aldehydes or ketones in a reductive amination reaction to give compounds (Ib) (introduction of $R^1$, methods K and L). Alternatively, an alkylation, addition, acylation or sulfonylation reaction can be performed with A-15 to additional compounds of formula (Ib).

Compounds (Ib) have been tested for their activity to affect MDM2-p53 interaction in their racemic form or alternatively as the enantiopure form. Each of the two enantiomers of a racemic mixture may have activity against MDM2 although with a different binding mode.

Enantiopure compounds are marked with the label "Chiral". Compounds listed in any table below that are labeled "Chiral" (both intermediates as well as compounds (Ib) according to the invention) can be separated by chiral SFC chromatography from their enantiomer or are synthesized from enantiopure starting material which is separated by chiral SFC.

EXAMPLE

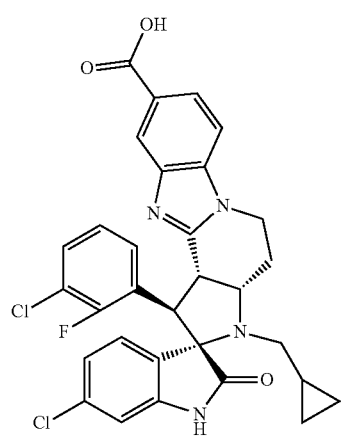
A

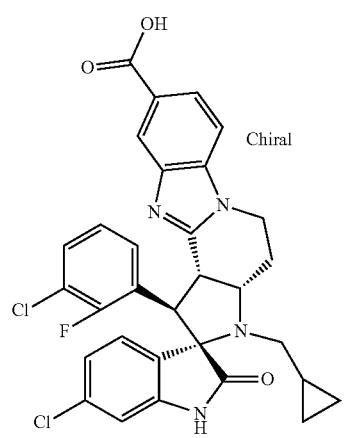
B  Chiral

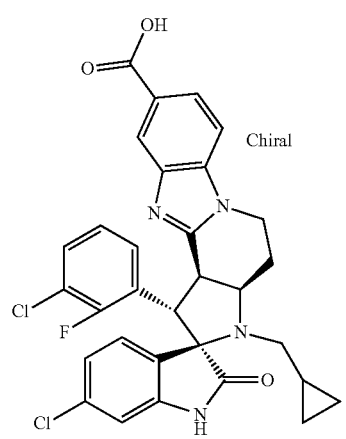
C  Chiral

Structure A defines the racemic mixture of compounds with structure B and C, i.e. structure A encompasses two structures (compounds B and C), whereas structures B and C, respectively, are enantiopure and only define one specific compound. Thus, formulae (Ib) and (Ib*)

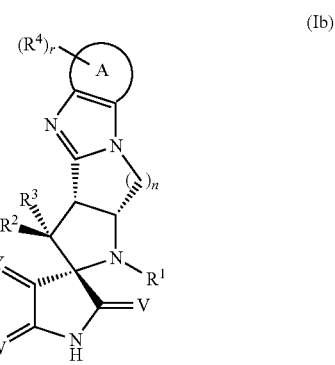
(Ib)

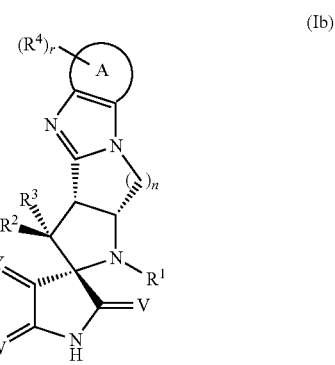
(Ib*)
Chiral with a set of specific definitions for groups $R^1$ to $R^4$, $R^7$, V, W, X, Y, n, r and q represent the racemic mixture of two enantiomers (→(Ib); structure A above is one specific example of such a racemic mixture) or a single enantiomer (→(Ib*); structure B above is one specific enantiomer), unless there are additional stereocenters present in one or more of the substituents. The same definition applies to synthetic intermediates.

Synthesis of Intermediates A-2

Experimental Procedure for the Synthesis of A-2a

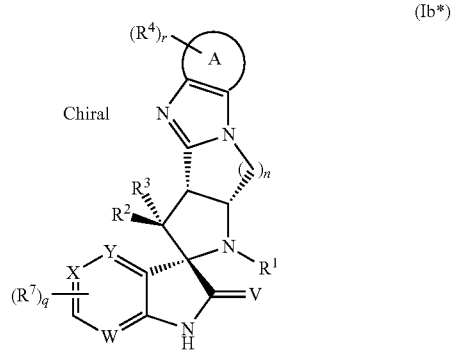
D-1a

225
-continued

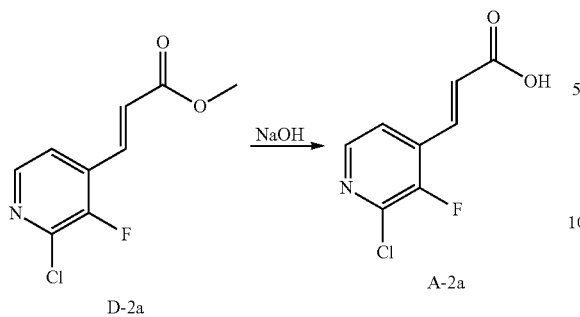

2-Chloro-3-fluoro-pyridine-4-carbaldehyde D-1a (1 g, 6.3 mmol) is dissolved in anhydrous MTBE (10 mL) under an argon atmosphere. Methyl (triphenylphosphoranylidene)acetate (2.1 g, 6.3 mmol) is added in one portion and the reaction mixture is stirred at rt for 1 h. Water and EtOAc is added and the phases are separated. The organic phase is dried with MgSO$_4$, filtered and the solvent is removed under reduced pressure. The residue is purified by reversed phase column chromatography giving pure (E)-3-(2-chloro-3-fluoro-pyridin-4-yl)-acrylic acid methyl ester D-2a.

D-2a (780 mg, 3.6 mmol) is dissolved in THF (3 mL) and 2 M NaOH is added (3.6 mL, 7.2 mmol). The reaction mixture is stirred at 60° C. for 1 h before it is quenched by the addition of 2 M HCl. Extraction with EtOAc and subsequent drying of the organic phase using MgSO$_4$ yields crude A-2a upon removal of the solvents under reduced pressure. Reversed phase column chromatography gives pure (E)-3-(2-chloro-3-fluoro-pyridin-4-yl)-acrylic acid A-2a.

Further building blocks A-2 are available in an analogous manner starting from different carbaldehydes D-1.

TABLE 16

| # | structure | t$_{ret}$ [min] | [M + H]$^+$ | HPLC method |
|---|---|---|---|---|
| A-2a | ![structure] | 0.0 | 202 | A |

226
Synthesis of Intermediates A-3 (Method A)

Experimental Procedure for the Synthesis of A-3a

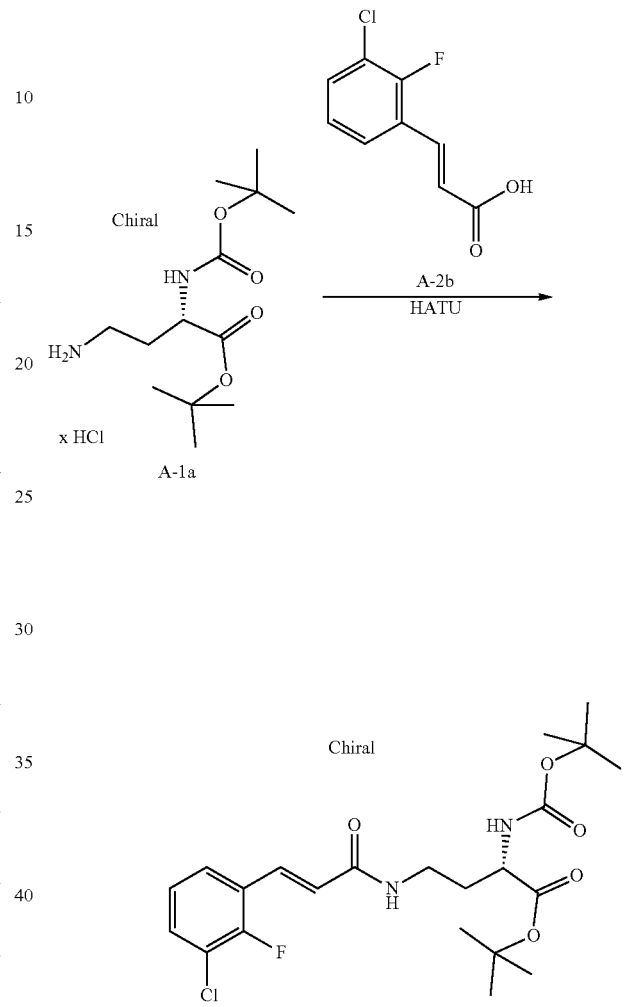

3-Chloro-2-fluoro cinnamic acid A-2b (10.3 g, 50.67 mmol) is suspended in anhydrous DMF (300 mL) at 0° C. and DIPEA (19.5 mL, 120.65 mmol) and HATU (20.39 g, 53.09 mmol) are added to the reaction mixture. The reaction mixture is stirred at 0° C. for 30 min. A solution of (S)-4-amino-2-tert-butoxycarbonylamino-butyric acid tert-butyl ester hydrochloride A-1a (15.0 g, 48.26 mmol) in DMF (100 mL) is added dropwise over a period of 15 min. The reaction mixture is stirred for additional 60 min and sat. aq. NH$_4$Cl solution is added. Deionized water is added and the mixture is extracted with a 1:1 mixture of EtOAc and cyclohexane. The layers are separated and the organic phase is washed with deionized water and dried with MgSO$_4$. The solvents are removed under reduced pressure and (S)-2-tert-butoxycarbonylamino-4-[(E)-3-(3-chloro-2-fluoro-phenyl)-acryloylamino]-butyric acid tert-butyl ester A-3a is used without further purification.

The following intermediates A-3 (table 17) are available in analogous manner starting from different acrylic acids A-2 and protected amino acids A-1.

TABLE 17
| # | structure | $t_{ret}$ [min] | $[M + H]^+$ | HPLC method |
|---|---|---|---|---|
| A-3a | 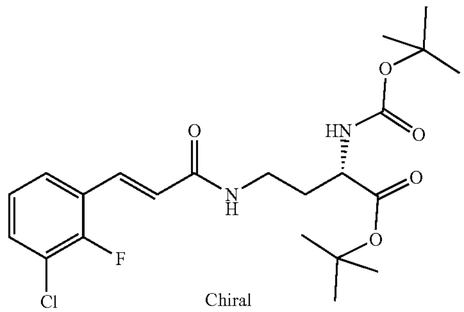 [SMILES: CC(C)(C)OC(=O)N[C@@H](CCNC(=O)/C=C/c1cccc(Cl)c1F)C(=O)OC(C)(C)C ; "Chiral"] | 1.56 | $[M + H\text{-Boc}]^+$ 357 | A |
| A-3b | 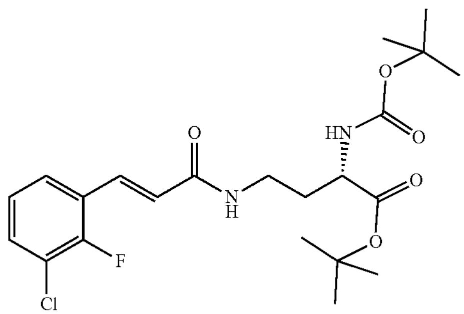 [SMILES: CC(C)(C)OC(=O)N[C@@H](CCNC(=O)/C=C/c1cccc(Cl)c1F)C(=O)OC(C)(C)C] | 1.56 | $[M + H\text{-Boc}]^+$ 357 | A |
| A-3c | 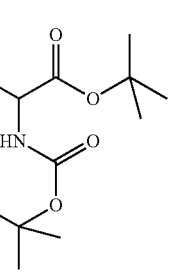 | 0.82 | 443 | G |
| A-3d | 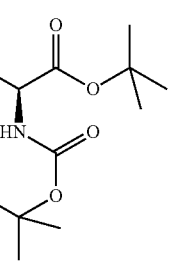 | 0.82 | 443 | G |
| A-3e | 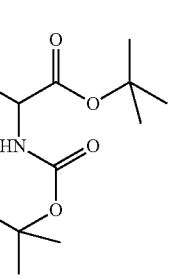 | n.a. | n.a. | |

TABLE 17-continued
| # | structure | $t_{ret}$ [min] | $[M + H]^+$ | HPLC method |
|---|---|---|---|---|
| A-3f | 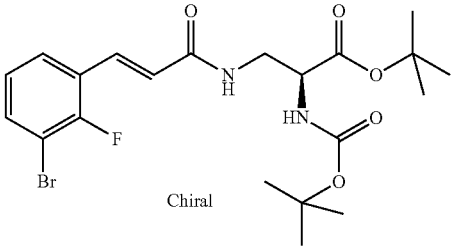 [SMILES: CC(C)(C)OC(=O)N[C@@H](CNC(=O)/C=C/c1cccc(Br)c1F)C(=O)OC(C)(C)C ; "Chiral"] | n.a. | n.a. | |
| A-3g | 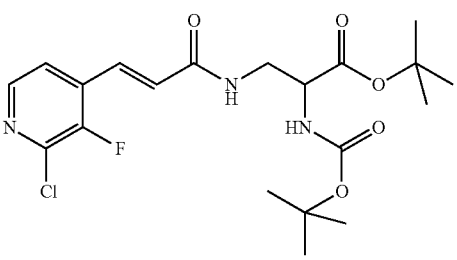 [SMILES: CC(C)(C)OC(=O)NC(CNC(=O)/C=C/c1ccnc(Cl)c1F)C(=O)OC(C)(C)C] | 1.44 | 466 | A |
| A-3h | 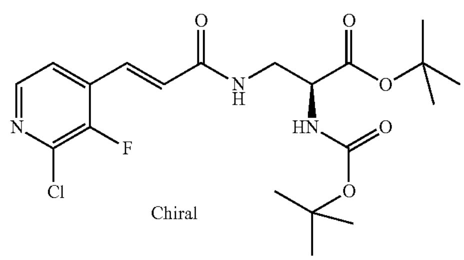 [SMILES: CC(C)(C)OC(=O)N[C@@H](CNC(=O)/C=C/c1ccnc(Cl)c1F)C(=O)OC(C)(C)C ; "Chiral"] | 1.44 | 466 | A |
| A-3i | 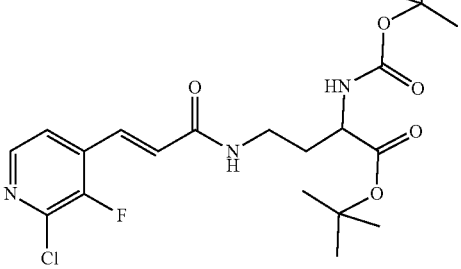 | n.a. | n.a. | |
| A-3j | 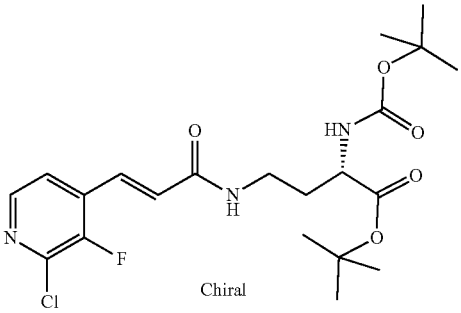 [SMILES: CC(C)(C)OC(=O)N[C@@H](CCNC(=O)/C=C/c1ccnc(Cl)c1F)C(=O)OC(C)(C)C ; "Chiral"] | n.a. | n.a. | |

Synthesis of Intermediates A-4 (Method B)

Experimental Procedure for the Synthesis of A-4a

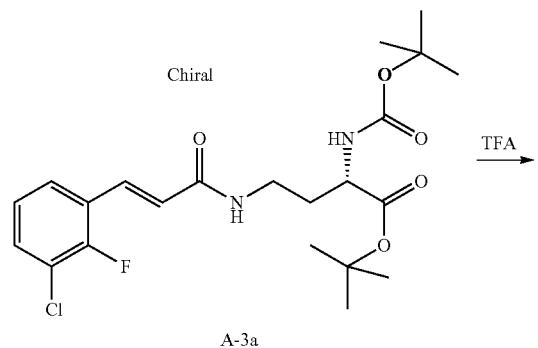

A-3a

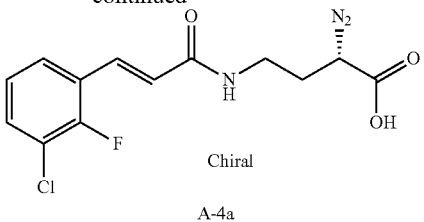

A-4a (S)-2-tert-Butoxycarbonylamino-4-[(E)-3-(3-chloro-2-fluoro-phenyl)-acryloylamino]-butyric acid tert-butyl ester A-3a (22.4 g, 48.9 mmol) is dissolved in DCM (150 mL). TFA (35 mL) is added at 0° C. and the reaction mixture is slowly warmed to rt. The reaction mixture is heated to reflux for 24 h. Before it is concentrated in vacuo, aq. NaOH (4 M) is added at 0° C. until a pH of 12 is reached. Addition of aq. HCl (2 M) results in the formation of a precipitate at pH 6-7 which is filtered off. The solid residue (S)-2-amino-4-[(E)-3-(3-chloro-2-fluoro-phenyl)-acryloylamino]-butyric acid hydrochloride A-4a is washed with water and acetonitrile and dried at 50° C. under reduced pressure.

The following intermediates A-4 (table 18) are available in an analogous manner starting from different intermediates A-3.

TABLE 18

| # | structure | $t_{ret}$ [min] | $[M + H]^+$ | HPLC method |
|---|---|---|---|---|
| A-4a | 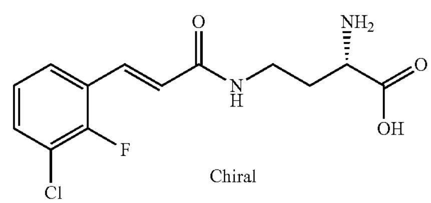 [SMILES: N[C@@H](CCNC(=O)/C=C/c1cccc(Cl)c1F)C(=O)O ; "Chiral"] | 0.91 | 301 | A |
| A-4b | 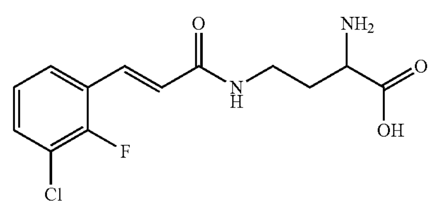 [SMILES: NC(CCNC(=O)/C=C/c1cccc(Cl)c1F)C(=O)O] | 0.91 | 301 | A |
| A-4c | 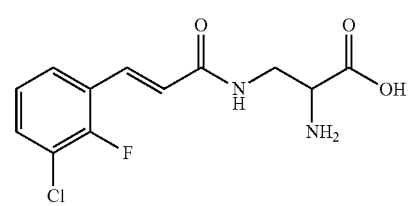 [SMILES: NC(CNC(=O)/C=C/c1cccc(Cl)c1F)C(=O)O] | 0.63 | 287 | A |
| A-4d | 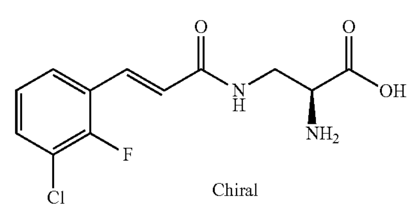 [SMILES: N[C@@H](CNC(=O)/C=C/c1cccc(Cl)c1F)C(=O)O ; "Chiral"] | 0.63 | 287 | A |

TABLE 18-continued
| # | structure | $t_{ret}$ [min] | [M + H]⁺ | HPLC method |
|---|---|---|---|---|
| A-4e | 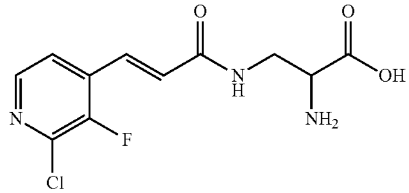 [SMILES: NC(CNC(=O)/C=C/c1ccnc(Cl)c1F)C(=O)O] | 0.21 | 288 | A |
| A-4f | Chiral | 0.21 | 288 | A |
| A-4g | 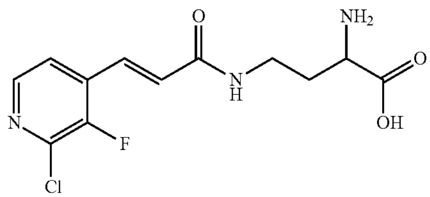 [SMILES: NC(CCNC(=O)/C=C/c1ccnc(Cl)c1F)C(=O)O] | 1.40 | 302 | M |
| A-4h | Chiral | 1.40 | 302 | M |
Synthesis of Intermediate A-5 (Method C)
Experimental Procedure for the Synthesis of A-5a and A-5c
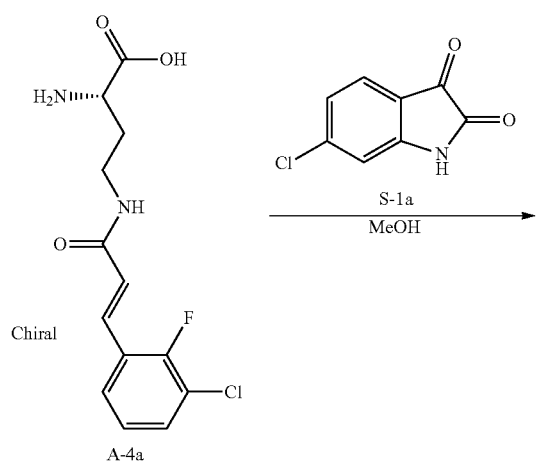
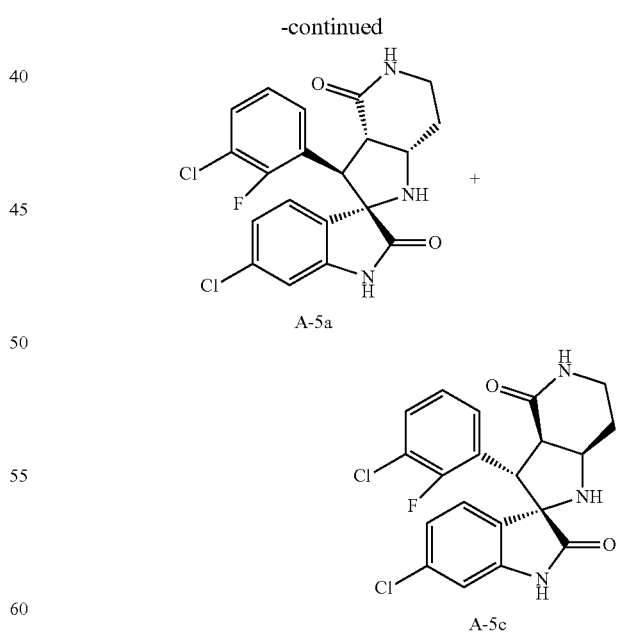
(S)-2-Amino-4-[(E)-3-(3-chloro-2-fluoro-phenyl)-acryloylamino]-butyric acid A-4a (0.34 g, 1.13 mmol), 6-chloro-1H-indole-2,3-dione S-1a (2.1 g, 1.13 mmol) and ground, activated 4 Å molecular sieves are suspended in anhydrous MeOH (15 mL) in a microwave vial. The reaction vessel is sealed with Teflon caps and irradiated for 30 min at a final temperature of 100° C. After cooling to rt, the crude mixture is filtered over a pad of Celite© and solvents are removed under reduced pressure. The crude reaction mixture is purified by reversed phase HPLC which gives diastereomers A-5a and A-5c.

The following intermediates A-5 (Table 19) are available in analogous manner starting from different intermediates A-4 and S-1.

TABLE 19

| # | structure | $t_{ret}$ [min] | $[M + H]^+$ | HPLC method |
|---|---|---|---|---|
| A-5a | 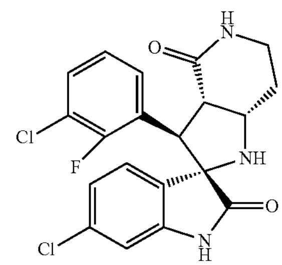 | 0.49 | 420 | G |
| A-5b | 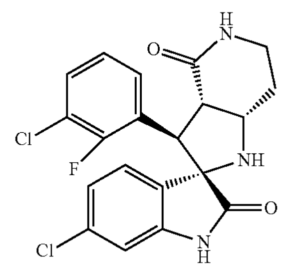 | 0.49 | 420 | G |
| A-5c | 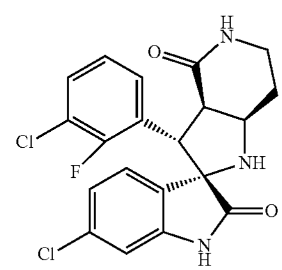 [SMILES: O=C1NCC[C@H]2N[C@@]3(C(=O)Nc4cc(Cl)ccc43)[C@H](c3cccc(Cl)c3F)[C@@H]12] | 0.45 | 420 | G |
| A-5d | 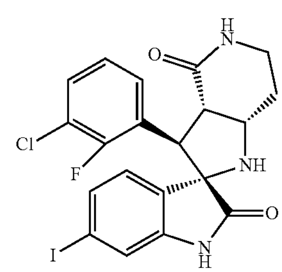 [SMILES: O=C1NCC[C@@H]2N[C@@]3(C(=O)Nc4cc(I)ccc43)[C@@H](c3cccc(Cl)c3F)[C@H]12] | 0.53 | 512 | G |
| A-5e | 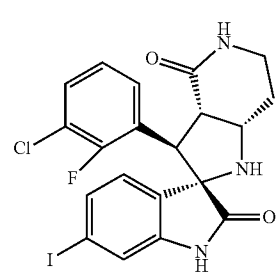 | 0.53 | 512 | G |

TABLE 19-continued

| # | structure | $t_{ret}$ [min] | [M + H]⁺ | HPLC method |
|---|---|---|---|---|
| A-5f | 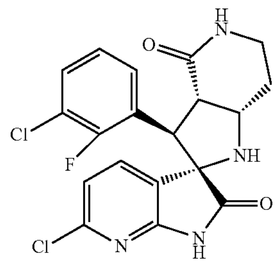 [SMILES: O=C1NCC[C@@H]2N[C@@]3(C(=O)Nc4nc(Cl)ccc43)[C@@H](c3cccc(Cl)c3F)[C@H]12] | 0.93 | 421 | A |
| A-5g | Chiral | 0.93 | 421 | A |
| A-5h | 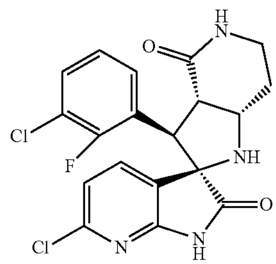 [SMILES: O=C1NCC[C@@H]2N[C@]3(C(=O)Nc4nc(Cl)ccc43)[C@@H](c3cccc(Cl)c3F)[C@H]12] | 0.89 | 421 | A |
| A-5i | 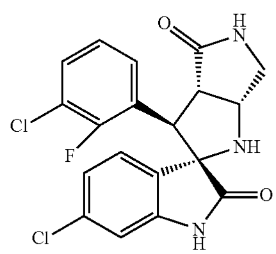 [SMILES: O=C1NC[C@@H]2N[C@@]3(C(=O)Nc4cc(Cl)ccc43)[C@@H](c3cccc(Cl)c3F)[C@H]12] | 0.99 | 406 | A |
| A-5j | Chiral | 0.99 | 406 | A |
| A-5k | Chiral | 0.99 | 406 | A |

TABLE 19-continued

| # | structure | $t_{ret}$ [min] | $[M + H]^+$ | HPLC method |
|---|---|---|---|---|
| A-5l | 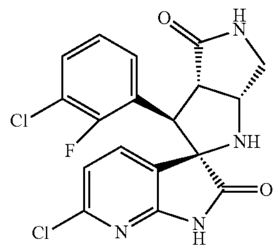 [SMILES: O=C1NC[C@@H]2N[C@]3(C(=O)Nc4nc(Cl)ccc43)[C@@H](c3cccc(Cl)c3F)[C@H]12] | 0.93 | 421 | A |
| A-5m | Chiral | 0.93 | 421 | A |
| A-5n | 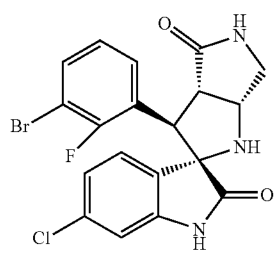 | 0.50 | 451 | G |
| A-5o | Chiral | 0.50 | 451 | G |
| A-5p | 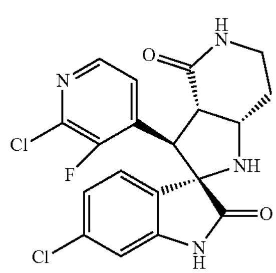 | 0.91 | 421 | A |
| A-5q | Chiral | 0.91 | 421 | A |

Synthesis of Intermediates A-8 (Method D)

Experimental Procedure for the Synthesis of A-8a

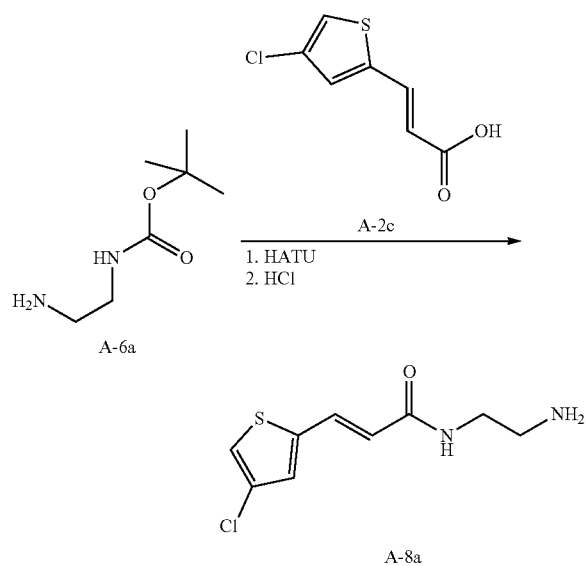

(E)-3-(4-Chloro-thiophen-2-yl)-acrylic acid A-2c (554 mg, 2.94 mmol) is suspended in anhydrous DMF (5 mL) at 0° C. and DIPEA (1.14 g, 129.3 mmol) and HATU (1.34 g, 3.52 mmol) are added to the reaction mixture. The mixture is stirred at 0° C. for 30 min. A solution of (2-amino-ethyl) carbamic acid tert-butyl ester A-6a (470 mg, 2.94 mmol) in DMF (1 mL) is added dropwise over a period of 15 min. The reaction mixture is stirred for additional 30 min. Concentrated HCl (2.89 g, 29.37 mmol) is added and the mixture is heated to 90° C. and stirred for 90 min. Sodium hydroxide (8 N in $H_2O$) is added until a pH of 12 is reached and the mixture is extracted with EtOAc. The layers are separated and the organic phase is washed with deionized water and dried with $MgSO_4$. The solvents are removed under reduced pressure and the crude reaction mixture is purified by reversed phase HPLC if necessary to obtain intermediate A-8a.

The following intermediates A-8 (table 20) are available in an analogous manner starting from different acrylic acids A-2 and amines A-6.

TABLE 20

| # | structure | $t_{ret}$ [min] | $[M + H]^+$ | HPLC method |
|---|---|---|---|---|
| A-8a | 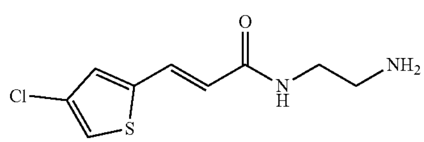 [SMILES: NCCNC(=O)/C=C/c1cc(Cl)cs1] | 0.28 | 231 | G |
| A-8b | 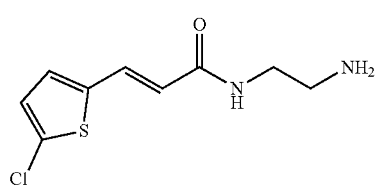 [SMILES: NCCNC(=O)/C=C/c1ccc(Cl)s1] | 0.29 | 231 | G |
| A-8c | 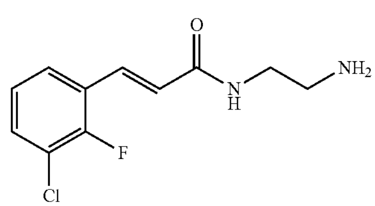 [SMILES: NCCNC(=O)/C=C/c1cccc(Cl)c1F] | 0.86 | 243 | A |
| A-8d | 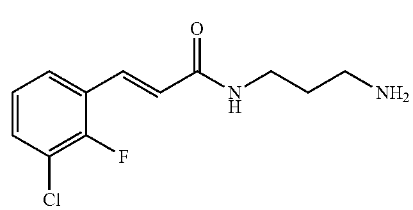 [SMILES: NCCCNC(=O)/C=C/c1cccc(Cl)c1F] | 0.86 | 257 | A |

Synthesis of Additional Intermediates A-5 (Method E)

Experimental Procedure for the Synthesis of A-5r and A-5t

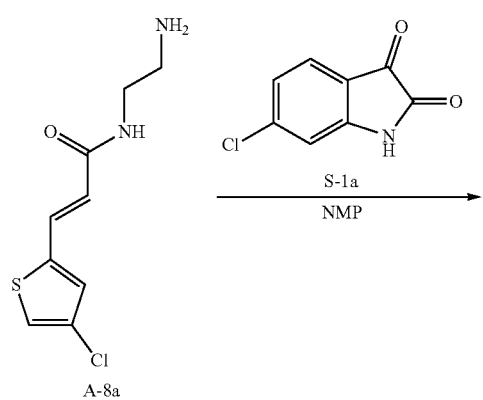

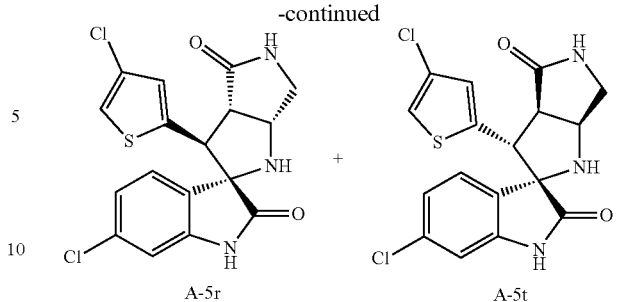

(E)-N-(2-Amino-ethyl)-3-(4-chloro-thiophen-2-yl)acrylamide A-8a (0.37 g, 1.60 mmol), 6-chloro-1H-indole-2,3-dione S-1a (306 mg, 1.60 mmol) and triethylamine (162 mg, 1.60 mmol) are suspended in anhydrous NMP (12 mL) in a microwave vial. The reaction vessel is sealed with a Teflon cap and irradiated for 30 min at a final temperature of 110° C. After cooling to rt the solvents are removed under reduced pressure. The product is used crude for the next step or purified by reversed phase HPLC which gives diastereomers A-5r and A-5t.

The following intermediates A-5 (table 21) are available in analogous manner starting from different intermediates S-1 and A-8.

TABLE 21

| # | structure | $t_{ret}$ [min] | $[M + H]^+$ | HPLC method |
|---|---|---|---|---|
| A-5r | 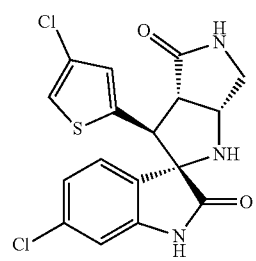 [SMILES: O=C1NC[C@@H]2N[C@@]3(C(=O)Nc4cc(Cl)ccc43)[C@@H](c3cc(Cl)cs3)[C@H]12] | 0.47 | 394 | G |
| A-5s | 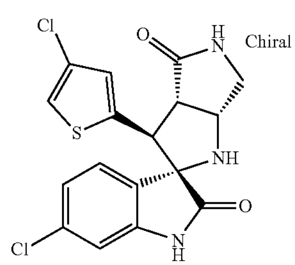 | 0.47 | 394 | G |
| A-5t | 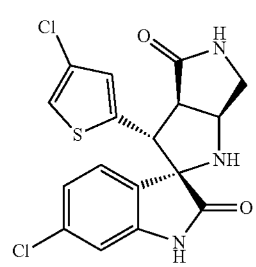 [SMILES: O=C1NC[C@H]2N[C@@]3(C(=O)Nc4cc(Cl)ccc43)[C@H](c3cc(Cl)cs3)[C@@H]12] | 0.47 | 394 | G |

TABLE 21-continued
| # | structure | $t_{ret}$ [min] | [M + H]$^+$ | HPLC method |
|---|---|---|---|---|
| A-5u | 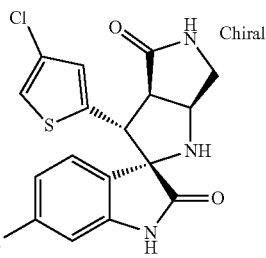 | 0.47 | 394 | G |
| A-5v | 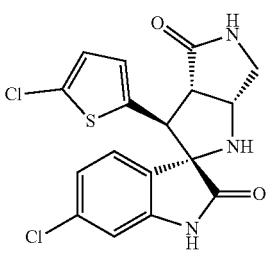 [SMILES: O=C1NC[C@@H]2N[C@@]3(C(=O)Nc4cc(Cl)ccc43)[C@@H](c3ccc(Cl)s3)[C@H]12] | 0.39 | 394 | A |
| A-5w | 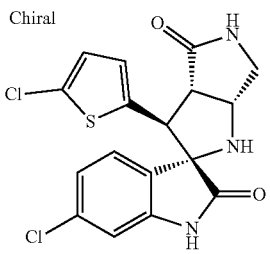 | 0.39 | 394 | A |
| A-5x | 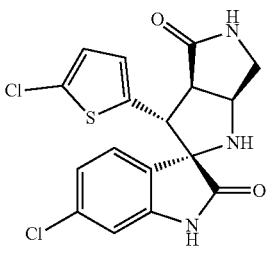 [SMILES: O=C1NC[C@H]2N[C@@]3(C(=O)Nc4cc(Cl)ccc43)[C@H](c3ccc(Cl)s3)[C@@H]12] | 0.39 | 394 | A |
| A-5y | 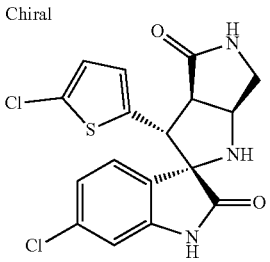 | 0.39 | 394 | A |
| A-5z | 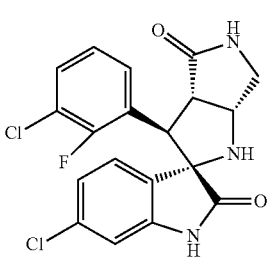 [SMILES: O=C1NC[C@@H]2N[C@@]3(C(=O)Nc4cc(Cl)ccc43)[C@@H](c3cccc(Cl)c3F)[C@H]12] | 0.99 | 406 | A |

TABLE 21-continued
| # | structure | $t_{ret}$ [min] | [M + H]⁺ | HPLC method |
|---|---|---|---|---|
| A-5aa | 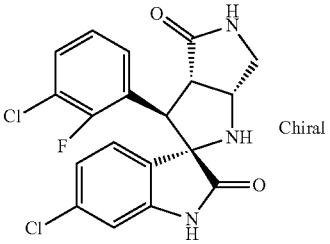 | 0.99 | 406 | A |
| A-5ab | 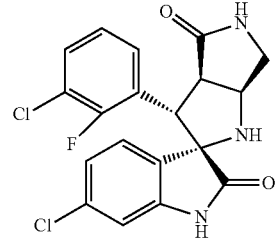 [SMILES: O=C1NC[C@H]2N[C@@]3(C(=O)Nc4cc(Cl)ccc43)[C@H](c3cccc(Cl)c3F)[C@@H]12] | 0.80 | 406 | K |
| A-5ac | 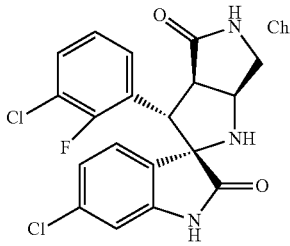 | 0.80 | 406 | K |
| A-5ad | 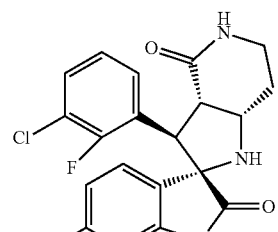 | 0.49 | 420 | G |
| A-5ae | 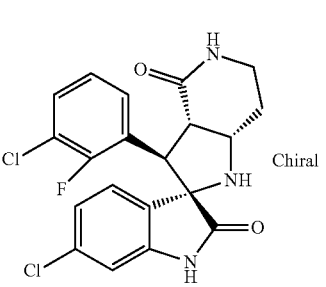 | 0.49 | 420 | G |
| A-5af | 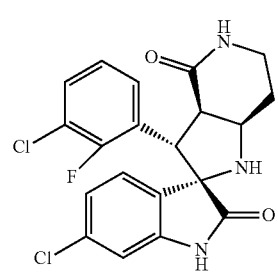 [SMILES: O=C1NCC[C@H]2N[C@@]3(C(=O)Nc4cc(Cl)ccc43)[C@H](c3cccc(Cl)c3F)[C@@H]12] | 0.45 | 420 | G |

Synthesis of Intermediates A-9 (Method F)

Experimental Procedure for the Synthesis of A-9a

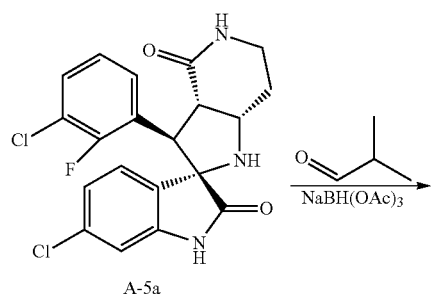

A-5a

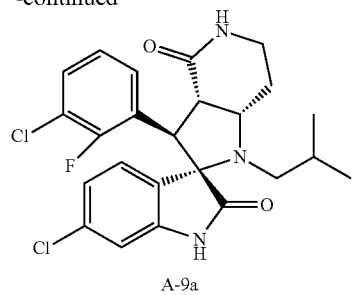

A-9a

A-5a (120 mg, 0.29 mmol) and isobutyraldehyde (62 mL, 0.86 mmol) are dissolved in AcOH (5 mL), and sodium triacetoxyborohydride (0.30 g, 1.43 mmol) is added. The reaction mixture is stirred at rt for 30 min and another portion of sodium triacetoxyborohydride (0.30 g, 1.43 mmol) is added and stirring is continued for additional 30 min before deionized water is added. EtOAc is added and the phases are separated. After washing with water, the organic phase is dried with $MgSO_4$ and the solvents are removed under reduced pressure. If needed the product is purified using reversed phase HPLC resulting in purified A-9a.

The following intermediates A-9 (table 22) are available in analogous manner starting from different intermediates A-5.

TABLE 22

| # | structure | $t_{ret}$ [min] | $[M + H]^+$ | HPLC method |
|---|---|---|---|---|
| A-9a | 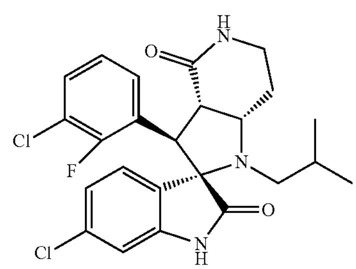 [SMILES: CC(C)CN1[C@H]2CCNC(=O)[C@H]2[C@H](c2cccc(Cl)c2F)[C@]12C(=O)Nc1cc(Cl)ccc12] | 0.74 | 476 | G |
| A-9b | Chiral | 0.74 | 476 | G |
| A-9c | 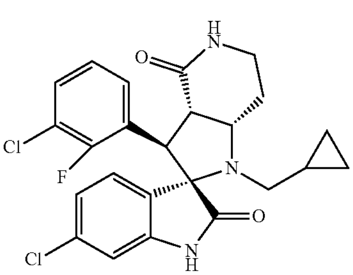 [SMILES: O=C1NCC[C@H]2[C@@H]1[C@H](c1cccc(Cl)c1F)[C@]1(C(=O)Nc3cc(Cl)ccc31)N2CC1CC1] | 1.29 | 474 | A |

TABLE 22-continued

| # | structure | $t_{ret}$ [min] | $[M + H]^+$ | HPLC method |
|---|---|---|---|---|
| A-9d | 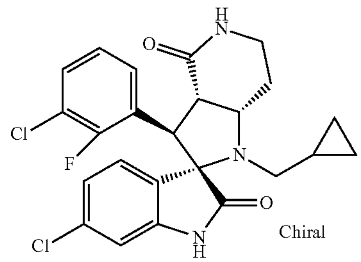 | 1.29 | 474 | A |
| A-9e | 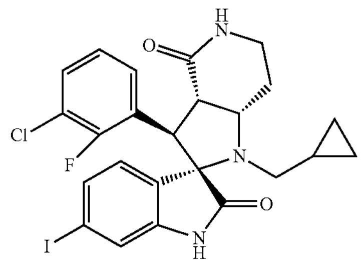 [SMILES: O=C1NCC[C@H]2[C@@H]1[C@H](c1cccc(Cl)c1F)[C@]1(C(=O)Nc3cc(I)ccc31)N2CC1CC1] | 0.73 | 566 | G |
| A-9f | 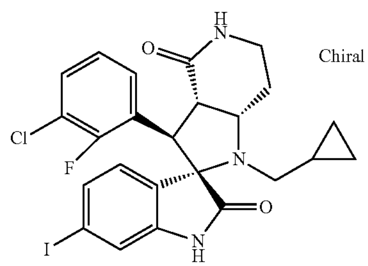 [SMILES: O=C1NCC[C@H]2[C@@H]1[C@H](c1cccc(Cl)c1F)[C@]1(C(=O)Nc3cc(I)ccc31)N2CC1CC1 ; "Chiral"] | n.a. | n.a. | |
| A-9g | 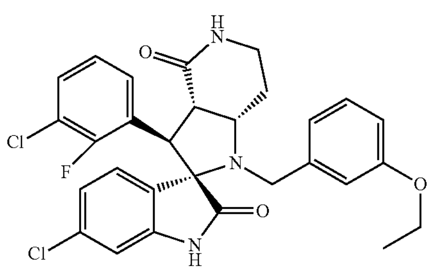 [SMILES: CCOc1cccc(CN2[C@H]3CCNC(=O)[C@H]3[C@H](c3cccc(Cl)c3F)[C@]23C(=O)Nc2cc(Cl)ccc23)c1] | 1.38 | 554 | A |
| A-9h | 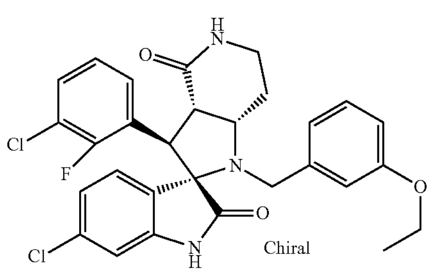 | 1.38 | 554 | A |
| A-9i | 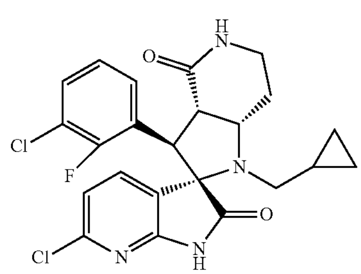 [SMILES: O=C1NCC[C@H]2[C@@H]1[C@H](c1cccc(Cl)c1F)[C@]1(C(=O)Nc3nc(Cl)ccc31)N2CC1CC1] | 1.19 | 475 | A |

TABLE 22-continued
| # | structure | $t_{ret}$ [min] | $[M + H]^+$ | HPLC method |
|---|---|---|---|---|
| A-9j | 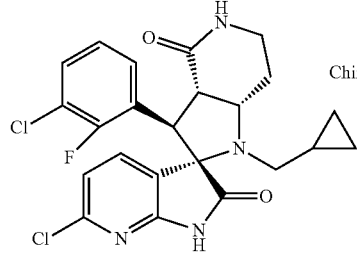 Chiral | 1.19 | 475 | A |
| A-9k | 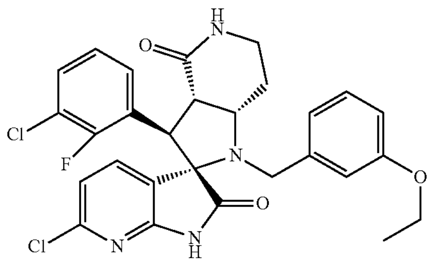 [SMILES: CCOc1cccc(CN2[C@H]3CCNC(=O)[C@H]3[C@H](c3cccc(Cl)c3F)[C@]23C(=O)Nc2nc(Cl)ccc23)c1] | 1.28 | 555 | A |
| A-9l |  Chiral | 1.28 | 555 | A |
| A-9m | 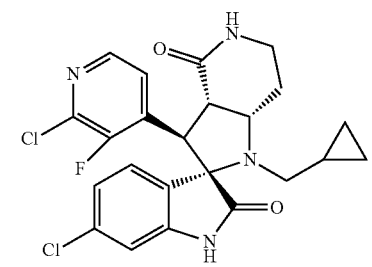 | 1.20 | 475 | A |
| A-9n | 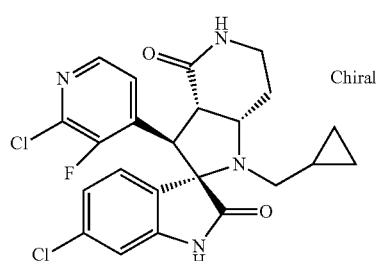 Chiral | 1.20 | 475 | A |
| A-9o | 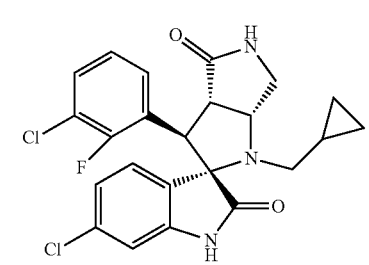 [SMILES: O=C1NC[C@H]2[C@@H]1[C@H](c1cccc(Cl)c1F)[C@]1(C(=O)Nc3cc(Cl)ccc31)N2CC1CC1] | 1.24 | 460 | A |

TABLE 22-continued

| # | structure | $t_{ret}$ [min] | [M + H]⁺ | HPLC method |
|---|---|---|---|---|
| A-9p | 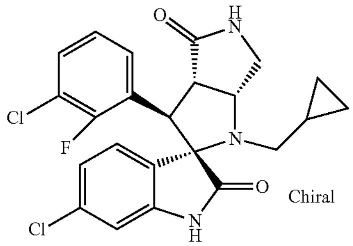 | 1.23 | 460 | A |
| A-9q | 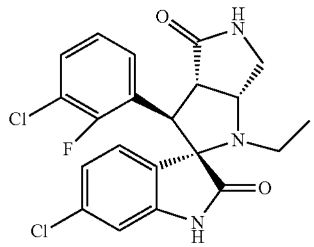 [SMILES: CCN1[C@H]2CNC(=O)[C@H]2[C@H](c2cccc(Cl)c2F)[C@]12C(=O)Nc1cc(Cl)ccc12] | 0.62 | 434 | G |
| A-9r | 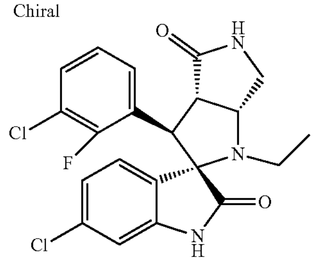 | 0.62 | 434 | G |
| A-9s | 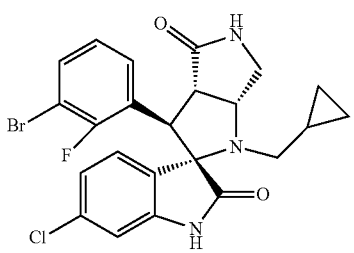 | 1.21 | 504 | A |
| A-9t | 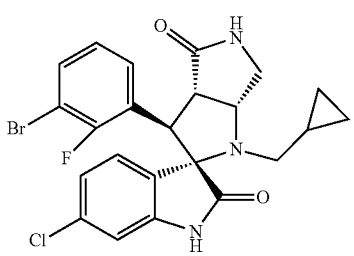 | 1.21 | 504 | A |
| A-9u | 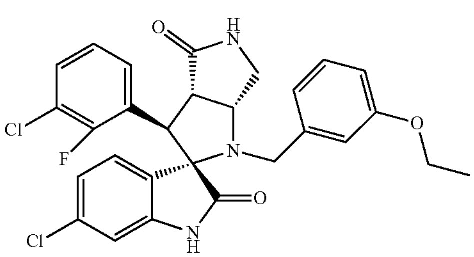 [SMILES: CCOc1cccc(CN2[C@H]3CNC(=O)[C@H]3[C@H](c3cccc(Cl)c3F)[C@]23C(=O)Nc2cc(Cl)ccc23)c1] | 1.47 | 540 | A |

TABLE 22-continued
| # | structure | $t_{ret}$ [min] | $[M + H]^+$ | HPLC method |
|---|---|---|---|---|
| A-9v | 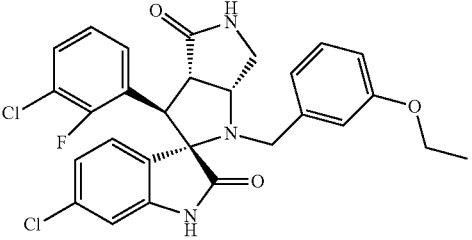 [SMILES: CCOc1cccc(CN2[C@H]3CNC(=O)[C@H]3[C@H](c3cccc(Cl)c3F)[C@]23C(=O)Nc2cc(Cl)ccc23)c1] | 1.47 | 540 | A |
| A-9w | 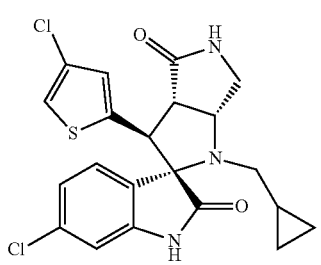 [SMILES: O=C1NC[C@H]2[C@@H]1[C@H](c1cc(Cl)cs1)[C@]1(C(=O)Nc3cc(Cl)ccc31)N2CC1CC1] | 1.19 | 448 | A |
| A-9x | 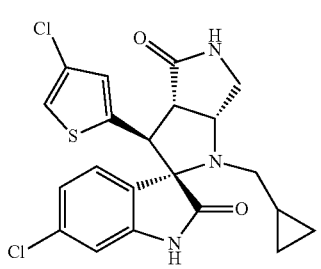 [SMILES: O=C1NC[C@H]2[C@@H]1[C@H](c1cc(Cl)cs1)[C@]1(C(=O)Nc3cc(Cl)ccc31)N2CC1CC1] | 1.19 | 448 | A |
| A-9y | 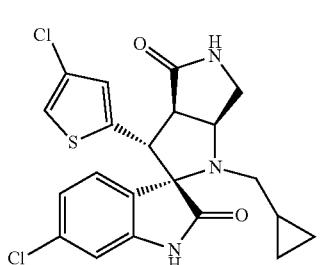 | 1.14 | 448 | A |
| A-9z | 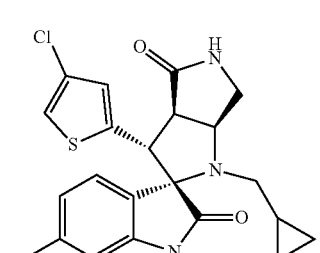 | 1.14 | 448 | A |
| A-9aa | 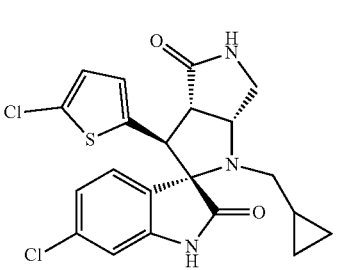 [SMILES: O=C1NC[C@H]2[C@@H]1[C@H](c1ccc(Cl)s1)[C@]1(C(=O)Nc3cc(Cl)ccc31)N2CC1CC1] | 1.19 | 448 | A |

TABLE 22-continued

| # | structure | $t_{ret}$ [min] | $[M + H]^+$ | HPLC method |
|---|---|---|---|---|
| A-9ab | 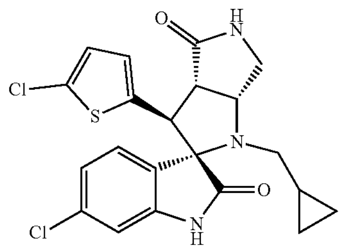 [SMILES: O=C1NC[C@H]2[C@@H]1[C@H](c1ccc(Cl)s1)[C@]1(C(=O)Nc3cc(Cl)ccc31)N2CC1CC1] | 1.19 | 448 | A |
| A-9ac | 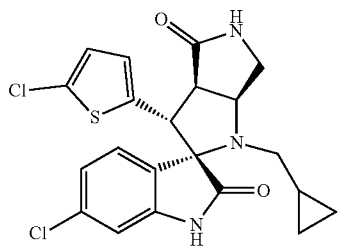 [SMILES: O=C1NC[C@@H]2[C@H]1[C@@H](c1ccc(Cl)s1)[C@]1(C(=O)Nc3cc(Cl)ccc31)N2CC1CC1] | 1.14 | 448 | A |
| A-9ad | 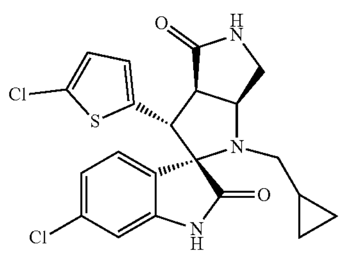 [SMILES: O=C1NC[C@@H]2[C@H]1[C@@H](c1ccc(Cl)s1)[C@]1(C(=O)Nc3cc(Cl)ccc31)N2CC1CC1] | 1.14 | 448 | A |
| A-9ae | 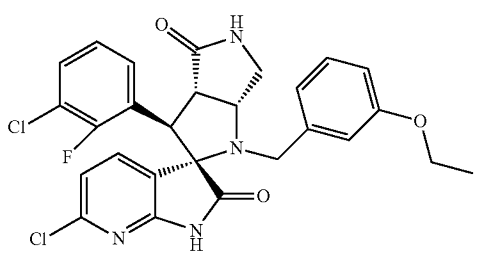 [SMILES: CCOc1cccc(CN2[C@H]3CNC(=O)[C@H]3[C@H](c3cccc(Cl)c3F)[C@]23C(=O)Nc2nc(Cl)ccc23)c1] | 1.25 | 541 | A |
| A-9af | 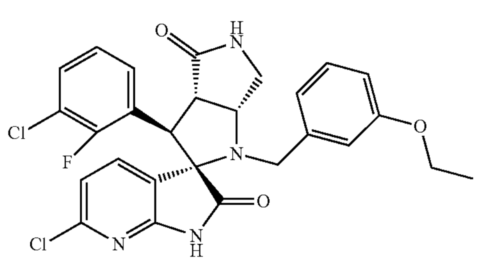 [SMILES: CCOc1cccc(CN2[C@H]3CNC(=O)[C@H]3[C@H](c3cccc(Cl)c3F)[C@]23C(=O)Nc2nc(Cl)ccc23)c1] | 1.25 | 541 | A |

Synthesis of Intermediates A-11 (Method G)

Experimental Procedure for the Synthesis of A-11a

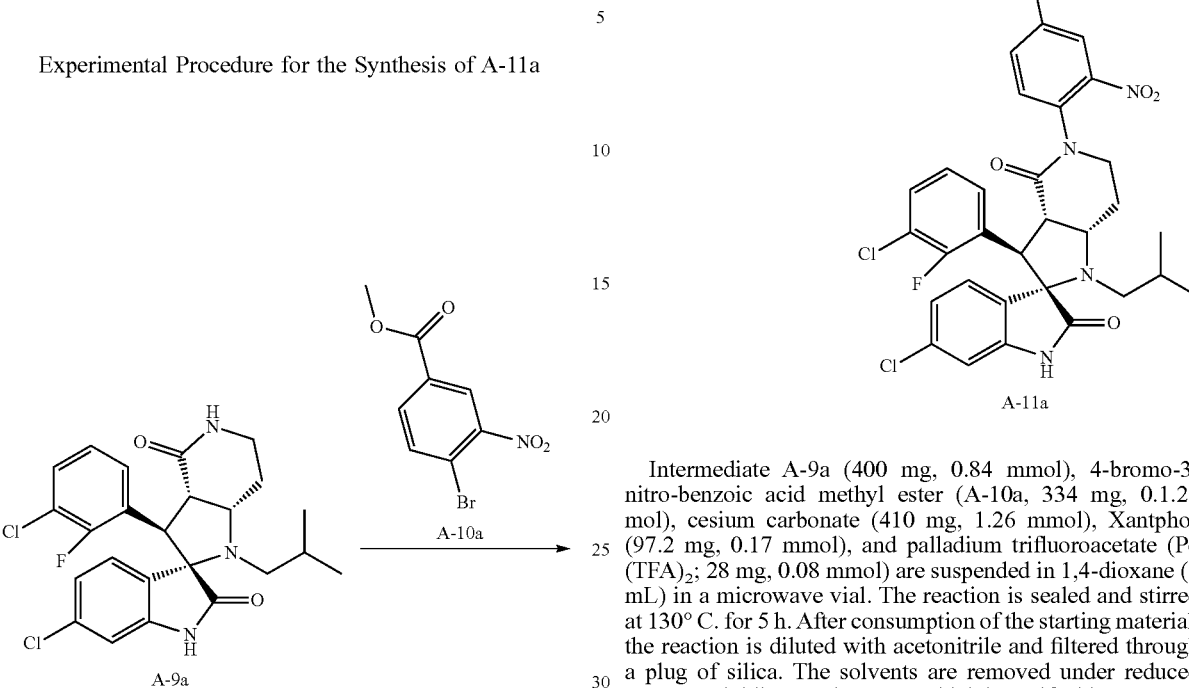

Intermediate A-9a (400 mg, 0.84 mmol), 4-bromo-3-nitro-benzoic acid methyl ester (A-10a, 334 mg, 0.1.26 mol), cesium carbonate (410 mg, 1.26 mmol), Xantphos (97.2 mg, 0.17 mmol), and palladium trifluoroacetate (Pd (TFA)$_2$; 28 mg, 0.08 mmol) are suspended in 1,4-dioxane (8 mL) in a microwave vial. The reaction is sealed and stirred at 130° C. for 5 h. After consumption of the starting material, the reaction is diluted with acetonitrile and filtered through a plug of silica. The solvents are removed under reduced pressure yielding crude A-11a which is purified by reversed phase column chromatography if necessary.

The following intermediates A-11 (table 23) are available in an analogous manner starting from different intermediates A-9 and A-10.

TABLE 23

| # | structure | $t_{ret}$ [min] | [M + H]+ | HPLC methold |
|---|-----------|-----------------|----------|--------------|
| A-11a | 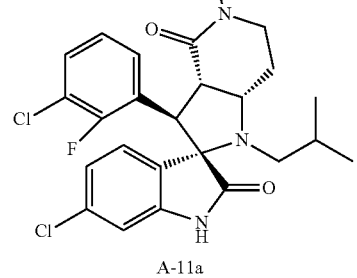 | 1.00 | 655 | G |

TABLE 23-continued

| # | structure | t_ret [min] | [M + H]+ | HPLC method |
|---|-----------|-------------|----------|-------------|
| A-11b | Chiral | 0.93 | 655 | D |
| A-11c | 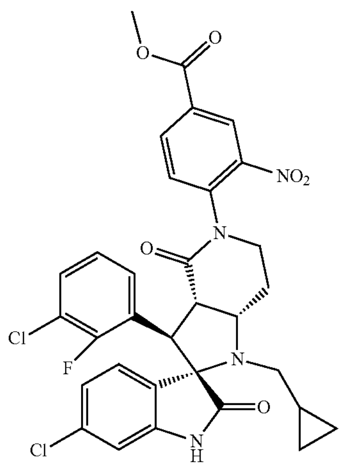 [SMILES: COC(=O)c1ccc(N2CC[C@H]3[C@@H](C2=O)[C@H](c2cccc(Cl)c2F)[C@]2(C(=O)Nc4cc(Cl)ccc42)N3CC2CC2)c([N+](=O)[O-])c1] | 0.88 | 653 | G |
| A-11d | Chiral | 0.90 | 653 | D |

TABLE 23-continued
| # | structure | $t_{ret}$ [min] | [M + H]+ | HPLC methold |
|---|---|---|---|---|
| A-11e | Chiral 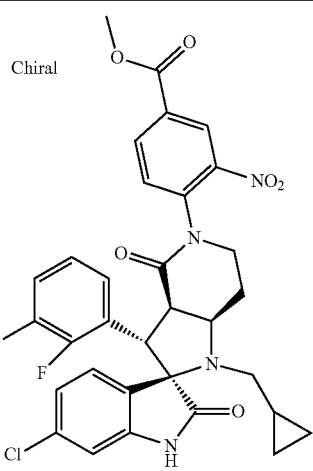 | 0.90 | 653 | D |
| A-11f | 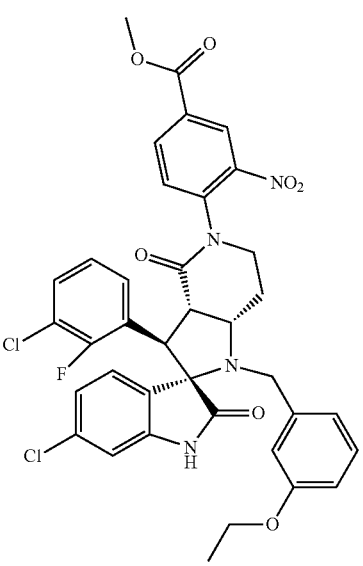 [SMILES: CCOc1cccc(CN2[C@H]3CCN(c4ccc(C(=O)OC)cc4[N+](=O)[O-])C(=O)[C@H]3[C@H](c3cccc(Cl)c3F)[C@]23C(=O)Nc2cc(Cl)ccc23)c1] | 0.91 | 733 | G |
| A-11g | Chiral 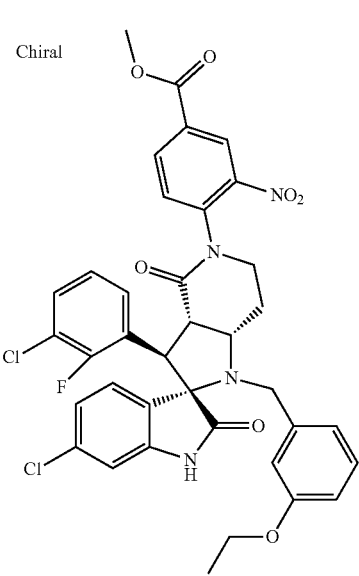 [SMILES: CCOc1cccc(CN2[C@H]3CCN(c4ccc(C(=O)OC)cc4[N+](=O)[O-])C(=O)[C@H]3[C@H](c3cccc(Cl)c3F)[C@]23C(=O)Nc2cc(Cl)ccc23)c1 ; "Chiral"] | 0.91 | 733 | G |

TABLE 23-continued
| # | structure | $t_{ret}$ [min] | [M + H]+ | HPLC methold |
|---|---|---|---|---|
| A-11h | 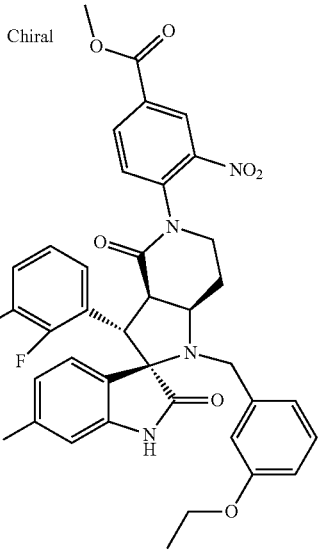 | 0.91 | 733 | G |
| A-11i | 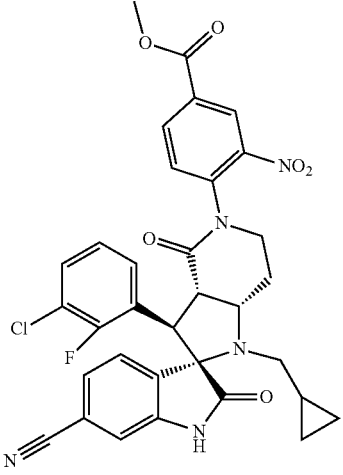 [SMILES: COC(=O)c1ccc(N2CC[C@H]3[C@@H](C2=O)[C@H](c2cccc(Cl)c2F)[C@]2(C(=O)Nc4cc(C#N)ccc42)N3CC2CC2)c([N+](=O)[O-])c1] | 0.80 | 644 | G |
| A-11j | 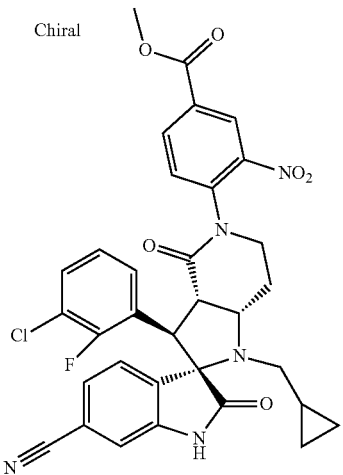 [SMILES: COC(=O)c1ccc(N2CC[C@H]3[C@@H](C2=O)[C@H](c2cccc(Cl)c2F)[C@]2(C(=O)Nc4cc(C#N)ccc42)N3CC2CC2)c([N+](=O)[O-])c1 ; "Chiral"] | 0.80 | 644 | G |

TABLE 23-continued
| # | structure | $t_{ret}$ [min] | [M + H]+ | HPLC methold |
|---|---|---|---|---|
| A-11k | 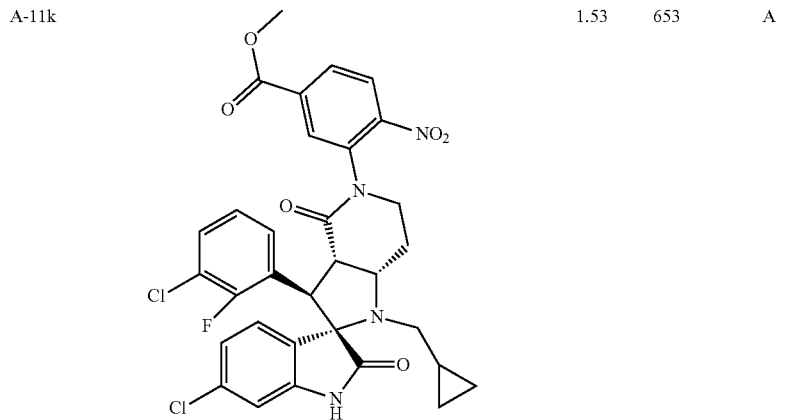 | 1.53 | 653 | A |
| A-11l | 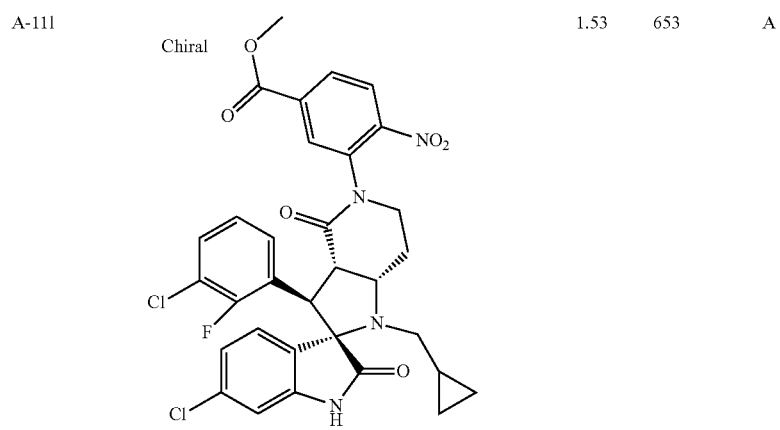 Chiral | 1.53 | 653 | A |
| A-11m | 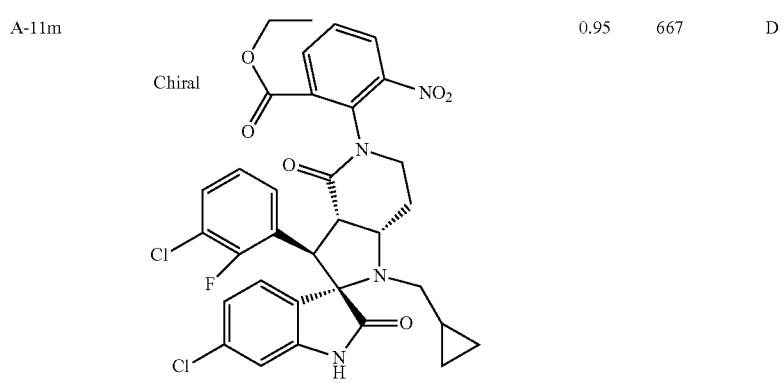 Chiral | 0.95 | 667 | D |

TABLE 23-continued

| # | structure | t_ret [min] | [M + H]+ | HPLC methold |
|---|---|---|---|---|
| A-11n | 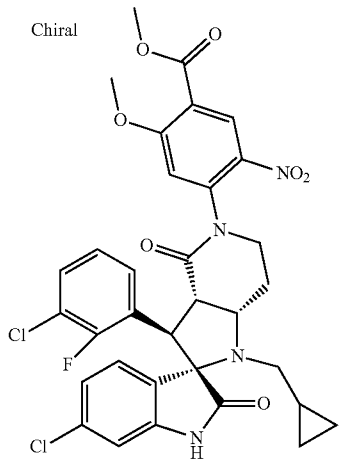 [SMILES: COC(=O)c1cc([N+](=O)[O-])c(N2CC[C@H]3[C@@H](C2=O)[C@H](c2cccc(Cl)c2F)[C@]2(C(=O)Nc4cc(Cl)ccc42)N3CC2CC2)cc1OC ; "Chiral"] | 0.85 | 683 | G |
| A-11o | 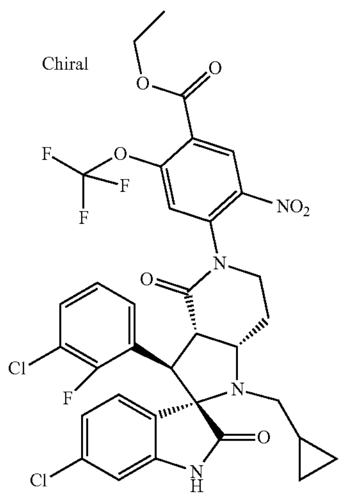 | 0.97 | 751 | G |
| A-11p | 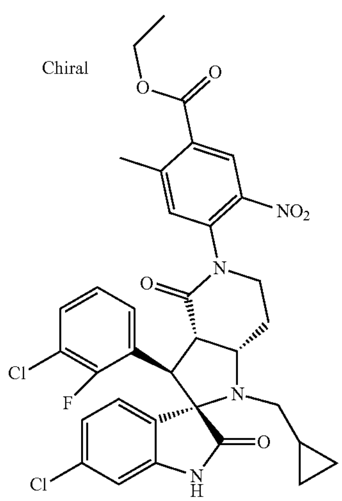 | 0.97 | 681 | D |

TABLE 23-continued
| # | structure | $t_{ret}$ [min] | [M + H]+ | HPLC methold |
|---|-----------|-----------------|----------|--------------|
| A-11q | 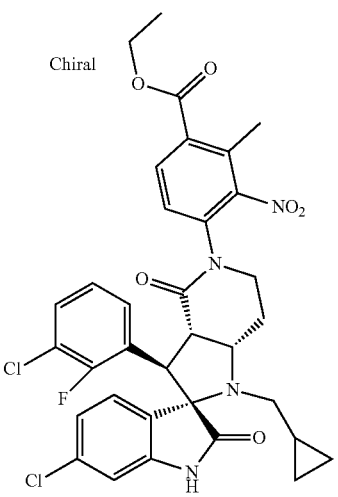 | 0.90 | 667 | G |
| A-11r | 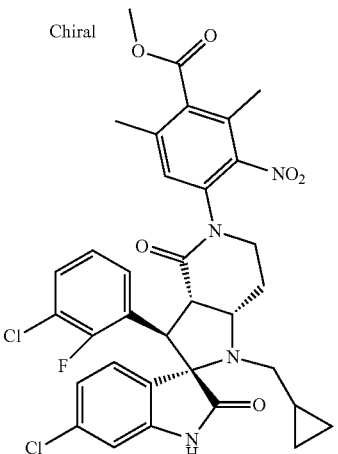 | 0.91 | 681 | G |
| A-11s | 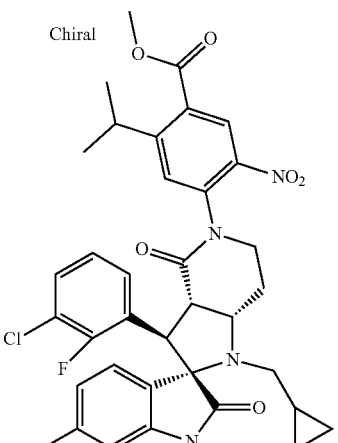 | 0.96 | 695 | G |

TABLE 23-continued
| # | structure | $t_{ret}$ [min] | [M + H]+ | HPLC methold |
|---|---|---|---|---|
| A-11t | 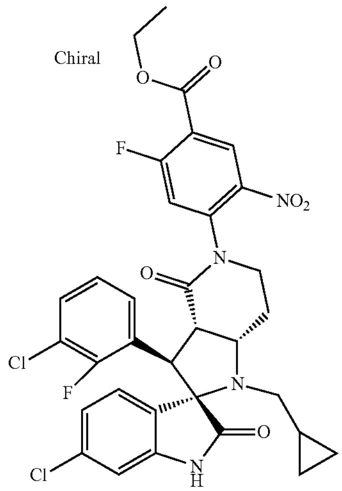 | 0.96 | 685 | D |
| A-11u | 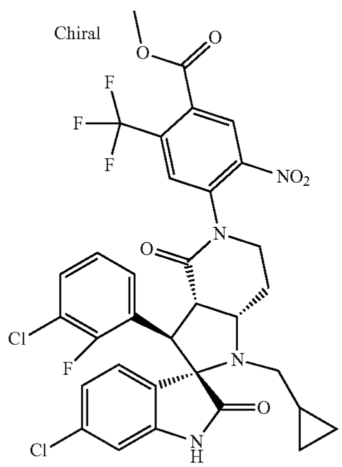 | 0.92 | 721 | G |
| A-11v | 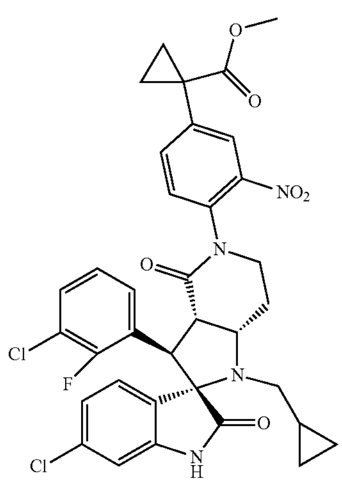 [SMILES: COC(=O)C1(c2ccc(N3CC[C@H]4[C@@H](C3=O)[C@H](c3cccc(Cl)c3F)[C@]3(C(=O)Nc5cc(Cl)ccc53)N4CC3CC3)c([N+](=O)[O-])c2)CC1] | 0.89 | 693 | G |

TABLE 23-continued
| # | structure | t_ret [min] | [M + H]+ | HPLC methold |
|---|---|---|---|---|
| A-11w | 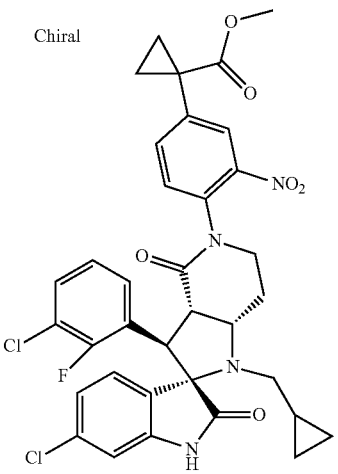 [SMILES: COC(=O)C1(c2ccc(N3CC[C@H]4[C@@H](C3=O)[C@H](c3cccc(Cl)c3F)[C@]3(C(=O)Nc5cc(Cl)ccc53)N4CC3CC3)c([N+](=O)[O-])c2)CC1 ; "Chiral"] | 0.89 | 693 | G |
| A-11x | 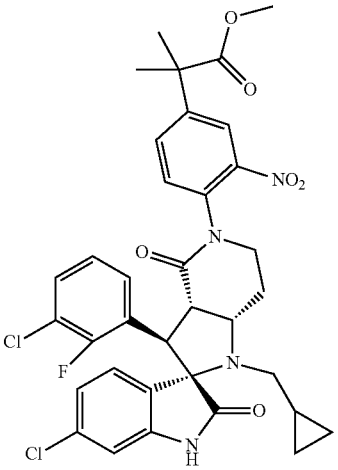 [SMILES: COC(=O)C(C)(C)c1ccc(N2CC[C@H]3[C@@H](C2=O)[C@H](c2cccc(Cl)c2F)[C@]2(C(=O)Nc4cc(Cl)ccc42)N3CC2CC2)c([N+](=O)[O-])c1] | 0.91 | 695 | G |
| A-11y | 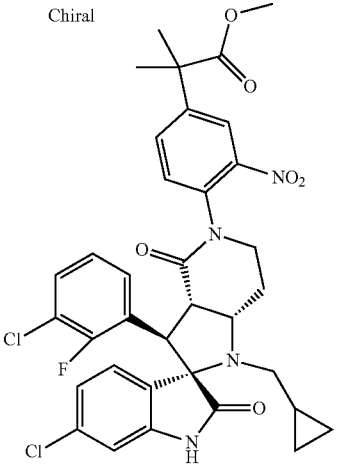 [SMILES: COC(=O)C(C)(C)c1ccc(N2CC[C@H]3[C@@H](C2=O)[C@H](c2cccc(Cl)c2F)[C@]2(C(=O)Nc4cc(Cl)ccc42)N3CC2CC2)c([N+](=O)[O-])c1 ; "Chiral"] | 0.91 | 695 | G |

TABLE 23-continued

| # | structure | $t_{ret}$ [min] | [M + H]+ | HPLC methold |
|---|---|---|---|---|
| A-11z | 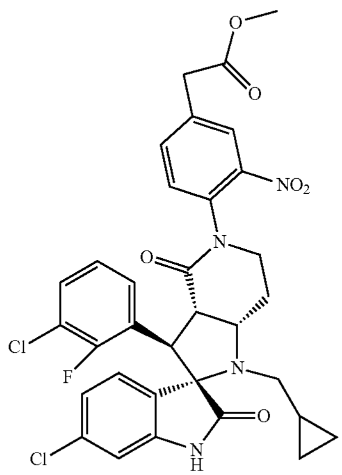 [SMILES: COC(=O)Cc1ccc(N2CC[C@H]3[C@@H](C2=O)[C@H](c2cccc(Cl)c2F)[C@]2(C(=O)Nc4cc(Cl)ccc42)N3CC2CC2)c([N+](=O)[O-])c1] | 0.85 | 667 | G |
| A-11aa | Chiral | 0.85 | 667 | G |
| A-11ab | 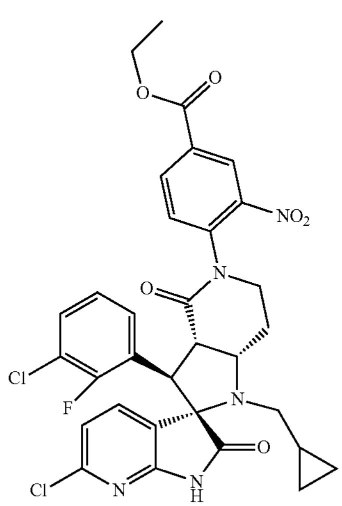 [SMILES: CCOC(=O)c1ccc(N2CC[C@H]3[C@@H](C2=O)[C@H](c2cccc(Cl)c2F)[C@]2(C(=O)Nc4nc(Cl)ccc42)N3CC2CC2)c([N+](=O)[O-])c1] | 0.55 | 640 | E |

TABLE 23-continued
| # | structure | $t_{ret}$ [min] | [M + H]+ | HPLC methold |
|---|---|---|---|---|
| A-11ac | 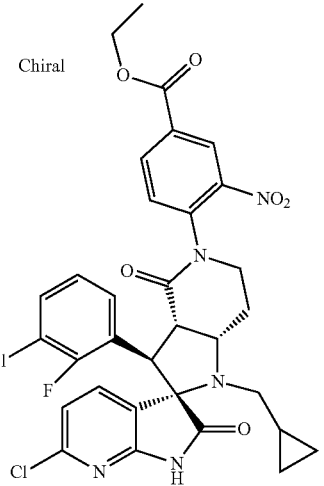 Chiral | 0.55 | 640 | E |
| A-11ad | 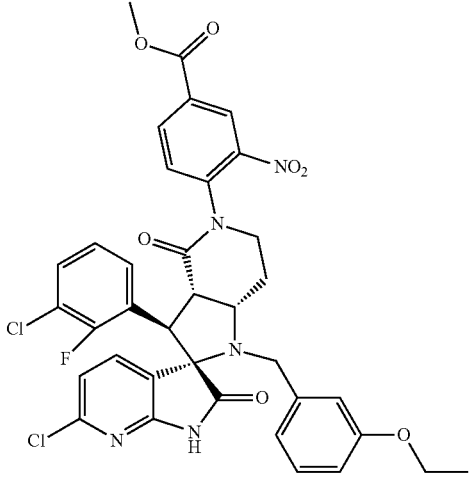 [SMILES: CCOc1cccc(CN2[C@H]3CCN(c4ccc(C(=O)OC)cc4[N+](=O)[O-])C(=O)[C@H]3[C@H](c3cccc(Cl)c3F)[C@]23C(=O)Nc2nc(Cl)ccc23)c1] | 0.89 | 734 | F |
| A-11ae | 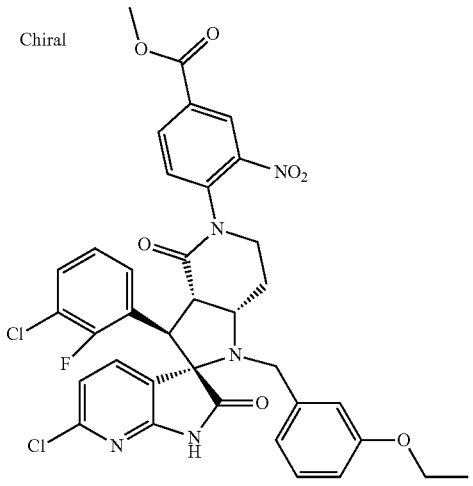 [SMILES: CCOc1cccc(CN2[C@H]3CCN(c4ccc(C(=O)OC)cc4[N+](=O)[O-])C(=O)[C@H]3[C@H](c3cccc(Cl)c3F)[C@]23C(=O)Nc2nc(Cl)ccc23)c1 ; "Chiral"] Chiral | 0.89 | 734 | F |

TABLE 23-continued
| # | structure | t_ret [min] | [M + H]+ | HPLC methold |
|---|---|---|---|---|
| A-11af | 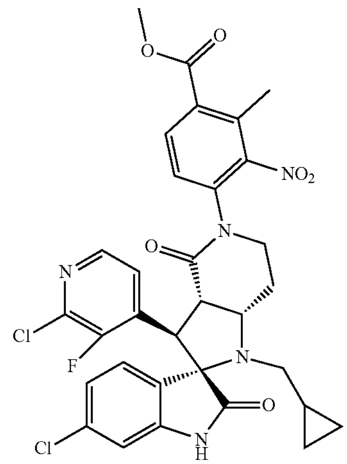 [SMILES: COC(=O)c1ccc(N2CC[C@H]3[C@@H](C2=O)[C@H](c2ccnc(Cl)c2F)[C@]2(C(=O)Nc4cc(Cl)ccc42)N3CC2CC2)c([N+](=O)[O-])c1C] | 0.86 | 668 | G |
| A-11ag | 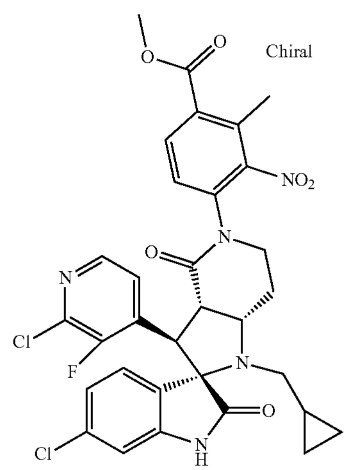 | 0.86 | 668 | G |
| A-11ah | 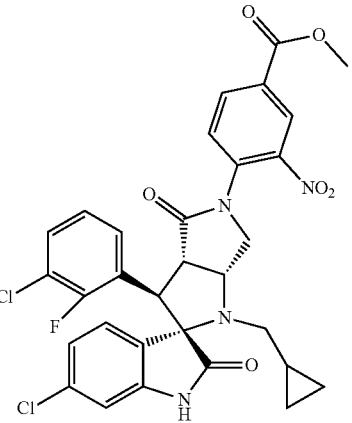 | 0.87 | 639 | G |

TABLE 23-continued
| # | structure | $t_{ret}$ [min] | [M + H]+ | HPLC methold |
|---|---|---|---|---|
| A-11ai | Chiral 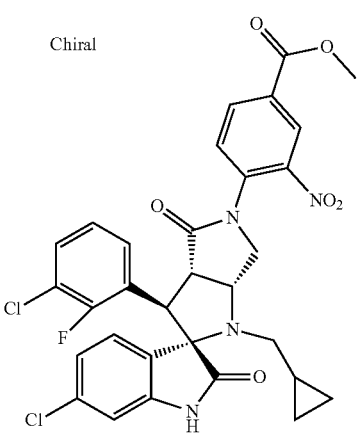 [SMILES: COC(=O)c1ccc(N2C[C@H]3[C@@H](C2=O)[C@H](c2cccc(Cl)c2F)[C@]2(C(=O)Nc4cc(Cl)ccc42)N3CC2CC2)c([N+](=O)[O-])c1 ; "Chiral"] | 0.88 | 639 | G |
| A-11aj | Chiral 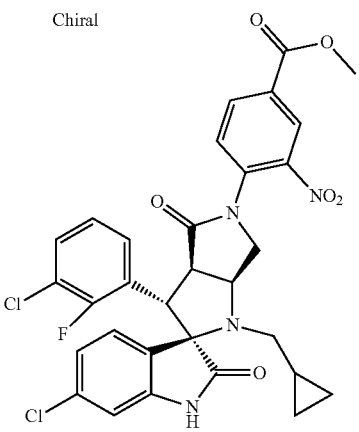 [SMILES: COC(=O)c1ccc(N2C[C@@H]3[C@H](C2=O)[C@@H](c2cccc(Cl)c2F)[C@@]2(C(=O)Nc4cc(Cl)ccc42)N3CC2CC2)c([N+](=O)[O-])c1 ; "Chiral"] | 0.88 | 639 | G |
| A-11ak | 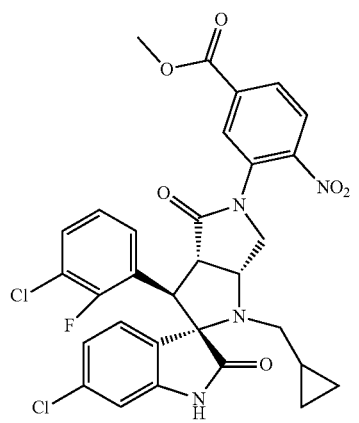 [SMILES: COC(=O)c1ccc([N+](=O)[O-])c(N2C[C@H]3[C@@H](C2=O)[C@H](c2cccc(Cl)c2F)[C@]2(C(=O)Nc4cc(Cl)ccc42)N3CC2CC2)c1] | 0.89 | 639 | F |

TABLE 23-continued

| # | structure | t_ret [min] | [M + H]+ | HPLC methold |
|---|---|---|---|---|
| A-11al | 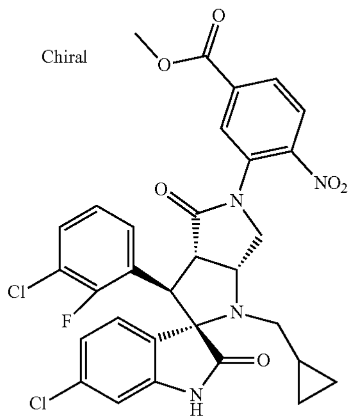 [SMILES: COC(=O)c1ccc([N+](=O)[O-])c(N2C[C@H]3[C@@H](C2=O)[C@H](c2cccc(Cl)c2F)[C@]2(C(=O)Nc4cc(Cl)ccc42)N3CC2CC2)c1] | 0.89 | 639 | F |
| A-11am | 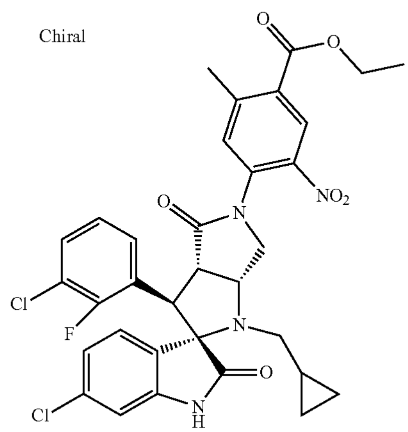 [SMILES: CCOC(=O)c1cc([N+](=O)[O-])c(N2C[C@H]3[C@@H](C2=O)[C@H](c2cccc(Cl)c2F)[C@]2(C(=O)Nc4cc(Cl)ccc42)N3CC2CC2)cc1C ; "Chiral"] | 0.93 | 677 | G |
| A-11an | 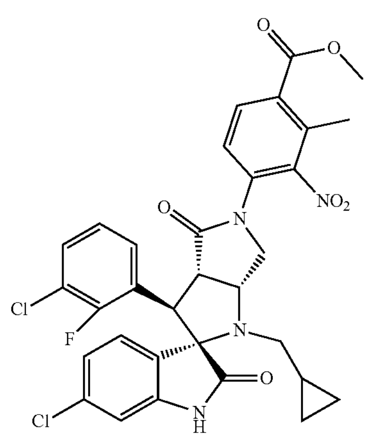 [SMILES: COC(=O)c1ccc(N2C[C@H]3[C@@H](C2=O)[C@H](c2cccc(Cl)c2F)[C@]2(C(=O)Nc4cc(Cl)ccc42)N3CC2CC2)c([N+](=O)[O-])c1C] | 0.89 | 653 | G |

TABLE 23-continued
| # | structure | $t_{ret}$ [min] | [M + H]+ | HPLC method |
|---|---|---|---|---|
| A-11ao | Chiral 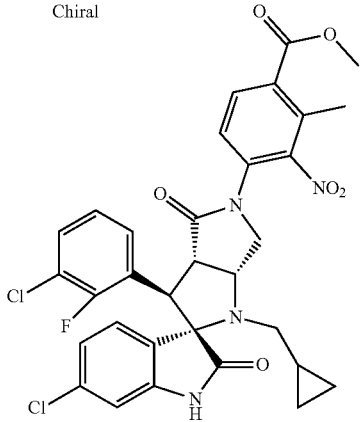 [SMILES: COC(=O)c1ccc(N2C[C@H]3[C@@H](C2=O)[C@H](c2cccc(Cl)c2F)[C@]2(C(=O)Nc4cc(Cl)ccc42)N3CC2CC2)c([N+](=O)[O-])c1C ; "Chiral"] | 0.89 | 653 | G |
| A-11ap | 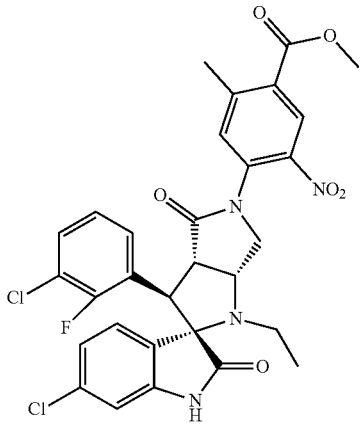 [SMILES: CCN1[C@H]2CN(c3cc(C)c(C(=O)OC)cc3[N+](=O)[O-])C(=O)[C@H]2[C@H](c2cccc(Cl)c2F)[C@]12C(=O)Nc1cc(Cl)ccc12] | 0.87 | 627 | G |
| A-11aq | Chiral 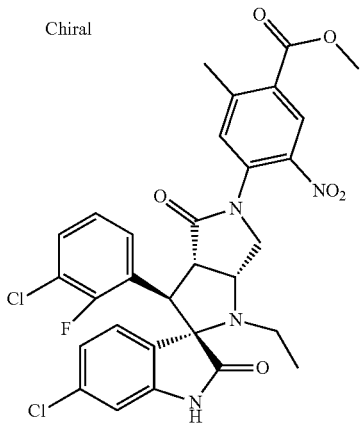 [SMILES: CCN1[C@H]2CN(c3cc(C)c(C(=O)OC)cc3[N+](=O)[O-])C(=O)[C@H]2[C@H](c2cccc(Cl)c2F)[C@]12C(=O)Nc1cc(Cl)ccc12 ; "Chiral"] | 0.87 | 627 | G |

TABLE 23-continued

| # | structure | $t_{ret}$ [min] | [M + H]+ | HPLC methold |
|---|---|---|---|---|
| A-11ar | 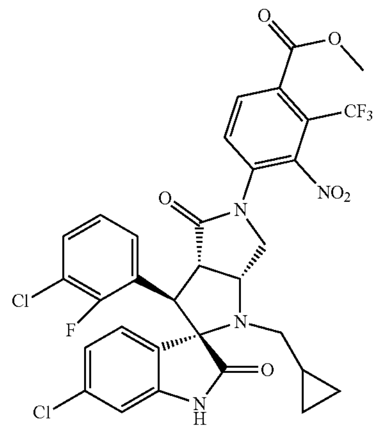 [SMILES: COC(=O)c1ccc(N2C[C@H]3[C@@H](C2=O)[C@H](c2cccc(Cl)c2F)[C@]2(C(=O)Nc4cc(Cl)ccc42)N3CC2CC2)c([N+](=O)[O-])c1C(F)(F)F] | 0.92 | 707 | G |
| A-11as | Chiral | 0.92 | 707 | G |
| A-11at | 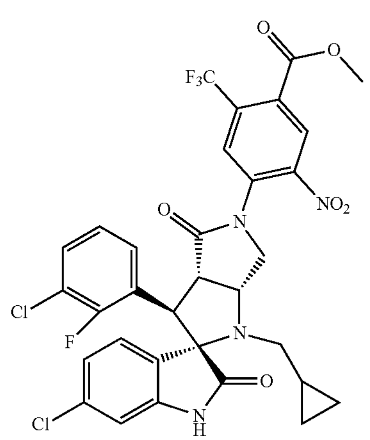 [SMILES: COC(=O)c1cc([N+](=O)[O-])c(N2C[C@H]3[C@@H](C2=O)[C@H](c2cccc(Cl)c2F)[C@]2(C(=O)Nc4cc(Cl)ccc42)N3CC2CC2)cc1C(F)(F)F] | 0.92 | 707 | G |

TABLE 23-continued
| # | structure | $t_{ret}$ [min] | [M + H]+ | HPLC method |
|---|---|---|---|---|
| A-11au | 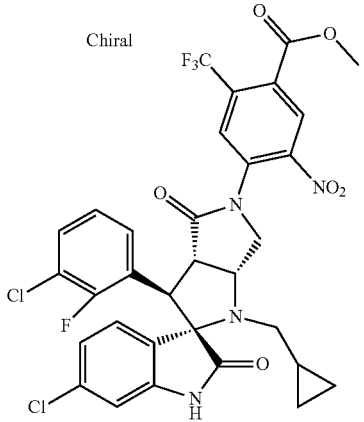 [SMILES: COC(=O)c1cc([N+](=O)[O-])c(N2C[C@H]3[C@@H](C2=O)[C@H](c2cccc(Cl)c2F)[C@]2(C(=O)Nc4cc(Cl)ccc42)N3CC2CC2)cc1C(F)(F)F ; "Chiral"] | 0.92 | 707 | G |
| A-11av | 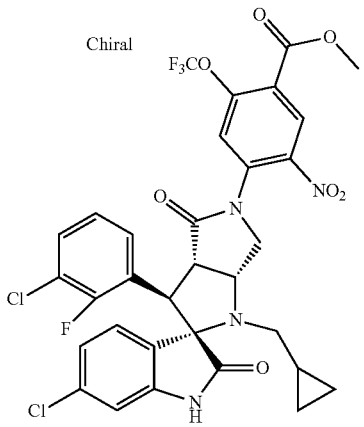 [SMILES: COC(=O)c1cc([N+](=O)[O-])c(N2C[C@H]3[C@@H](C2=O)[C@H](c2cccc(Cl)c2F)[C@]2(C(=O)Nc4cc(Cl)ccc42)N3CC2CC2)cc1OC(F)(F)F ; "Chiral"] | 0.96 | 737 | G |
| A-11aw | 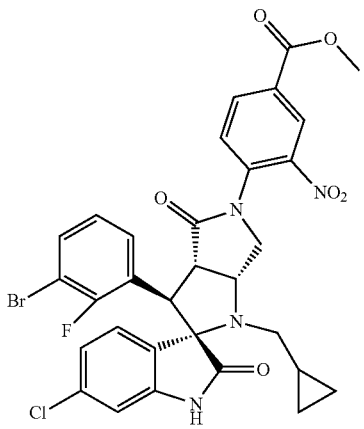 | 0.89 | 683 | G |

TABLE 23-continued
| # | structure | $t_{ret}$ [min] | [M + H]+ | HPLC methold |
|---|---|---|---|---|
| A-11ax | 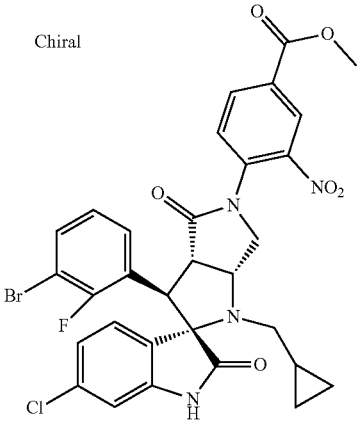 Chiral | 0.89 | 683 | G |
| A-11ay | 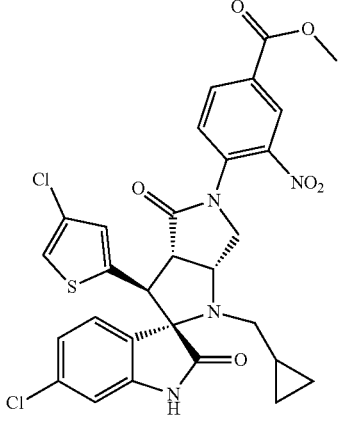 [SMILES: COC(=O)c1ccc(N2C[C@H]3[C@@H](C2=O)[C@H](c2cc(Cl)cs2)[C@]2(C(=O)Nc4cc(Cl)ccc42)N3CC2CC2)c([N+](=O)[O-])c1] | 0.87 | 627 | G |
| A-11az | 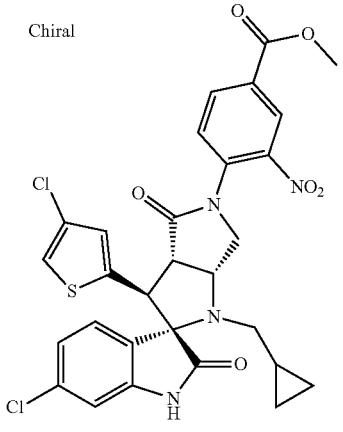 [SMILES: COC(=O)c1ccc(N2C[C@H]3[C@@H](C2=O)[C@H](c2cc(Cl)cs2)[C@]2(C(=O)Nc4cc(Cl)ccc42)N3CC2CC2)c([N+](=O)[O-])c1 ; "Chiral"] Chiral | 0.87 | 627 | G |

TABLE 23-continued

| # | structure | $t_{ret}$ [min] | [M + H]+ | HPLC methold |
|---|---|---|---|---|
| A-11ba | 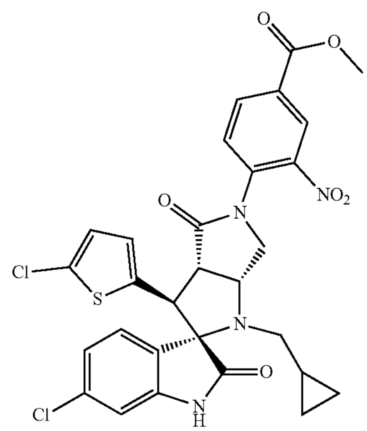 [SMILES: COC(=O)c1ccc(N2C[C@H]3[C@@H](C2=O)[C@H](c2ccc(Cl)s2)[C@]2(C(=O)Nc4cc(Cl)ccc42)N3CC2CC2)c([N+](=O)[O-])c1] | 0.88 | 627 | G |
| A-11bb | Chiral | 0.88 | 627 | G |
| A-11bc | 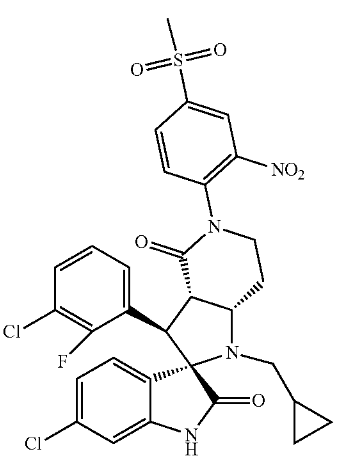 [SMILES: CS(=O)(=O)c1ccc(N2CC[C@H]3[C@@H](C2=O)[C@H](c2cccc(Cl)c2F)[C@]2(C(=O)Nc4cc(Cl)ccc42)N3CC2CC2)c([N+](=O)[O-])c1] | 0.80 | 673 | G |

TABLE 23-continued

| # | structure | $t_{ret}$ [min] | [M + H]+ | HPLC methold |
|---|---|---|---|---|
| A-11bd | Chiral | 0.81 | 673 | G |
| A-11be | 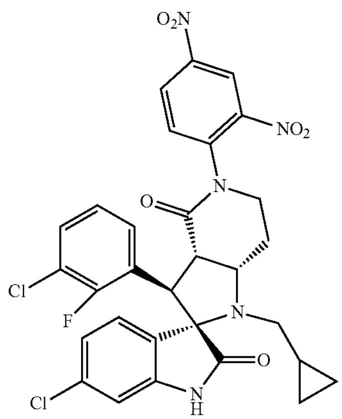 [SMILES: O=C1[C@@H]2[C@H](CCN1c1ccc([N+](=O)[O-])cc1[N+](=O)[O-])N(CC1CC1)[C@@]1(C(=O)Nc3cc(Cl)ccc31)[C@H]2c1cccc(Cl)c1F] | 1.50 | 640 | A |
| A-11bf | Chiral | 1.50 | 640 | A |

TABLE 23-continued
| # | structure | t_ret [min] | [M + H]+ | HPLC methold |
|---|---|---|---|---|
| A-11bg | Chiral 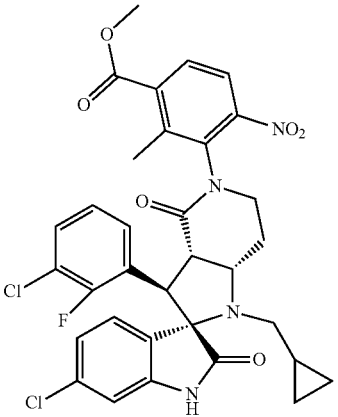 | 0.91 | 667 | E |
| A-11bh | Chiral 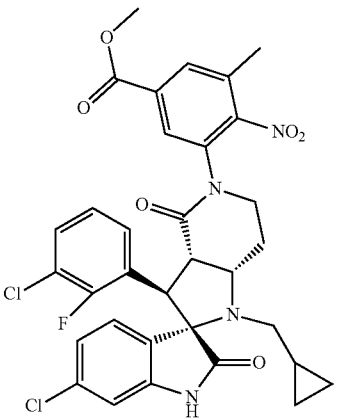 | 0.93 | 667 | E |
| A-11bi | Chiral 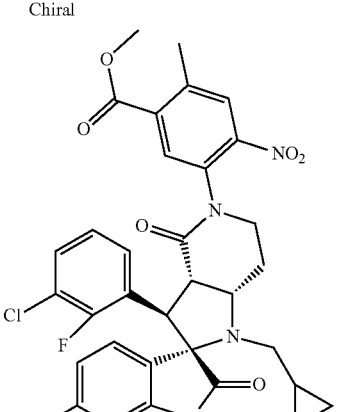 | 0.92 | 667 | E |

Synthesis of Compounds (Ib) According to the Invention (Method H)

Experimental Procedure for the Synthesis of Ib-1

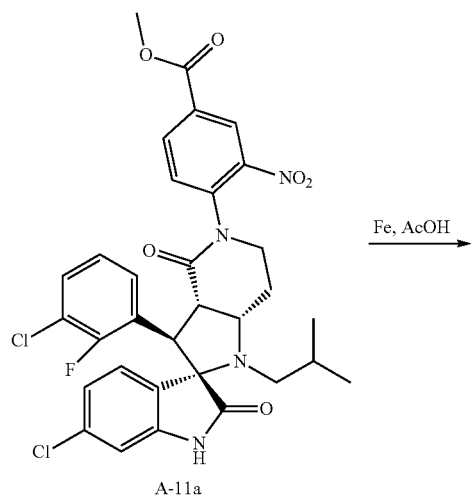

A-11a

Fe, AcOH →

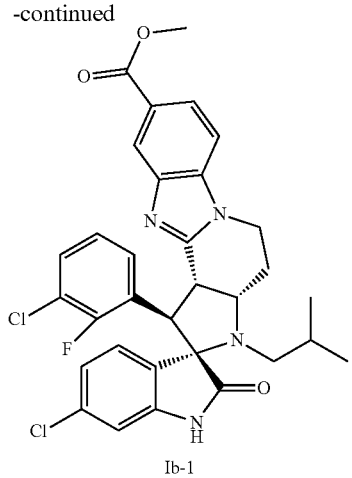

Ib-1

A-11a (533 mg, 0.8 mmol) is dissolved in acetic acid (10 mL) and iron powder (469 mg, 8.4 mmol) is added. The suspension is heated to 130° C. overnight. After addition of EtOAc and saturated aqueous $Na_2CO_3$ solution, the phases are separated and the organic phase is dried by the addition of $MgSO_4$. Removal of the solvents yields crude Ib-1, which is of sufficient purity for the further derivatisation or purified by reversed phase column chromatography.

The following compounds (Ib) according to the invention (table 24) are available in an analogous manner starting from different intermediates A-11.

TABLE 24

| # | structure | $t_{ret}$ [min] | $[M + H]^+$ | HPLC method |
|---|---|---|---|---|
| Ib-1 | 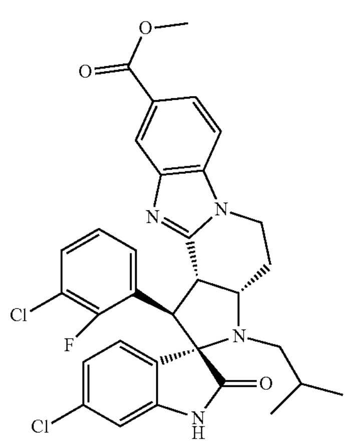 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CC(C)C] | 0.86 | 607 | G |

TABLE 24-continued
| # | structure | $t_{ret}$ [min] | $[M + H]^+$ | HPLC method |
|---|---|---|---|---|
| Ib-2 | 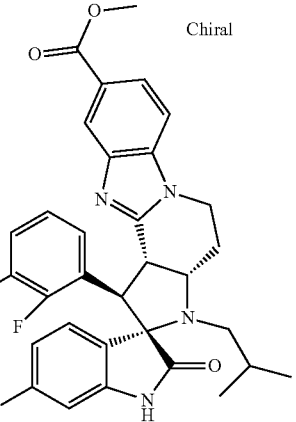 Chiral | 0.92 | 607 | B |
| Ib-3 | 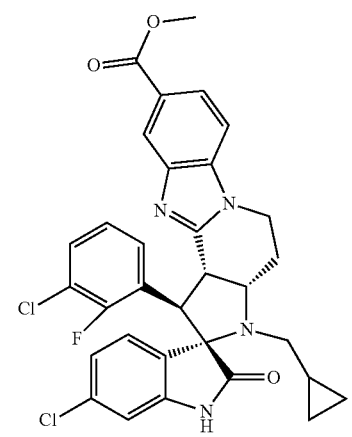 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CC1CC1] | 1.52 | 605 | A |
| Ib-4 | 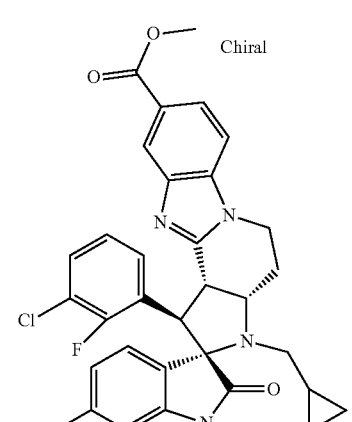 Chiral | 1.52 | 605 | A |

TABLE 24-continued
| # | structure | $t_{ret}$ [min] | $[M + H]^+$ | HPLC method |
|---|---|---|---|---|
| Ib-5 | 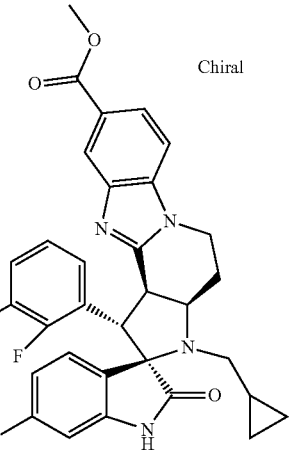 | 1.52 | 605 | A |
| Ib-6 | 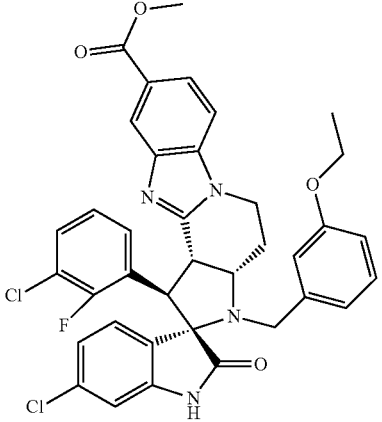 [SMILES: CCOc1cccc(CN2[C@H]3CCn4c(nc5cc(C(=O)OC)ccc54)[C@H]3[C@H](c3cccc(Cl)c3F)[C@]23C(=O)Nc2cc(Cl)ccc23)c1] | 0.54 | 685 | D |
| Ib-7 | 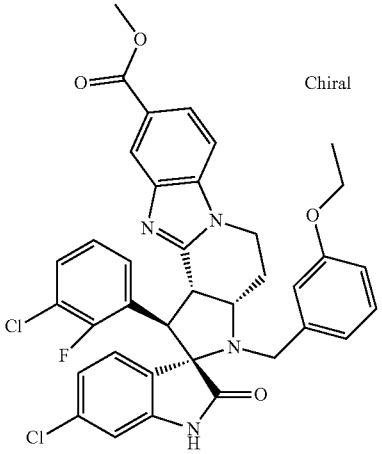 [SMILES: CCOc1cccc(CN2[C@H]3CCn4c(nc5cc(C(=O)OC)ccc54)[C@H]3[C@H](c3cccc(Cl)c3F)[C@]23C(=O)Nc2cc(Cl)ccc23)c1 ; "Chiral"] | 0.54 | 685 | D |

TABLE 24-continued
| # | structure | $t_{ret}$ [min] | $[M + H]^+$ | HPLC method |
|---|---|---|---|---|
| Ib-8 | 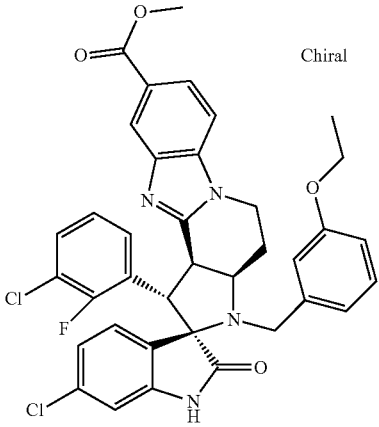 [SMILES: CCOc1cccc(CN2[C@@H]3CCn4c(nc5cc(C(=O)OC)ccc54)[C@@H]3[C@@H](c3cccc(Cl)c3F)[C@@]23C(=O)Nc2cc(Cl)ccc23)c1 ; "Chiral"] Chiral | 0.54 | 685 | D |
| Ib-9 | 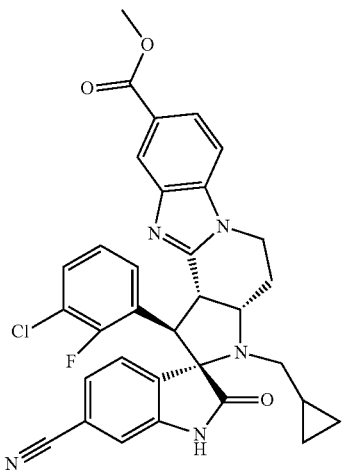 [SMILES: COC(=O)c1ccc2c(c1)nc1n2CC[C@H]2[C@@H]1[C@H](c1cccc(Cl)c1F)[C@]1(C(=O)Nc3cc(C#N)ccc31)N2CC1CC1] | 0.74 | 596 | G |
| Ib-10 | 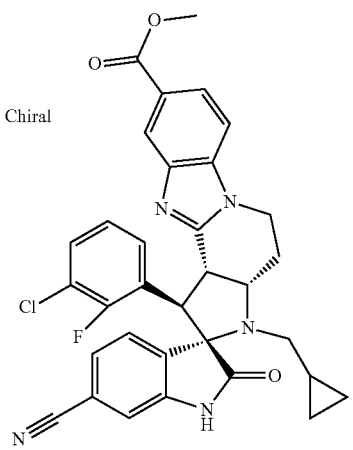 [SMILES: COC(=O)c1ccc2c(c1)nc1n2CC[C@H]2[C@@H]1[C@H](c1cccc(Cl)c1F)[C@]1(C(=O)Nc3cc(C#N)ccc31)N2CC1CC1 ; "Chiral"] Chiral | 0.74 | 596 | G |

TABLE 24-continued

| # | structure | t_ret [min] | [M + H]+ | HPLC method |
|---|---|---|---|---|
| Ib-11 | | 0.81 | 605 | G |
| Ib-12 Chiral | | 0.81 | 605 | G |
| Ib-13 Chiral | | 0.97 | 619 | D |

TABLE 24-continued
| # | structure | t_ret [min] | [M + H]+ | HPLC method |
|---|---|---|---|---|
| Ib-14 | 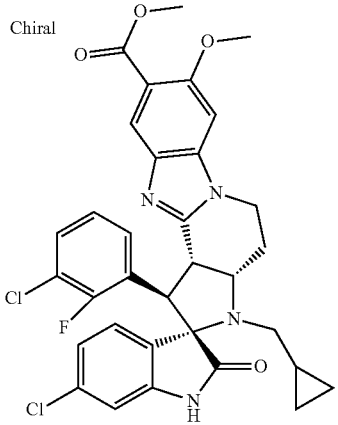 | 0.73 | 635 | G |
| Ib-15 | 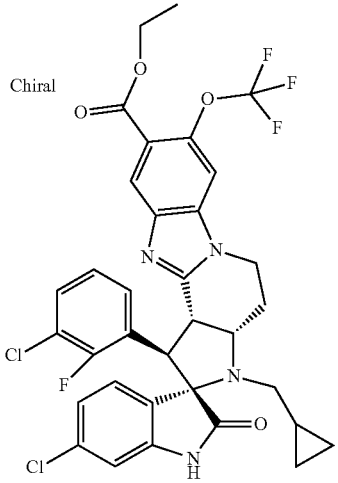 | 0.97 | 703 | G |
| Ib-16 | 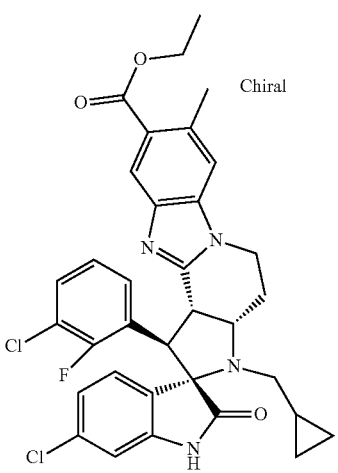 [SMILES: CCOC(=O)c1cc2nc3n(c2cc1C)CC[C@H]1[C@@H]3[C@H](c2cccc(Cl)c2F)[C@]2(C(=O)Nc3cc(Cl)ccc32)N1CC1CC1 ; "Chiral"] | 0.87 | 633 | G |

TABLE 24-continued
| # | structure | t_ret [min] | [M + H]+ | HPLC method |
|---|---|---|---|---|
| Ib-17 | 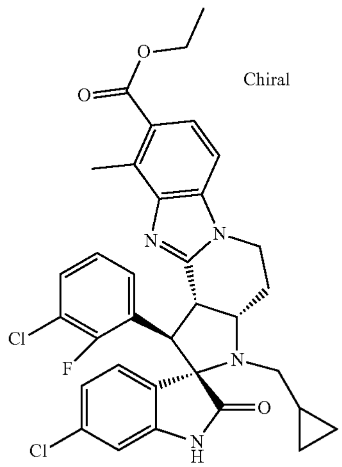 [SMILES: CCOC(=O)c1ccc2c(nc3n2CC[C@H]2[C@@H]3[C@H](c3cccc(Cl)c3F)[C@]3(C(=O)Nc4cc(Cl)ccc43)N2CC2CC2)c1C ; "Chiral"] | 0.85 | 619 | G |
| Ib-18 | 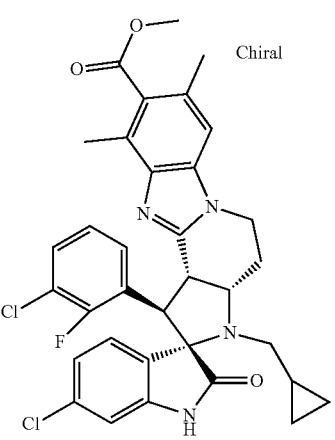 [SMILES: COC(=O)c1c(C)cc2c(nc3n2CC[C@H]2[C@@H]3[C@H](c3cccc(Cl)c3F)[C@]3(C(=O)Nc4cc(Cl)ccc43)N2CC2CC2)c1C ; "Chiral"] | 0.83 | 633 | G |
| Ib-19 | 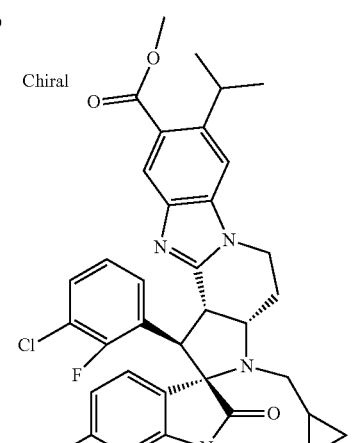 | 0.89 | 647 | G |

TABLE 24-continued
| # | structure | t_ret [min] | [M + H]+ | HPLC method |
|---|---|---|---|---|
| Ib-20 | 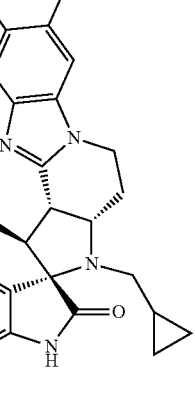 | 0.96 | 685 | D |
| Ib-21 | 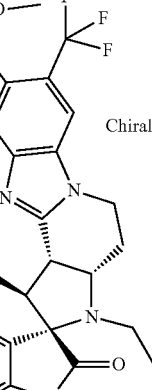 | 0.92 | 673 | G |
| Ib-22 | 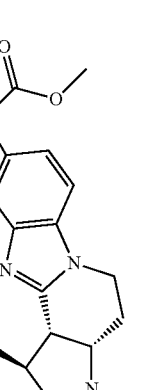 | 0.81 | 645 | G |

TABLE 24-continued
| # | structure | t_ret [min] | [M + H]+ | HPLC method |
|---|---|---|---|---|
| Ib-23 | 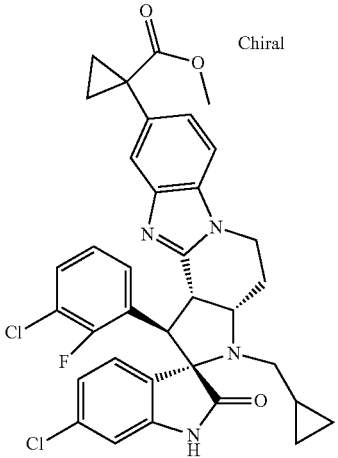 Chiral | 0.81 | 645 | G |
| Ib-24 | 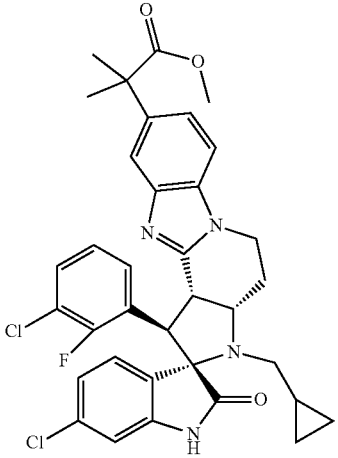 [SMILES: COC(=O)C(C)(C)c1ccc2c(c1)nc1n2CC[C@H]2[C@@H]1[C@H](c1cccc(Cl)c1F)[C@]1(C(=O)Nc3cc(Cl)ccc31)N2CC1CC1] | 0.80 | 647 | G |
| Ib-25 | 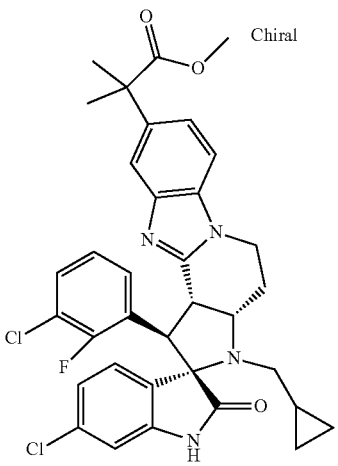 Chiral | 0.80 | 647 | G |

TABLE 24-continued

| # | structure | $t_{ret}$ [min] | $[M + H]^+$ | HPLC method |
|---|---|---|---|---|
| Ib-26 | 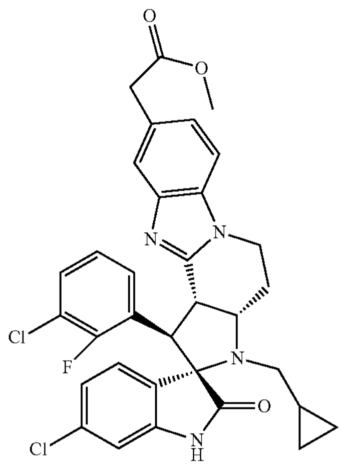 [SMILES: COC(=O)Cc1ccc2c(c1)nc1n2CC[C@H]2[C@@H]1[C@H](c1cccc(Cl)c1F)[C@]1(C(=O)Nc3cc(Cl)ccc31)N2CC1CC1] | 0.73 | 619 | G |
| Ib-27 | 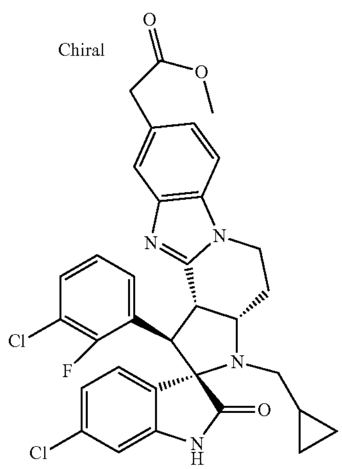 | 0.73 | 619 | G |
| Ib-28 | 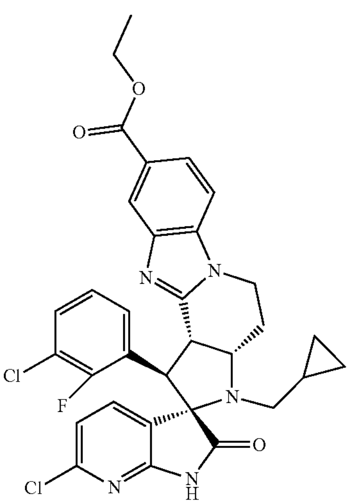 [SMILES: CCOC(=O)c1ccc2c(c1)nc1n2CC[C@H]2[C@@H]1[C@H](c1cccc(Cl)c1F)[C@]1(C(=O)Nc3nc(Cl)ccc31)N2CC1CC1] | n.a. | n.a. | n.a. |

TABLE 24-continued
| # | structure | $t_{ret}$ [min] | $[M + H]^+$ | HPLC method |
|---|---|---|---|---|
| Ib-29 | 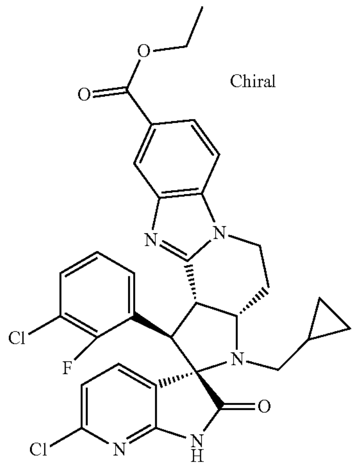 | n.a. | n.a. | n.a. |
| Ib-30 | 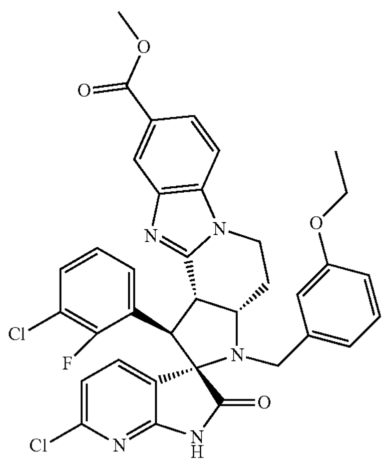 [SMILES: CCOc1cccc(CN2[C@H]3CCn4c(nc5cc(C(=O)OC)ccc54)[C@H]3[C@H](c3cccc(Cl)c3F)[C@]23C(=O)Nc2nc(Cl)ccc23)c1] | n.a. | n.a. | n.a. |
| Ib-31 | 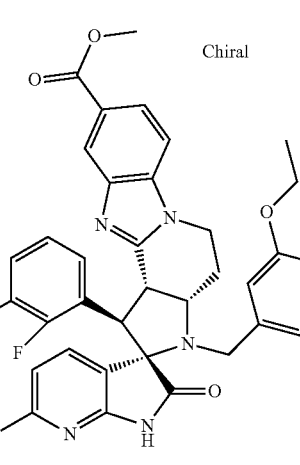 | n.a. | n.a. | n.a. |

TABLE 24-continued

| # | structure | t$_{ret}$ [min] | [M + H]$^+$ | HPLC method |
|---|---|---|---|---|
| Ib-32 | 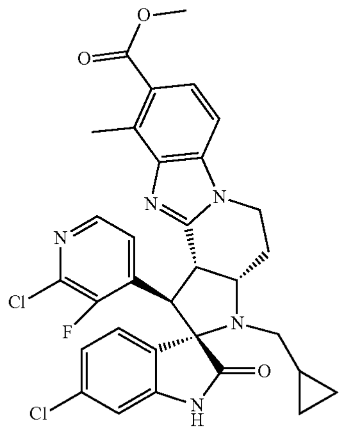 [SMILES: COC(=O)c1ccc2c(nc3n2CC[C@H]2[C@@H]3[C@H](c3ccnc(Cl)c3F)[C@]3(C(=O)Nc4cc(Cl)ccc43)N2CC2CC2)c1C] | 0.84 | 620 | G |
| Ib-33 | (Chiral) | 0.84 | 620 | G |
| Ib-34 | 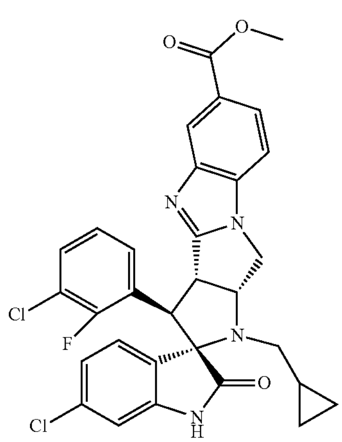 [SMILES: COC(=O)c1ccc2c(c1)nc1n2C[C@H]2[C@@H]1[C@H](c1cccc(Cl)c1F)[C@]1(C(=O)Nc3cc(Cl)ccc31)N2CC1CC1] | 0.84 | 591 | G |

TABLE 24-continued
| # | structure | $t_{ret}$ [min] | $[M + H]^+$ | HPLC method |
|---|---|---|---|---|
| Ib-35 | 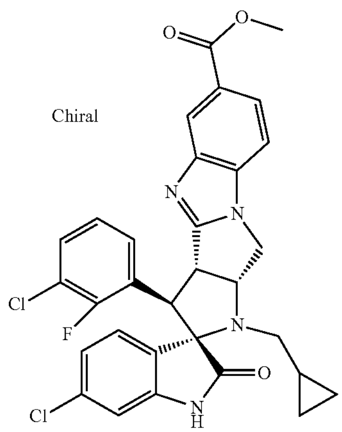 [SMILES: COC(=O)c1ccc2c(c1)nc1n2C[C@H]2[C@@H]1[C@H](c1cccc(Cl)c1F)[C@]1(C(=O)Nc3cc(Cl)ccc31)N2CC1CC1 ; "Chiral"] | 0.84 | 591 | G |
| Ib-36 | 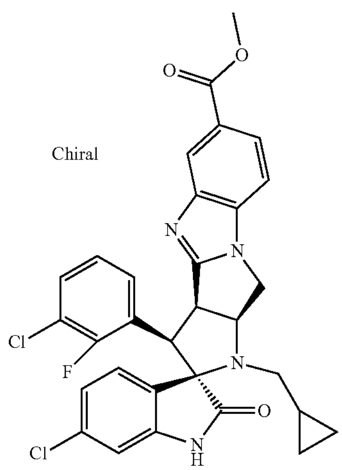 [SMILES: COC(=O)c1ccc2c(c1)nc1n2C[C@@H]2[C@H]1[C@H](c1cccc(Cl)c1F)[C@@]1(C(=O)Nc3cc(Cl)ccc31)N2CC1CC1 ; "Chiral"] | 0.84 | 591 | G |
| Ib-37 | 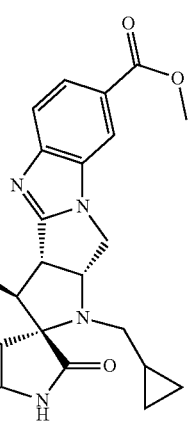 | 0.89 | 591 | E |

TABLE 24-continued
| # | structure | $t_{ret}$ [min] | $[M + H]^+$ | HPLC method |
|---|---|---|---|---|
| Ib-38 | 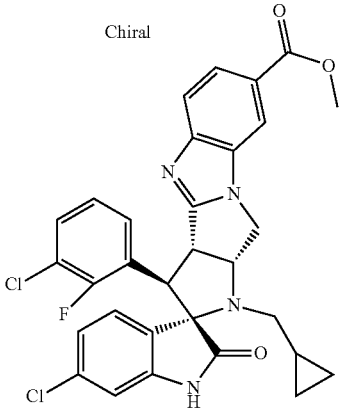 [SMILES: COC(=O)c1ccc2nc3n(c2c1)C[C@H]1[C@@H]3[C@H](c2cccc(Cl)c2F)[C@]2(C(=O)Nc3cc(Cl)ccc32)N1CC1CC1 ; "Chiral"] Chiral | 0.89 | 591 | E |
| Ib-39 | 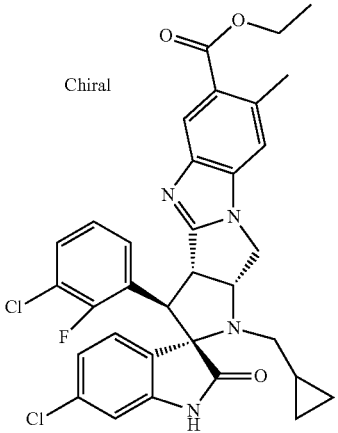 [SMILES: CCOC(=O)c1cc2nc3n(c2cc1C)C[C@H]1[C@@H]3[C@H](c2cccc(Cl)c2F)[C@]2(C(=O)Nc3cc(Cl)ccc32)N1CC1CC1 ; "Chiral"] Chiral | 0.90 | 619 | G |
| Ib-40 | 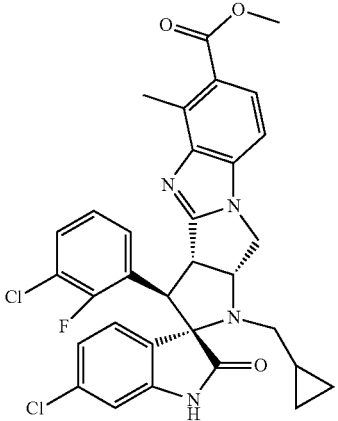 [SMILES: COC(=O)c1ccc2c(nc3n2C[C@H]2[C@@H]3[C@H](c3cccc(Cl)c3F)[C@]3(C(=O)Nc4cc(Cl)ccc43)N2CC2CC2)c1C] | 0.87 | 605 | G |

TABLE 24-continued
| # | structure | $t_{ret}$ [min] | $[M + H]^+$ | HPLC method |
|---|---|---|---|---|
| Ib-41 | 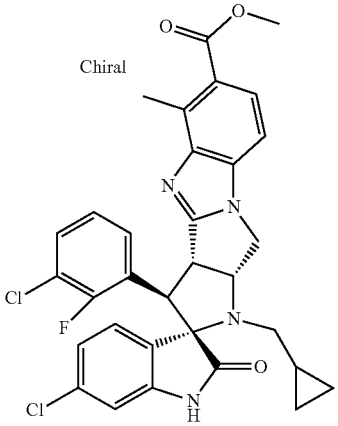 | 0.87 | 605 | G |
| Ib-42 | 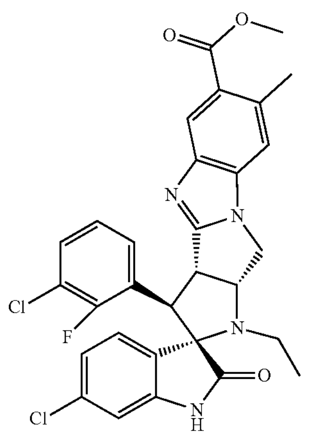 [SMILES: CCN1[C@H]2Cn3c(nc4cc(C(=O)OC)c(C)cc43)[C@H]2[C@H](c2cccc(Cl)c2F)[C@]12C(=O)Nc1cc(Cl)ccc12] | 0.83 | 579 | G |
| Ib-43 | 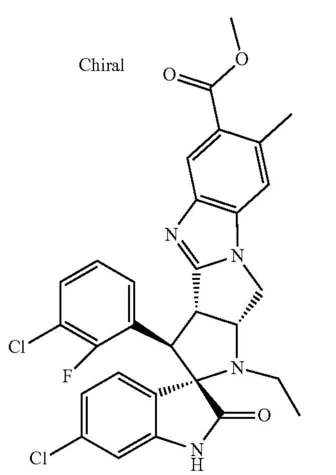 | 0.83 | 579 | G |

TABLE 24-continued
| # | structure | t_ret [min] | [M + H]+ | HPLC method |
|---|---|---|---|---|
| Ib-44 | 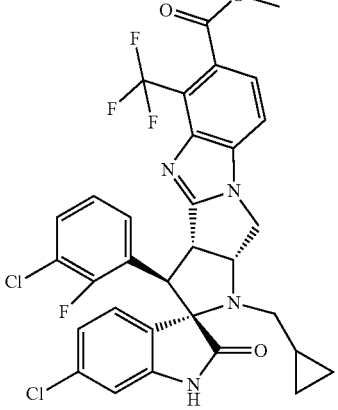 | 0.92 | 659 | G |
| Ib-45 | 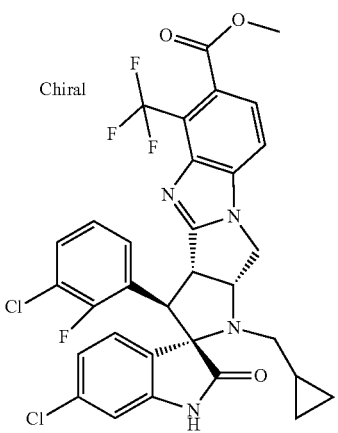 Chiral | 0.92 | 659 | G |
| Ib-46 | 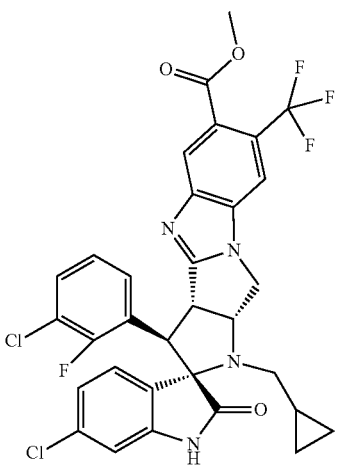 [SMILES: COC(=O)c1cc2nc3n(c2cc1C(F)(F)F)C[C@H]1[C@@H]3[C@H](c2cccc(Cl)c2F)[C@]2(C(=O)Nc3cc(Cl)ccc32)N1CC1CC1] | 0.90 | 659 | G |

TABLE 24-continued
| # | structure | $t_{ret}$ [min] | $[M + H]^+$ | HPLC method |
|---|---|---|---|---|
| Ib-47 | 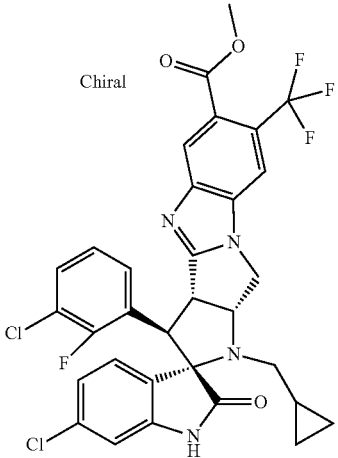 | 0.90 | 659 | G |
| Ib-48 | 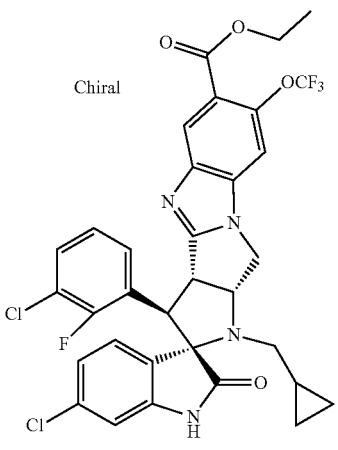 [SMILES: CCOC(=O)c1cc2nc3n(c2cc1OC(F)(F)F)C[C@H]1[C@@H]3[C@H](c2cccc(Cl)c2F)[C@]2(C(=O)Nc3cc(Cl)ccc32)N1CC1CC1 ; "Chiral"] | 0.97 | 689 | G |
| Ib-49 | 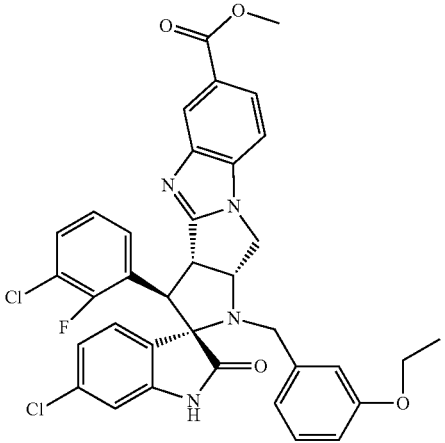 [SMILES: CCOc1cccc(CN2[C@H]3Cn4c(nc5cc(C(=O)OC)ccc54)[C@H]3[C@H](c3cccc(Cl)c3F)[C@]23C(=O)Nc2cc(Cl)ccc23)c1] | 1.60 | 671 | A |

TABLE 24-continued
| # | structure | $t_{ret}$ [min] | $[M + H]^+$ | HPLC method |
|---|---|---|---|---|
| Ib-50 | 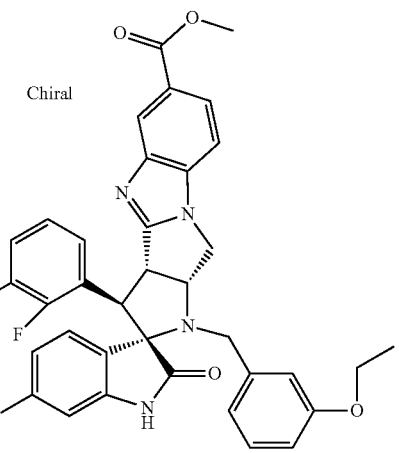 | 1.60 | 671 | A |
| Ib-51 | 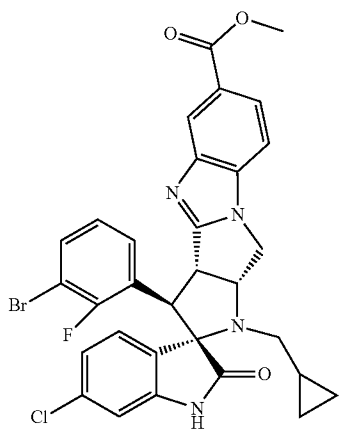 | 0.87 | 637 | G |
| Ib-52 | 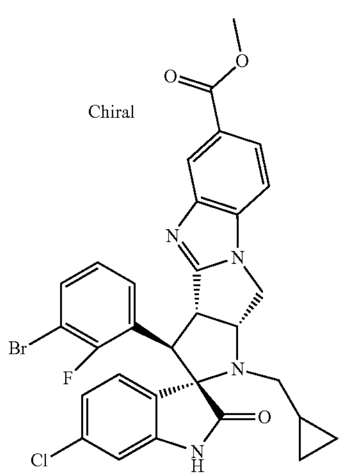 | 0.87 | 637 | G |

TABLE 24-continued
| # | structure | t_ret [min] | [M + H]+ | HPLC method |
|---|-----------|-------------|----------|-------------|
| Ib-53 | 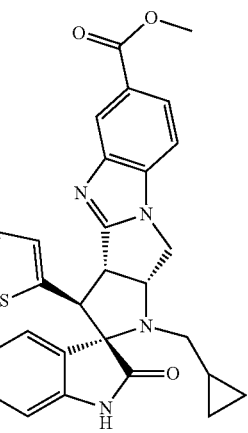 | 0.84 | 579 | G |
| Ib-54 Chiral | 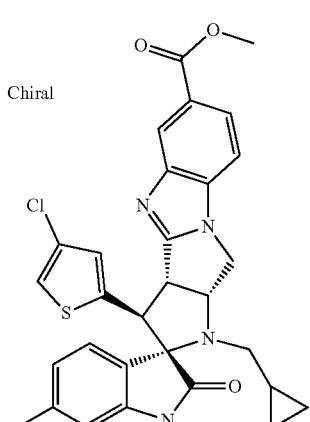 | 0.84 | 579 | G |
| Ib-55 | 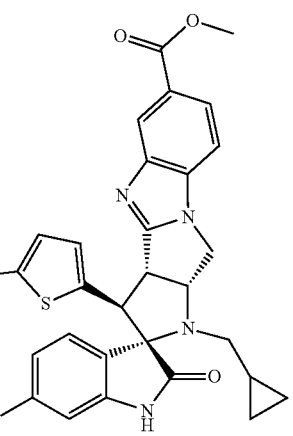 | 0.85 | 579 | G |

TABLE 24-continued
| # | structure | $t_{ret}$ [min] | $[M + H]^+$ | HPLC method |
|---|---|---|---|---|
| Ib-56 | 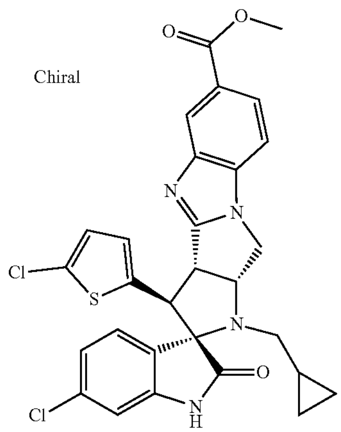 [SMILES: COC(=O)c1ccc2c(c1)nc1n2C[C@H]2[C@@H]1[C@H](c1ccc(Cl)s1)[C@]1(C(=O)Nc3cc(Cl)ccc31)N2CC1CC1 ; "Chiral"] | 0.85 | 579 | G |
| Ib-57 | 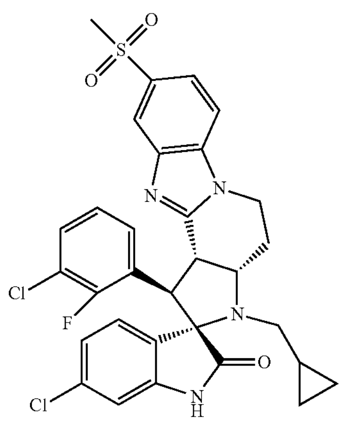 [SMILES: CC(C1CC1)N1[C@H]2CCn3c(nc4cc(S(C)(=O)=O)ccc43)[C@H]2[C@H](c2cccc(Cl)c2F)[C@]12C(=O)Nc1cc(Cl)ccc12] | 1.40 | 625 | A |
| Ib-58 | 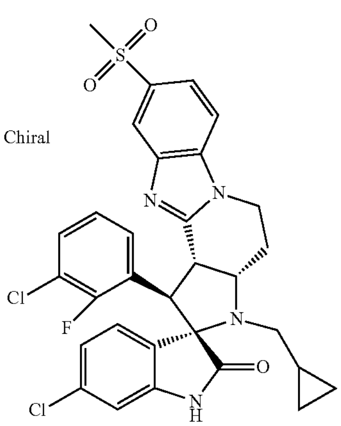 [SMILES: CC(C1CC1)N1[C@H]2CCn3c(nc4cc(S(C)(=O)=O)ccc43)[C@H]2[C@H](c2cccc(Cl)c2F)[C@]12C(=O)Nc1cc(Cl)ccc12 ; "Chiral"] | 1.40 | 625 | A |

TABLE 24-continued

| # | structure | t_ret [min] | [M + H]+ | HPLC method |
|---|---|---|---|---|
| Ib-59 | 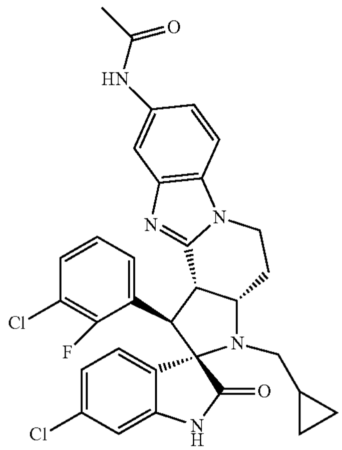 [SMILES: CC(=O)Nc1ccc2c(c1)nc1n2CC[C@H]2[C@@H]1[C@H](c1cccc(Cl)c1F)[C@]1(C(=O)Nc3cc(Cl)ccc31)N2C(C)C1CC1] | 1.33 | 604 | A |
| Ib-60 | Chiral | 1.33 | 604 | A |
| Ib-61 | Chiral | 0.90 | 619 | E |

TABLE 24-continued

| # | structure | $t_{ret}$ [min] | $[M + H]^+$ | HPLC method |
|---|---|---|---|---|
| Ib-62 | 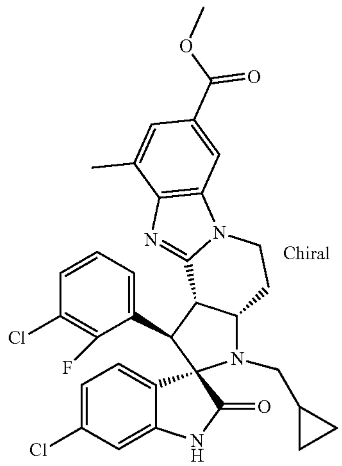 | 0.93 | 619 | E |
| Ib-63 | 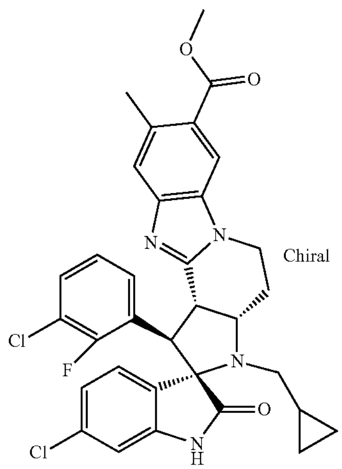 | 0.92 | 619 | E |

Synthesis of Intermediates A-12 (Method I)

Experimental Procedure for the Synthesis of A-12a

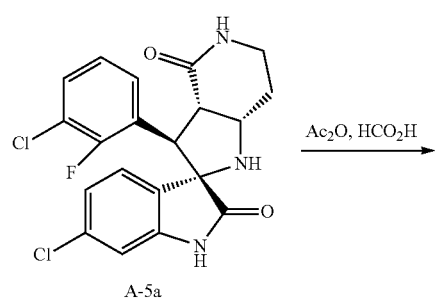

A-5a

Ac₂O, HCO₂H →

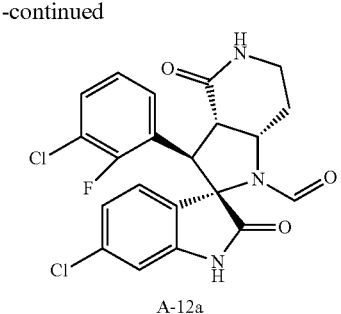

A-12a

Intermediate A-5a (2.0 g, 4.8 mmol) is dissolved in formic acid (10 mL) and acetic anhydride is added (3.5 mL, 38.1 mmol). The reaction mixture is stirred at 50° C. for 16 h and subsequently quenched by the addition of water. Purification by reversed phase column chromatography yields intermediate A-12a.

The following intermediates A-12 (Table 25) are available in an analogous manner starting from different intermediates A-5.

TABLE 25
| # | structure | $t_{ret}$ [min] | $[M+H]^+$ | HPLC method |
|---|---|---|---|---|
| A-12a | 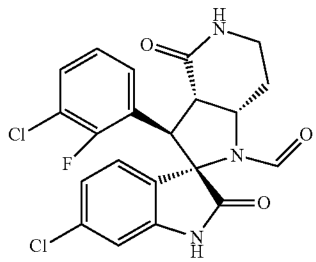 [SMILES: O=CN1[C@H]2CCNC(=O)[C@H]2[C@H](c2cccc(Cl)c2F)[C@]12C(=O)Nc1cc(Cl)ccc12] | 0.99 | 448 | A |
| A-12b Chiral | | 0.99 | 448 | A |
| A-12c | 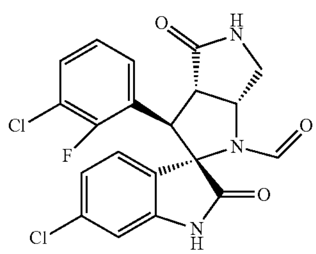 [SMILES: O=CN1[C@H]2CNC(=O)[C@H]2[C@H](c2cccc(Cl)c2F)[C@]12C(=O)Nc1cc(Cl)ccc12] | 0.49 | 434 | G |
| A-12d Chiral | | 0.49 | 434 | G |
Synthesis of Intermediates A-13 (Method G)
Synthesis of A-13a
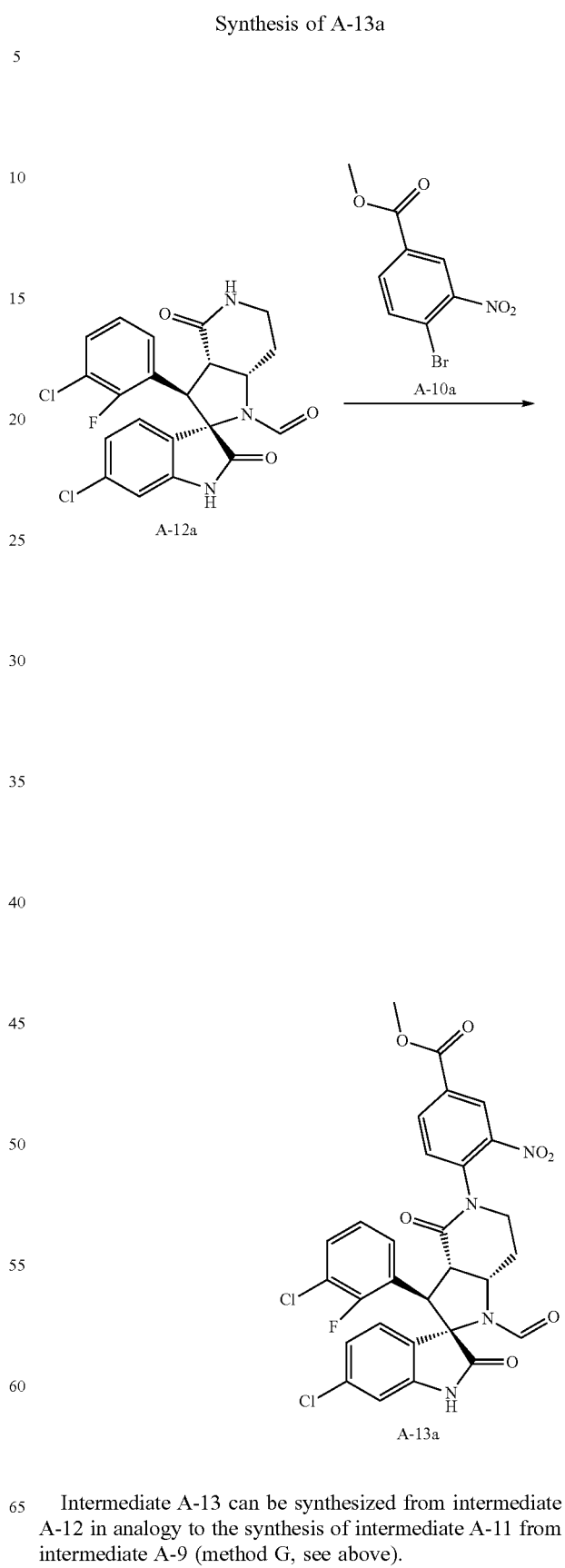
Intermediate A-13 can be synthesized from intermediate A-12 in analogy to the synthesis of intermediate A-11 from intermediate A-9 (method G, see above).

TABLE 26

| # | structure | $t_{ret}$ [min] | $[M + H]^+$ | HPLC method |
|---|---|---|---|---|
| A-13a | 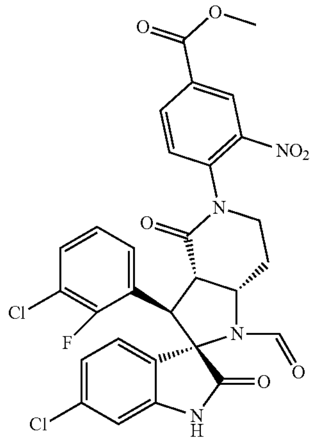 [SMILES: COC(=O)c1ccc(N2CC[C@H]3[C@@H](C2=O)[C@H](c2cccc(Cl)c2F)[C@]2(C(=O)Nc4cc(Cl)ccc42)N3C=O)c([N+](=O)[O-])c1] | 0.70 | 627 | G |
| A-13b | Chiral | 0.70 | 627 | G |
| A-13c | 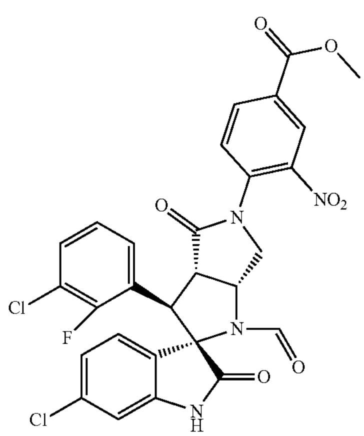 [SMILES: COC(=O)c1ccc(N2C[C@H]3[C@@H](C2=O)[C@H](c2cccc(Cl)c2F)[C@]2(C(=O)Nc4cc(Cl)ccc42)N3C=O)c([N+](=O)[O-])c1] | 0.70 | 613 | G |

TABLE 26-continued
| # | structure | $t_{ret}$ [min] | [M + H]$^+$ | HPLC method |
|---|---|---|---|---|
| A-13d Chiral | 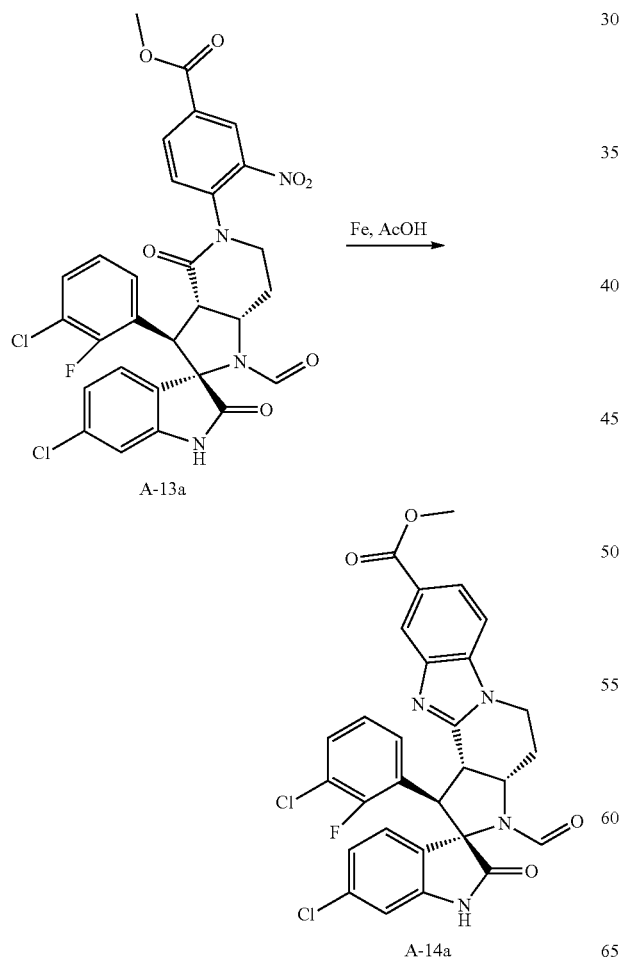 | 0.70 | 613 | G |
Synthesis of Intermediate A-14 (Method H)
Synthesis of A-14a
Intermediate A-14 can be synthesized from intermediate A-13 in analogy to the synthesis of compounds (Ib) according to the invention from intermediate A-11 (method H, see above).
TABLE 27
| # | structure | $t_{ret}$ [min] | [M + H]$^+$ | HPLC method |
|---|---|---|---|---|
| A-14a | 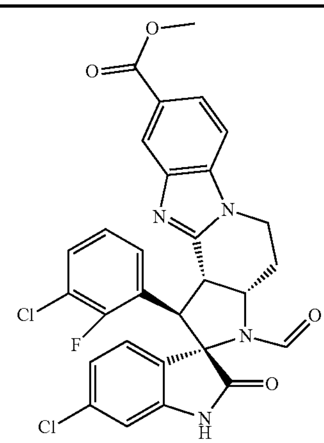 | 0.65 | 579 | G |
| A-14b Chiral | | 0.65 | 579 | G |

TABLE 27-continued

| # | structure | $t_{ret}$ [min] | [M + H]$^+$ | HPLC method |
|---|---|---|---|---|
| A-14c | (structure shown) | 0.66 | 565 | G |
| A-14d | Chiral (structure shown) | 0.66 | 565 | G |

Synthesis of Intermediates A-15 (Method J)

Experimental Procedure for the Synthesis of A-15a

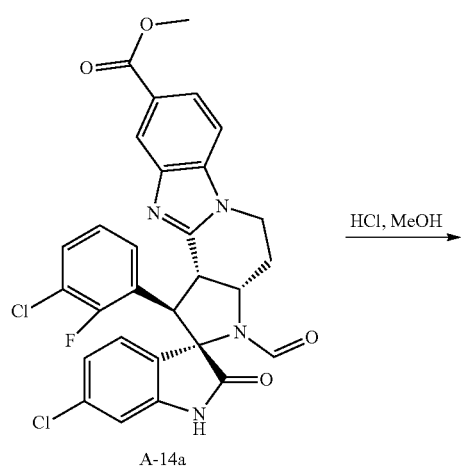

A-14a → HCl, MeOH →

A-14a (840 mg, 1.45 mmol) is dissolved in MeOH (2 mL) and conc. HCl (37%, 500 µL) is added. The reaction mixture is heated to 100° C. for 30 min. The reaction is quenched by the addition of sat. aq. NaHCO₃ and subsequently extracted with EtOAc. Phases are separated and the organic phase is dried with MgSO₄. The solvents are removed under reduced pressure. Reverses phase column chromatography gives pure A-15a.

The following compounds A-15 (table 28) are available in an analogous manner starting from different compounds A-14.

TABLE 28

| # | structure | $t_{ret}$ [min] | [M + H]$^+$ | HPLC method |
|---|---|---|---|---|
| A-15a | 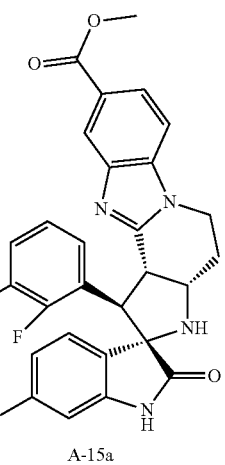 | 0.67 | 551 | G |

TABLE 28-continued

| # | structure | $t_{ret}$ [min] | [M + H]$^+$ | HPLC method |
|---|---|---|---|---|
| A-15b | (Chiral structure shown) | 0.67 | 551 | G |
| A-15c | (structure shown) | 0.68 | 537 | G |
| A-15d | (Chiral structure shown) | 0.68 | 537 | G |

Synthesis of Intermediates A-17 (Method M)

Experimental Procedure for the Synthesis of A-17a

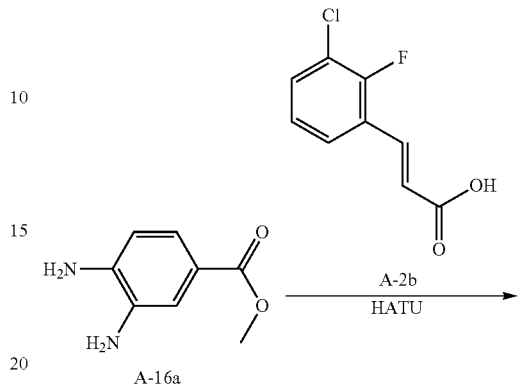

A-17a

3-Chloro-2-fluoro cinnamic acid A-2b (3.0 g, 14.81 mmol) is suspended in anhydrous DMF (25 mL) at 0° C. and DIPEA (3.6 mL, 22.21 mmol) and HATU (5.6 g, 14.73 mmol) are added to the reaction mixture. The reaction mixture is stirred at 0° C. for 30 min. A solution of 3,4-diamino-benzoic acid methyl ester A-16a (2.95 g, 17.77 mmol) in DMF (5 mL) is added dropwise over a period of 15 min. The reaction mixture is stirred for additional 3 h and aq. $K_2CO_3$ solution (8 mL, 2 N) is added. Deionized water is added and the mixture is extracted with DCM. The layers are separated and the organic phase is washed with deionized water and dried with $MgSO_4$. The solvents are removed under reduced pressure and the mixture is used without further purification or is purified by reversed phase column chromatography to yield A-17a.

The following intermediates A-17 (table 29) are available in an analogous manner starting from different intermediates A-2 and A-16.

TABLE 29

| # | structure | $t_{ret}$ [min] | $[M + H]^+$ | HPLC method |
|---|---|---|---|---|
| A-17a | 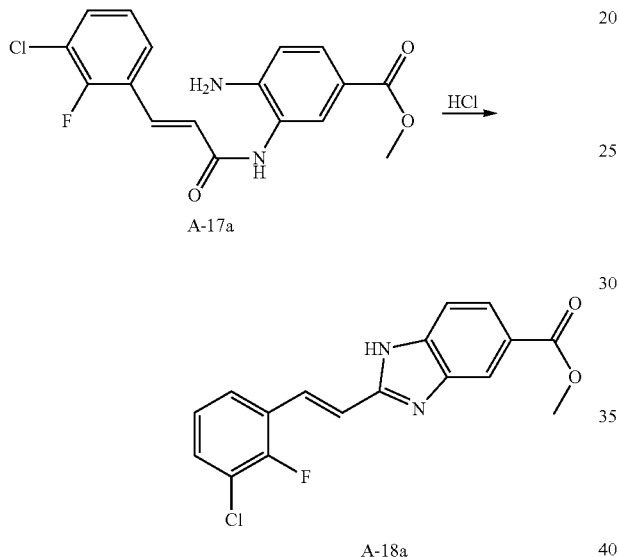 | 1.16 | 349 | A |

Synthesis of Intermediate A-18 (Method N)

Experimental Procedure for the Synthesis of A-18a

Intermediate A-17a (839 mg, 2.4 mmol) is dissolved in dioxane (5 mL) and conc. HCl (1.76 g) and MeOH (24 mL) is added. The resulting mixture is stirred for 15 h at 70° C. The mixture is diluted with EtOAc and aq. NaOH (4 N) is added until pH=10 is reached. Conc. HCl is added and the resulting solid is collected by filtration. Intermediate A-18a is used without further purification for the next step.

The following intermediates A-18 (table 30) are available in an analogous manner starting from different intermediates A-17.

TABLE 30

| # | structure | $t_{ret}$ [min] | $[M + H]^+$ | HPLC method |
|---|---|---|---|---|
| A-18a | 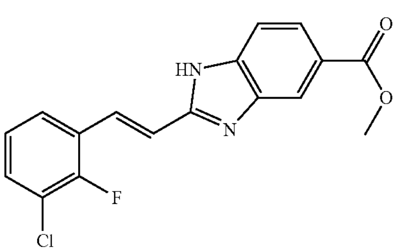 [SMILES: COC(=O)c1ccc2[nH]c(/C=C/c3cccc(Cl)c3F)nc2c1] | 1.22 | 331 | A |

Synthesis of Intermediate A-20 (Method O)

Experimental Procedure for the Synthesis of A-20a and A-20b

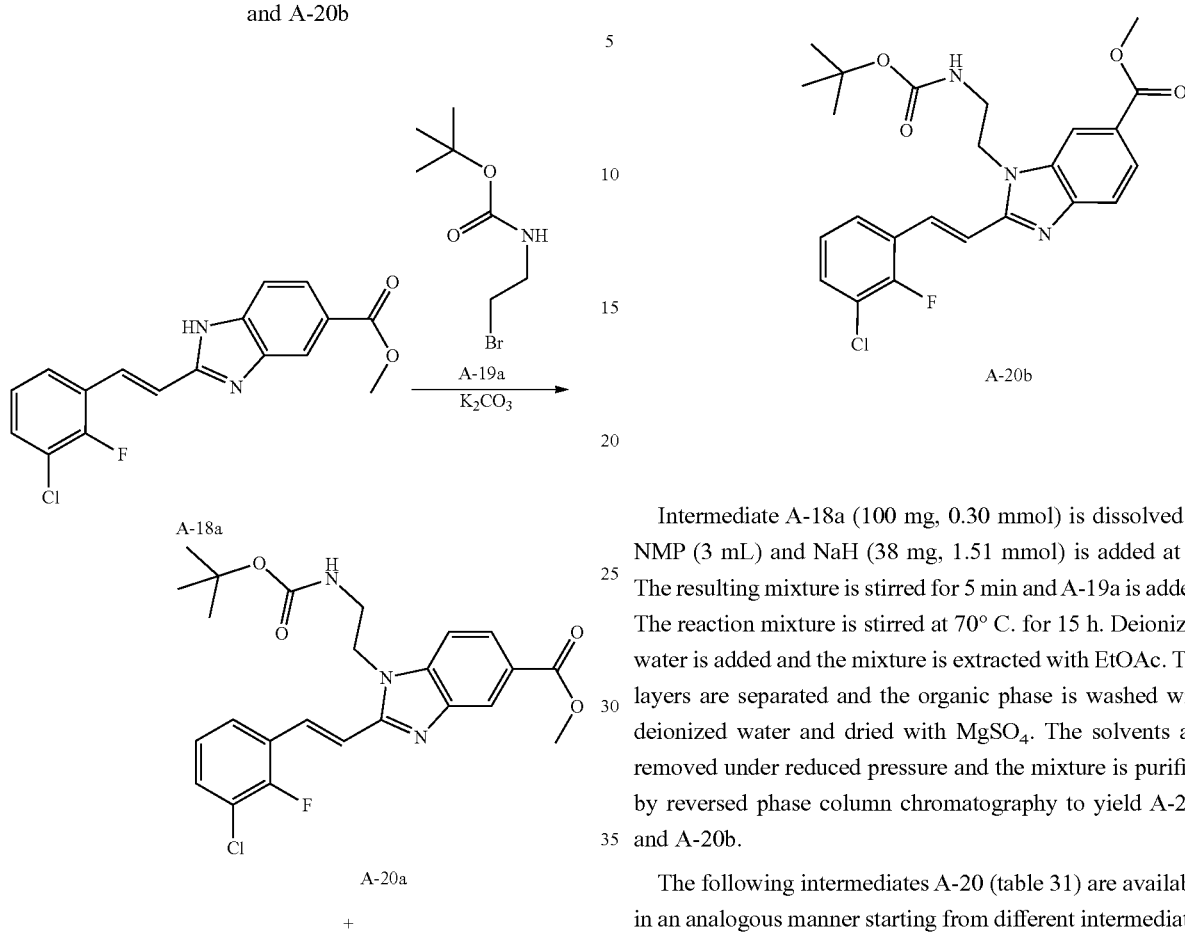

Intermediate A-18a (100 mg, 0.30 mmol) is dissolved in NMP (3 mL) and NaH (38 mg, 1.51 mmol) is added at rt. The resulting mixture is stirred for 5 min and A-19a is added. The reaction mixture is stirred at 70° C. for 15 h. Deionized water is added and the mixture is extracted with EtOAc. The layers are separated and the organic phase is washed with deionized water and dried with MgSO$_4$. The solvents are removed under reduced pressure and the mixture is purified by reversed phase column chromatography to yield A-20a and A-20b.

The following intermediates A-20 (table 31) are available in an analogous manner starting from different intermediates A-18 and/or A-19.

TABLE 31

| # | structure | t$_{ret}$ [min] | [M + H]$^+$ | HPLC method |
|---|---|---|---|---|
| A-20a | 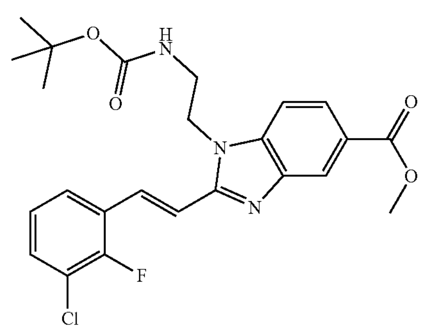 [SMILES: COC(=O)c1ccc2c(c1)nc(/C=C/c1cccc(Cl)c1F)n2CCNC(=O)OC(C)(C)C] | 1.38 | 474 | A |

TABLE 31-continued

| # | structure | $t_{ret}$ [min] | $[M + H]^+$ | HPLC method |
|---|---|---|---|---|
| A-20b | 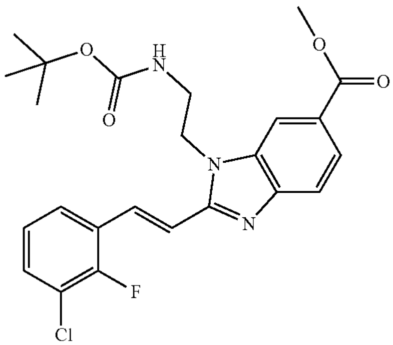 [SMILES: COC(=O)c1ccc2nc(/C=C/c3cccc(Cl)c3F)n(CCNC(=O)OC(C)(C)C)c2c1] | 1.38 | 474 | A |

Synthesis of Intermediate A-21 (Method P)

Experimental Procedure for the Synthesis of A-21a

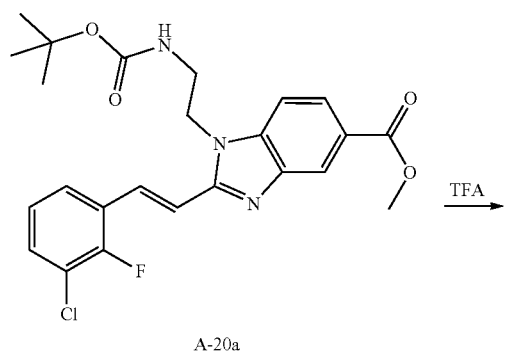

A-20a

TFA →

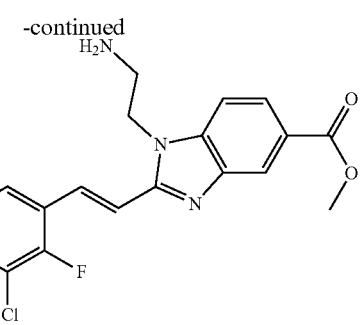

-continued

A-21a

Intermediate A-20a (50 mg, 0.05 mmol) is dissolved in DCM (1 mL). TFA (40 µL) is added at 0° C. and the reaction mixture is slowly warmed to rt. The reaction mixture is heated to reflux for 24 h and concentrated in vacuo. The residue is dissolved in EtOAc and water and aq. NaOH (4 M) is added until a pH of 12 is reached. The layers are separated and the aqueous phase is extracted with EtOAc. The combined organic layers are dried with MgSO$_4$. The solvents are removed under reduced pressure and the mixture is purified by reversed phase column chromatography to yield A-21a.

The following intermediates A-21 (Table 32) are available in an analogous manner starting from different intermediates A-20.

TABLE 32

| # | structure | $t_{ret}$ [min] | $[M + H]^+$ | HPLC method |
|---|---|---|---|---|
| A-21a | 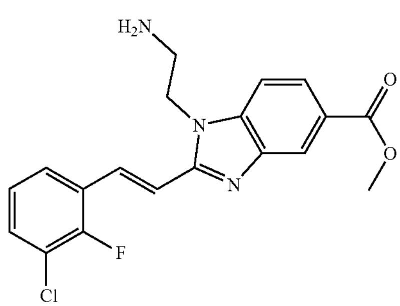 [SMILES: COC(=O)c1ccc2c(c1)nc(/C=C/c1cccc(Cl)c1F)n2CCN] | 1.14 | 374 | A |

TABLE 32-continued

| # | structure | $t_{ret}$ [min] | $[M + H]^+$ | HPLC method |
|---|---|---|---|---|
| A-21b | 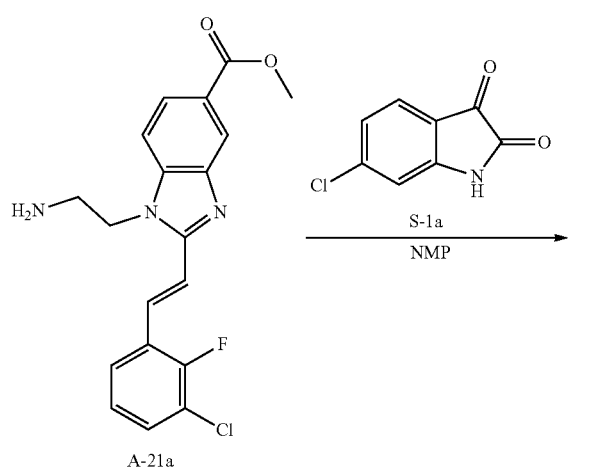 | 1.14 | 374 | A |

Synthesis of Additional Intermediates A-15
(Method Q)

Experimental Procedure for the Synthesis of A-15c
(Alternative Synthesis, See Also Method J)

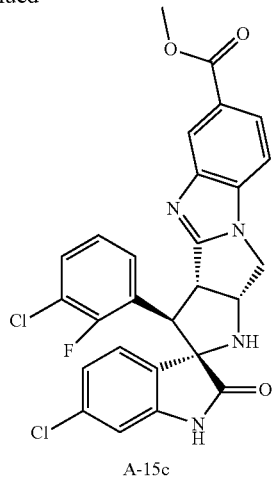

Intermediate A-21a (20 mg, 0.027 mmol), 6-chloro-1H-indole-2,3-dione S-1a (5 mg, 0.027 mmol) and triethylamine (17 µL, 0.13 mmol) are suspended in anhydrous NMP (500 µL) in a microwave vial. The reaction vessel is sealed with a Teflon cap and irradiated for 45 min at a final temperature of 100° C. After cooling to rt the solvents are removed under reduced pressure. The product is purified by reversed phase HPLC which gives intermediate A-15c.

The following intermediates A-15 (table 33) are available in an analogous manner starting from different intermediates A-21 and/or S-1.

TABLE 33

| # | structure | $t_{ret}$ [min] | $[M + H]^+$ | HPLC method |
|---|---|---|---|---|
| A-15c | 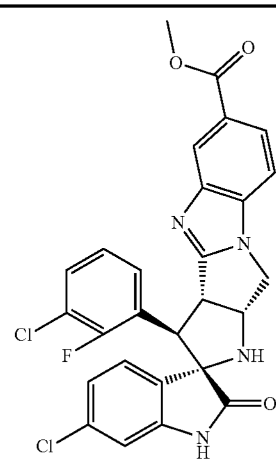 | 1.26 | 537 | A |

TABLE 33-continued

| # | structure | t_ret [min] | [M + H]+ | HPLC method |
|---|---|---|---|---|
| A-15d | 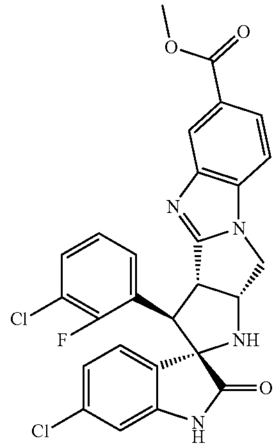 [SMILES: COC(=O)c1ccc2c(c1)nc1n2C[C@@H]2N[C@@]3(C(=O)Nc4cc(Cl)ccc43)[C@@H](c3cccc(Cl)c3F)[C@H]12] | 1.26 | 537 | A |
| A-15e | 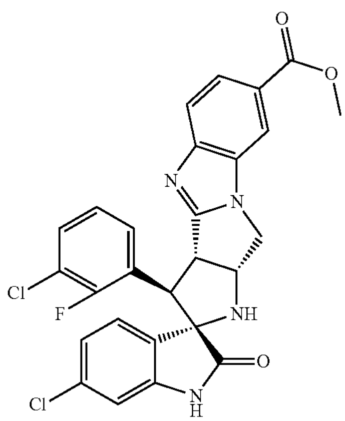 [SMILES: COC(=O)c1ccc2nc3n(c2c1)C[C@@H]1N[C@@]2(C(=O)Nc4cc(Cl)ccc42)[C@@H](c2cccc(Cl)c2F)[C@H]31] | 1.26 | 537 | A |
| A-15f | 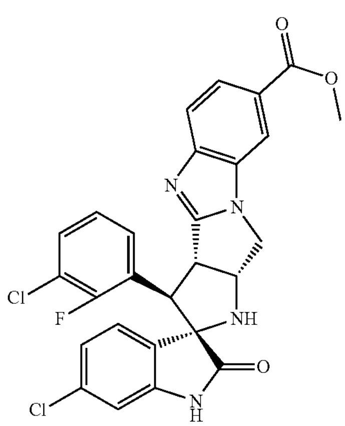 [SMILES: COC(=O)c1ccc2nc3n(c2c1)C[C@@H]1N[C@@]2(C(=O)Nc4cc(Cl)ccc42)[C@@H](c2cccc(Cl)c2F)[C@H]31] | 1.26 | 537 | A |

Synthesis of Further Compounds (Ib) According to the Invention (Method K)

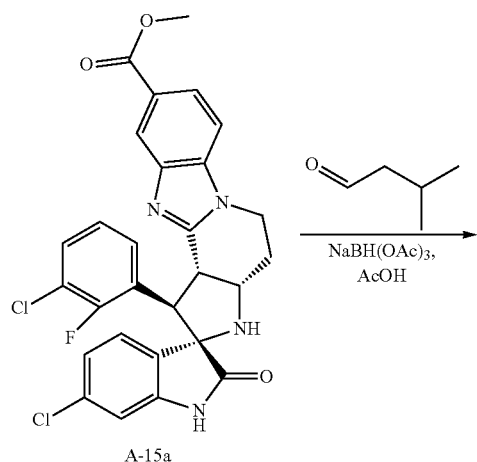

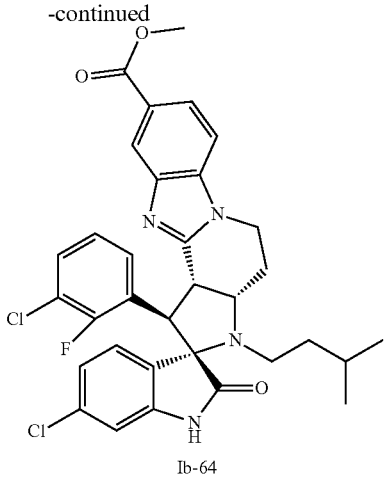

A-15a (0.030 g, 0.054 mmol) and 3-methyl-butyraldehyde (0.14 mg, 0.163 mmol) are dissolved in acetic acid (1 mL) and sodium triacetoxyborohydride (0.06 g, 0.272 mmol) is added. The reaction mixture is allowed to stir at ambient temperature for 1 h before it is quenched by the careful addition of sat. aq. NaHCO$_3$ solution at 0° C. Deionized water and EtOAc are added and the phases are separated. After washing with sat. aq. NaHCO$_3$ and water, the organic phase is dried with MgSO$_4$ and the solvent is removed under reduced pressure. Reversed phase column chromatography gives pure Ib-64.

The following compounds (Ib) (table 34) are available in an analogous manner starting from different intermediates A-15.

TABLE 34

| # | structure | $t_{ret}$ [min] | $[M + H]^+$ | HPLC method |
|---|---|---|---|---|
| Ib-64 | 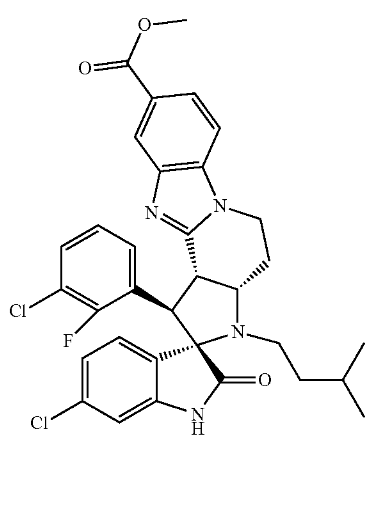 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CCC(C)C] | 0.90 | 621 | G |

TABLE 34-continued

| # | structure | $t_{ret}$ [min] | $[M + H]^+$ | HPLC method |
|---|---|---|---|---|
| Ib-65 | 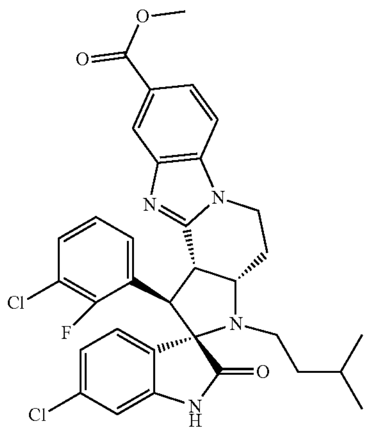 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CCC(C)C] | 0.90 | 621 | G |
| Ib-66 | 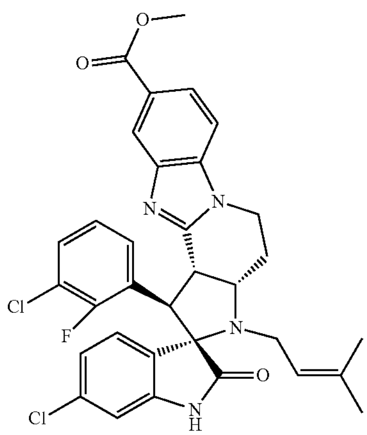 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CC=C(C)C] | 1.55 | 619 | A |
| Ib-67 | 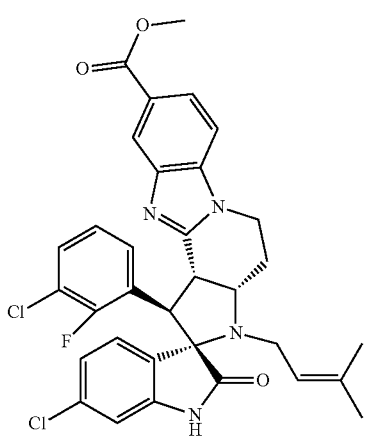 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CC=C(C)C] | 1.55 | 619 | A |

TABLE 34-continued

| # | structure | $t_{ret}$ [min] | [M + H]$^+$ | HPLC method |
|---|---|---|---|---|
| Ib-68 | 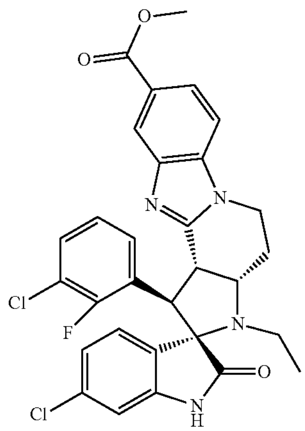 [SMILES: CCN1[C@H]2CCn3c(nc4cc(C(=O)OC)ccc43)[C@H]2[C@H](c2cccc(Cl)c2F)[C@]12C(=O)Nc1cc(Cl)ccc12] | 0.78 | 579 | G |
| Ib-69 | 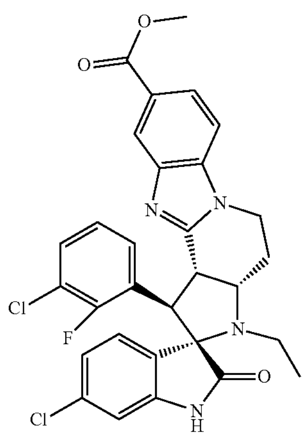 [SMILES: CCN1[C@H]2CCn3c(nc4cc(C(=O)OC)ccc43)[C@H]2[C@H](c2cccc(Cl)c2F)[C@]12C(=O)Nc1cc(Cl)ccc12] | 0.78 | 579 | G |
| Ib-70 | 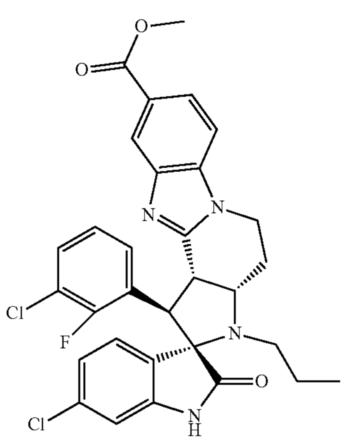 [SMILES: CCCN1[C@H]2CCn3c(nc4cc(C(=O)OC)ccc43)[C@H]2[C@H](c2cccc(Cl)c2F)[C@]12C(=O)Nc1cc(Cl)ccc12] | 0.83 | 593 | G |

TABLE 34-continued

| # | structure | $t_{ret}$ [min] | $[M + H]^+$ | HPLC method |
|---|---|---|---|---|
| Ib-71 | 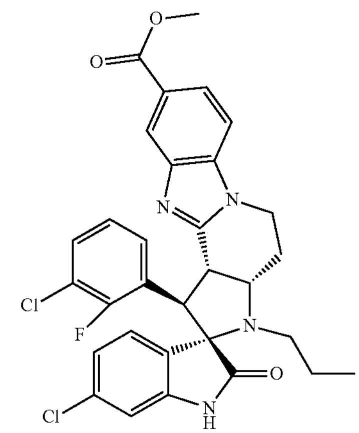 [SMILES: CCCN1[C@H]2CCn3c(nc4cc(C(=O)OC)ccc43)[C@H]2[C@H](c2cccc(Cl)c2F)[C@]12C(=O)Nc1cc(Cl)ccc12] | 0.83 | 593 | G |
| Ib-72 | 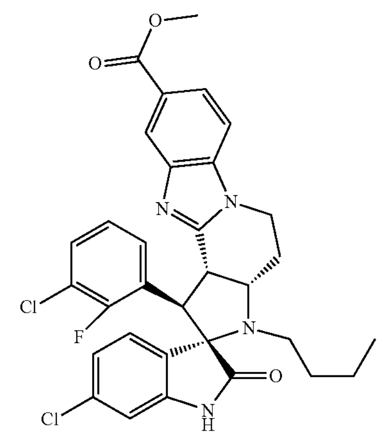 [SMILES: CCCCN1[C@H]2CCn3c(nc4cc(C(=O)OC)ccc43)[C@H]2[C@H](c2cccc(Cl)c2F)[C@]12C(=O)Nc1cc(Cl)ccc12] | 0.87 | 607 | G |
| Ib-73 | 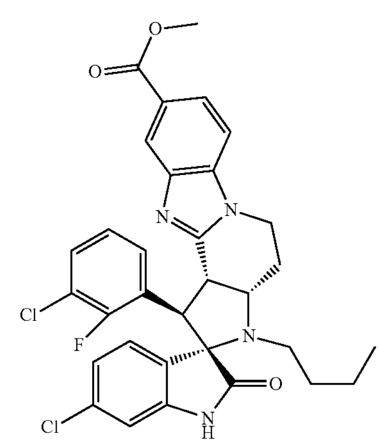 [SMILES: CCCCN1[C@H]2CCn3c(nc4cc(C(=O)OC)ccc43)[C@H]2[C@H](c2cccc(Cl)c2F)[C@]12C(=O)Nc1cc(Cl)ccc12] | 0.87 | 607 | G |

TABLE 34-continued

| # | structure | $t_{ret}$ [min] | $[M + H]^+$ | HPLC method |
|---|---|---|---|---|
| Ib-74 | 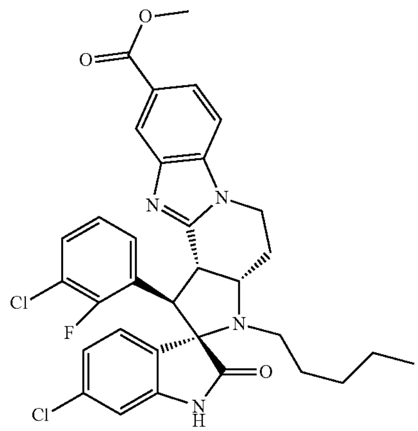 [SMILES: CCCCCN1[C@H]2CCn3c(nc4cc(C(=O)OC)ccc43)[C@H]2[C@H](c2cccc(Cl)c2F)[C@]12C(=O)Nc1cc(Cl)ccc12] | 0.90 | 621 | G |
| Ib-75 | Chiral | 0.90 | 621 | G |
| Ib-76 | 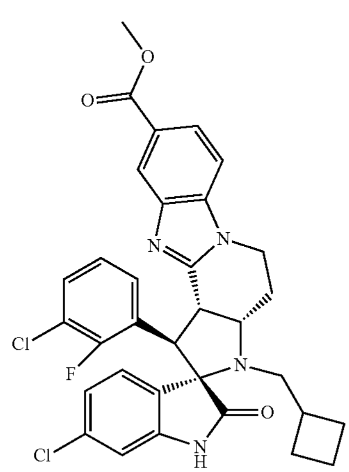 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CC1CCC1] | 0.88 | 619 | G |

TABLE 34-continued
| # | structure | $t_{ret}$ [min] | [M + H]$^+$ | HPLC method |
|---|---|---|---|---|
| Ib-77 | 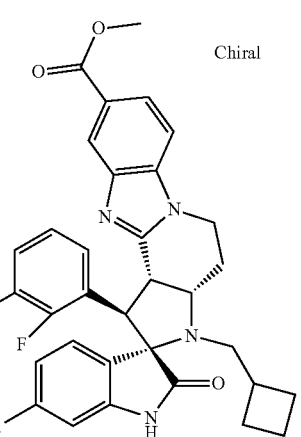 Chiral | 0.88 | 619 | G |
| Ib-78 | 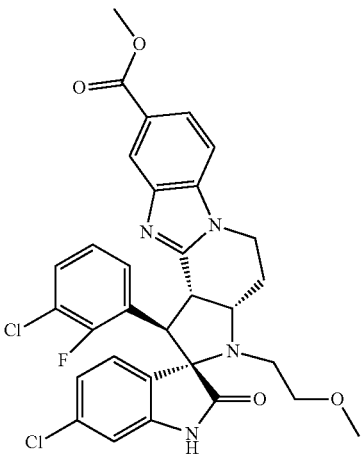 [SMILES: COCCN1[C@H]2CCn3c(nc4cc(C(=O)OC)ccc43)[C@H]2[C@H](c2cccc(Cl)c2F)[C@]12C(=O)Nc1cc(Cl)ccc12] | n.a. | n.a. | n.a. |
| Ib-79 | 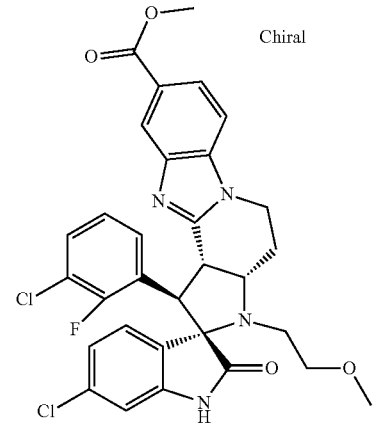 [SMILES: COCCN1[C@H]2CCn3c(nc4cc(C(=O)OC)ccc43)[C@H]2[C@H](c2cccc(Cl)c2F)[C@]12C(=O)Nc1cc(Cl)ccc12 ; "Chiral"] Chiral | n.a. | n.a. | n.a. |

TABLE 34-continued

| # | structure | $t_{ret}$ [min] | [M + H]$^+$ | HPLC method |
|---|---|---|---|---|
| Ib-80 | 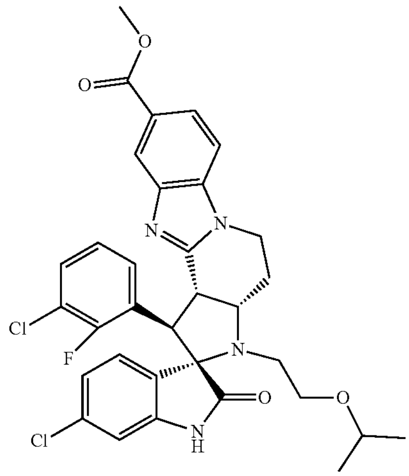 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CCOC(C)C] | 0.81 | 637 | G |
| Ib-81 | Chiral | 0.81 | 637 | G |
| Ib-82 | 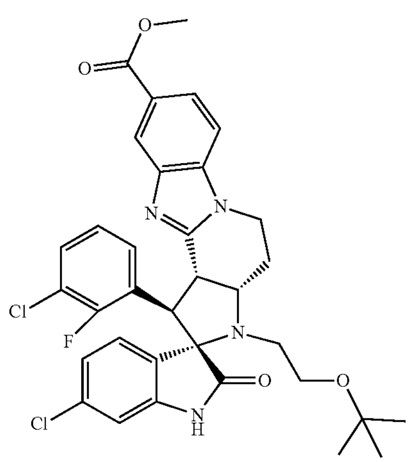 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CCOC(C)(C)C] | 0.88 | 651 | G |

TABLE 34-continued
| # | structure | $t_{ret}$ [min] | $[M + H]^+$ | HPLC method |
|---|---|---|---|---|
| Ib-83 | 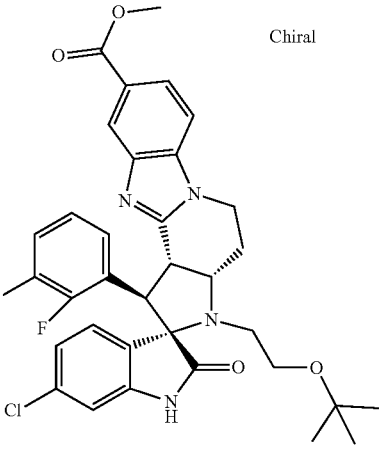 Chiral | 0.88 | 651 | G |
| Ib-84 | 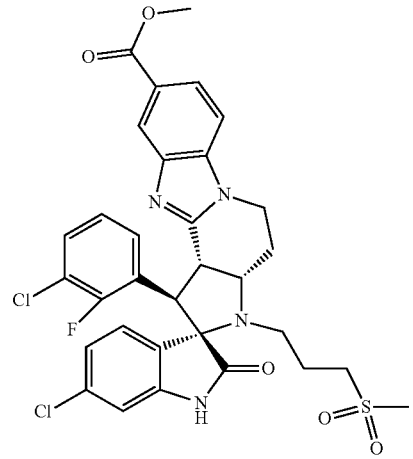 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CCCS(C)(=O)=O] | 0.67 | 671 | G |
| Ib-85 | 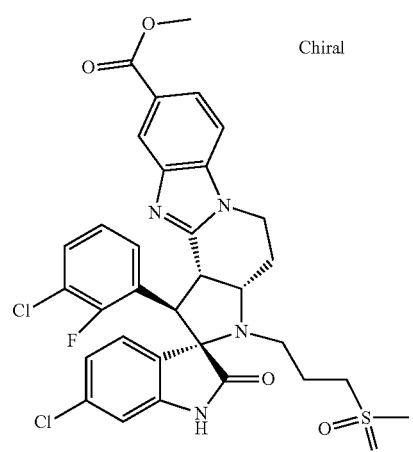 Chiral | 0.67 | 671 | G |

TABLE 34-continued
| # | structure | $t_{ret}$ [min] | [M + H]⁺ | HPLC method |
|---|---|---|---|---|
| Ib-86 | 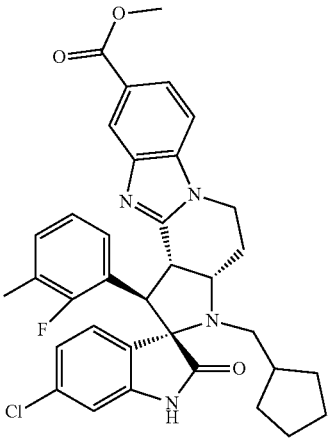 | 0.93 | 633 | G |
| Ib-87 | 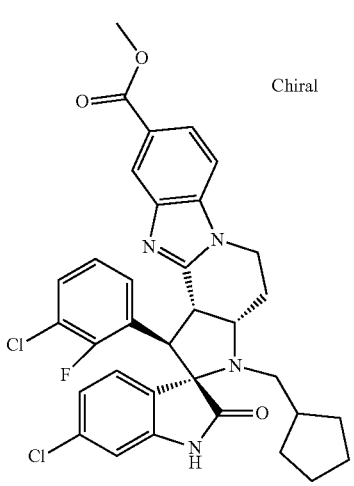 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CC1CCCC1 ; "Chiral"] Chiral | 0.93 | 633 | G |
| Ib-88 | 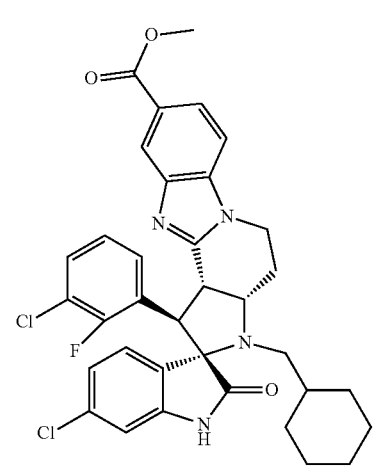 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CC1CCCCC1] | 0.95 | 647 | G |

TABLE 34-continued
| # | structure | $t_{ret}$ [min] | [M + H]$^+$ | HPLC method |
|---|---|---|---|---|
| Ib-89 | 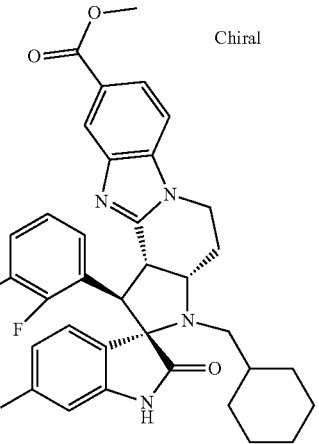 Chiral | 0.95 | 647 | G |
| Ib-90 | 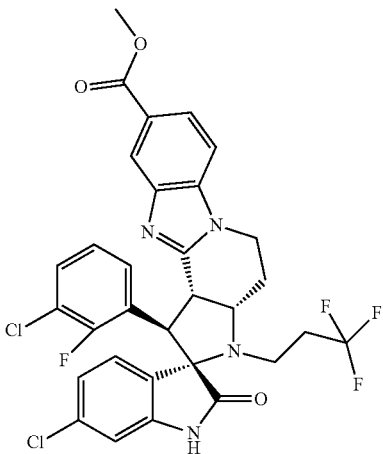 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CCC(F)(F)F] | 0.81 | 647 | G |
| Ib-91 | 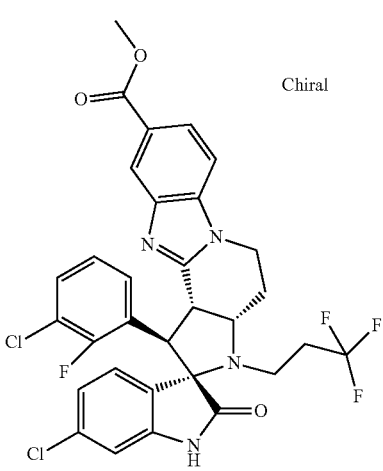 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CCC(F)(F)F ; "Chiral"] Chiral | 0.81 | 647 | G |

TABLE 34-continued

| # | structure | $t_{ret}$ [min] | $[M + H]^+$ | HPLC method |
|---|---|---|---|---|
| Ib-92 | 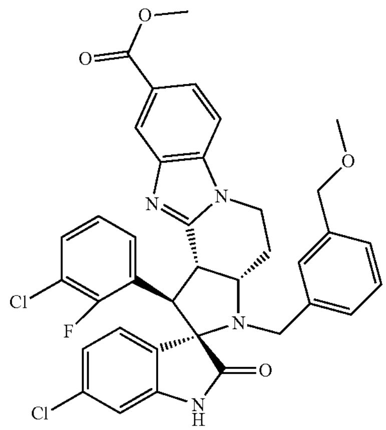 [SMILES: COCc1cccc(CN2[C@H]3CCn4c(nc5cc(C(=O)OC)ccc54)[C@H]3[C@H](c3cccc(Cl)c3F)[C@]23C(=O)Nc2cc(Cl)ccc23)c1] | 0.88 | 685 | D |
| Ib-93 | 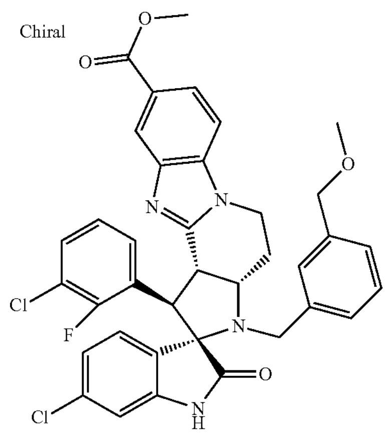 [SMILES: COCc1cccc(CN2[C@H]3CCn4c(nc5cc(C(=O)OC)ccc54)[C@H]3[C@H](c3cccc(Cl)c3F)[C@]23C(=O)Nc2cc(Cl)ccc23)c1 ; "Chiral"] | 0.88 | 685 | D |
| Ib-94 | 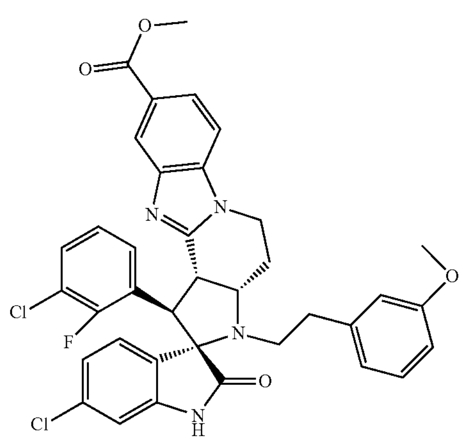 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CCc1cccc(OC)c1] | 0.87 | 685 | G |

TABLE 34-continued
| # | structure | $t_{ret}$ [min] | [M + H]$^+$ | HPLC method |
|---|---|---|---|---|
| Ib-95 | 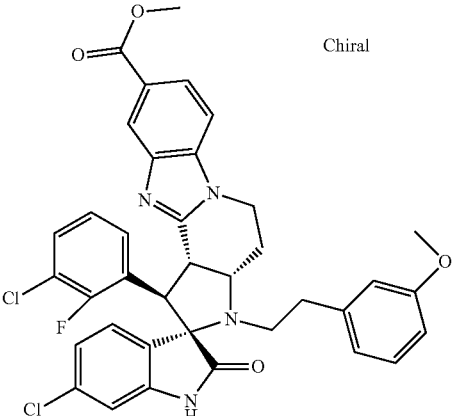 | 0.87 | 685 | G |
| Ib-96 | 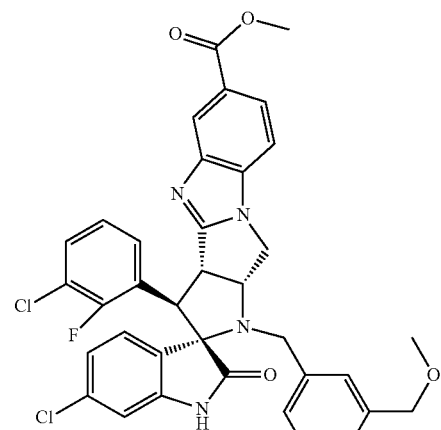 | 1.11 | 671 | K |
| Ib-97 | 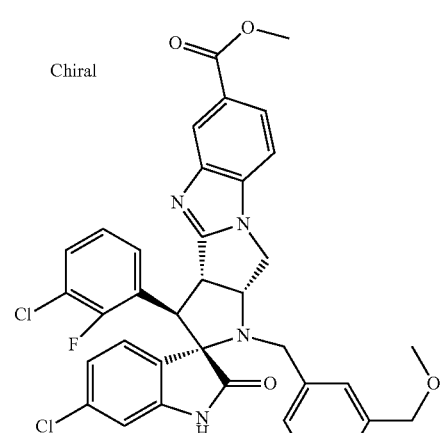 | 1.11 | 671 | K |

TABLE 34-continued

| # | structure | $t_{ret}$ [min] | $[M + H]^+$ | HPLC method |
|---|---|---|---|---|
| Ib-98 | 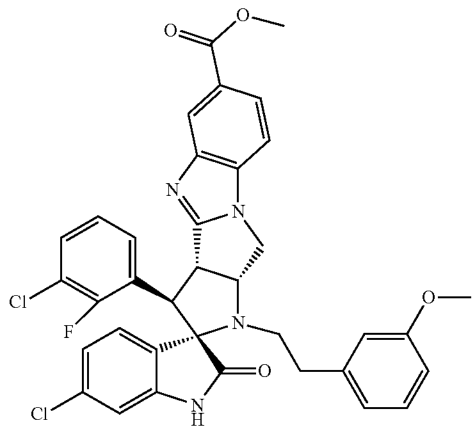 [SMILES: COC(=O)c1ccc2c(c1)nc1n2C[C@H]2[C@@H]1[C@H](c1cccc(Cl)c1F)[C@]1(C(=O)Nc3cc(Cl)ccc31)N2CCc1cccc(OC)c1] | 1.13 | 671 | K |
| Ib-99 | Chiral | 1.13 | 671 | K |

Synthesis of Further Compounds (Ib) According to the Invention (Method L)

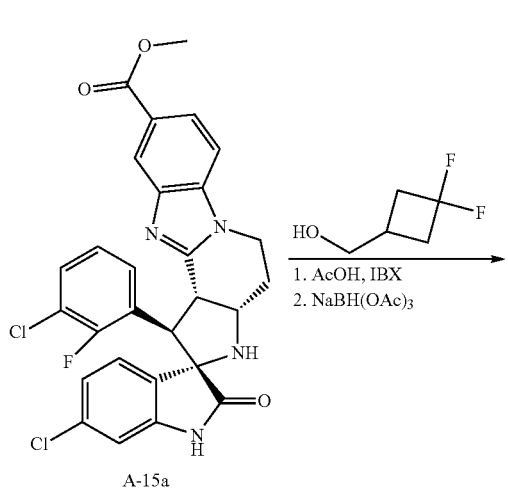

(3,3-difluorocyclobutyl)methanol (100 mg, 0.819 mmol) is dissolved in acetic acid (500 μL) and IBX (298 mg, 1.065 mmol) is added. The reaction mixture is stirred at 40° C. for 3 h before it is filtered through a plug of Celite©. To the filtrate, a solution of A-15a (30 mg, 0.054 mmol) in acetic acid (500 μL) is added at rt. Sodium triacetoxyborohydride (58 mg, 0.272 mmol) is added in one portion to the reaction mixture and the reaction is allowed to stir at rt for 30 min before it is quenched by the careful addition of sat. aq. NaHCO₃ solution at 0° C. Deionized water and EtOAc are added and the phases are separated. After washing with sat.

aq. NaHCO₃ and water, the organic phase is dried with MgSO₄ and the solvent is removed under reduced pressure. Reversed phase column chromatography gives pure Ib-100.

The following compounds (Ib) (table 35) are available in an analogous manner starting from different intermediates A-15 and/or different alcohols.

TABLE 35

| # | structure | t_ret [min] | [M + H]⁺ | HPLC method |
|---|---|---|---|---|
| Ib-100 | 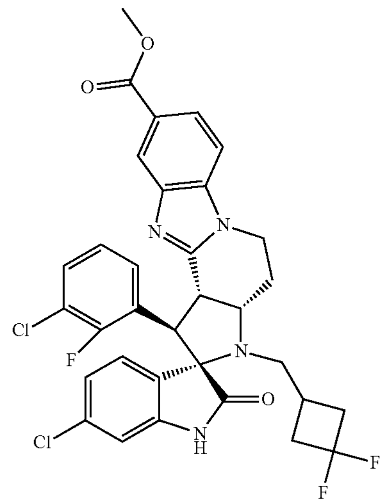 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CC1CC(F)(F)C1] | 0.82 | 655 | G |
| Ib-101 | Chiral | 0.82 | 655 | G |
| Ib-102 | 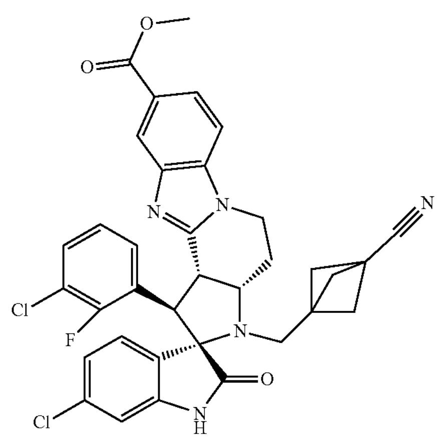 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CC12CC(C#N)(C1)C2] | 0.78 | 656 | G |

TABLE 35-continued
| # | structure | $t_{ret}$ [min] | $[M + H]^+$ | HPLC method |
|---|---|---|---|---|
| Ib-103 | 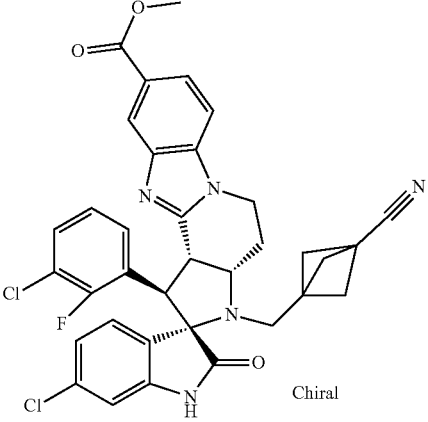 | 0.78 | 656 | G |
| Ib-104 | 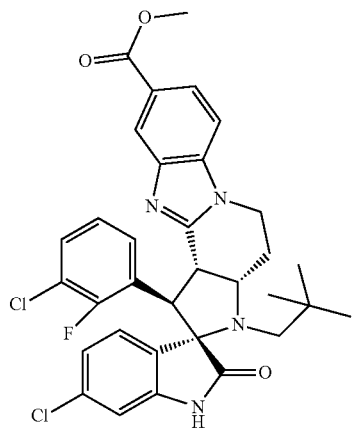 [SMILES: COC(=O)c1ccc2c(c1)nc1n2CC[C@H]2[C@@H]1[C@H](c1cccc(Cl)c1F)[C@]1(C(=O)Nc3cc(Cl)ccc31)N2CC(C)(C)C] | 0.96 | 621 | D |
| Ib-105 | 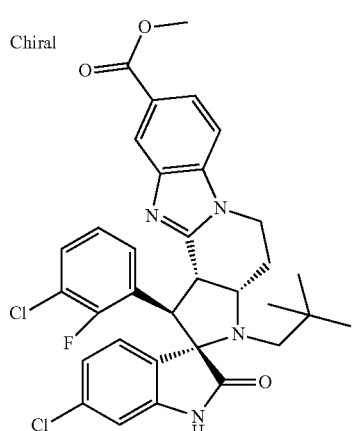 | 0.96 | 621 | D |

Synthesis of Further Compounds (Ib) by Ester Saponification

Experimental Procedure for the Synthesis of Ib-106

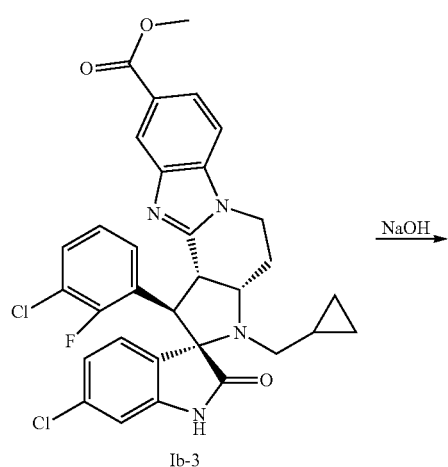

Ib-3

NaOH →

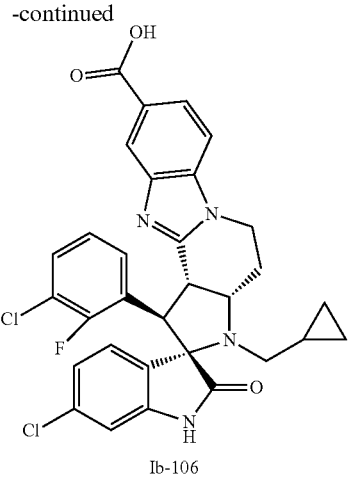

Ib-106

Ib-3 (484 mg, 0.8 mmol) is dissolved in MeOH (10 mL) and aq. NaOH solution (2 mL, 4 M) is added. The reaction mixture is heated to reflux for 1 h. After acidification with 2 M aq. HCl and extraction with EtOAc the organic phase is dried with MgSO$_4$. Purification with reversed phase HPLC leads to pure Ib-106.

The following compounds (Ib) (Table 36) are available in an analogous manner starting from initially obtained compounds (Ib).

TABLE 36

| # | structure | $t_{ret}$ [min] | [M + H]$^+$ | HPLC method |
|---|---|---|---|---|
| Ib-106 | 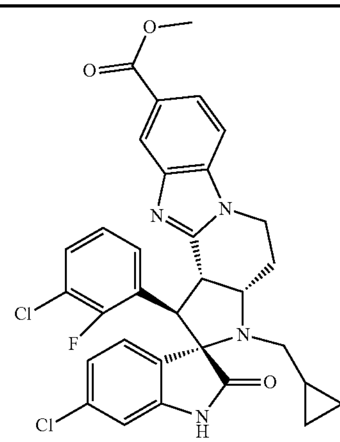 | 1.21 | 591 | A |
| Ib-107 | Chiral | 1.03 | 591 | A |

TABLE 36-continued
| # | structure | t_ret [min] | [M + H]+ | HPLC method |
|---|-----------|-------------|----------|-------------|
| Ib-108 | 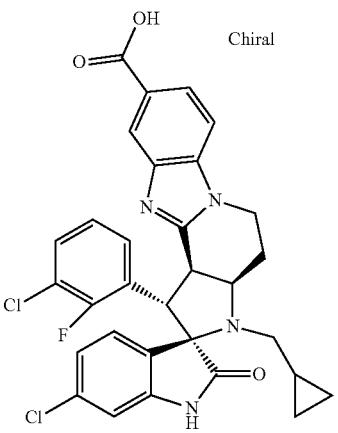 [SMILES: O=C(O)c1ccc2c(c1)nc1n2CC[C@@H]2[C@H]1[C@@H](c1cccc(Cl)c1F)[C@@]1(C(=O)Nc3cc(Cl)ccc31)N2CC1CC1 ; "Chiral"] Chiral | 1.03 | 591 | A |
| Ib-109 | 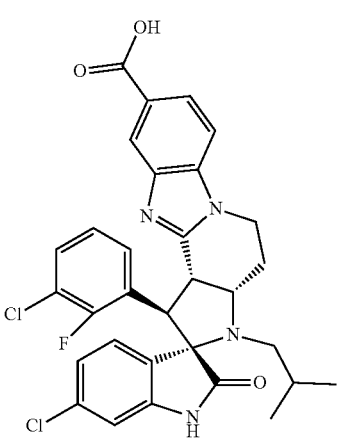 [SMILES: CC(C)CN1[C@H]2CCn3c(nc4cc(C(=O)O)ccc43)[C@H]2[C@H](c2cccc(Cl)c2F)[C@]12C(=O)Nc1cc(Cl)ccc12] | 1.12 | 593 | A |
| Ib-110 | 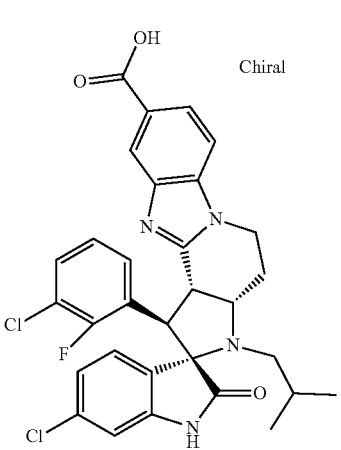 [SMILES: CC(C)CN1[C@H]2CCn3c(nc4cc(C(=O)O)ccc43)[C@H]2[C@H](c2cccc(Cl)c2F)[C@]12C(=O)Nc1cc(Cl)ccc12 ; "Chiral"] Chiral | 1.08 | 593 | A |

TABLE 36-continued

| # | structure | t_ret [min] | [M + H]+ | HPLC method |
|---|---|---|---|---|
| Ib-111 | 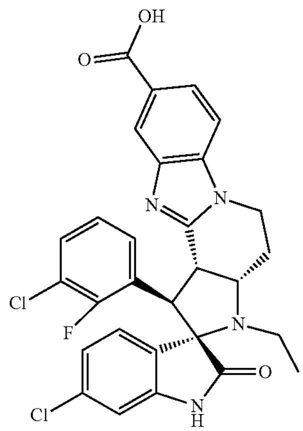 [SMILES: CCN1[C@H]2CCn3c(nc4cc(C(=O)O)ccc43)[C@H]2[C@H](c2cccc(Cl)c2F)[C@]12C(=O)Nc1cc(Cl)ccc12] | 1.01 | 565 | A |
| Ib-112 | 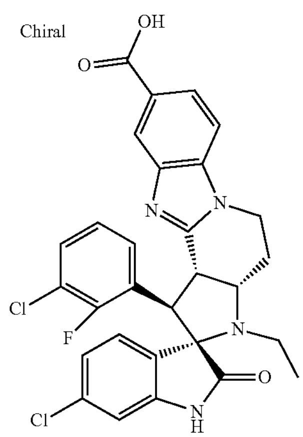 [SMILES: CCN1[C@H]2CCn3c(nc4cc(C(=O)O)ccc43)[C@H]2[C@H](c2cccc(Cl)c2F)[C@]12C(=O)Nc1cc(Cl)ccc12 ; "Chiral"] | 1.01 | 565 | A |
| Ib-113 | 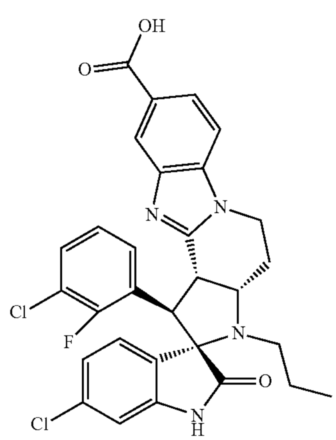 [SMILES: CCCN1[C@H]2CCn3c(nc4cc(C(=O)O)ccc43)[C@H]2[C@H](c2cccc(Cl)c2F)[C@]12C(=O)Nc1cc(Cl)ccc12] | 1.09 | 579 | A |

TABLE 36-continued

| # | structure | $t_{ret}$ [min] | $[M + H]^+$ | HPLC method |
|---|---|---|---|---|
| Ib-114 | 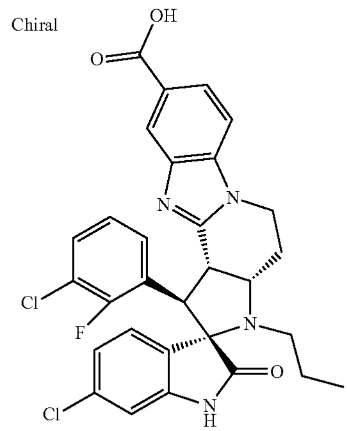 | 1.09 | 579 | A |
| Ib-115 | 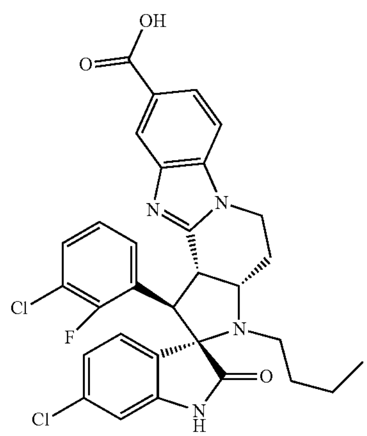 [SMILES: CCCCN1[C@H]2CCn3c(nc4cc(C(=O)O)ccc43)[C@H]2[C@H](c2cccc(Cl)c2F)[C@]12C(=O)Nc1cc(Cl)ccc12] | 1.11 | 593 | A |
| Ib-116 | 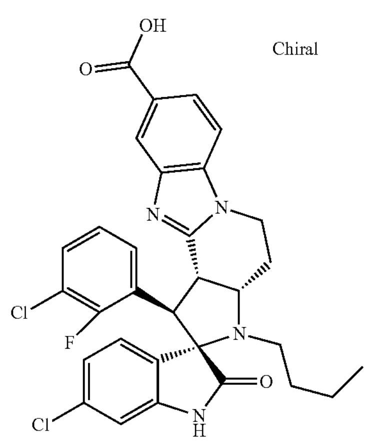 [SMILES: CCCCN1[C@H]2CCn3c(nc4cc(C(=O)O)ccc43)[C@H]2[C@H](c2cccc(Cl)c2F)[C@]12C(=O)Nc1cc(Cl)ccc12 ; "Chiral"] | 1.11 | 593 | A |

TABLE 36-continued
| # | structure | $t_{ret}$ [min] | $[M + H]^+$ | HPLC method |
|---|---|---|---|---|
| Ib-117 | 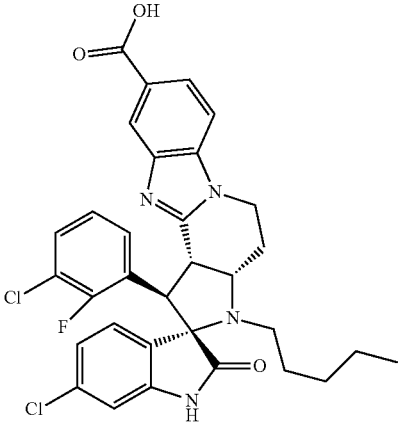 [SMILES: CCCCCN1[C@H]2CCn3c(nc4cc(C(=O)O)ccc43)[C@H]2[C@H](c2cccc(Cl)c2F)[C@]12C(=O)Nc1cc(Cl)ccc12] | 1.14 | 607 | A |
| Ib-118 | 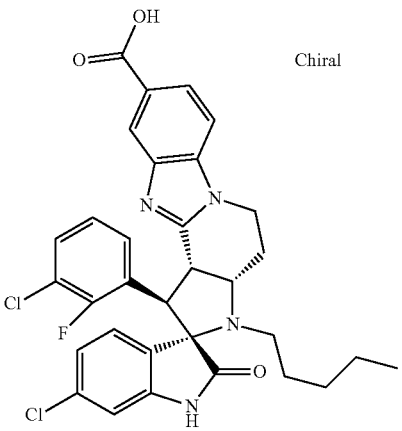 [SMILES: CCCCCN1[C@H]2CCn3c(nc4cc(C(=O)O)ccc43)[C@H]2[C@H](c2cccc(Cl)c2F)[C@]12C(=O)Nc1cc(Cl)ccc12 ; "Chiral"] Chiral | 1.14 | 607 | A |
| Ib-119 | 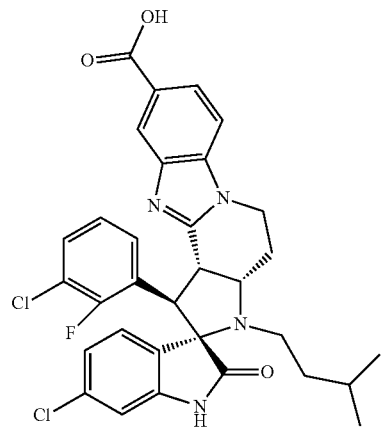 [SMILES: CC(C)CCN1[C@H]2CCn3c(nc4cc(C(=O)O)ccc43)[C@H]2[C@H](c2cccc(Cl)c2F)[C@]12C(=O)Nc1cc(Cl)ccc12] | 1.13 | 607 | A |

TABLE 36-continued
| # | structure | t_ret [min] | [M + H]+ | HPLC method |
|---|-----------|-------------|----------|-------------|
| Ib-120 | 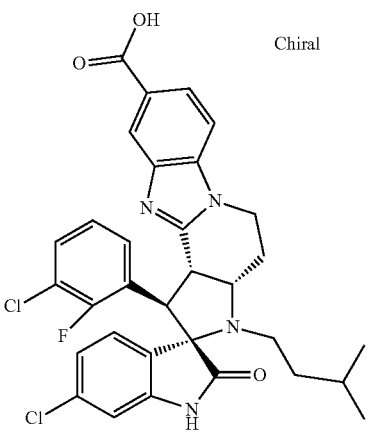 [SMILES: CC(C)CCN1[C@H]2CCn3c(nc4cc(C(=O)O)ccc43)[C@H]2[C@H](c2cccc(Cl)c2F)[C@]12C(=O)Nc1cc(Cl)ccc12 ; "Chiral"] Chiral | 1.13 | 607 | A |
| Ib-121 | 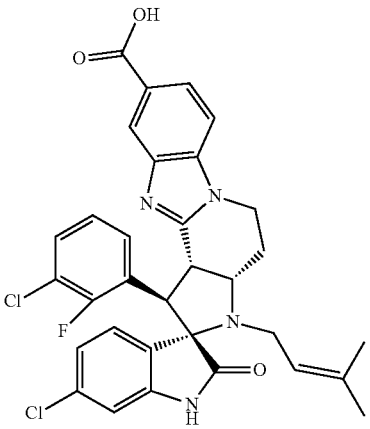 [SMILES: CC(C)=CCN1[C@H]2CCn3c(nc4cc(C(=O)O)ccc43)[C@H]2[C@H](c2cccc(Cl)c2F)[C@]12C(=O)Nc1cc(Cl)ccc12] | 1.10 | 605 | A |
| Ib-122 | 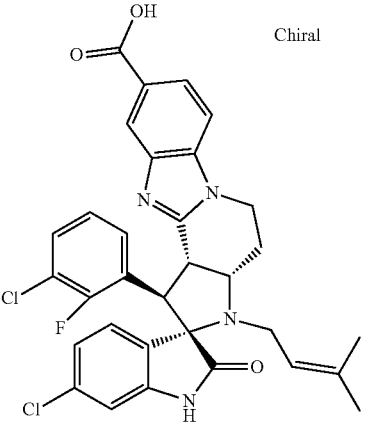 [SMILES: CC(C)=CCN1[C@H]2CCn3c(nc4cc(C(=O)O)ccc43)[C@H]2[C@H](c2cccc(Cl)c2F)[C@]12C(=O)Nc1cc(Cl)ccc12 ; "Chiral"] Chiral | 1.10 | 605 | A |

TABLE 36-continued
| # | structure | $t_{ret}$ [min] | [M + H]$^+$ | HPLC method |
|---|---|---|---|---|
| Ib-123 | 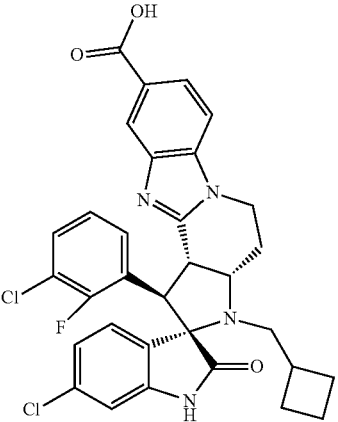 [SMILES: O=C(O)c1ccc2c(c1)nc1n2CC[C@H]2[C@@H]1[C@H](c1cccc(Cl)c1F)[C@]1(C(=O)Nc3cc(Cl)ccc31)N2CC1CCC1] | 1.11 | 605 | A |
| Ib-124 | 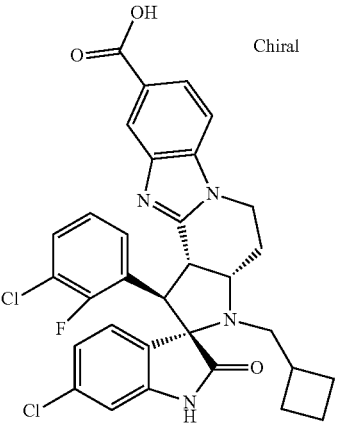 [SMILES: O=C(O)c1ccc2c(c1)nc1n2CC[C@H]2[C@@H]1[C@H](c1cccc(Cl)c1F)[C@]1(C(=O)Nc3cc(Cl)ccc31)N2CC1CCC1 ; "Chiral"] Chiral | 1.11 | 605 | A |
| Ib-125 | 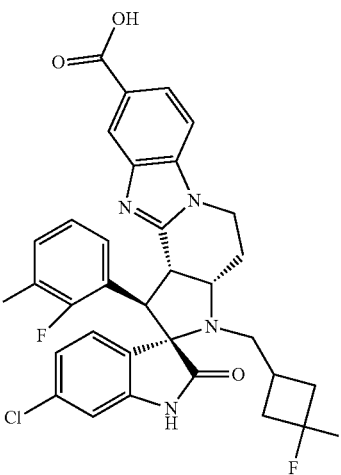 | 1.06 | 641 | A |

TABLE 36-continued
| # | structure | $t_{ret}$ [min] | [M + H]⁺ | HPLC method |
|---|---|---|---|---|
| Ib-126 | 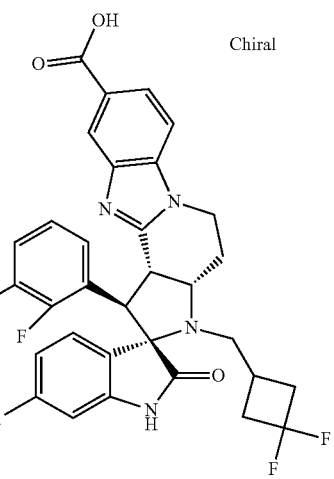 | 1.06 | 641 | A |
| Ib-127 | 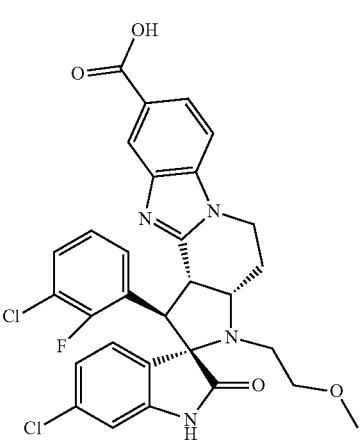 [SMILES: COCCN1[C@H]2CCn3c(nc4cc(C(=O)O)ccc43)[C@H]2[C@H](c2cccc(Cl)c2F)[C@]12C(=O)Nc1cc(Cl)ccc12] | 0.95 | 595 | A |
| Ib-128 | 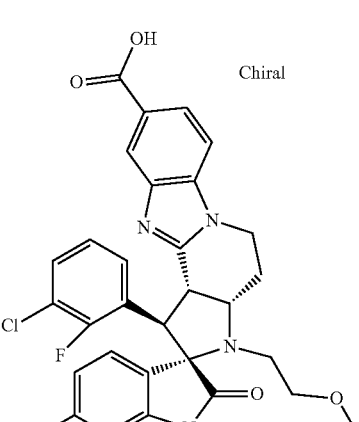 | 0.95 | 595 | A |

TABLE 36-continued

| # | structure | $t_{ret}$ [min] | $[M + H]^+$ | HPLC method |
|---|---|---|---|---|
| Ib-129 | 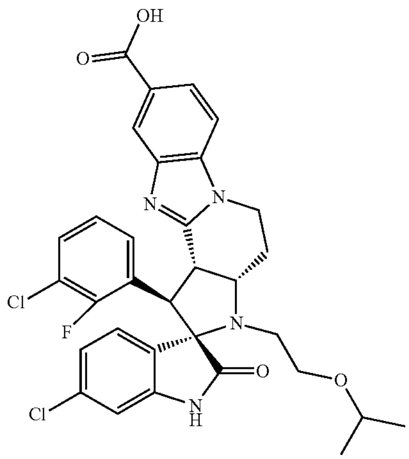 [SMILES: CC(C)OCCN1[C@H]2CCn3c(nc4cc(C(=O)O)ccc43)[C@H]2[C@H](c2cccc(Cl)c2F)[C@]12C(=O)Nc1cc(Cl)ccc12] | 1.05 | 623 | A |
| Ib-130 | Chiral | 1.05 | 623 | A |
| Ib-131 | 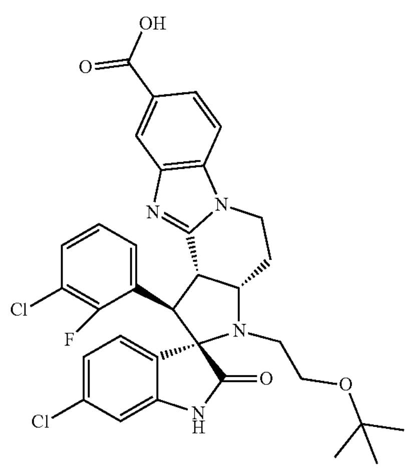 [SMILES: CC(C)(C)OCCN1[C@H]2CCn3c(nc4cc(C(=O)O)ccc43)[C@H]2[C@H](c2cccc(Cl)c2F)[C@]12C(=O)Nc1cc(Cl)ccc12] | 1.09 | 637 | A |

TABLE 36-continued
| # | structure | $t_{ret}$ [min] | $[M + H]^+$ | HPLC method |
|---|---|---|---|---|
| Ib-132 | 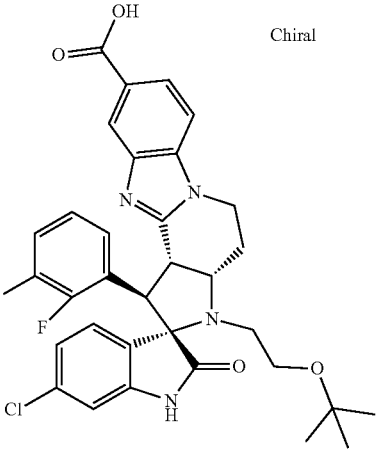 Chiral | 1.09 | 637 | A |
| Ib-133 | 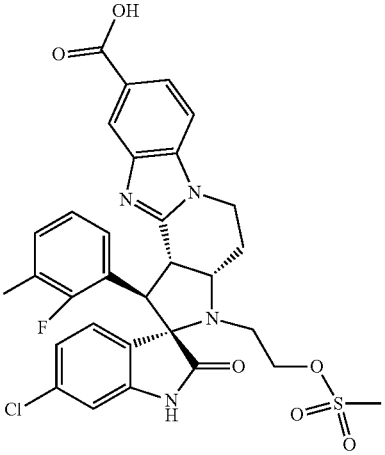 | 0.86 | 657 | A |
| Ib-134 | 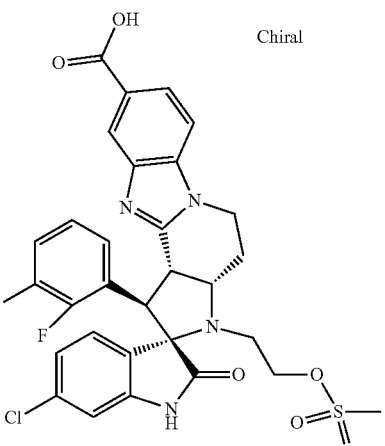 Chiral | 0.86 | 657 | A |

TABLE 36-continued
| # | structure | $t_{ret}$ [min] | [M + H]$^+$ | HPLC method |
|---|---|---|---|---|
| Ib-135 | 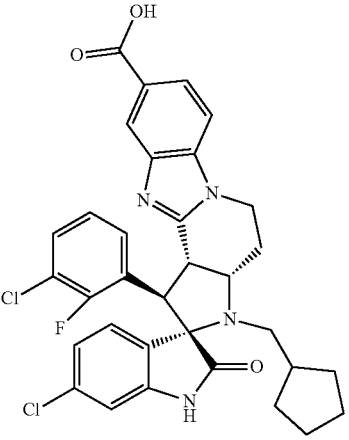 [SMILES: O=C(O)c1ccc2c(c1)nc1n2CC[C@H]2[C@@H]1[C@H](c1cccc(Cl)c1F)[C@]1(C(=O)Nc3cc(Cl)ccc31)N2CC1CCCC1] | 1.14 | 619 | A |
| Ib-136 | 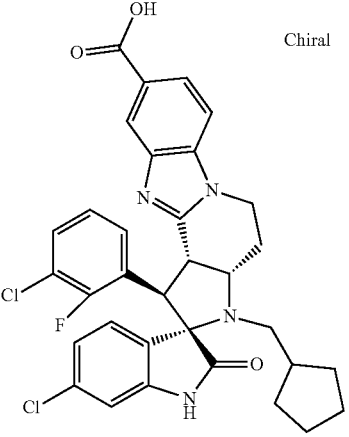 [SMILES: O=C(O)c1ccc2c(c1)nc1n2CC[C@H]2[C@@H]1[C@H](c1cccc(Cl)c1F)[C@]1(C(=O)Nc3cc(Cl)ccc31)N2CC1CCCC1 ; "Chiral"] Chiral | 1.14 | 619 | A |
| Ib-137 | 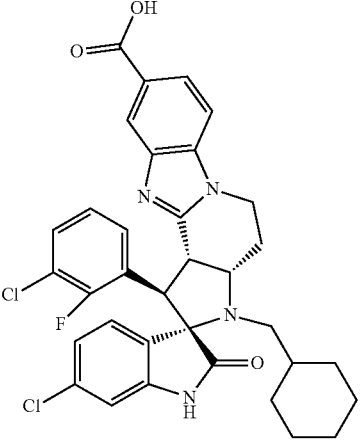 [SMILES: O=C(O)c1ccc2c(c1)nc1n2CC[C@H]2[C@@H]1[C@H](c1cccc(Cl)c1F)[C@]1(C(=O)Nc3cc(Cl)ccc31)N2CC1CCCCC1] | 1.19 | 633 | A |

TABLE 36-continued
| # | structure | $t_{ret}$ [min] | $[M + H]^+$ | HPLC method |
|---|---|---|---|---|
| Ib-138 | 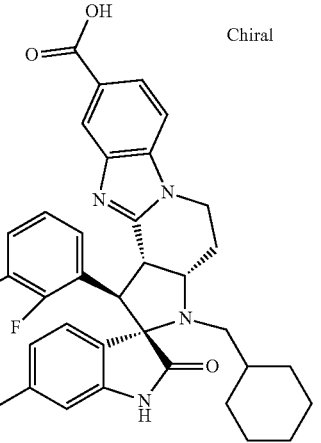 Chiral | 1.19 | 633 | A |
| Ib-139 | 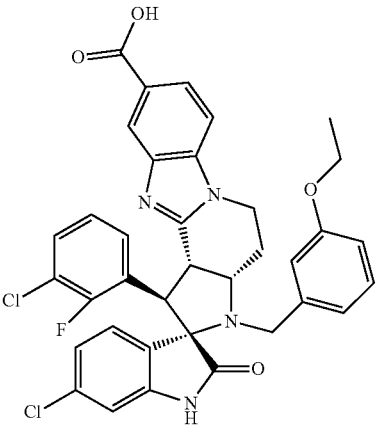 [SMILES: CCOc1cccc(CN2[C@H]3CCn4c(nc5cc(C(=O)O)ccc54)[C@H]3[C@H](c3cccc(Cl)c3F)[C@]23C(=O)Nc2cc(Cl)ccc23)c1] | 1.09 | 671 | A |
| Ib-140 | 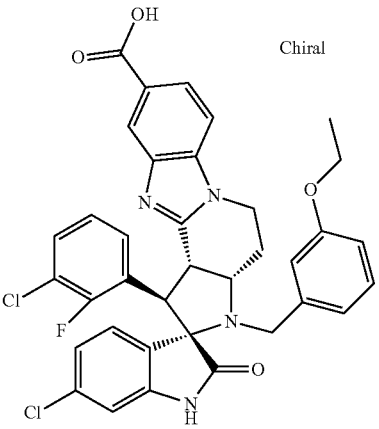 [SMILES: CCOc1cccc(CN2[C@H]3CCn4c(nc5cc(C(=O)O)ccc54)[C@H]3[C@H](c3cccc(Cl)c3F)[C@]23C(=O)Nc2cc(Cl)ccc23)c1 ; "Chiral"] Chiral | 1.09 | 671 | A |

TABLE 36-continued
| # | structure | $t_{ret}$ [min] | [M + H]$^+$ | HPLC method |
|---|---|---|---|---|
| Ib-141 | 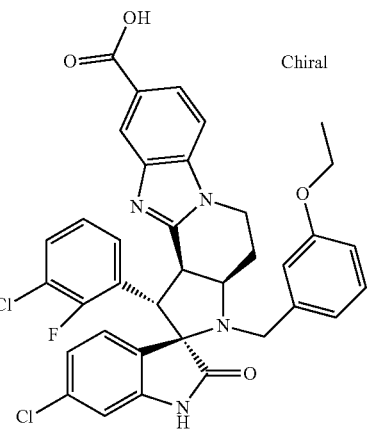 Chiral | 1.09 | 671 | A |
| Ib-142 | 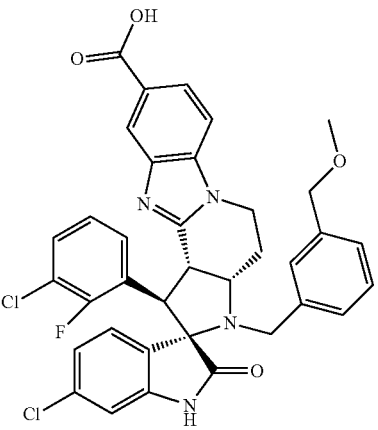 | 1.08 | 671 | A |
| Ib-143 | 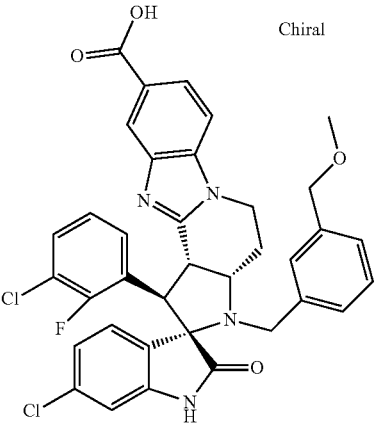 [SMILES: COCc1cccc(CN2[C@H]3CCn4c(nc5cc(C(=O)O)ccc54)[C@H]3[C@H](c3cccc(Cl)c3F)[C@]23C(=O)Nc2cc(Cl)ccc23)c1 ; "Chiral"] Chiral | 1.08 | 671 | A |

TABLE 36-continued

| # | structure | $t_{ret}$ [min] | $[M + H]^+$ | HPLC method |
|---|---|---|---|---|
| Ib-144 | 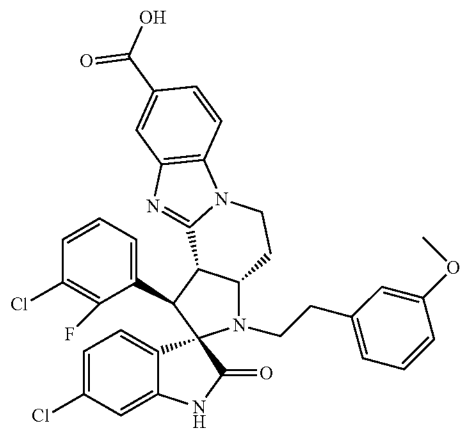 | 1.12 | 671 | A |
| Ib-145 | Chiral | 1.12 | 671 | A |
| Ib-146 | 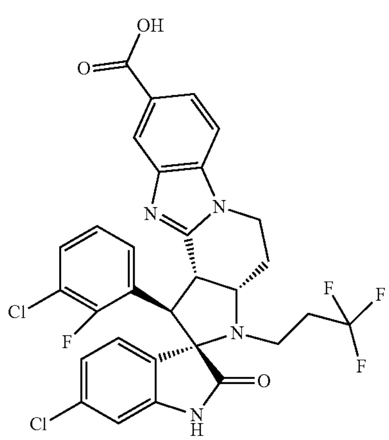 [SMILES: O=C(O)c1ccc2c(c1)nc1n2CC[C@H]2[C@@H]1[C@H](c1cccc(Cl)c1F)[C@]1(C(=O)Nc3cc(Cl)ccc31)N2CCC(F)(F)F] | 1.09 | 633 | A |

TABLE 36-continued
| # | structure | $t_{ret}$ [min] | [M + H]⁺ | HPLC method |
|---|---|---|---|---|
| Ib-147 | 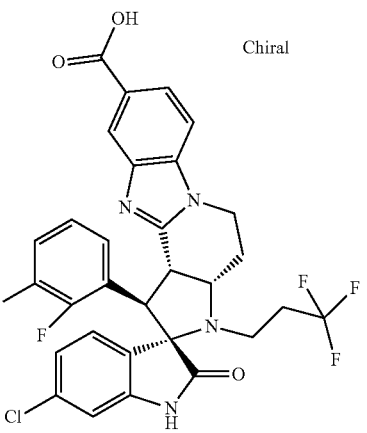 Chiral | 1.09 | 633 | A |
| Ib-148 | 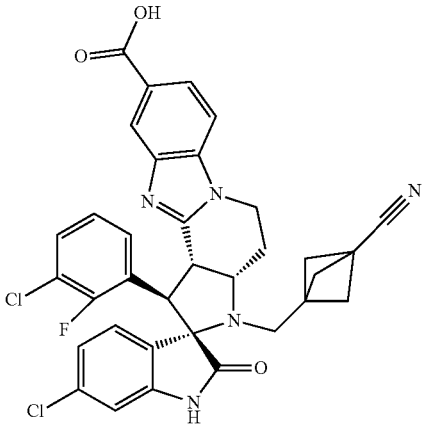 [SMILES: N#CC12CC(CN3[C@H]4CCn5c(nc6cc(C(=O)O)ccc65)[C@H]4[C@H](c4cccc(Cl)c4F)[C@]34C(=O)Nc3cc(Cl)ccc34)(C1)C2] | 1.03 | 642 | A |
| Ib-149 | 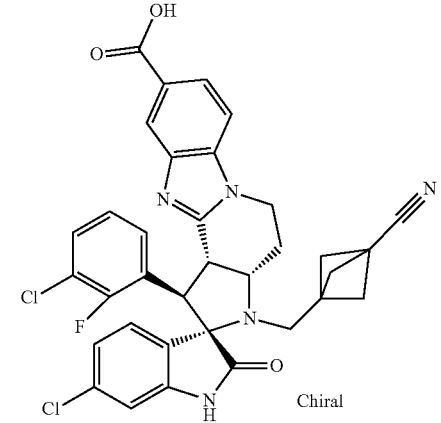 Chiral | 1.03 | 642 | A |

TABLE 36-continued
| # | structure | t_ret [min] | [M + H]+ | HPLC method |
|---|---|---|---|---|
| Ib-150 | 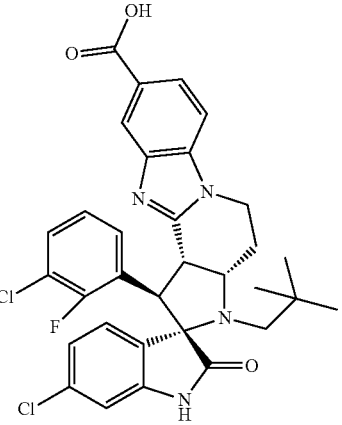 | 1.15 | 607 | A |
| Ib-151 | 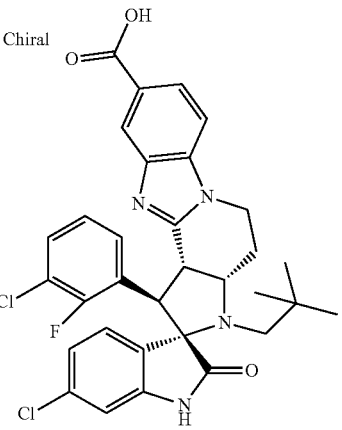 | 1.15 | 607 | A |
| Ib-152 | 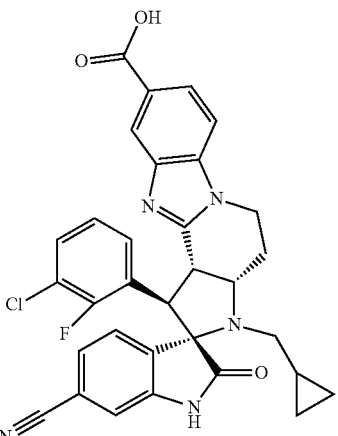 | 0.97 | 582 | A |

TABLE 36-continued
| # | structure | $t_{ret}$ [min] | [M + H]⁺ | HPLC method |
|---|---|---|---|---|
| Ib-153 | 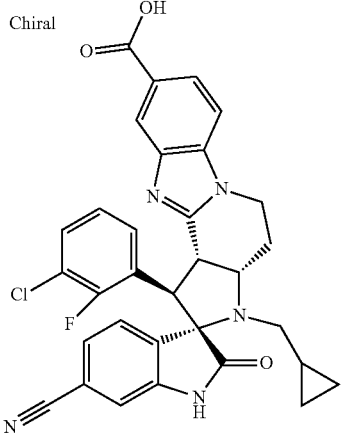 | 0.97 | 582 | A |
| Ib-154 | 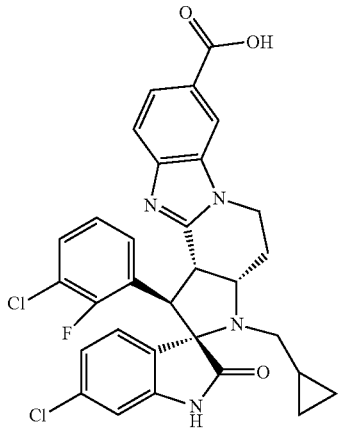 [SMILES: O=C(O)c1ccc2nc3n(c2c1)CC[C@H]1[C@@H]3[C@H](c2cccc(Cl)c2F)[C@]2(C(=O)Nc3cc(Cl)ccc32)N1CC1CC1] | 1.03 | 591 | A |
| Ib-155 | 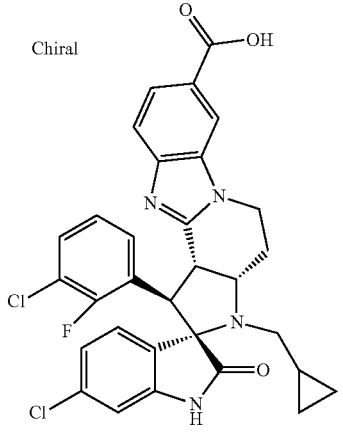 [SMILES: O=C(O)c1ccc2nc3n(c2c1)CC[C@H]1[C@@H]3[C@H](c2cccc(Cl)c2F)[C@]2(C(=O)Nc3cc(Cl)ccc32)N1CC1CC1 ; "Chiral"] | 1.05 | 591 | A |

TABLE 36-continued

| # | structure | $t_{ret}$ [min] | $[M + H]^+$ | HPLC method |
|---|---|---|---|---|
| Ib-156 | Chiral | 0.97 | 591 | A |
| Ib-157 | Chiral | 1.09 | 621 | A |
| Ib-158 | Chiral | 1.16 | 675 | A |

TABLE 36-continued
| # | structure | $t_{ret}$ [min] | [M + H]$^+$ | HPLC method |
|---|---|---|---|---|
| Ib-159 | 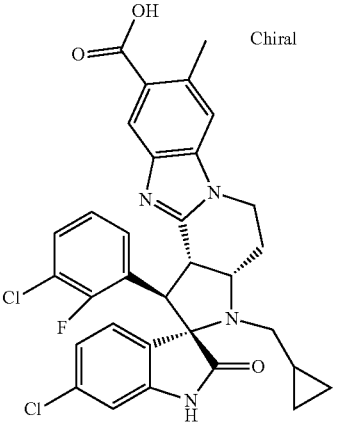 [SMILES: Cc1cc2c(cc1C(=O)O)nc1n2CC[C@H]2[C@@H]1[C@H](c1cccc(Cl)c1F)[C@]1(C(=O)Nc3cc(Cl)ccc31)N2CC1CC1 ; "Chiral"] | 1.08 | 605 | A |
| Ib-160 | 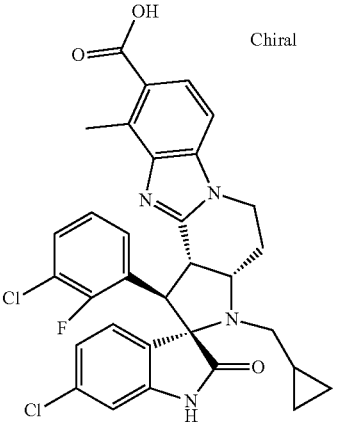 [SMILES: Cc1c(C(=O)O)ccc2c1nc1n2CC[C@H]2[C@@H]1[C@H](c1cccc(Cl)c1F)[C@]1(C(=O)Nc3cc(Cl)ccc31)N2CC1CC1 ; "Chiral"] | 1.05 | 605 | A |
| Ib-161 | 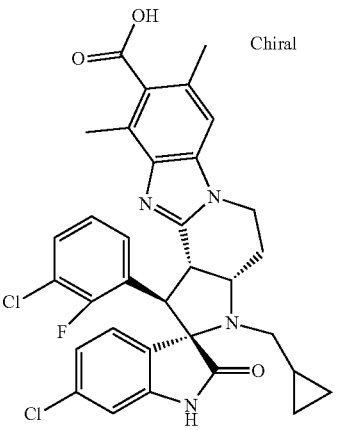 [SMILES: Cc1cc2c(nc3n2CC[C@H]2[C@@H]3[C@H](c3cccc(Cl)c3F)[C@]3(C(=O)Nc4cc(Cl)ccc43)N2CC2CC2)c(C)c1C(=O)O ; "Chiral"] | 1.08 | 619 | A |

TABLE 36-continued
| # | structure | $t_{ret}$ [min] | $[M + H]^+$ | HPLC method |
|---|---|---|---|---|
| Ib-162 | 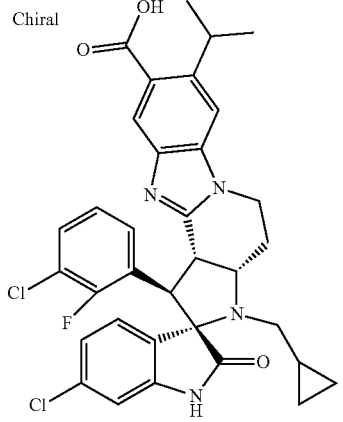 | 1.14 | 633 | A |
| Ib-163 | 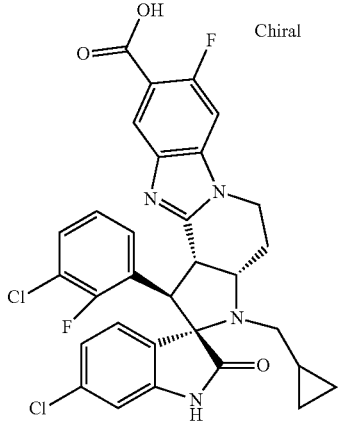 | 1.05 | 609 | A |
| Ib-164 | 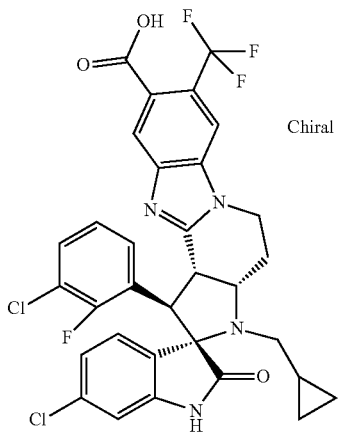 [SMILES: O=C(O)c1cc2nc3n(c2cc1C(F)(F)F)CC[C@H]1[C@@H]3[C@H](c2cccc(Cl)c2F)[C@]2(C(=O)Nc3cc(Cl)ccc32)N1CC1CC1 ; "Chiral"] | 1.12 | 659 | A |

TABLE 36-continued
| # | structure | $t_{ret}$ [min] | [M + H]$^+$ | HPLC method |
|---|---|---|---|---|
| Ib-165 | 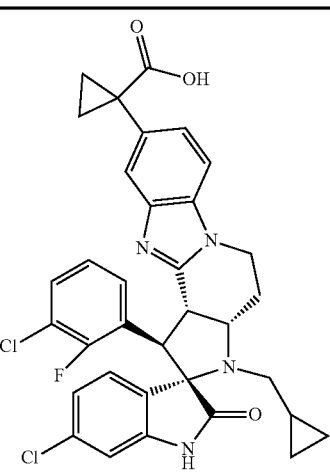 | 1.11 | 631 | A |
| Ib-166 | 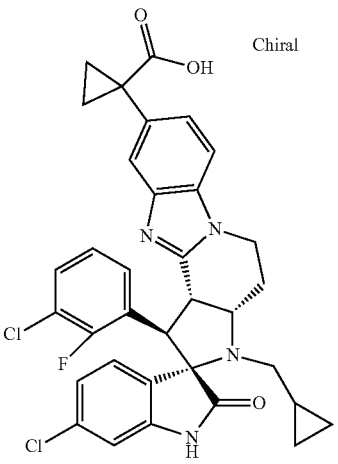 [SMILES: O=C(O)C1(c2ccc3c(c2)nc2n3CC[C@H]3[C@@H]2[C@H](c2cccc(Cl)c2F)[C@]2(C(=O)Nc4cc(Cl)ccc42)N3CC2CC2)CC1 ; "Chiral"] Chiral | 1.11 | 631 | A |
| Ib-167 | 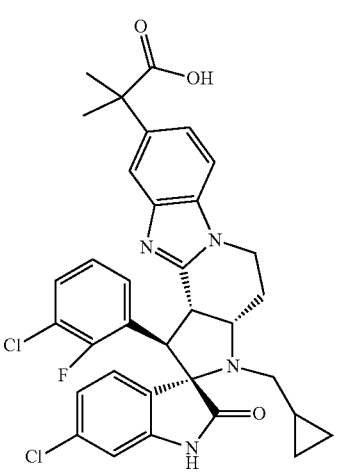 [SMILES: CC(C)(C(=O)O)c1ccc2c(c1)nc1n2CC[C@H]2[C@@H]1[C@H](c1cccc(Cl)c1F)[C@]1(C(=O)Nc3cc(Cl)ccc31)N2CC1CC1] | 1.11 | 633 | A |

TABLE 36-continued
| # | structure | $t_{ret}$ [min] | $[M + H]^+$ | HPLC method |
|---|---|---|---|---|
| Ib-168 | 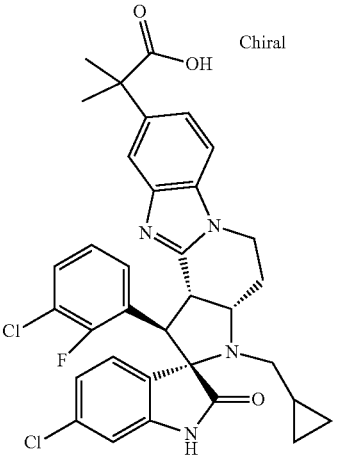 | 1.11 | 633 | A |
| Ib-169 | 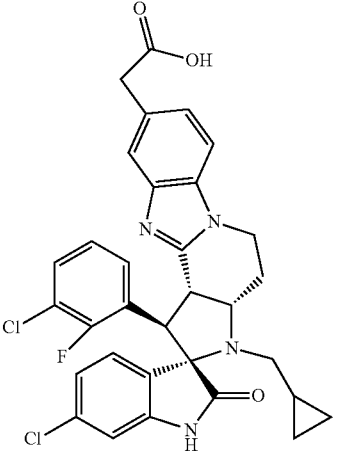 [SMILES: O=C(O)Cc1ccc2c(c1)nc1n2CC[C@H]2[C@@H]1[C@H](c1cccc(Cl)c1F)[C@]1(C(=O)Nc3cc(Cl)ccc31)N2CC1CC1] | 1.05 | 605 | A |
| Ib-170 | 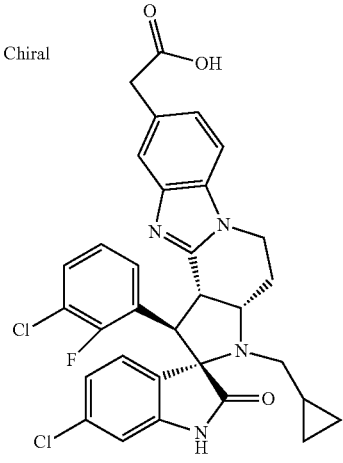 [SMILES: "Chiral" ; O=C(O)Cc1ccc2c(c1)nc1n2CC[C@H]2[C@@H]1[C@H](c1cccc(Cl)c1F)[C@]1(C(=O)Nc3cc(Cl)ccc31)N2CC1CC1] | 1.05 | 605 | A |

| # | structure | $t_{ret}$ [min] | [M + H]⁺ | HPLC method |
|---|---|---|---|---|
| Ib-171 | 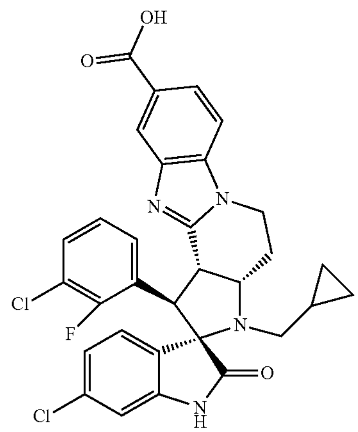 [SMILES: O=C(O)c1ccc2c(c1)nc1n2CC[C@H]2[C@@H]1[C@H](c1cccc(Cl)c1F)[C@]1(C(=O)Nc3cc(Cl)ccc31)N2CC1CC1] | 1.02 | 592 | A |
| Ib-172 | Chiral | 1.02 | 592 | A |
| Ib-173 | 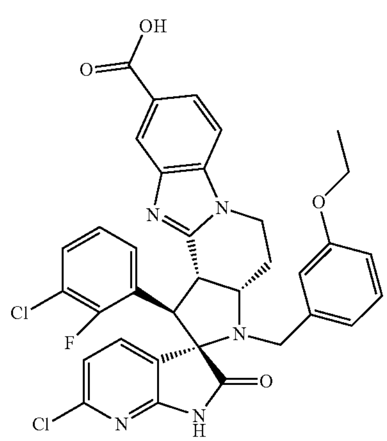 | 1.08 | 672 | A |

TABLE 36-continued
| # | structure | $t_{ret}$ [min] | [M + H]$^+$ | HPLC method |
|---|---|---|---|---|
| Ib-174 | 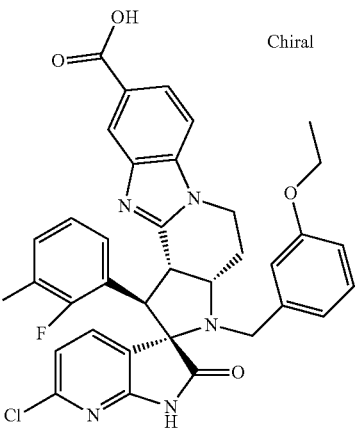 | 1.08 | 672 | A |
| Ib-175 | 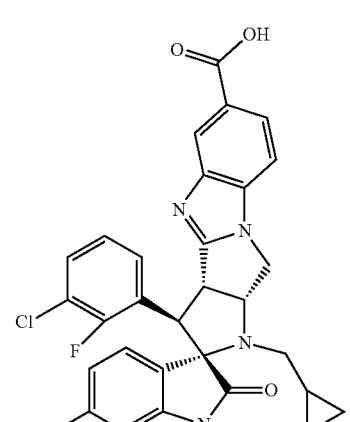 | 1.08 | 577 | A |
| Ib-176 | 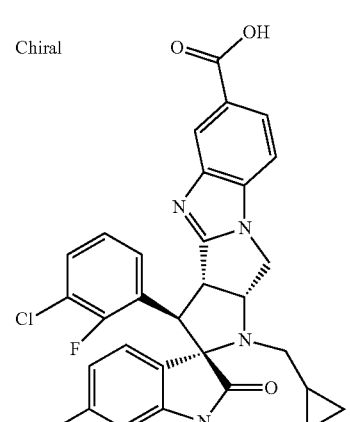 | 1.01 | 577 | A |

TABLE 36-continued
| # | structure | $t_{ret}$ [min] | [M + H]$^+$ | HPLC method |
|---|---|---|---|---|
| Ib-177 | 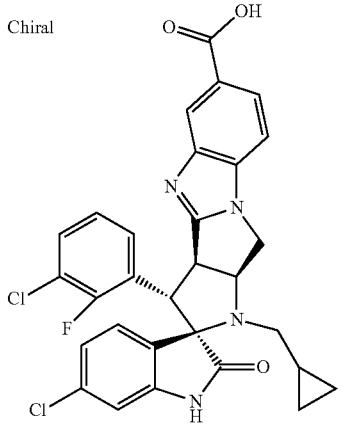 [SMILES: O=C(O)c1ccc2c(c1)nc1n2C[C@@H]2[C@H]1[C@@H](c1cccc(Cl)c1F)[C@@]1(C(=O)Nc3cc(Cl)ccc31)N2CC1CC1 ; "Chiral"] Chiral | 1.01 | 577 | A |
| Ib-178 | 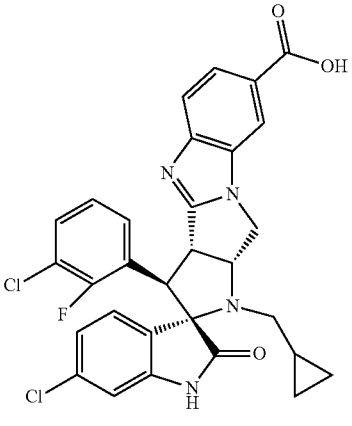 [SMILES: O=C(O)c1ccc2nc3n(c2c1)C[C@H]1[C@@H]3[C@H](c2cccc(Cl)c2F)[C@]2(C(=O)Nc3cc(Cl)ccc32)N1CC1CC1] | 0.99 | 577 | A |
| Ib-179 | 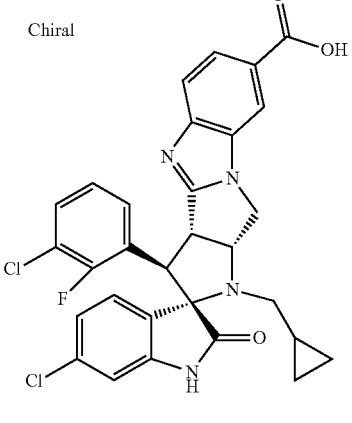 Chiral | 0.99 | 577 | A |

TABLE 36-continued
| # | structure | $t_{ret}$ [min] | [M + H]$^+$ | HPLC method |
|---|---|---|---|---|
| Ib-180 | 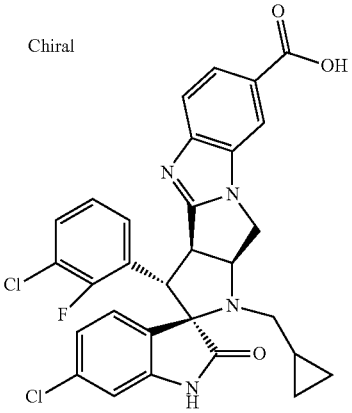 [SMILES: O=C(O)c1ccc2nc3n(c2c1)C[C@@H]1[C@H]3[C@@H](c2cccc(Cl)c2F)[C@@]2(C(=O)Nc3cc(Cl)ccc32)N1CC1CC1 ; "Chiral"] | 0.99 | 577 | A |
| Ib-181 | 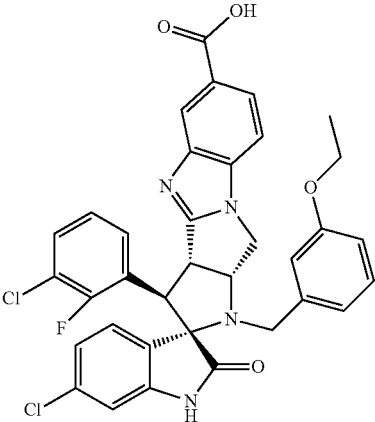 | 1.13 | 657 | A |
| Ib-182 | 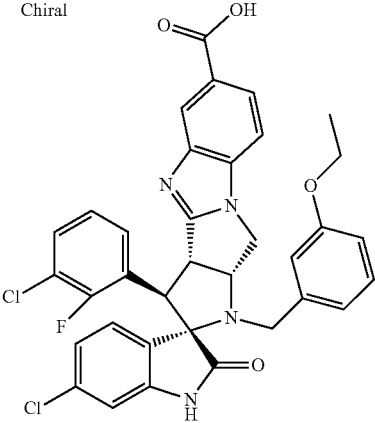 [SMILES: CCOc1cccc(CN2[C@H]3Cn4c(nc5cc(C(=O)O)ccc54)[C@H]3[C@H](c3cccc(Cl)c3F)[C@]23C(=O)Nc2cc(Cl)ccc23)c1 ; "Chiral"] | 1.13 | 657 | A |

TABLE 36-continued

| # | structure | $t_{ret}$ [min] | $[M + H]^+$ | HPLC method |
|---|---|---|---|---|
| Ib-183 | | 1.05 | 657 | A |
| Ib-184 Chiral | | 1.05 | 657 | A |
| Ib-185 Chiral | | 1.05 | 657 | A |

TABLE 36-continued
| # | structure | t_ret [min] | [M + H]+ | HPLC method |
|---|---|---|---|---|
| Ib-186 | 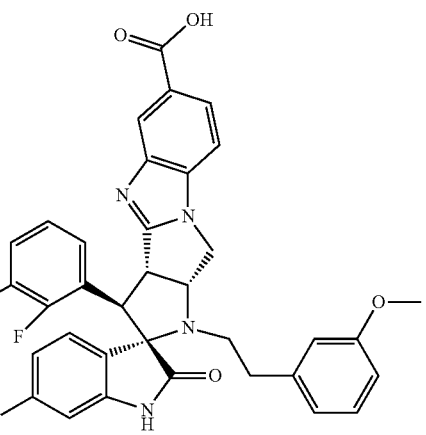 | 1.08 | 657 | A |
| Ib-187 Chiral | 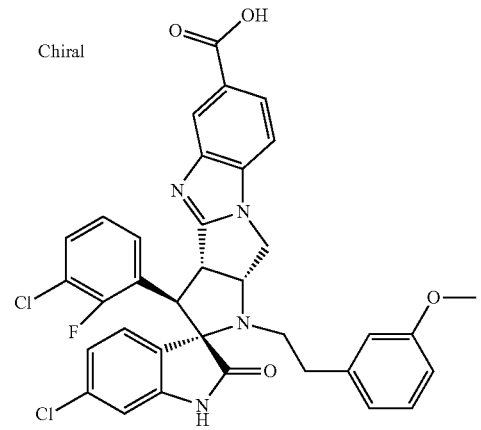 [SMILES: COc1cccc(CCN2[C@H]3Cn4c(nc5cc(C(=O)O)ccc54)[C@H]3[C@H](c3cccc(Cl)c3F)[C@]23C(=O)Nc2cc(Cl)ccc23)c1 ; "Chiral"] | 1.08 | 657 | A |
| Ib-188 Chiral | 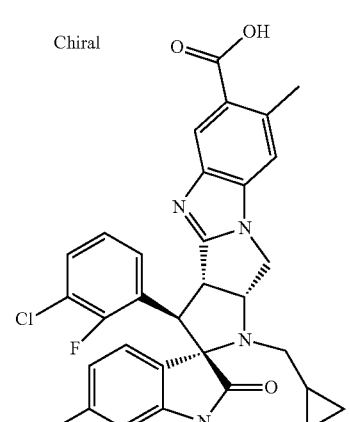 | 1.05 | 591 | A |

TABLE 36-continued
| # | structure | $t_{ret}$ [min] | [M + H]⁺ | HPLC method |
|---|---|---|---|---|
| Ib-189 | 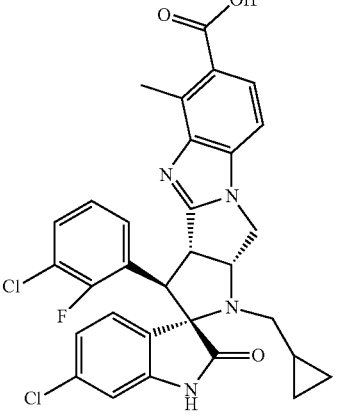 | 1.01 | 591 | A |
| Ib-190 | 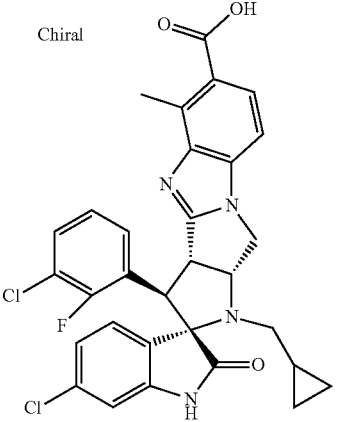 [SMILES: Cc1c(C(=O)O)ccc2c1nc1n2C[C@H]2[C@@H]1[C@H](c1cccc(Cl)c1F)[C@]1(C(=O)Nc3cc(Cl)ccc31)N2CC1CC1 ; "Chiral"] | 1.02 | 591 | A |
| Ib-191 | 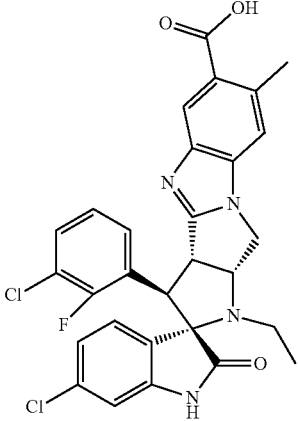 [SMILES: CCN1[C@H]2Cn3c(nc4cc(C(=O)O)c(C)cc43)[C@H]2[C@H](c2cccc(Cl)c2F)[C@]12C(=O)Nc1cc(Cl)ccc12] | 0.99 | 565 | A |

TABLE 36-continued

| # | structure | t_ret [min] | [M + H]+ | HPLC method |
|---|---|---|---|---|
| Ib-192 | Chiral | 0.99 | 565 | A |
| Ib-193 | 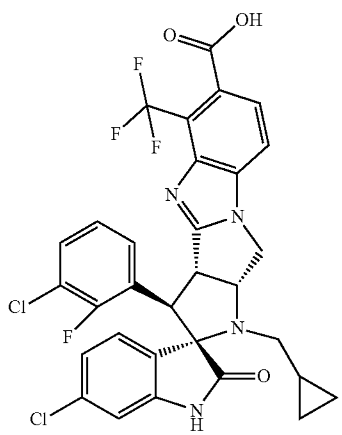 | 1.03 | 645 | A |
| Ib-194 | Chiral | 1.03 | 645 | A |

TABLE 36-continued
| # | structure | $t_{ret}$ [min] | [M + H]$^+$ | HPLC method |
|---|---|---|---|---|
| Ib-195 | 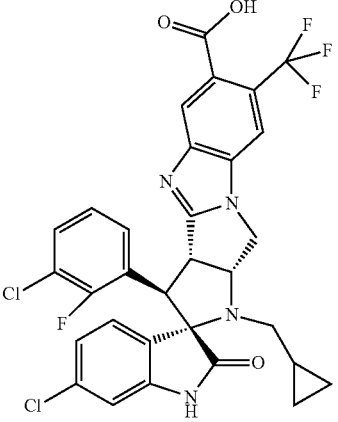 [SMILES: O=C(O)c1cc2nc3n(c2cc1C(F)(F)F)C[C@H]1[C@@H]3[C@H](c2cccc(Cl)c2F)[C@]2(C(=O)Nc3cc(Cl)ccc32)N1CC1CC1] | 1.08 | 645 | A |
| Ib-196 | 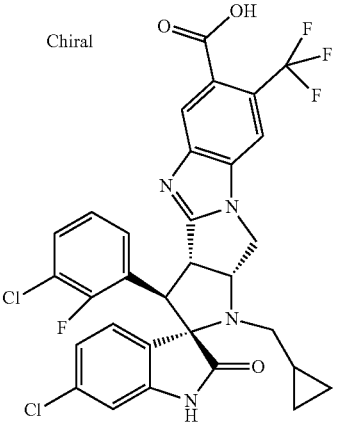 [SMILES: O=C(O)c1cc2nc3n(c2cc1C(F)(F)F)C[C@H]1[C@@H]3[C@H](c2cccc(Cl)c2F)[C@]2(C(=O)Nc3cc(Cl)ccc32)N1CC1CC1 ; "Chiral"] Chiral | 1.08 | 645 | A |
| Ib-197 | 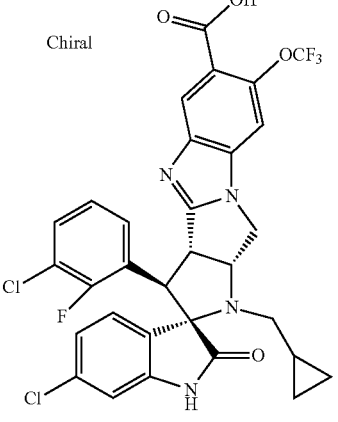 Chiral | 1.10 | 661 | A |

TABLE 36-continued
| # | structure | $t_{ret}$ [min] | $[M + H]^+$ | HPLC method |
|---|---|---|---|---|
| Ib-198 | 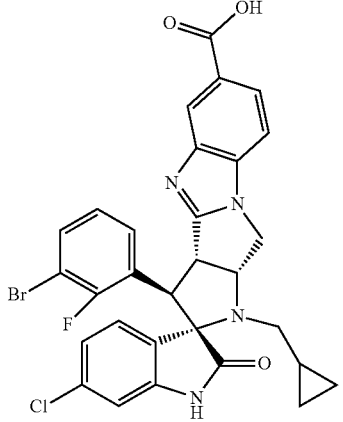 | 1.06 | 621 | A |
| Ib-199 | Chiral 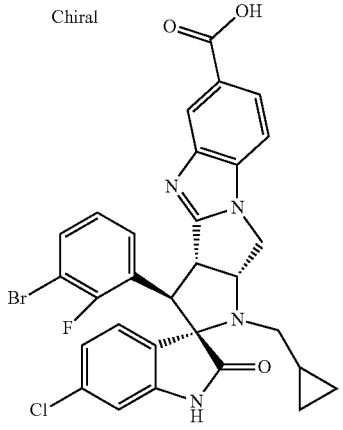 [SMILES: O=C(O)c1ccc2c(c1)nc1n2C[C@H]2[C@@H]1[C@H](c1cccc(Br)c1F)[C@]1(C(=O)Nc3cc(Cl)ccc31)N2CC1CC1 ; "Chiral"] | 1.06 | 621 | A |
| Ib-200 | 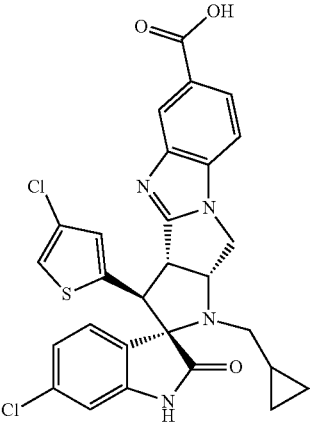 [SMILES: O=C(O)c1ccc2c(c1)nc1n2C[C@H]2[C@@H]1[C@H](c1cc(Cl)cs1)[C@]1(C(=O)Nc3cc(Cl)ccc31)N2CC1CC1] | 1.01 | 565 | A |

TABLE 36-continued
| # | structure | $t_{ret}$ [min] | $[M + H]^+$ | HPLC method |
|---|---|---|---|---|
| Ib-201 | 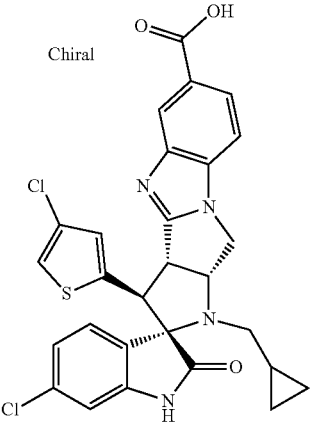 | 1.01 | 565 | A |
| Ib-202 | 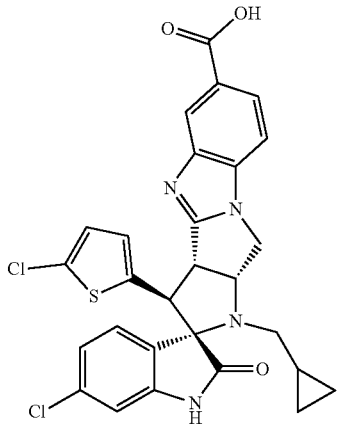 [SMILES: O=C(O)c1ccc2c(c1)nc1n2C[C@H]2[C@@H]1[C@H](c1ccc(Cl)s1)[C@]1(C(=O)Nc3cc(Cl)ccc31)N2CC1CC1] | 1.03 | 565 | A |
| Ib-203 | 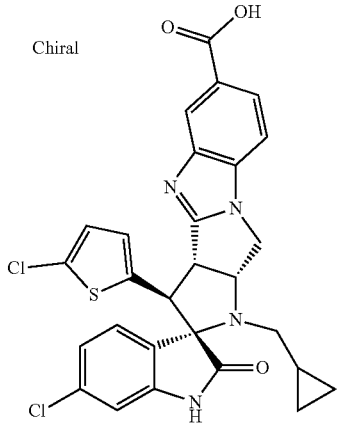 [SMILES: O=C(O)c1ccc2c(c1)nc1n2C[C@H]2[C@@H]1[C@H](c1ccc(Cl)s1)[C@]1(C(=O)Nc3cc(Cl)ccc31)N2CC1CC1 ; "Chiral"] | 1.03 | 565 | A |

TABLE 36-continued
| # | structure | t_ret [min] | [M + H]+ | HPLC method |
|---|---|---|---|---|
| Ib-204 | 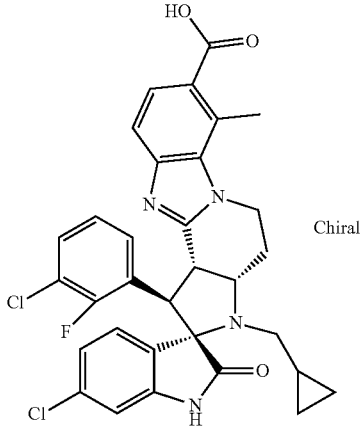 | 1.01 | 605 | A |
| Ib-205 | 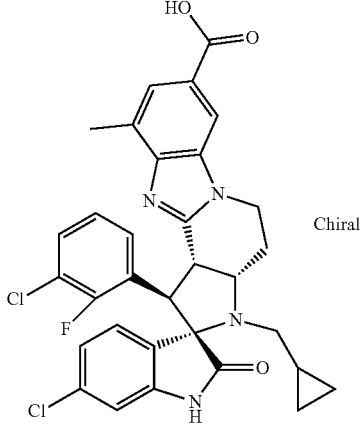 | 1.02 | 605 | A |
| Ib-206 | 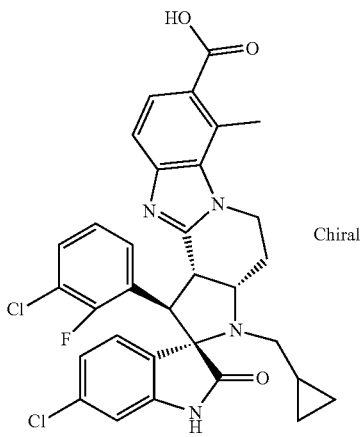 | 1.01 | 605 | A |

TABLE 36-continued

| # | structure | $t_{ret}$ [min] | [M + H]⁺ | HPLC method |
|---|---|---|---|---|
| Ib-207 | 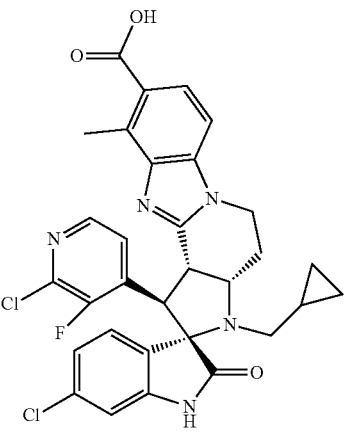 [SMILES: Cc1c(C(=O)O)ccc2c1nc1n2CC[C@H]2[C@@H]1[C@H](c1ccnc(Cl)c1F)[C@]1(C(=O)Nc3cc(Cl)ccc31)N2CC1CC1] | 1.03 | 606 | A |
| Ib-208 | 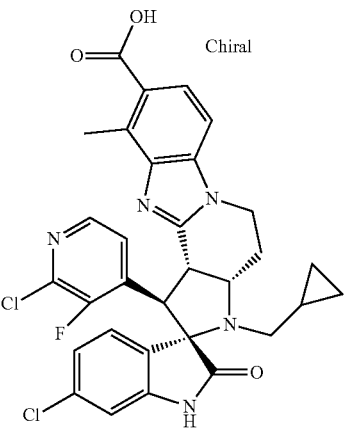 [SMILES: Cc1c(C(=O)O)ccc2c1nc1n2CC[C@H]2[C@@H]1[C@H](c1ccnc(Cl)c1F)[C@]1(C(=O)Nc3cc(Cl)ccc31)N2CC1CC1 ; "Chiral"] | 1.03 | 606 | A |

Synthesis of Further Compounds (Ib) by Amidation

Experimental Procedure for the Synthesis of Ib-209

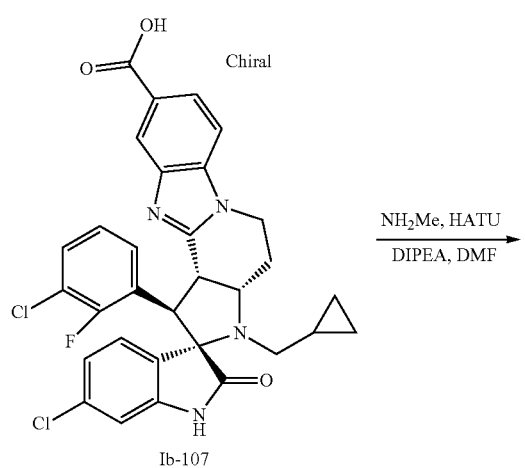

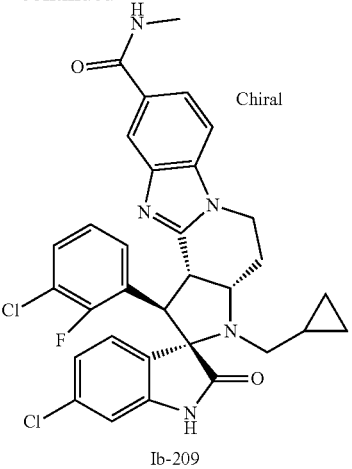

Ib-107 (52 mg, 0.09 mmol) is dissolved in anhydrous DMF (1 mL) and HATU (40 mg, 0.11 mmol) is added at rt. After addition of DIPEA (44.7 µL, 0.26 mmol) the reaction mixture is allowed to stir at rt for 15 min. Methyl amine (2 M in THF, 52.6 µL, 0.11 mmol) is added and the reaction is allowed to stir for additional 30 min. The crude reaction mixture is submitted to reversed phase column chromatography yielding pure Ib-209.

The following compounds (Ib) (table 37) are available in an analogous manner starting from initially obtained compounds (Ib).

TABLE 37

| # | structure | $t_{ret}$ [min] | [M + H]$^+$ | HPLC method |
|---|---|---|---|---|
| Ib-209 | 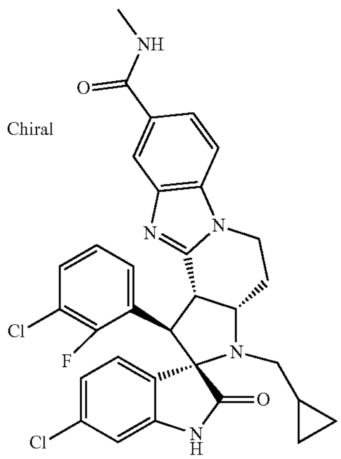 | 1.34 | 604 | A |
| Ib-210 | 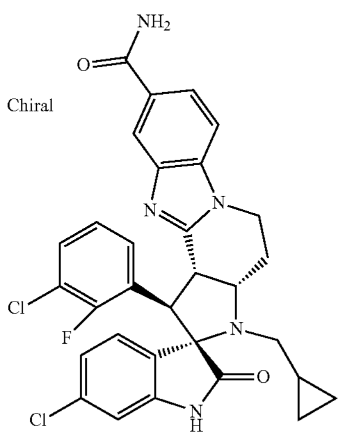 | 1.29 | 590 | A |
| Ib-211 | 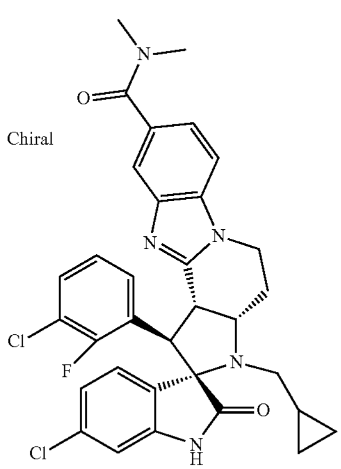 | 1.39 | 618 | A |

TABLE 37-continued
| # | structure | t_ret [min] | [M + H]+ | HPLC method |
|---|---|---|---|---|
| Ib-212 | 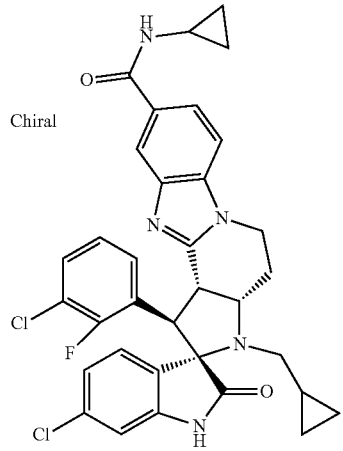 | 1.36 | 630 | A |
| Ib-213 | 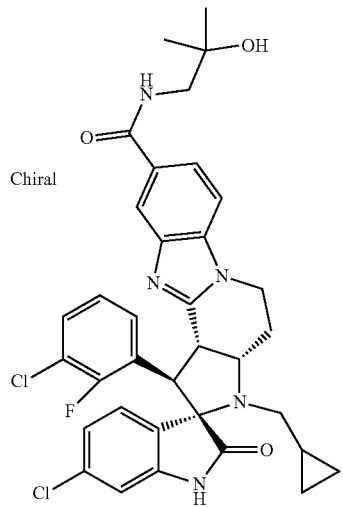 | 1.32 | 662 | A |
| Ib-214 | 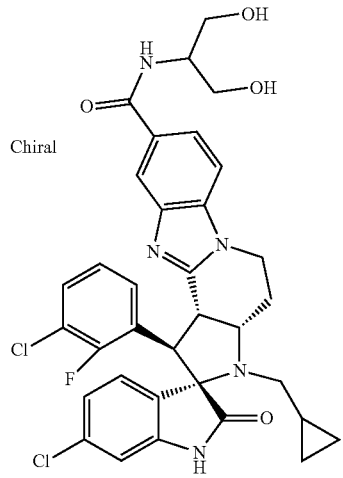 | 1.22 | 664 | A |

TABLE 37-continued
| # | structure | $t_{ret}$ [min] | [M + H]$^+$ | HPLC method |
|---|---|---|---|---|
| Ib-215 | 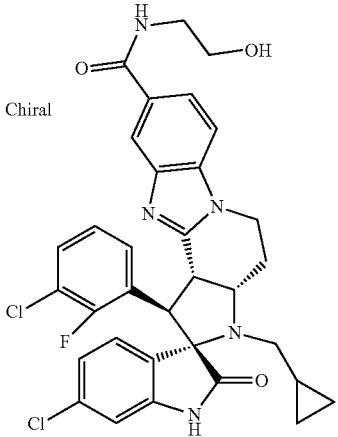 | 1.25 | 634 | A |
| Ib-216 | 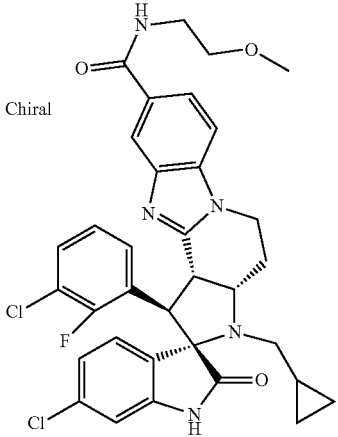 | 1.34 | 648 | A |
| Ib-217 | 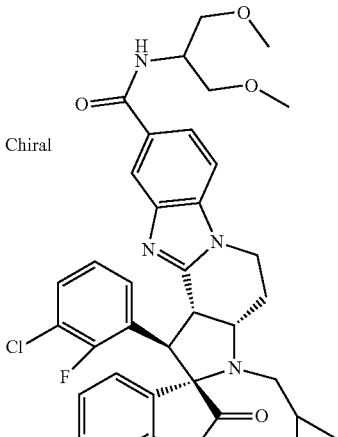 | 1.38 | 692 | A |

473
474
TABLE 37-continued
| # | structure | $t_{ret}$ [min] | [M + H]⁺ | HPLC method |
|---|---|---|---|---|
| Ib-218 | 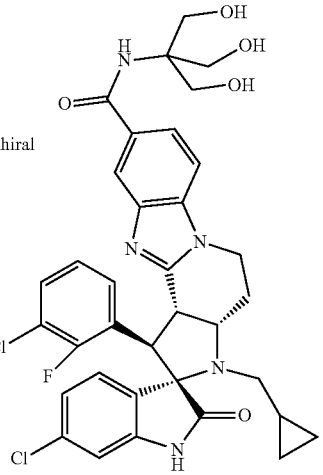 | 1.23 | 694 | A |
| Ib-219 | 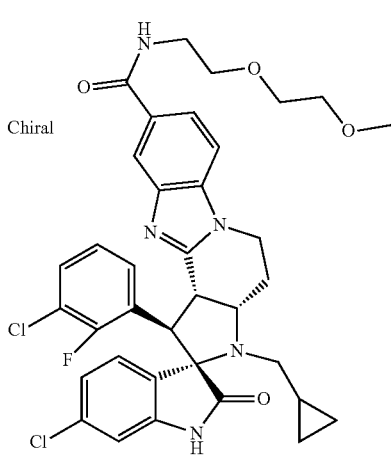 | 1.37 | 692 | A |
| Ib-220 | 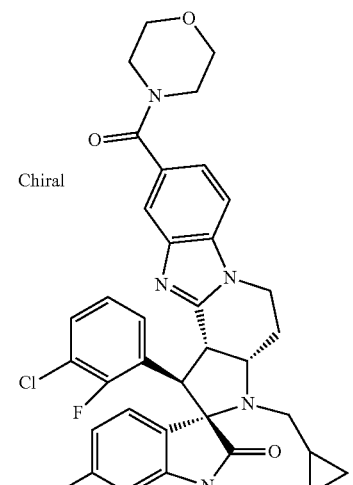 | 1.35 | 660 | A |

TABLE 37-continued
| # | structure | $t_{ret}$ [min] | [M + H]⁺ | HPLC method |
|---|---|---|---|---|
| Ib-221 | 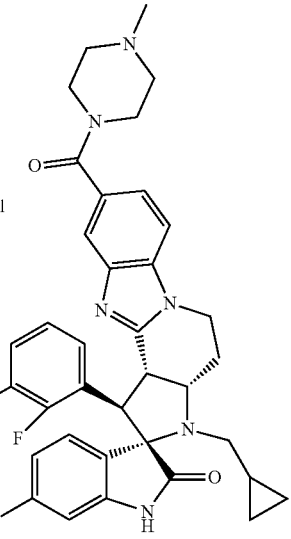 | 1.34 | 673 | A |
| Ib-222 | 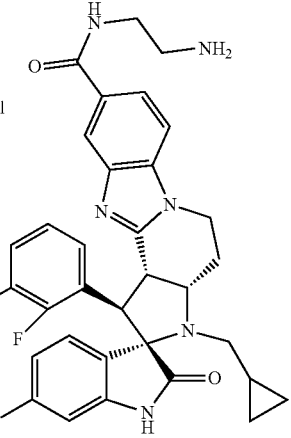 | 1.35 | 633 | A |
| Ib-223 | 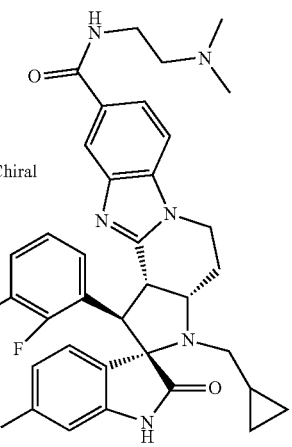 | 1.37 | 661 | A |

TABLE 37-continued
| # | structure | $t_{ret}$ [min] | [M + H]⁺ | HPLC method |
|---|---|---|---|---|
| Ib-224 | 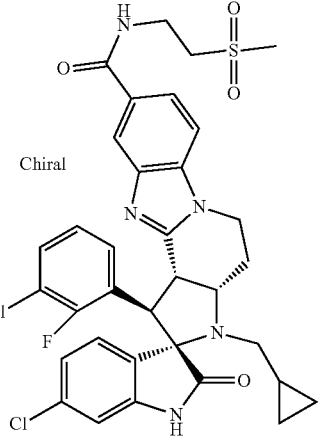 | 1.29 | 596 | A |
| Ib-225 | 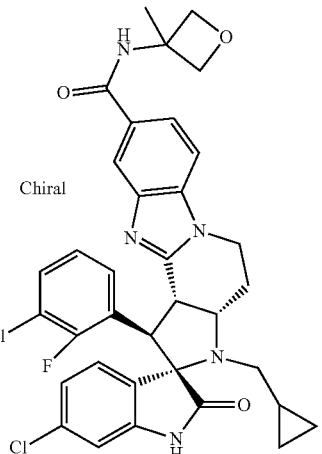 | 1.34 | 660 | A |
| Ib-226 | 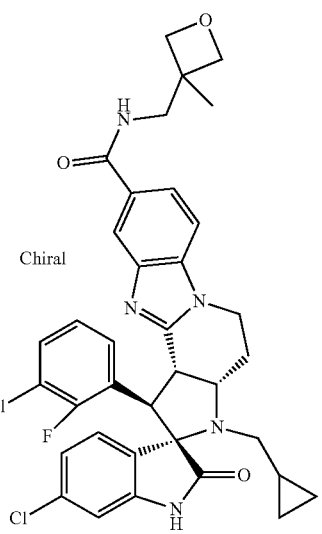 | 1.34 | 674 | A |

TABLE 37-continued
| # | structure | t_ret [min] | [M + H]+ | HPLC method |
|---|---|---|---|---|
| Ib-227 | 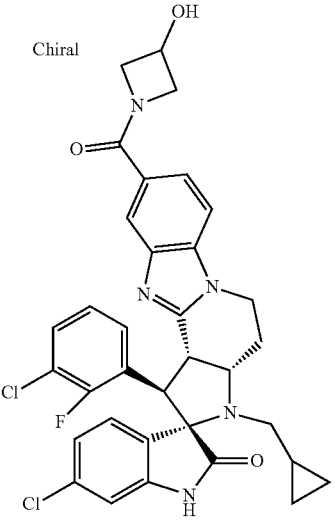 | 1.26 | 646 | A |
| Ib-228 | 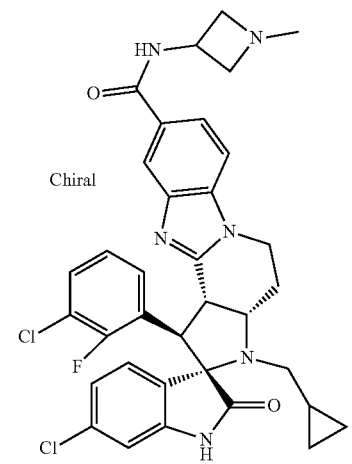 | 1.33 | 659 | A |
| Ib-229 | 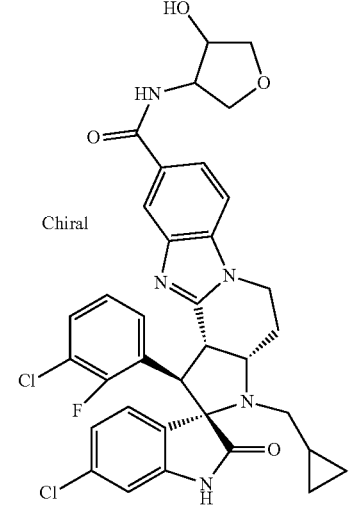 [SMILES: O=C(NC1COCC1O)c1ccc2c(c1)nc1n2CC[C@H]2[C@@H]1[C@H](c1cccc(Cl)c1F)[C@]1(C(=O)Nc3cc(Cl)ccc31)N2CC1CC1 ; "Chiral"] | 1.27 | 676 | A |

TABLE 37-continued
| # | structure | $t_{ret}$ [min] | [M + H]$^+$ | HPLC method |
|---|---|---|---|---|
| Ib-230 | 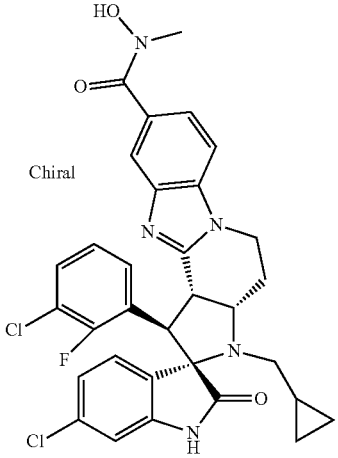 [SMILES: CN(O)C(=O)c1ccc2c(c1)nc1n2CC[C@H]2[C@@H]1[C@H](c1cccc(Cl)c1F)[C@]1(C(=O)Nc3cc(Cl)ccc31)N2CC1CC1 ; "Chiral"] | 1.34 | 620 | A |
| Ib-231 | 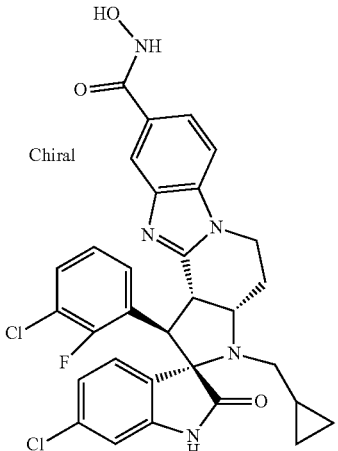 | 1.28 | 606 | A |
| Ib-232 | 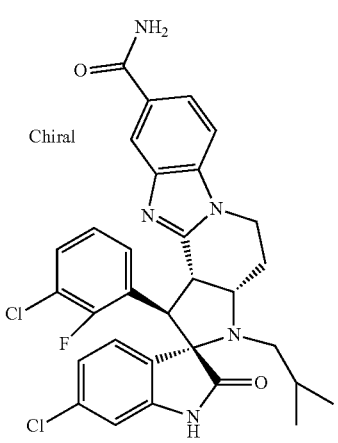 | 1.32 | 592 | A |

TABLE 37-continued
| # | structure | t_ret [min] | [M + H]+ | HPLC method |
|---|---|---|---|---|
| Ib-233 | 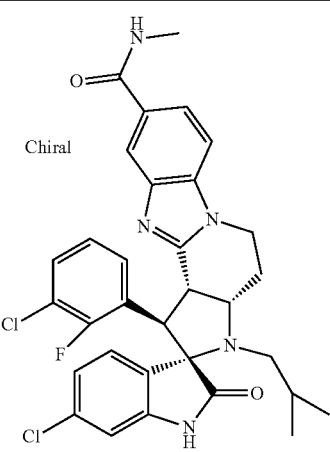 | 1.36 | 606 | A |
| Ib-234 | 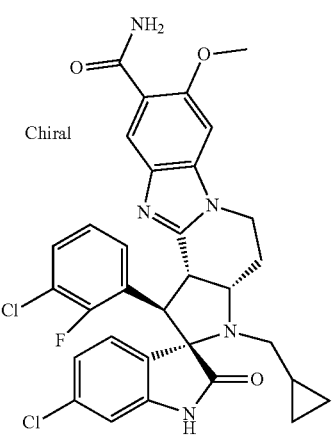 | 1.34 | 620 | A |
| Ib-235 | 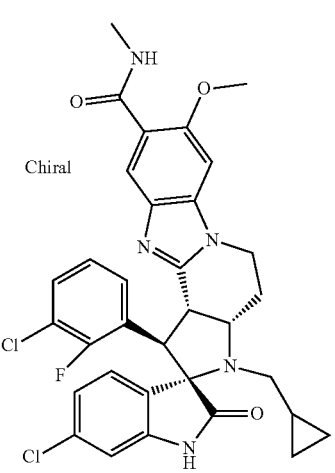 | 1.38 | 634 | A |

TABLE 37-continued
| # | structure | $t_{ret}$ [min] | [M + H]$^+$ | HPLC method |
|---|---|---|---|---|
| Ib-236 | 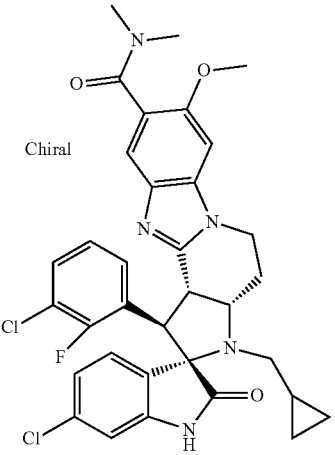 | 1.40 | 648 | A |
| Ib-237 | 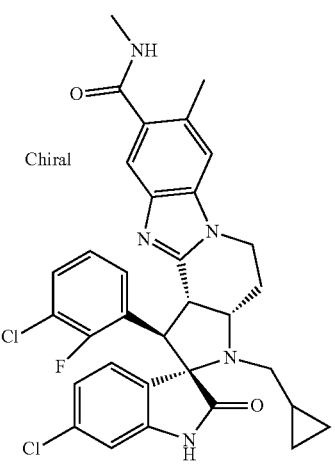 | 1.34 | 618 | A |
| Ib-238 | 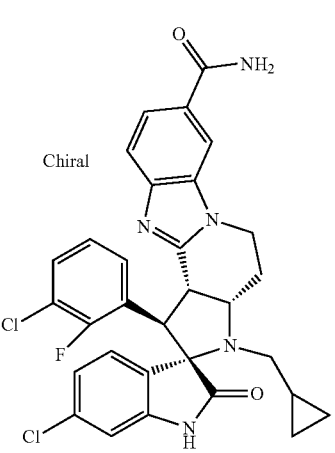 | 1.27 | 590 | A |

TABLE 37-continued
| # | structure | $t_{ret}$ [min] | [M + H]$^+$ | HPLC method |
|---|---|---|---|---|
| Ib-239 | 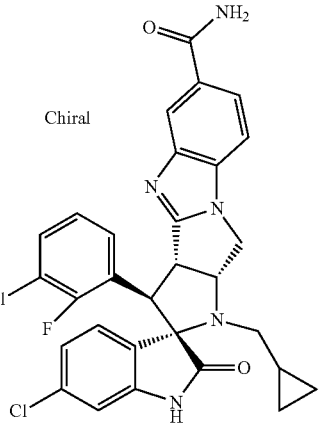 | 1.25 | 576 | A |
| Ib-240 | 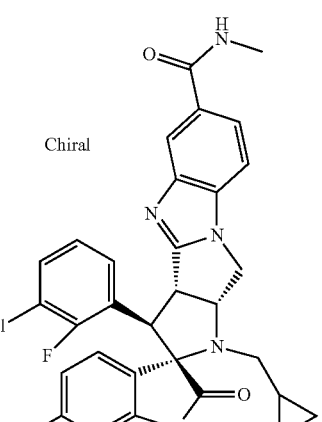 | 1.29 | 590 | A |
| Ib-241 | 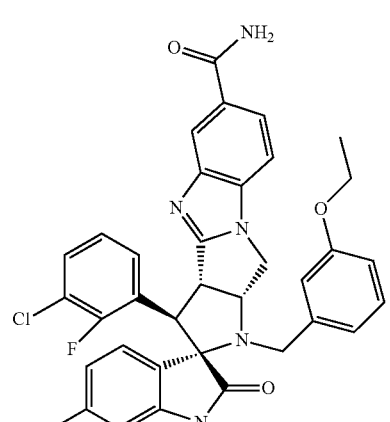 | 1.36 | 656 | A |

TABLE 37-continued
| # | structure | t_ret [min] | [M + H]+ | HPLC method |
|---|---|---|---|---|
| Ib-242 | 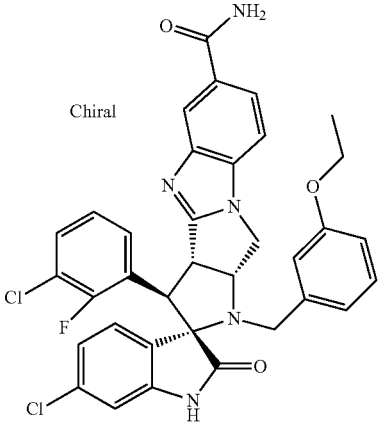 [SMILES: CCOc1cccc(CN2[C@H]3Cn4c(nc5cc(C(N)=O)ccc54)[C@H]3[C@H](c3cccc(Cl)c3F)[C@]23C(=O)Nc2cc(Cl)ccc23)c1 ; "Chiral"] | 1.36 | 656 | A |
| Ib-243 | 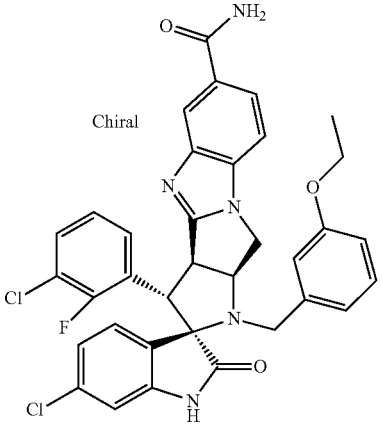 | 1.36 | 656 | A |
| Ib-244 | 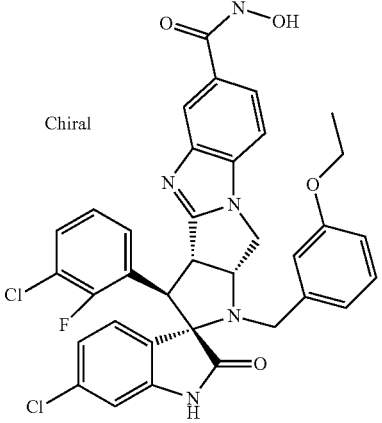 | 1.33 | 672 | A |

Synthesis of Further Compounds (Ib) by Ester Reduction

Experimental Procedure for the Synthesis of Ib-245

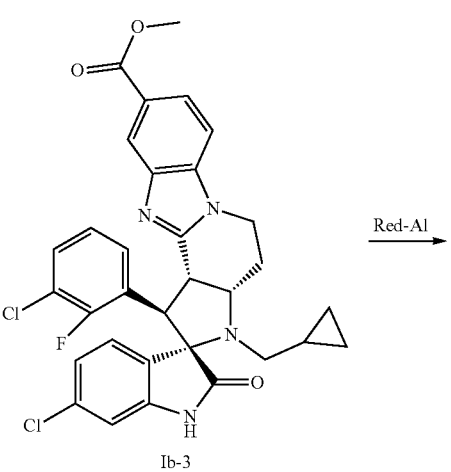

Ib-3

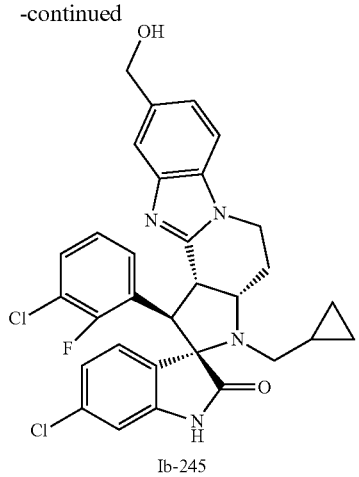

Ib-245

Ib-3 (30 mg, 0.05 mmol) is dissolved in anhydrous toluene (1 mL) and a solution of Red-Al® (60% in toluene, 48 µL) is added. The reaction mixture is heated to 90° C. for 16 h. After that period of time, additional Red-Al (24 µL) is added and heating is continued for 1 h. The reaction is quenched by the addition of water and extracted with EtOAc. The organic layer is dried with $MgSO_4$ and solvents are removed under reduced pressure. Reversed phase column chromatography gives pure Ib-245.

The following compounds (Ib) (table 38) are available in an analogous manner starting from initially obtained compounds (Ib).

TABLE 38

| # | structure | $t_{ret}$ [min] | $[M + H]^+$ | HPLC method |
|---|---|---|---|---|
| Ib-245 | (structure shown) | 1.38 | 577 | A |

TABLE 38-continued

| # | structure | t_ret [min] | [M + H]+ | HPLC method |
|---|---|---|---|---|
| Ib-246 Chiral | | 1.38 | 577 | A |

Synthesis of Further Compounds (Ib) by Deacylation

Experimental Procedure for the Synthesis of Ib-247

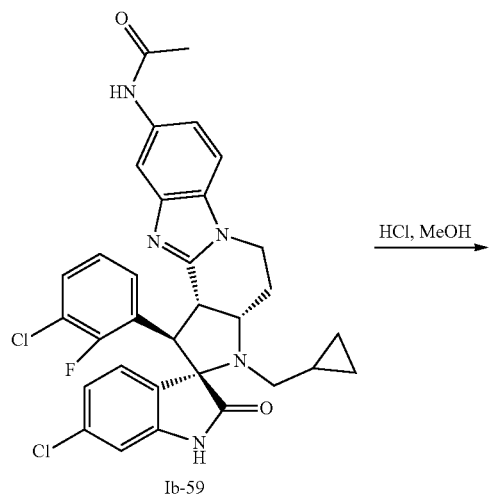

HCl, MeOH

-continued

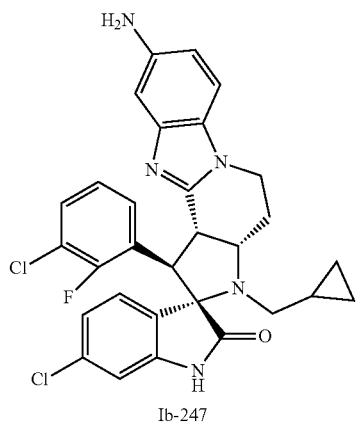

Ib-247

Ib-59 (55 mg, 0.09 mmol) is dissolved in MeOH (500 µL) and conc. aq. HCl (37%, 40 µL) is added. The reaction mixture is heated to 65° C. for 3 h. The reaction is quenched by the addition of 4 M NaOH and EtOAc. The phases are separated and the organic phase is dried with MgSO$_4$. After removal of the solvents under reduced pressure, reversed phase column chromatography gives Ib-247.

The following compounds (Ib) (table 39) are available in an analogous manner starting from initially obtained compounds (Ib).

TABLE 39

| # | structure | t_ret [min] | [M + H]+ | HPLC method |
|---|---|---|---|---|
| I-247 | 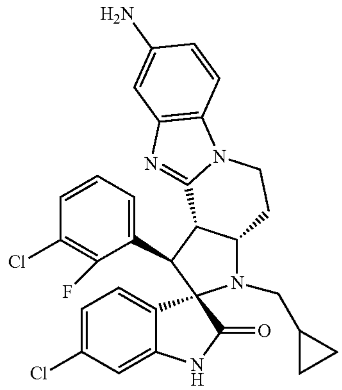 [SMILES: Nc1ccc2c(c1)nc1n2CC[C@H]2[C@@H]1[C@H](c1cccc(Cl)c1F)[C@]1(C(=O)Nc3cc(Cl)ccc31)N2CC1CC1] | 1.35 | 562 | A |
| I-248 | Chiral | 1.35 | 562 | A |

Synthesis of Further Compounds (Ib) by Reductive Amination

Experimental Procedure for the Synthesis of Ib-249

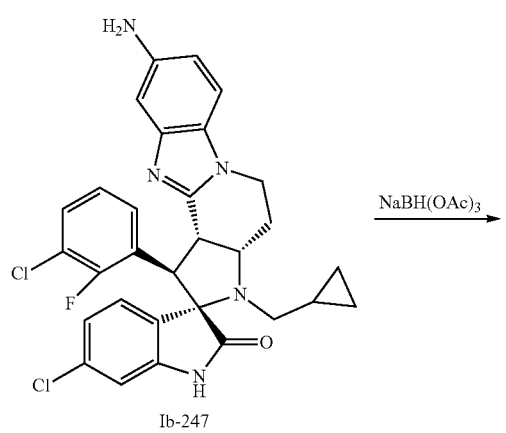

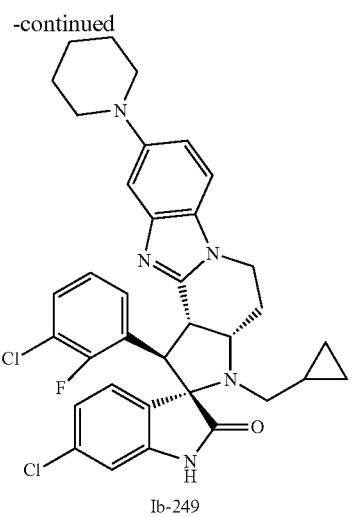

Glutyraldehyde (25% in water, 20 μL, 0.055 mmol) is dissolved in DMF (600 μL) and Ib-247 (10 mg, 0.018 mmol) is added as a solution in DMF (400 μL). The reaction mixture is treated with AcOH (5.1 μL, 0.05 mmol) and stirred at rt for 15 min. After that period of time, sodium triacetoxyborohydride (11.3 mg, 0.05 mmol) is added in one portion and the reaction mixture is allowed to stir at ambient temperature for 2 h. The reaction is quenched by the addition of water, filtered through syringe filter and purified by reversed phase column chromatography to give Ib-249.

The following compounds (Ib) (Table 40) are available in an analogous manner starting from different compounds (Ib).

TABLE 40

| # | structure | $t_{ret}$ [min] | [M + H]$^+$ | HPLC method |
|---|---|---|---|---|
| Ib-249 | 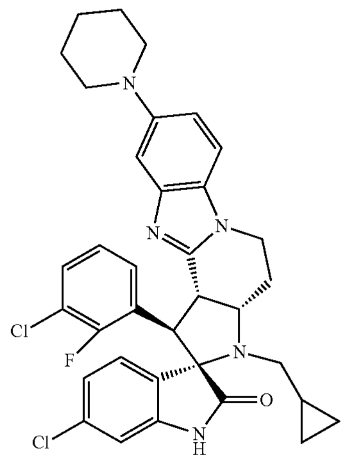 [SMILES: O=C1Nc2cc(Cl)ccc2[C@@]12[C@@H](c1cccc(Cl)c1F)[C@@H]1c3nc4cc(N5CCCCC5)ccc4n3CC[C@@H]1N2CC1CC1] | 1.64 | 630 | A |
| Ib-250 | Chiral | 1.64 | 630 | A |
| Ib-251 | 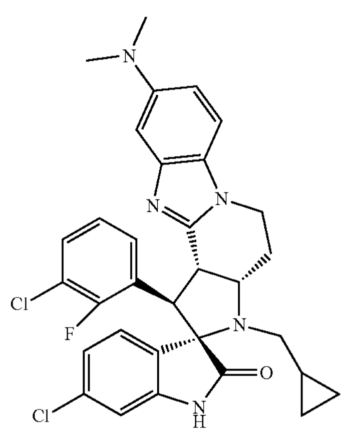 [SMILES: CN(C)c1ccc2c(c1)nc1n2CC[C@H]2[C@@H]1[C@H](c1cccc(Cl)c1F)[C@]1(C(=O)Nc3cc(Cl)ccc31)N2CC1CC1] | 1.35 | 562 | A |

TABLE 40-continued

| # | structure | $t_{ret}$ [min] | $[M + H]^+$ | HPLC method |
|---|---|---|---|---|
| Ib-252 | 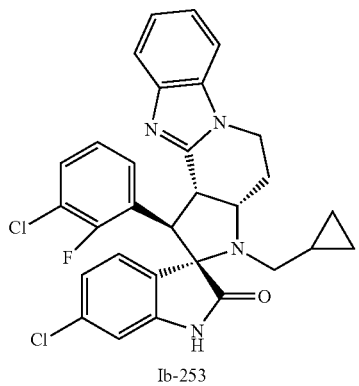 | 1.35 | 562 | A |

Synthesis of Further Compounds (Ib) by Amine Cleavage

Experimental Procedure for the Synthesis of Ib-253

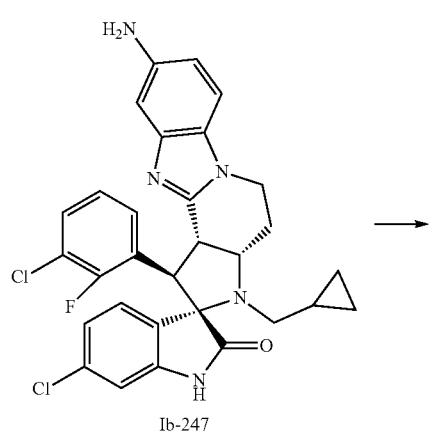
Ib-247

→

Ib-247 (12 mg, 0.021 mmol) is added to a mixture of hypophosphorous acid (50% in water, 300 μL, 2.7 mmol), sulfuric acid (15 μL, 0.26 mmol), and copper(II)sulfate (3.75 mg, 0.023 mmol). The reaction mixture is stirred at rt for 5 min before sodium nitrite (6 mg, 0.085 mmol) and a couple of drops of water are added. The reaction is allowed to stir for 5 min. After quenching by the addition of diluted NaOH and extraction with EtOAc, phases are separated and the organic phase is dried with MgSO₄. Solvents are removed under reduced pressure and reversed phase column chromatography yields pure Ib-253.

The following compounds (Ib) (table 41) are available in an analogous manner starting from initially obtained compounds (Ib).

TABLE 41
| # | structure | $t_{ret}$ [min] | $[M + H]^+$ | HPLC method |
|---|---|---|---|---|
| Ib-253 | 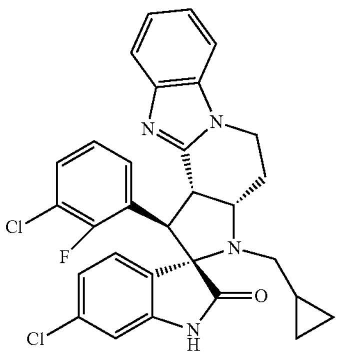 [SMILES: O=C1Nc2cc(Cl)ccc2[C@@]12[C@@H](c1cccc(Cl)c1F)[C@@H]1c3nc4ccccc4n3CC[C@@H]1N2CC1CC1] | 1.51 | 547 | A |
| Ib-254 Chiral | | 1.51 | 547 | A |
Compounds (Ic)
General Reaction Scheme and Summary of the Synthesis Route
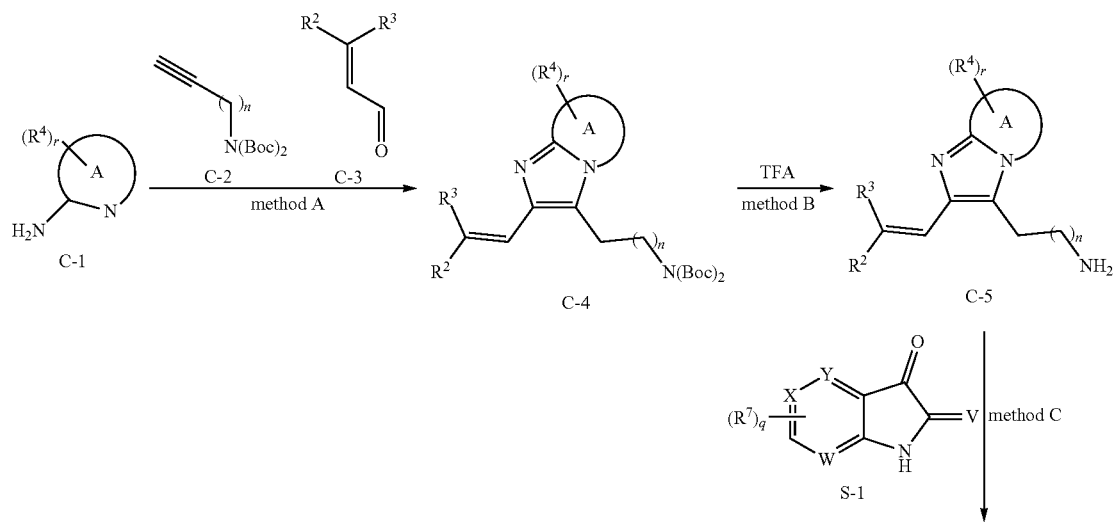
Scheme 6

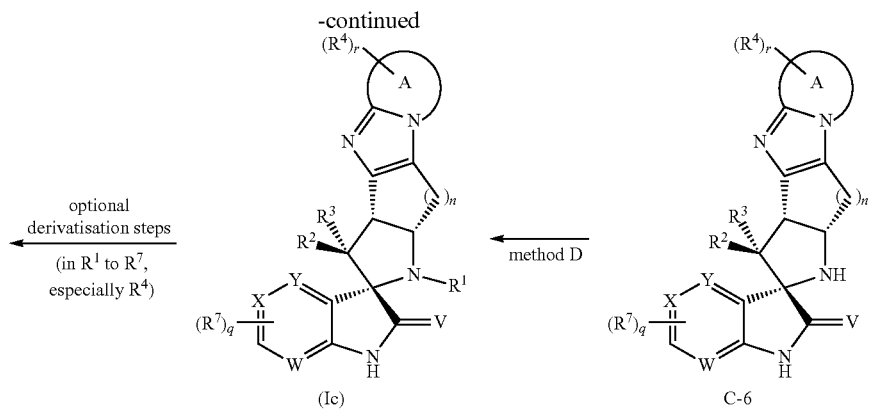

(Ic)    C-6

Novel compounds of structure (Ic) can be prepared stepwise with a synthesis route depicted in scheme 6 starting from (hetero)aryl amines C-1 via a copper-catalyzed three-component coupling reaction with protected alkynylamines C-2 (e.g. bis- or mono-Boc protected) and an α,β-unsaturated aldehyde C-3 to build up imidazo ring systems (e.g. imidazopyrimidyl) C-4 (*Angew. Chem. Int. Ed.* 2010, 49, 2743). The protecting group(s) on C-4 can be removed by an appropriate method. In case of mono- or di-Boc protection acidic conditions, like TFA in dioxane, can be used to generate intermediate C-5. Intermediates C-6 can be obtained from intermediates C-5 and isatin derivatives S-1 via a 1,3-dipolar cycloaddition to build up spiro systems as a racemic mixture potentially along with other regio- and/or diastereoisomers of C-6. The enantiomers of C-6 can be separated at this stage by chiral SFC or alternatively the racemic mixture can be separated at any later stage of the synthesis. Also all other means known for separation of enantiomers can be applied here or after any later synthetic step herein described, e.g. crystallisation, chiral resolution, chiral HPLC etc. (see also Enantiomers, racemates, and resolutions, Jean Jacques, André Collet, Samuel H Wilen John Wiley and Sons, N Y, 1981).

C-6 can be reacted with aldehydes or ketones in a reductive amination reaction to yield compounds (Ic). Alternatively, an alkylation, addition, acylation or sulfonylation reaction can be performed with C-6 to obtain additional compounds (Ic).

Compounds (Ic) which are initially obtained from C-6 can be derivatized in optional derivatization steps not explicitly depicted in the schemes in all residues, especially in $R^4$, if they carry functional groups, that can be further modified such as e.g. halogen atoms, amino and hydroxy groups (including cyclic amines), carboxylic acid or ester functions, nitrils etc. to further compounds (Ic) by well-established organic chemical transformations such as metal-catalyzed cross coupling reactions, acylation, amidation, addition, reduction or (reductive) alkylation or cleavage of protecting groups. These additional steps are not depicted in the general schemes. Likewise, it is also possible to include these additional steps in the synthetic routes depicted in the general schemes, i.e. to carry out derivatization reactions with intermediate compounds. In addition, it may also be possible that building blocks bearing protecting groups are used, i.e. further steps for deprotection are necessary.

Compounds (Ic) have been tested for their activity to affect MDM2-p53 interaction in their racemic form or alternatively as the enantiopure form. Each of the two enantiomers of a racemic mixture may have activity against MDM2 although with a different binding mode. Enantiopure compounds are marked with the label "Chiral". Compounds listed in any table below that are labeled "Chiral" (both intermediates as well as compounds (Ic) according to the invention) can be separated by chiral SFC chromatography from their enantiomer or are synthesized from enantiopure starting material which is separated by chiral SFC.

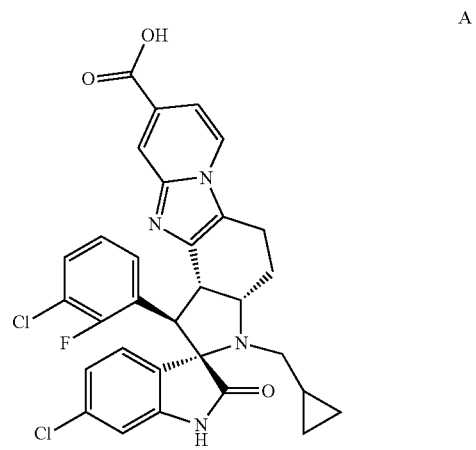

A

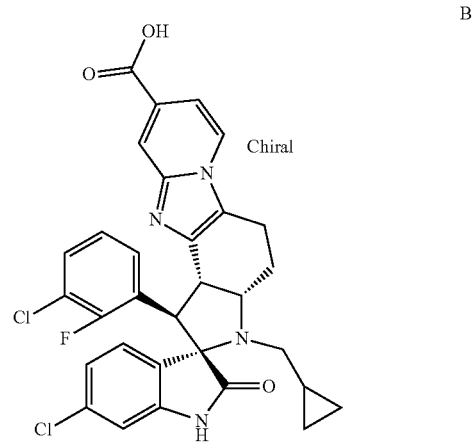

B

505
-continued

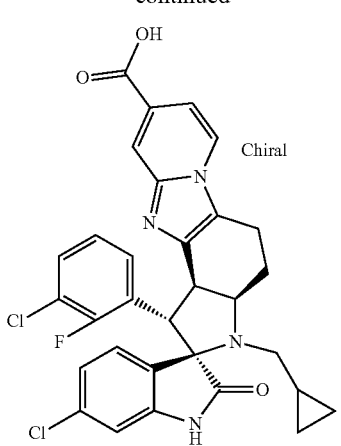
C

Structure A defines the racemic mixture of compounds with structure B and C, i.e. structure A encompasses two structures (compounds B and C), whereas structures B and C, respectively, are enantiopure and only define one specific compound. Thus, formulae (Ic) and (Ic*)

(Ic)

(Ic*)

with a set of specific definitions for groups $R^1$ to $R^7$, A, V, W, X, Y, n, r and q represent the racemic mixture of two enantiomers (→(Ic); structure A above is one specific example of such a racemic mixture) or a single enantiomer (→(Ic*); structure B above is one specific enantiomer), unless there are additional stereocenters present in one or more of the substituents. The same definition applies to synthetic intermediates.

Synthesis of Intermediates C-3

Experimental Procedure for the Synthesis of C-3a

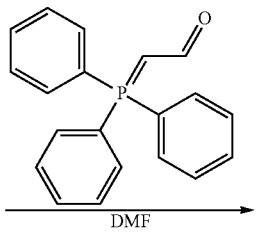

2-Chloro-3-fluoro-pyridine-4-carbaldehyde D-1a (1.00 g, 6.27 mmol) and (triphenylphos-phoranylidene)acetaldehyde (1.91 g, 6.27 mmol) are dissolved in DMF and stirred at rt for 16 h. The mixture is poured into ice-water and the precipitate is filtered. The crude product is purified by chromatography to deliver intermediate C-3a.

The following intermediates C-3a (table 42) are available in an analogous manner starting from different aldehydes D-1.

TABLE 42

| # | structure | $t_{ret}$ [min] | $[M + H]^+$ | HPLC method |
|---|---|---|---|---|
| C-3a | 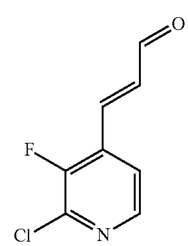 [SMILES: O=C/C=C/c1ccnc(Cl)c1F] | 0.45 | 185 | C |

Synthesis of Intermediates C-4

Experimental Procedure for the Synthesis of C-4a (Method A)

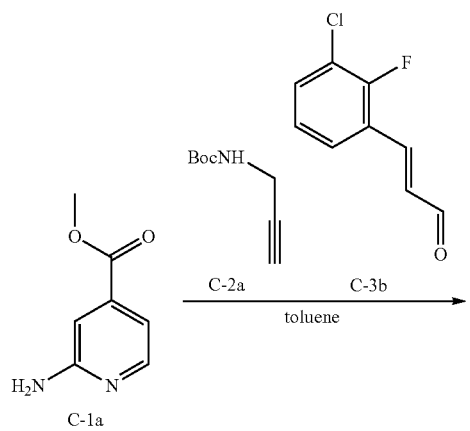

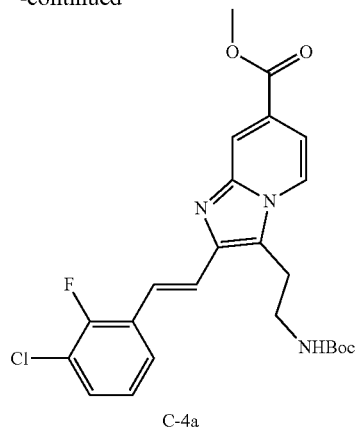

C-4a

2-Amino-isonicotinic acid methyl ester C-1a (1.00 g, 6.572 mmol), N-Boc prop-2-ynylamine C-2a (1.12 g, 7.230 mmol), E-3-(3-chloro-2-fluorophenyl) propenal C-3b (1.34 g, 7.23 mmol), Cu(OTf)$_2$ (0.24 g, 0.66 mmol) and CuCl (0.06 g, 0.07 mmol) are dissolved in toluene under argon and stirred at 100° C. for 20 h. The solvent is removed under vacuum and the crude product is purified by chromatography to deliver intermediate C-4a.

The following intermediates C-4 (table 43) are available in an analogous manner starting from different intermediates C-1, C-2 and C-3.

TABLE 43

| # | structure | t$_{ret}$ [min] | [M + H]$^+$ | HPLC method |
|---|---|---|---|---|
| C-4a | 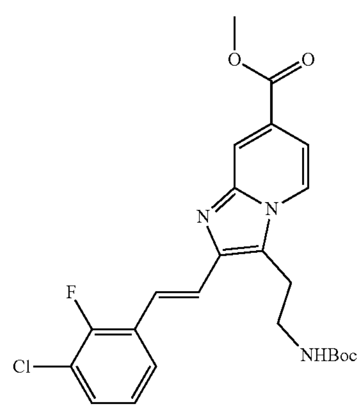 [SMILES: COC(=O)c1ccn2c(CCNC(=O)OC(C)(C)C)c(/C=C/c3cccc(Cl)c3F)nc2c1] | 1.41 | 474 | A |
| C-4b | 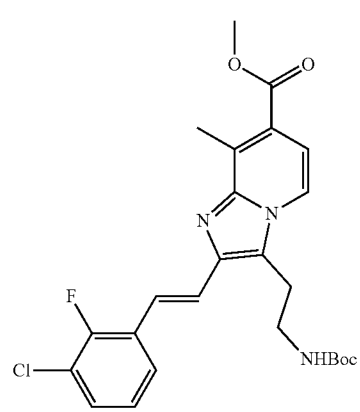 [SMILES: COC(=O)c1ccn2c(CCNC(=O)OC(C)(C)C)c(/C=C/c3cccc(Cl)c3F)nc2c1C] | 1.52 | 488 | A |

TABLE 43-continued
| # | structure | $t_{ret}$ [min] | [M + H]$^+$ | HPLC method |
|---|---|---|---|---|
| C-4c | 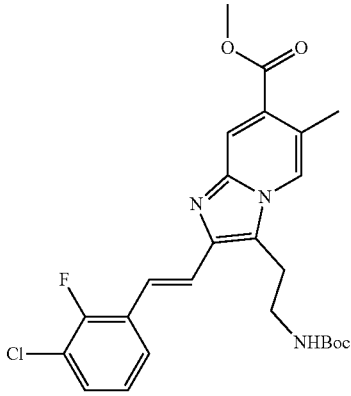 [SMILES: COC(=O)c1cc2nc(/C=C/c3cccc(Cl)c3F)c(CCNC(=O)OC(C)(C)C)n2cc1C] | 0.87 | 589 | C |
| C-4d | 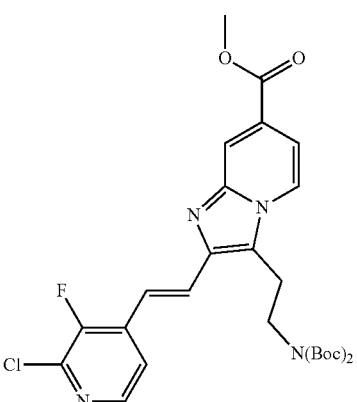 | 0.89 | 575 | C |
| C-4e | 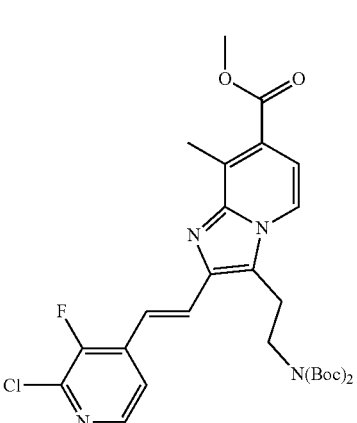 | n.a. | n.a. | n.a |

Synthesis of Intermediates C-5

Experimental Procedure for the Synthesis of C-5a (Method B)

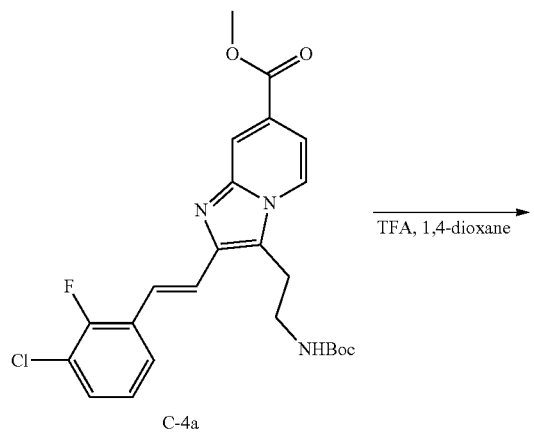

C-4a

→ TFA, 1,4-dioxane →

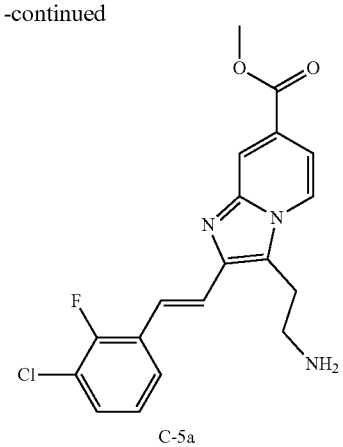

C-5a

Intermediate C-4a (1.00 g, 1.372 mmol) is dissolved in 1,4-dioxane and stirred at rt for 3 h. The solvent is removed under vacuum and the crude product is purified by chromatography if necessary to deliver intermediate C-5a.

The following intermediates C-5 (table 44) are available in an analogous manner starting from different intermediates C-4.

TABLE 44

| # | structure | $t_{ret}$ [min] | $[M + H]^+$ | HPLC method |
|---|-----------|-----------------|-------------|-------------|
| C-5a | 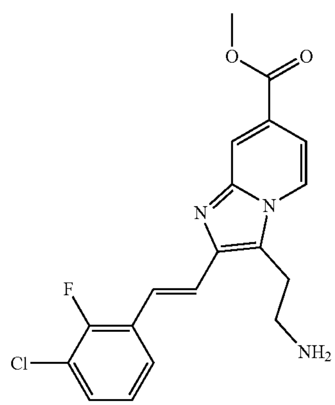 [SMILES: COC(=O)c1ccn2c(CCN)c(/C=C/c3cccc(Cl)c3F)nc2c1] | 1.16 | 374 | A |
| C-5b | 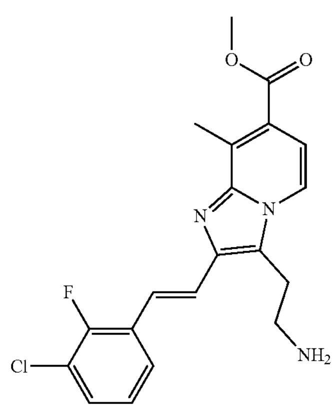 [SMILES: COC(=O)c1ccn2c(CCN)c(/C=C/c3cccc(Cl)c3F)nc2c1C] | 1.29 | 388 | A |

TABLE 44-continued
| # | structure | t_ret [min] | [M + H]+ | HPLC method |
|---|---|---|---|---|
| C-5c | 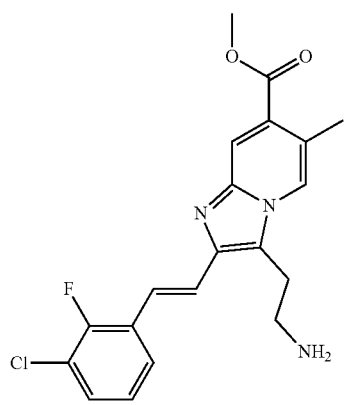 [SMILES: COC(=O)c1cc2nc(/C=C/c3cccc(Cl)c3F)c(CCN)n2cc1C] | 0.46 | 388 | C |
| C-5d | 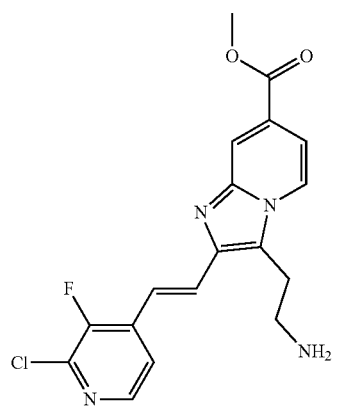 | 1.01 | 375 | A |
| C-5e | 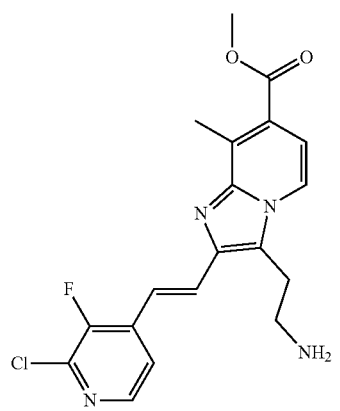 [SMILES: COC(=O)c1ccn2c(CCN)c(/C=C/c3ccnc(Cl)c3F)nc2c1C] | 1.12 | 389 | A |

TABLE 44-continued

| # | structure | $t_{ret}$ [min] | $[M + H]^+$ | HPLC method |
|---|---|---|---|---|
| C-5f | 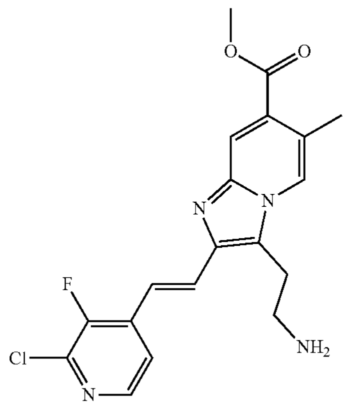 [SMILES: COC(=O)c1cc2nc(/C=C/c3ccnc(Cl)c3F)c(CCN)n2cc1C] | 1.06 | 389 | A |

Synthesis of Intermediates C-6

Experimental Procedure for the Synthesis of C-6a (Method C)

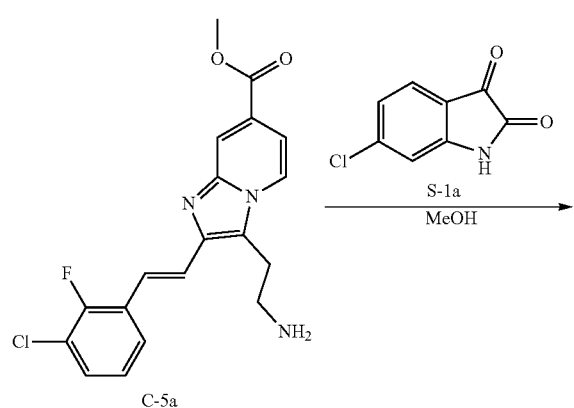

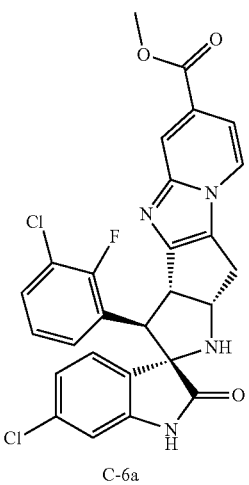

A solution of intermediate C-5a (735 mg, 1.792 mmol), 6-chloroisatin S-1a (813 mg, 4.479 mmol) and N-methylpyrrolidine (763 mg. 8.958 mmol) in MeOH (30 mL) is heated under microwave irradiation at 120° C. for 20 min. The reaction mixture is diluted with DCM and extracted with a saturated aqueous NaHCO₃ solution. The organic layer is separated and the solvents are removed under vacuum and the resulting crude product is purified by chromatography and reversed phase HPLC to deliver intermediate C-6a.

The following intermediates C-6 (table 45) are available in an analogous manner starting from different intermediates C-5 and S-1.

TABLE 45

| # | structure | t_ret [min] | [M + H]+ | HPLC method |
|---|---|---|---|---|
| C-6a | 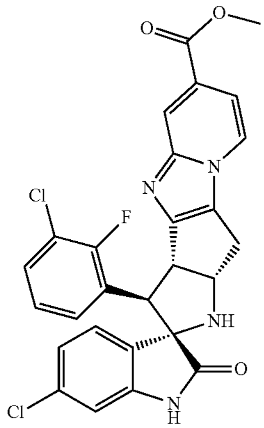 [SMILES: COC(=O)c1ccn2c3c(nc2c1)[C@@H]1[C@H](C3)N[C@@]2(C(=O)Nc3cc(Cl)ccc32)[C@H]1c1cccc(Cl)c1F] | 0.677 | 537 | C |
| C-6b | Chiral | 0.677 | 537 | C |
| C-6c | 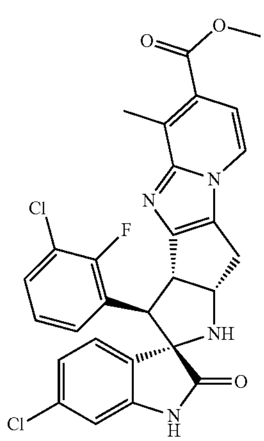 [SMILES: COC(=O)c1ccn2c3c(nc2c1C)[C@@H]1[C@H](C3)N[C@@]2(C(=O)Nc3cc(Cl)ccc32)[C@H]1c1cccc(Cl)c1F] | n.a. | n.a. | — |

TABLE 45-continued

| # | structure | $t_{ret}$ [min] | $[M + H]^+$ | HPLC method |
|---|---|---|---|---|
| C-6d | | Chiral | n.a. | n.a. | — |
| C-6e | 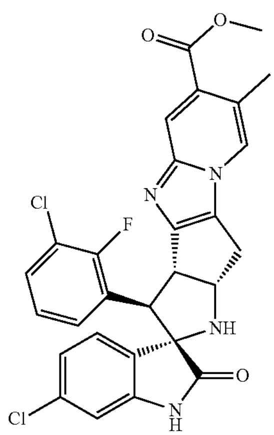 [SMILES: COC(=O)c1cc2nc3c(n2cc1C)C[C@@H]1N[C@@]2(C(=O)Nc4cc(Cl)ccc42)[C@@H](c2cccc(Cl)c2F)[C@H]31] | n.a. | n.a. | — |
| C-6f | | Chiral | n.a. | n.a. | — |

TABLE 45-continued

| # | structure | t_ret [min] | [M + H]+ | HPLC method |
|---|---|---|---|---|
| C-6g | 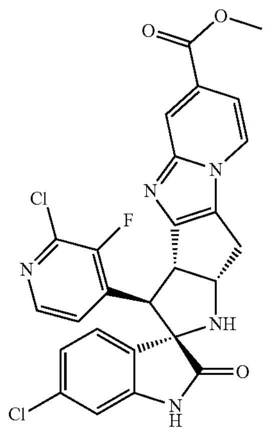 | 1.17 | 538 | A |
| C-6h | Chiral | 1.17 | 538 | A |
| C-6i | 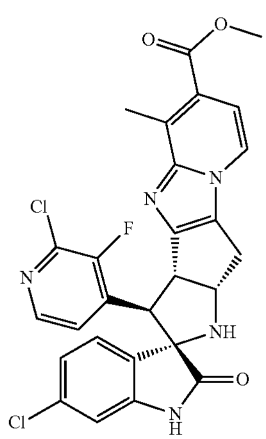 | 1.23 | 552 | A |

TABLE 45-continued
| # | structure | $t_{ret}$ [min] | [M + H]$^+$ | HPLC method |
|---|---|---|---|---|
| C-6j | 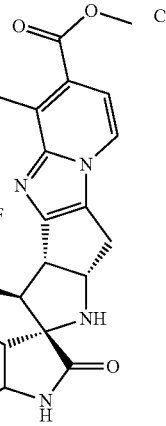 Chiral | 1.23 | 552 | A |
| C-6k | 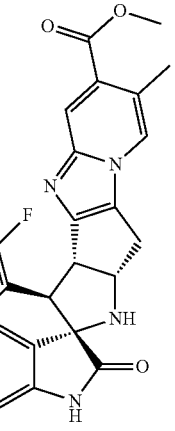 | 1.23 | 552 | A |
| C-6l | 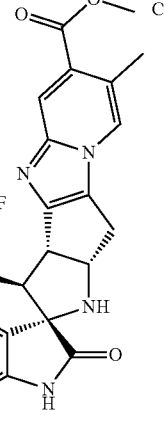 Chiral | 1.23 | 552 | A |

Synthesis of Compounds (Ic) According to the Invention

Experimental Procedure for the Synthesis of Ic-1 (Method D)

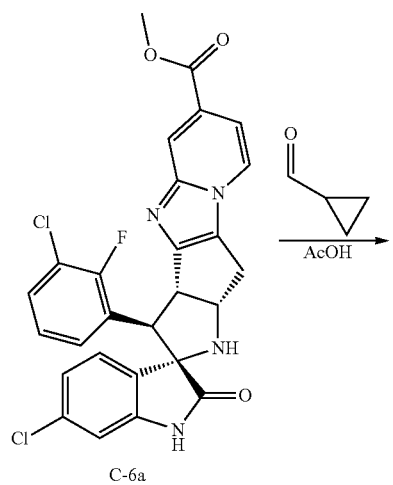

C-6a

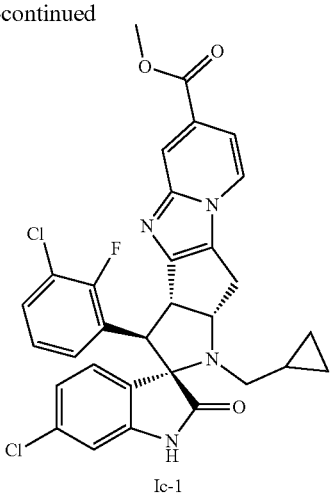

Ic-1

To a solution of cyclopropanecarbaldehyde (2.7 mg, 0.039 mmol) in AcOH (1 mL) is added intermediate C-6a (18 mg, 0.033 mmol) and the reaction mixture is stirred for 15 min. Sodium triacetoxyborohydride (14.2 g, 0.065 mmol) is added and the reaction mixture is stirred overnight. Water is added to the reaction mixture and it is extracted with EtOAc. The combined organic layer is dried ($MgSO_4$), filtered, concentrated in vacuo and the crude product is purified by chromatography to give compound Ic-1.

The following compounds (Ic) (table 46) are available in an analogous manner starting from different intermediates C-6 and different aldehydes.

TABLE 46

| # | structure | $t_{ret}$ [min] | [M + H]$^+$ | HPLC method |
|---|---|---|---|---|
| Ic-1 | 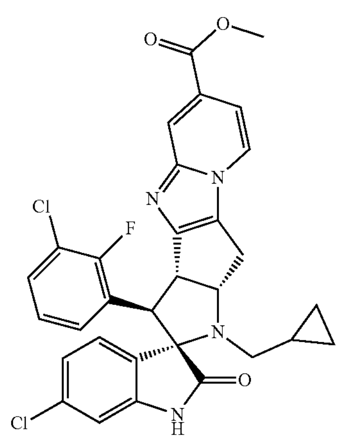 [SMILES: COC(=O)c1ccn2c3c(nc2c1)[C@@H]1[C@H](C3)N(CC2CC2)[C@@]2(C(=O)Nc3cc(Cl)ccc32)[C@H]1c1cccc(Cl)c1F] | 1.50 | 1.50 | A |

TABLE 46-continued
| # | structure | $t_{ret}$ [min] | [M + H]$^+$ | HPLC method |
|---|---|---|---|---|
| Ic-2 | 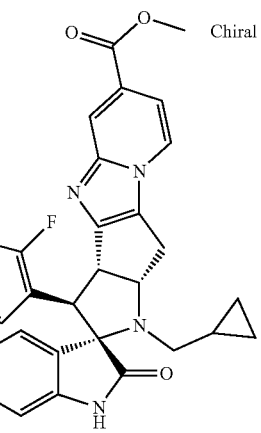 Chiral | 1.50 | 1.50 | A |
| Ic-3 | 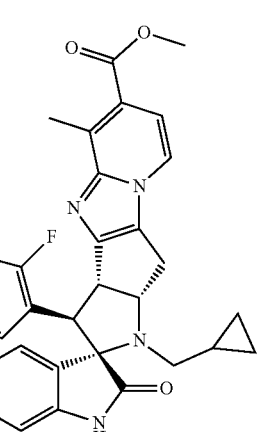 | n.a. | n.a. | — |
| Ic-4 | 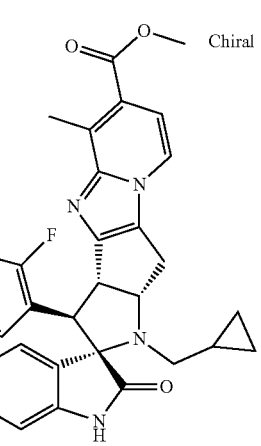 Chiral | n.a. | n.a. | — |

TABLE 46-continued
| # | structure | t_ret [min] | [M + H]+ | HPLC method |
|---|---|---|---|---|
| Ic-5 | 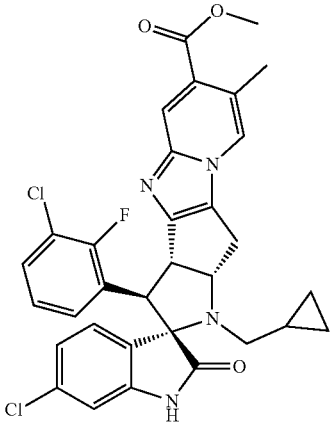 [SMILES: COC(=O)c1cc2nc3c(n2cc1C)C[C@H]1[C@@H]3[C@H](c2cccc(Cl)c2F)[C@]2(C(=O)Nc3cc(Cl)ccc32)N1CC1CC1] | n.a. | n.a. | — |
| Ic-6 | 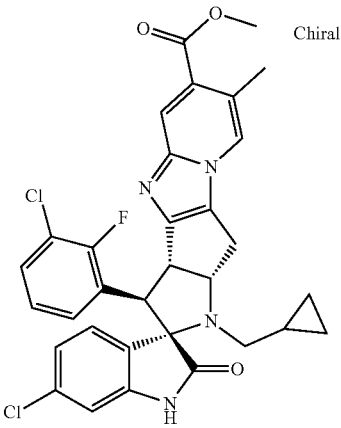 Chiral | n.a. | n.a. | — |
| Ic-7 | 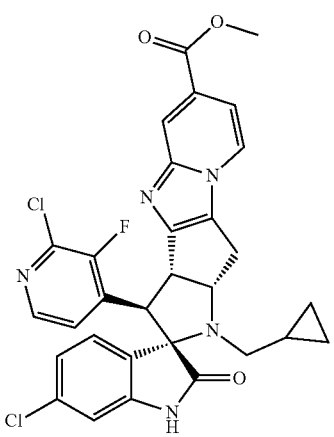 [SMILES: COC(=O)c1ccn2c3c(nc2c1)[C@@H]1[C@H](C3)N(CC2CC2)[C@@]2(C(=O)Nc3cc(Cl)ccc32)[C@H]1c1ccnc(Cl)c1F] | 1.44 | 592 | A |

TABLE 46-continued
| # | structure | $t_{ret}$ [min] | [M + H]$^+$ | HPLC method |
|---|---|---|---|---|
| Ic-8 | 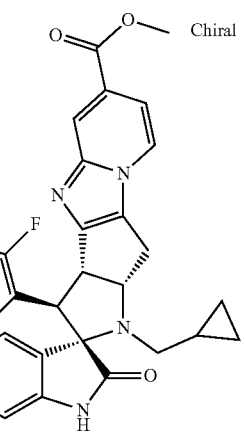 Chiral | 1.44 | 592 | A |
| Ic-9 | 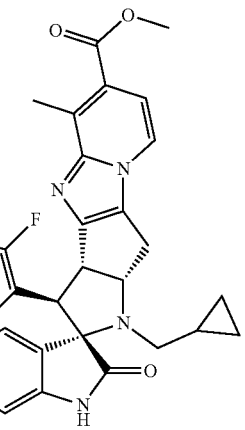 | 1.44 | 592 | A |
| Ic-10 | 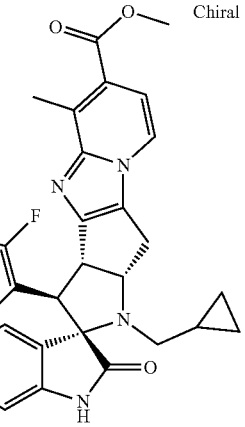 Chiral | 1.44 | 592 | A |

TABLE 46-continued
| # | structure | t_ret [min] | [M + H]+ | HPLC method |
|---|---|---|---|---|
| Ic-11 | 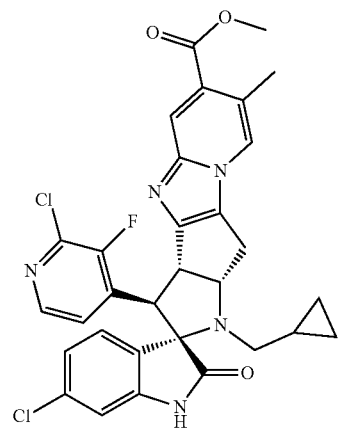 [SMILES: COC(=O)c1cc2nc3c(n2cc1C)C[C@H]1[C@@H]3[C@H](c2ccnc(Cl)c2F)[C@]2(C(=O)Nc3cc(Cl)ccc32)N1CC1CC1] | n.a. | n.a. | — |
| Ic-12 | 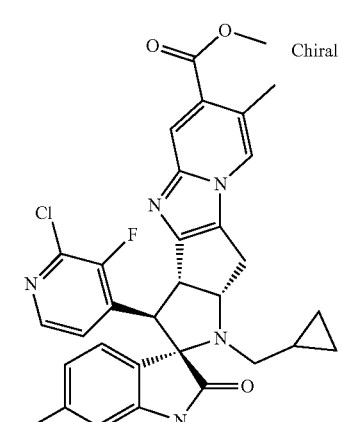 Chiral | n.a. | n.a. | — |
| Ic-13 | 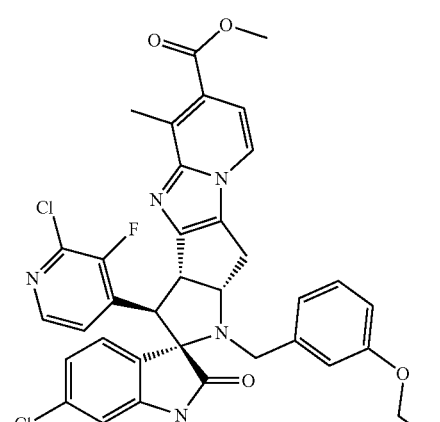 | 1.57 | 686 | A |

TABLE 46-continued

| # | structure | $t_{ret}$ [min] | $[M + H]^+$ | HPLC method |
|---|---|---|---|---|
| Ic-14 | 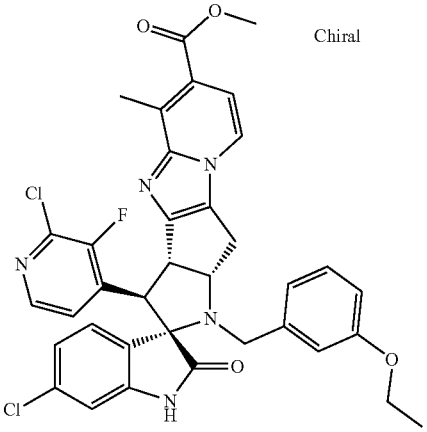 [SMILES: CCOc1cccc(CN2[C@H]3Cc4c(nc5c(C)c(C(=O)OC)ccn45)[C@H]3[C@H](c3ccnc(Cl)c3F)[C@]23C(=O)Nc2cc(Cl)ccc23)c1 ; "Chiral"] Chiral | 1.57 | 686 | A |

Synthesis of Further Compounds (Ic) by Ester Saponification

Experimental Procedure for the Synthesis of Ic-15 (Method E)

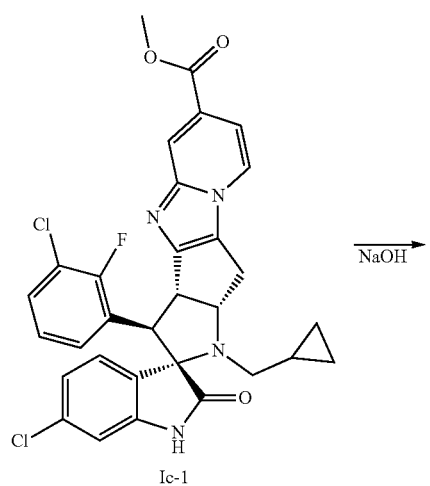

Ic-1

$\xrightarrow{\text{NaOH}}$

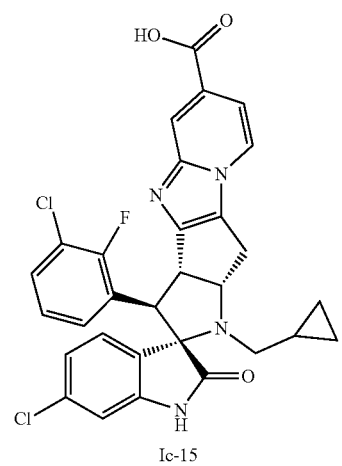

Ic-15

Ic-1 (12 mg, 0.022 mmol) is dissolved in THE (0.5 mL) and water (1 mL) and NaOH s (25 mg, 0.45 mmol) is added. The reaction mixture is stirred at 70° C. for 8 h. After acidification with 2 M aq. HCl and extraction with EtOAc the organic phase is dried with $MgSO_4$. Purification with reversed phase HPLC leads to pure Ic-15.

The following compounds (Ic) (table 47) are available in an analogous manner starting from initially obtained compounds (Ic).

TABLE 47
| # | structure | $t_{ret}$ [min] | $[M + H]^+$ | HPLC method |
|---|---|---|---|---|
| Ic-15 | 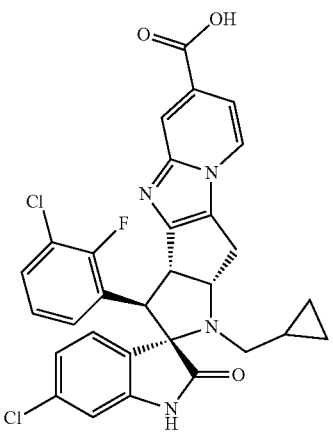 [SMILES: O=C(O)c1ccn2c3c(nc2c1)[C@@H]1[C@H](C3)N(CC2CC2)[C@@]2(C(=O)Nc3cc(Cl)ccc32)[C@H]1c1cccc(Cl)c1F] | 577 | 1.05 | A |
| Ic-16 | 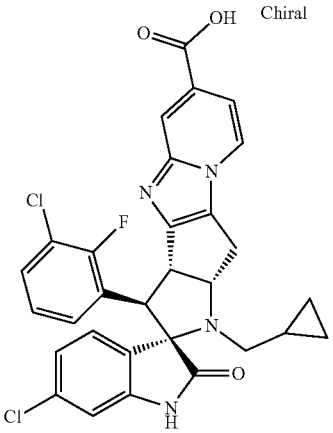 Chiral | 577 | 1.05 | A |
| Ic-17 | 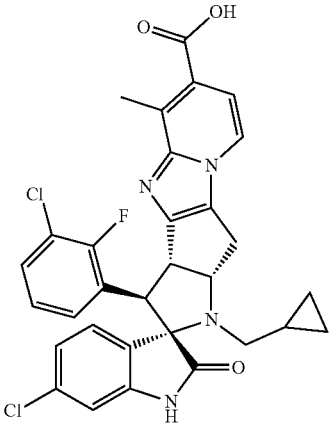 | n.a. | n.a. | — |

TABLE 47-continued
| # | structure | t_ret [min] | [M + H]+ | HPLC method |
|---|-----------|-------------|----------|-------------|
| Ic-18 | 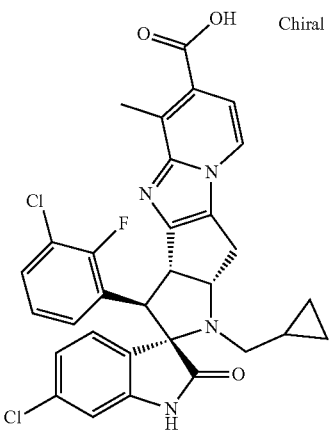 [SMILES: Cc1c(C(=O)O)ccn2c3c(nc12)[C@@H]1[C@H](C3)N(CC2CC2)[C@@]2(C(=O)Nc3cc(Cl)ccc32)[C@H]1c1cccc(Cl)c1F ; "Chiral"] Chiral | n.a. | n.a. | — |
| Ic-19 | 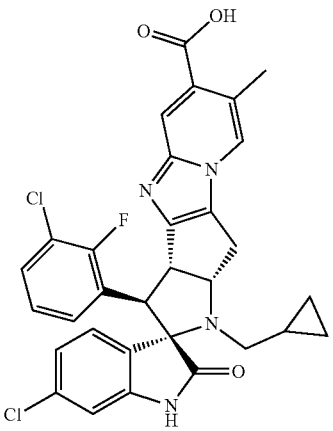 | n.a. | n.a. | — |
| Ic-20 | 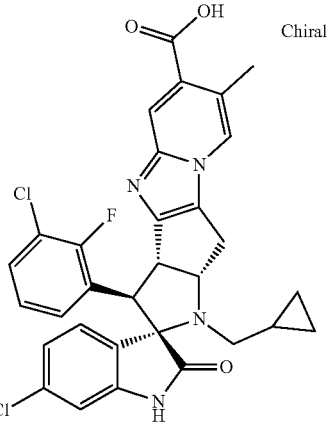 Chiral | n.a. | n.a. | — |

TABLE 47-continued
| # | structure | t_ret [min] | [M + H]+ | HPLC method |
|---|---|---|---|---|
| Ic-21 | 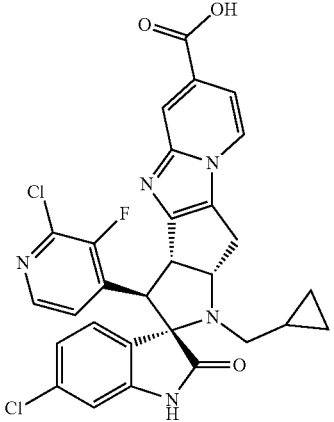 [SMILES: O=C(O)c1ccn2c3c(nc2c1)[C@@H]1[C@H](C3)N(CC2CC2)[C@@]2(C(=O)Nc3cc(Cl)ccc32)[C@H]1c1ccnc(Cl)c1F] | n.a. | n.a. | — |
| Ic-22 | 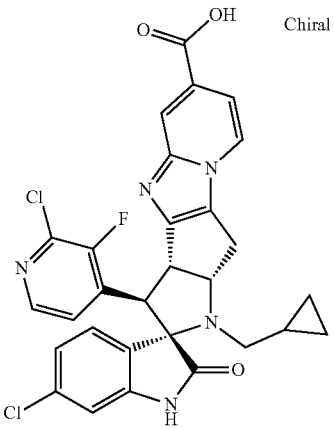 [SMILES: O=C(O)c1ccn2c3c(nc2c1)[C@@H]1[C@H](C3)N(CC2CC2)[C@@]2(C(=O)Nc3cc(Cl)ccc32)[C@H]1c1ccnc(Cl)c1F ; "Chiral"] Chiral | n.a. | n.a. | — |
| Ic-23 | 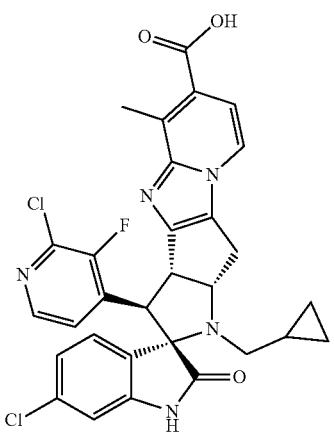 [SMILES: Cc1c(C(=O)O)ccn2c3c(nc12)[C@@H]1[C@H](C3)N(CC2CC2)[C@@]2(C(=O)Nc3cc(Cl)ccc32)[C@H]1c1ccnc(Cl)c1F] | 0.99 | 592 | A |

TABLE 47-continued
| # | structure | $t_{ret}$ [min] | $[M + H]^+$ | HPLC method |
|---|---|---|---|---|
| Ic-24 | 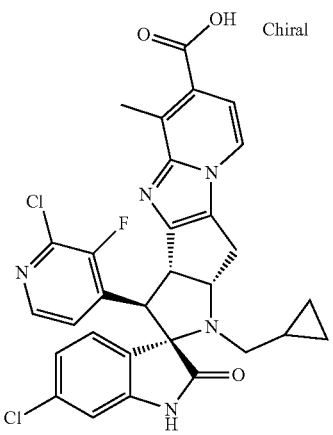 Chiral | 0.99 | 592 | A |
| Ic-25 | 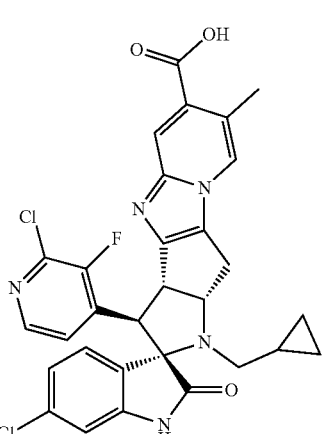 | n.a. | n.a. | — |
| Ic-26 | 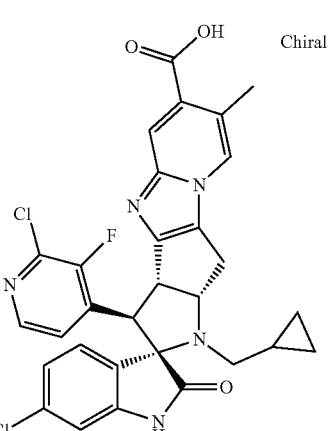 Chiral | n.a. | n.a. | — |

TABLE 47-continued

| # | structure | $t_{ret}$ [min] | $[M + H]^+$ | HPLC method |
|---|-----------|-----------------|-------------|-------------|
| Ic-27 | 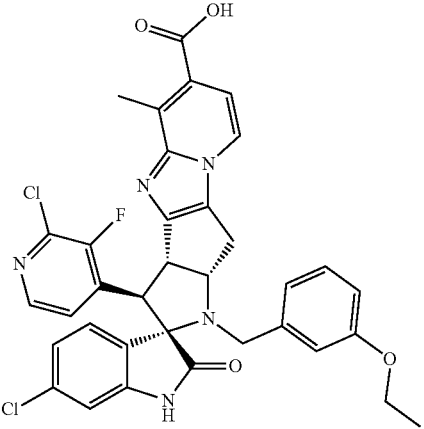 [SMILES: CCOc1cccc(CN2[C@H]3Cc4c(nc5c(C)c(C(=O)O)ccn45)[C@H]3[C@H](c3ccnc(Cl)c3F)[C@]23C(=O)Nc2cc(Cl)ccc23)c1] | 1.06 | 672 | A |
| Ic-28 | 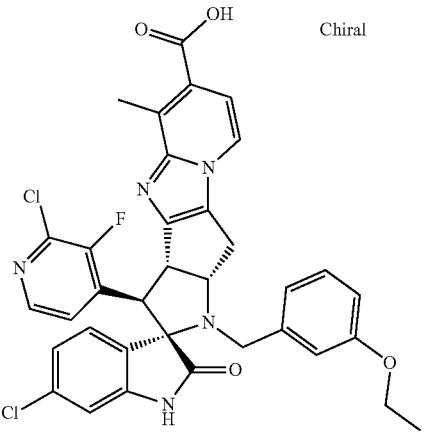 [SMILES: CCOc1cccc(CN2[C@H]3Cc4c(nc5c(C)c(C(=O)O)ccn45)[C@H]3[C@H](c3ccnc(Cl)c3F)[C@]23C(=O)Nc2cc(Cl)ccc23)c1 ; "Chiral"] Chiral | 1.06 | 672 | A |

Synthesis of Further Compounds (Ic) by Amidation

Experimental Procedure for the Synthesis of Ic-29 (Method F)

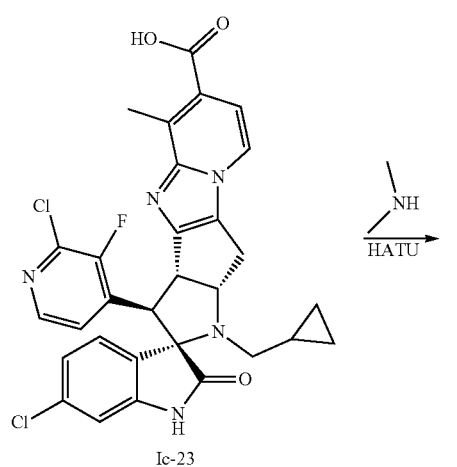

Ic-23

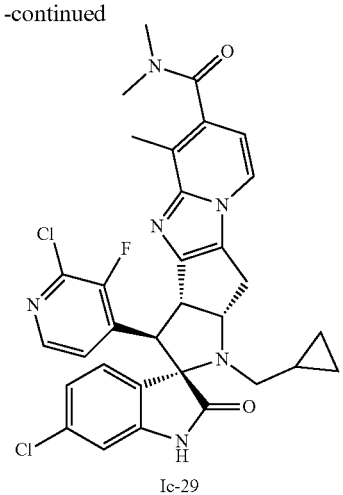

Ic-29

Ic-23 (7 mg, 0.012 mmol) is dissolved in anhydrous THF (1 mL) and HATU (5 mg, 0.05 mmol) is added at rt. After addition of DIPEA (5 mg, 0.05 mmol) the reaction mixture is allowed to stir at rt for 15 min. Dimethylamine (4 mg, 0.035 mmol) is added and the reaction is allowed to stir for additional 60 min. The crude reaction mixture is submitted to reversed phase column chromatography yielding pure Ic-29.

The following compounds (Ic) (table 48) are available in an analogous manner starting from initially obtained compounds (Ic).

TABLE 48

| # | structure | $t_{ret}$ [min] | $[M + H]^+$ | HPLC method |
|---|---|---|---|---|
| Ic-29 | 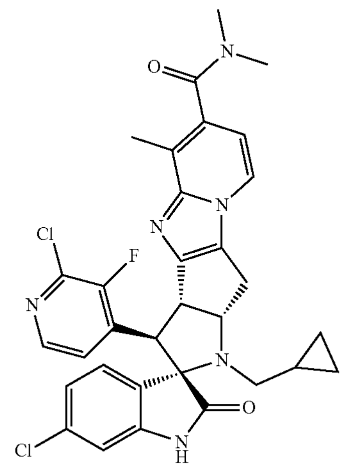 [SMILES: Cc1c(C(=O)N(C)C)ccn2c3c(nc12)[C@@H]1[C@H](C3)N(CC2CC2)[C@@]2(C(=O)Nc3cc(Cl)ccc32)[C@H]1c1ccnc(Cl)c1F] | 1.30 | 619 | A |
| Ic-30 | Chiral | 1.30 | 619 | A |
| Ic-31 | 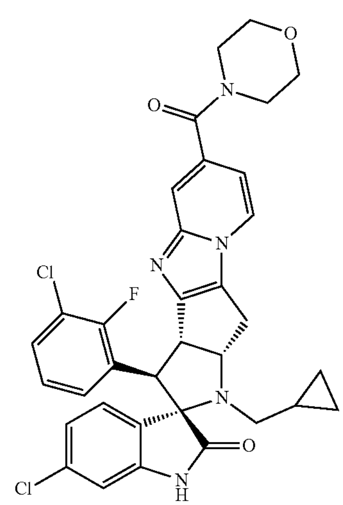 [SMILES: O=C(c1ccn2c3c(nc2c1)[C@@H]1[C@H](C3)N(CC2CC2)[C@@]2(C(=O)Nc3cc(Cl)ccc32)[C@H]1c1cccc(Cl)c1F)N1CCOCC1] | 0.63 | 646 | C |

TABLE 48-continued
| # | structure | t_{ret} [min] | [M + H]+ | HPLC method |
|---|---|---|---|---|
| Ic-32 | 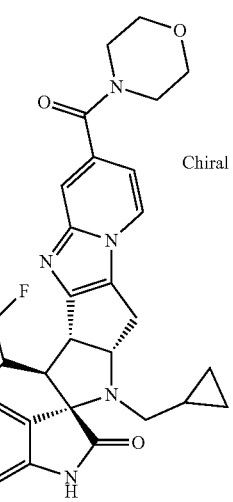 | 0.63 | 646 | C |
| Ic-33 | 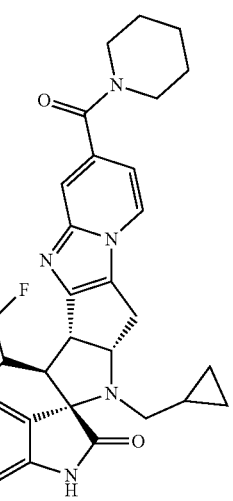 | 0.70 | 644 | C |
| Ic-34 | 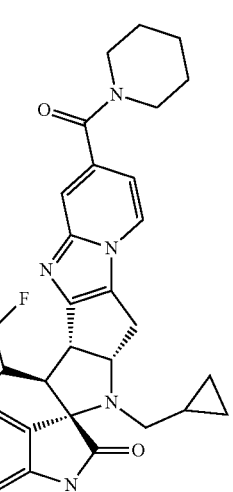 | 0.70 | 644 | C |

TABLE 48-continued

| # | structure | $t_{ret}$ [min] | [M + H]⁺ | HPLC method |
|---|---|---|---|---|
| Ic-35 | 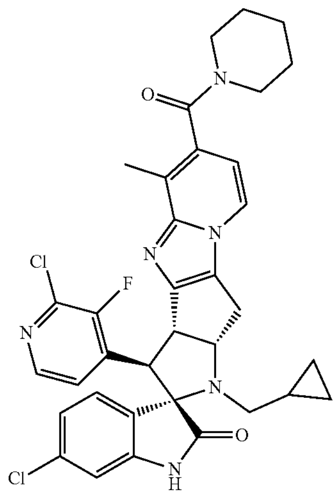 [SMILES: Cc1c(C(=O)N2CCCCC2)ccn2c3c(nc12)[C@@H]1[C@H](C3)N(CC2CC2)[C@@]2(C(=O)Nc3cc(Cl)ccc32)[C@H]1c1ccnc(Cl)c1F] | 1.45 | 659 | A |
| Ic-36 | Chiral | 1.45 | 659 | A |
| Ic-37 | 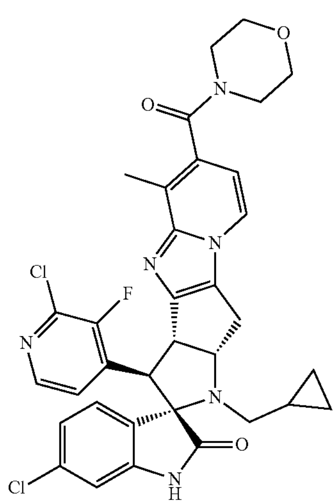 | 1.29 | 661 | A |

TABLE 48-continued

| # | structure | $t_{ret}$ [min] | $[M + H]^+$ | HPLC method |
|---|---|---|---|---|
| Ic-38 | 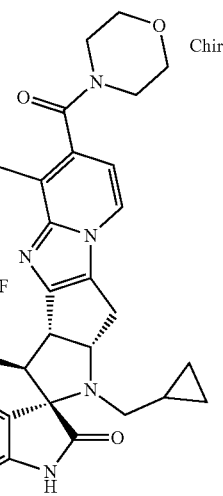 | 1.29 | 661 | A |

The following Examples describe the biological activity of the compounds according to the invention, without restricting the invention to these Examples.

Compounds of formulae (I), (Ia), (Ib), (Ic), (Ia*), (Ib*) and (Ic*) are characterised by their many possible applications in the therapeutic field. Particular mention should be made of those applications in which the inhibiting effect on the proliferation of cultivated human tumour cells but also on the proliferation of other cells such as endothelial cells, for example, are involved.

Mdm2-p53 Inhibition AlphaScreen

This assay is used to determine whether the compounds inhibit the p53-MDM2 interaction and thus restore p53 function.

15 µL of compound in 20% DMSO (serial pre-dilutions of compound are done in 100% DMSO) is pipetted to the wells of a white OptiPlate-96 (PerkinElmer). A mix consisting of 20 nM GST-MDM2 protein (aa 23-117) and 20 nM biotinylated p53 wt peptide (encompassing aa 16-27 of wt human p53, amino acid sequence QETFSDLWKLLP-Ttds-Lys-Biotin, molecular weight 2132.56 g/mol) is prepared in assay buffer (50 mM Tris/HCl pH 7.2; 120 mM NaCl; 0.1% bovine serum albumin (BSA); 5 mM dithiothreitol (DTT); 1 mM ethylenediaminetetraacetic acid (EDTA); 0.01% Tween 20). 30 µL of the mix is added to the compound dilutions and incubated for 15 min at rt while gently shaking the plate at 300 rounds per minute (rpm). Subsequently, 15 µL of premixed AlphaLISA Glutathione Acceptor Beads and AlphaScreen Streptavidin Donor Beads from PerkinElmer (in assay buffer at a concentration of 10 µg/mL each) are added and the samples are incubated for 30 min at rt in the dark (shaking 300 rpm). Afterwards, the signal is measured in a PerkinElmer Envision HTS Multilabel Reader using the AlphaScreen protocol from PerkinElmer.

Each plate contains negative controls where biotinylated p53-peptide and GST-MDM2 are left out and replaced by assay buffer. Negative control values are entered as low basis value when using the software GraphPad Prism for calculations. Furthermore, a positive control (5% DMSO instead of test compound; with protein/peptide mix) is pipetted. Determination of $IC_{50}$ values are carried out using GraphPad Prism 3.03 software (or updates thereof). Table 49 shows the $IC_{50}$ values of example compounds determined using the above assay.

TABLE 49

| # | $IC_{50}$ MDM2 [nM] |
|---|---|
| Ia-20 | 23 |
| Ia-25 | 2 |
| Ia-26 | 4 |
| Ia-27 | 2 |
| Ia-29 | 2 |
| Ia-30 | 2 |
| Ia-31 | 3 |
| Ia-32 | 2 |
| Ia-33 | 3 |
| Ia-34 | 2 |
| Ia-35 | 2 |
| Ia-36 | 5 |
| Ia-38 | 2 |
| Ia-39 | 4 |
| Ia-40 | 2 |
| Ia-41 | 3 |
| Ia-43 | 2 |
| Ia-46 | 8 |
| Ia-47 | 9 |
| Ia-48 | 10 |
| Ia-49 | 6 |
| Ia-50 | 4 |
| Ia-51 | 7 |
| Ia-52 | 69 |
| Ia-53 | 7 |
| Ia-54 | 13 |
| Ia-55 | 6 |
| Ia-56 | 5 |
| Ia-57 | 13 |
| Ib-49 | 5 |
| Ib-57 | 12 |
| Ib-58 | 7 |
| Ib-59 | 15 |
| Ib-66 | 166 |
| Ib-106 | 3 |
| Ib-107 | 2 |
| Ib-108 | 79 |
| Ib-109 | 8 |
| Ib-110 | 3 |
| Ib-111 | 7 |
| Ib-113 | 4 |
| Ib-115 | 7 |

TABLE 49-continued

| # | IC$_{50}$ MDM2 [nM] |
|---|---|
| Ib-117 | 8 |
| Ib-119 | 12 |
| Ib-121 | 11 |
| Ib-123 | 4 |
| Ib-125 | 14 |
| Ib-127 | 11 |
| Ib-129 | 10 |
| Ib-131 | 22 |
| Ib-133 | 58 |
| Ib-135 | 15 |
| Ib-137 | 34 |
| Ib-139 | 4 |
| Ib-140 | 2 |
| Ib-141 | 48 |
| Ib-142 | 3 |
| Ib-144 | 8 |
| Ib-146 | 11 |
| Ib-148 | 21 |
| Ib-150 | 20 |
| Ib-152 | 7 |
| Ib-154 | 3 |
| Ib-155 | 2 |
| Ib-156 | 5 |
| Ib-157 | 2 |
| Ib-158 | 3 |
| Ib-159 | 7 |
| Ib-160 | 4 |
| Ib-161 | 11 |
| Ib-162 | 6 |
| Ib-163 | 2 |
| Ib-164 | 3 |
| Ib-165 | 28 |
| Ib-167 | 22 |
| Ib-169 | 7 |
| Ib-171 | 10 |
| Ib-173 | 7 |
| Ib-175 | 3 |
| Ib-176 | 2 |
| Ib-177 | 53 |
| Ib-178 | 4 |
| Ib-179 | 2 |
| Ib-180 | 83 |
| Ib-183 | 3 |
| Ib-184 | 2 |
| Ib-185 | 14 |
| Ib-186 | 4 |
| Ib-188 | 3 |
| Ib-189 | 3 |
| Ib-190 | 2 |
| Ib-191 | 6 |
| Ib-193 | 3 |
| Ib-195 | 6 |
| Ib-197 | 2 |
| Ib-198 | 4 |
| Ib-200 | 3 |
| Ib-202 | 7 |
| Ib-204 | 2 |
| Ib-205 | 3 |
| Ib-206 | 4 |
| Ib-207 | 8 |
| Ib-209 | 3 |
| Ib-210 | 4 |
| Ib-211 | 11 |
| Ib-212 | 5 |
| Ib-213 | 7 |
| Ib-214 | 3 |
| Ib-215 | 4 |
| Ib-216 | 7 |
| Ib-217 | 4 |
| Ib-218 | 6 |
| Ib-219 | 5 |
| Ib-220 | 10 |
| Ib-221 | 10 |
| Ib-222 | 9 |
| Ib-223 | 5 |
| Ib-224 | 4 |
| Ib-225 | 5 |
| Ib-226 | 5 |
| Ib-227 | 4 |
| Ib-228 | 5 |
| Ib-229 | 4 |
| Ib-230 | 10 |
| Ib-231 | 4 |
| Ib-232 | 3 |
| Ib-233 | 4 |
| Ib-234 | 2 |
| Ib-235 | 3 |
| Ib-236 | 5 |
| Ib-237 | 10 |
| Ib-238 | 6 |
| Ib-239 | 3 |
| Ib-240 | 3 |
| Ib-241 | 4 |
| Ib-242 | 2 |
| Ib-243 | 99 |
| Ib-244 | 3 |
| Ib-245 | 20 |
| Ib-247 | 27 |
| Ib-249 | 240 |
| Ib-251 | 68 |
| Ib-253 | 72 |
| Ic-23 | 6 |
| Ic-27 | 13 |
| Ic-29 | 10 |
| Ic-35 | 10 |
| Ic-37 | 10 |

Cell Proliferation Assays

Cell Titer Glo assay for e.g. SJSA-1, SKOV-3, RS4-11 and KG-1 cells:

SJSA-1 cells (Osteosarcoma, wild-type p53, ATCC CRL-2098™) are seeded in duplicates at day 1 in flat bottom 96 well microtiter plates (white Packard View Plate 96 well Cat. No. 6005181) in 90 μL RPMI medium, 10% fetal calf serum (FCS, from e.g. JRH Biosciences #12103-500M, Lot.: 3N207) at a density of 2500 cells/well. Any other luminescence compatible plate format is possible.

Similarly, p53 mutant SKOV-3 cells (ovarian adenocarcinoma, ATCC HTB-77™) are seeded in duplicates in flat bottom 96 well microtiter plates in 90 μL McCoy medium, 10% FCS at a density of 3000 cells/well.

At day 2, 5 μL dilutions of the test compounds covering a concentration range between app. 0.6 and 50000 nM are added to the cells. Cells are incubated for three days in a humidified, CO$_2$-controlled incubator at 37° C.

wildtype p53 RS4-11 cells (acute lymphoblastic leukemia, ATCC CRL-1873™):

Day 1: RS4-11 cells are seeded in flat bottom 96 well microtiter plates (white Packard View Plate 96 well Cat. No. 6005181) in 90 μL RPMI medium, 10% fetal calf serum (FCS, from e.g. JRH Biosciences #12103-500M, Lot.: 3N0207) at a density of 5000 cells/well. Any other luminescence compatible plate format is possible.

Day 2: 5 μL dilutions of the test compounds covering a concentration range between app. 0.3 and 25000 nM (alternative dilution schemes are possible) are added to the cells. Cells are incubated for three days in a humidified, CO$_2$ controlled incubator at 37° C. The final DMSO-concentration is 0.5%.

p53 mutant KG-1 cells (acute myelogenous leukemia, ATCC CCL-246):

Day 1: KG-1 cells harboring a p53 mutation at the exon 6/intron 6 splice donor site are seeded in flat bottom 96 well microtiter plates (white Packard View Plate 96 well Cat. No. 6005181) in 90 μL IMDM medium, 10% FCS (JRH Biosciences #12103-500M, Lot.: 3N0207) at a density of 10000 cells/well. Any other luminescence compatible plate format is possible.

Day 2: 5 µL dilutions of the test compounds covering a concentration range between app. 0.3 and 25000 nM (alternative dilution schemes are possible) are added to the cells. Cells are incubated for three days in a humidified, $CO_2$ controlled incubator at 37° C. The final DMSO-concentration is 0.5%.

Evaluation of all Cell Titer Glo assays is done at day 5 after seeding. At day 5, 95 µL of Cell Titer Glo reagent (Cell titer Glo Luminescent Cat. No. G7571, Promega) are added to each well and incubated for additional 10 min at rt (with agitation). Luminescence is measured on a Wallac Victor using standard luminescence read out. $IC_{50}$ values are calculated using standard Levenburg Marquard algorithms (GraphPad Prism).

In addition, several other cancer cell lines from diverse tissue origins are sensitive to compounds (I), (Ia), (Ib), (Ic), (Ia*), (Ib*) and (Ic*). Examples include NCI-H460 (lung), Molp-8 (myeloma) and MV4-11 (AML).

On the basis of their biological properties the compounds of formula (I), (Ia), (Ib), (Ic), (Ia*), (Ib*) or (Ic*) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers/proliferative diseases may be treated with compounds according to the invention, without being restricted thereto:

brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, glioma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder and other urothelial cancers; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma, hormone receptor positive breast cancer (estrogen receptor positive breast cancer, progesterone receptor positive breast cancer), Her2 positive breast cancer, triple negative breast cancer; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma, multiple myeloma (MM), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, soft tissue sarcoma, liposarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); myelodysplastic syndromes (MDS); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer (e.g. castration-resistant prostate cancer); throat cancer or carcinomas of the pharynx such as for example nasopharynx carcinomas, oropharynx carcinomas and hypopharynx carcinomas; retinoblastoma, vaginal cancer or vaginal carcinoma, mesothelioma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra, cervical cancer, adenoid cystic carcinoma (AdCC), adrenocortical carcinoma and cancer of the vulva.

Preferably, the proliferative diseases/cancers to be treated have functional p53 and/or p53 wild-type status. Functional p53 means that p53 is able to bind to DNA and activate transcription of target genes.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of formula formula (I), (Ia), (Ib), (Ic), (Ia*), (Ib*) or (Ic*) may be used on their own or in combination with other active substances according to the invention, optionally also in combination with other pharmacologically active substances.

Therapeutic agents (=cytostatic and/or cytotoxic active substances) which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor (PDGF)", "fibroblast growth factor (FGF)", "vascular endothelial growth factor (VEGF)", "epidermal growth factor (EGF)", "insuline-like growth factors (IGF)", "human epidermal growth factor (HER, e.g. HER2, HER3, HER4)" and "hepatocyte growth factor (HGF)"), inhibitors are for example "growth factor" antibodies, "growth factor receptor" antibodies and tyrosine kinase inhibitors, such as for example cetuximab, gefitinib, imatinib, lapatinib, bosutinib and trastuzumab); antimetabolites (e.g. antifolates such as methotrexate, raltitrexed, pyrimidine analogues such as 5-fluorouracil (5-FU), capecitabine and gemcitabine, purine and adenosine analogues such as mercaptopurine, thioguanine, cladribine and pentostatin, cytarabine (ara C), fludarabine); antitumour antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors (e.g. sapacitabine), PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitros, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP activator, Mcl-1, MDM2/MDMX), MEK inhibitors (e.g. pimasertib), ERK inhibitors, FLT3 inhibitors (e.g. quizartinib), BRD4 inhibitors, IGF-1R inhibitors, TRAILR2 agonists, Bcl-xL inhibitors, Bcl-2 inhibitors (e.g. venetoclax), Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors (e.g. abiraterone, TAK-700), androgen receptor inhibitors (e.g. enzalutamide, ARN-509), immunotherapy (e.g. sipuleucel-T), DNMT inhibitors (e.g. SGI 110, temozolomide, vosaroxin), HDAC inhibitors (e.g. vorinostat, entinostat, pracinostat, panobinostat), ANG1/2 inhibitors (e.g. trebananib), CYP17 inhibitors (e.g. galeterone), radiopharmaceuticals (e.g. radium-223, alpharadin), immunotherapeutic agents (e.g. poxvirus-based vaccine, ipilimumab, immune checkpoint inhibitors) and various chemotherapeutic agents such as amifostin, anagrelid, clodronat, filgrastin, interferon, interferon alpha, leucovorin, rituximab, procarbazine, levamisole, mesna, mitotane, pamidronate and porfimer.

Other possible combination partners are 2-chlorodesoxyadenosine, 2-fluorodesoxycytidine, 2-methoxyoestradiol, 2C4, 3-alethine, 131-I-TM-601, 3CPA, 7-ethyl-10-hydroxycamptothecin, 16-aza-epothilone B, ABT-199, ABT-263/navitoclax, ABT-737, A 105972, A 204197, aldesleukin, alisertib/MLN8237, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), AMG-232, AMG-511, AMG 2520765, AMG 2112819, ARRY 162, ARRY 438162, ARRY-300, ARRY-142886/AZD-6244 (selumetinib), ARRY-704/AZD-8330, ATSP-7041, AR-12, AR-42, AS-703988, AXL-1717, AZD-1480, AZD-4547, AZD-8055, AZD-5363, AZD-6244, AZD-7762, ARQ-736, ARQ 680, AS-703026 (primasertib), avastin, AZD-2014, azacitidine (5-aza), azaepothilone B, azonafide, barasertib/AZD1152, BAY-43-9006, BAY 80-6946, BBR-3464, BBR-3576, bevacizumab, BEZ-235/dactolisib, biricodar dicitrate, birinapant, BCX-1777, BKM-120/buparlisib, bleocin, BLP-25, BMS-184476, BMS-247550, BMS-188797, BMS-275291, BMS-663513, BMS-754807, BNP-1350, BNP-7787, BIBW 2992/afatinib, BIBF 1120/nintedanib, BI 836845, BI 2536, BI 6727/volasertib, BI 836845, BI 847325, BI 853520, BIIB-022, bleomycinic acid, bleomycin A, bleomycin B, brivanib, bryostatin-1, bortezomib, brostallicin, busulphan, BYL-719/alpelisib, CA-4 prodrug, CA-4, cabazitaxel, cabozantinib, CapCell, calcitriol, canertinib, canfosfamide, capecitabine, carboxyphthalatoplatin, CCI-779, CC-115, CC-223, CEP-701, CEP-751, CBT-1 cefixime, ceflatonin, ceftriaxone, celecoxib, celmoleukin, cemadotin, CGM-097, CH4987655/RO-4987655, chlorotrianisene, cilengitide, ciclosporin, CD20 antibodies, CDA-II, CDC-394, CKD-602, CKI-27, clofarabine, colchicin, combretastatin A4, COT inhibitors, CHS-828, CH-5132799, CLL-Thera, CMT-3 cryptophycin 52, CPI-613, CTP-37, CTLA-4 monoclonal antibodies (e.g. ipilimumab), CP-461, crizotinib, CV-247, cyanomorpholinodoxorubicin, cytarabine, D 24851, dasatinib, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, DS-3032, E7010, E-6201, edatrexat, edotreotide, efaproxiral, eflornithine, EGFR inhibitors, EKB-569, EKB-509, enzastaurin, elesclomol, elsamitrucin, epothilone B, epratuzumab, EPZ-004777, ER-86526, erlotinib, ET-18-

OCH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fostamatinib, fotemustine, galarubicin, gallium maltolate, ganetespib, gefinitib, gemtuzumab, gemtuzumab ozogamicin, gimatecan, glufosfamide, GCS-IOO, GDC-0623, GDC-0941 (pictrelisib), GDC-0980, GDC-0032, GDC-0068, GDC-0349, GDC-0879, G17DT immunogen, GMK, GMX-1778, GPX-100, gp100-peptide vaccines, GSK-5126766, GSK-690693, GSK-1120212 (trametinib), GSK-1995010, GSK-2118436 (dabrafenib), GSK-2126458, GSK-2132231A, GSK-2334470, GSK-2110183, GSK-2141795, GSK-2636771, GSK-525762A/I-BET-762, GW2016, granisetron, herceptine, hexamethylmelamine, histamine, homoharringtonine, hyaluronic acid, hydroxyurea, hydroxyprogesterone caproate, HDM-201, ibandronate, ibritumomab, ibrutinib/PCI-32765, idasanutlin, idatrexate, idelalisib/CAL-101, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, iproplatin, irofulven, isohomohalichondrin-B, isoflavone, isotretinoin, ixabepilone, JRX-2, JSF-154, JQ-1, J-107088, conjugated oestrogens, kahalid F, ketoconazole, KW-2170, KW-2450, KU-55933, LCL-161, lobaplatin, leflunomide, lenalidomide, lenograstim, leuprolide, leuporelin, lexidronam, LGD-1550, linezolid, lovastatin, lutetium texaphyrin, lometrexol, lonidamine, losoxantrone, LU 223651, lurbinectedin, lurtotecan, LY-S6AKT1, LY-2780301, LY-2109761/galunisertib, mafosfamide, marimastat, masoprocol, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, MLN-0128, MLN-2480, motexafin gadolinium, MS-209, MS-275, MX6, neridronate, neratinib, Nexavar, neovastat, nilotinib, nimesulide, nitroglycerin, nolatrexed, norelin, N-acetylcysteine, NU-7441 06-benzylguanine, oblimersen, omeprazole, olaparib, oncophage, oncoVEX$^{GM-CSF}$, ormiplatin, ortataxel, OX44 antibodies, OSI-027, OSI-906 (linsitinib), 4-1BB antibodies, oxantrazole, oestrogen, onapristone, palbociclib/PD-0332991, panitumumab, panobinostat, patupilone, pazopanib, pegfilgrastim, PCK-3145, pegfilgrastim, PBI-1402, PBI-05204, PD0325901, PD-1 and PD-L1 antibodies (e.g. pembrolizumab, nivolumab, pidilizumab, MEDI-4736/durvalumab, RG-7446/atezolizumab), PD-616, PEG-paclitaxel, albumin-stabilized paclitaxel, PEP-005, PF-05197281, PF-05212384, PF-04691502, PF-3758309, PHA-665752, PHT-427, P-04, PKC412, P54, PI-88, pelitinib, pemetrexed, pentrix, perifosine, perillylalcohol, pertuzumab, pevonedistat, P13K inhibitors, P13K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PK1166, plevitrexed, plicamycin, polyprenic acid, ponatinib, porfiromycin, posaconazole, prednisone, prednisolone, PRT-062607, quinamed, quinupristin, quizartinib/AC220, R115777, RAF-265, ramosetron, ranpirnase, RDEA-119/BAY 869766, RDEA-436, rebeccamycin analogues, receptor tyrosine kinase (RTK) inhibitors, revimid, RG-7167, RG-7112, RG-7304, RG-7421, RG-7321, RG-7356, RG 7440, RG-7775, rhizoxin, rhu-MAb, rigosertib rinfabate, risedronate, rituximab, robatumumab, rofecoxib, romidepsin, RO-4929097, RO-31-7453, RO-5126766, RO-5068760, RPR 109881A, rubidazone, rubitecan, R-flurbiprofen, RX-0201, ruxolitinib, S-9788, sabarubicin, SAHA, sapacitabine, SAR-405838, sargramostim, satraplatin, SB-408075, SB-431542, Se-015/Ve-015, SU5416, SU6668, SDX-101, selinexor, semustin, seocalcitol, SM-11355, SN-38, SN-4071, SR-27897, SR-31747, SR-13668, SRL-172, sorafenib, spiroplatin, squalamine, STF-31, suberanilohydroxamic acid, sutent, T 900607, T 138067, TAE-684, TAK-733, TAS-103, tacedinaline, talaporfin, tanespimycin, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, tosedostat. trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valproic acid, valrubicin, vandetanib, vatalanib, vincristine, vinflunine, virulizin, vismodegib, vosaroxin, WX-UK1, WX-554, vectibix, XAV-939, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat and zosuquidar.

Particularly preferred are methods of treatment and medical uses including the use of the compounds (I) of the invention in combination with immunotherapeutic agents, e.g. checkpoint inhibitors including anti-PD-1 and anti-PD-L1 agents (such as e.g. pembrolizumab, nivolumab, pidilizumab, MEDI-4736/durvalumab and RG-7446/atezolizumab) and anti-LAG3 agents. Thus, one aspect of the invention are methods of treatment and medical uses including the use of a compound (I) of the invention in combination with an anti-PD-1 or an anti-PD-1 agent (such as e.g. pembrolizumab, nivolumab, pidilizumab, MEDI-4736/durvalumab and RG-7446/atezolizumab). Another aspect of the invention are methods of treatment and medical uses including the use of a compound (I) of the invention in combination with an anti-LAG3 agent. A further aspect of the invention are methods of treatment and medical uses including the use of a compound (I) of the invention in combination with an anti-PD-1 agent and an anti-LAG3 agent.

Suitable preparations include for example tablets, pills, capsules, suppositories, lozenges, troches, solutions—particularly solutions for injection (s.c., iv., i.m.) and infusion (injectables)—elixirs, syrups, sachets, emulsions, inhalatives or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc, agents for delaying release, such as carboxymethyl cellulose, cellulose acetate phthalate, or polyvinyl acetate, carriers, adjuvants, surfactants. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage range of the compounds of formula (I), (a), (Ib), (Ic), (Ia*), (Ib*) or (c*) applicable per day is usually from 1 mg to 2000 mg, preferably from 50 to 1000 mg, more preferably from 100 to 500 mg.

The dosage for intravenous use is from 1 mg to 1000 mg per hour, preferably between 5 mg and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope (active substance in all examples is a compound according to formula (I), (Ia), (Ib), (Ic), (Ia*), (Ib*) or (Ic*)):

Examples of Pharmaceutical Formulations

| A) | |
| --- | --- |
| Tablets | per tablet |
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | |
| --- | --- |
| Tablets | per tablet |
| active substance | 80 mg |
| lactose | 55 mg |
| corn starch | 190 mg |
| microcrystalline cellulose | 35 mg |
| polyvinylpyrrolidone | 15 mg |
| sodiumcarboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | |
| --- | --- |
| Tablets | per tablet |
| active substance | 25 mg |
| lactose | 50 mg |
| microcrystalline cellulose | 24 mg |
| magnesium stearate | 1 mg |
| | 100 mg |

The active substance, lactose and cellulose are mixed together. The mixture is screened, then either moistened with water, kneaded, wet-granulated and dried or dry-granulated or directely final blend with the magnesium stearate and compressed to tablets of suitable shape and size. When wet-granulated, additional lactose or cellulose and magnesium stearate is added and the mixture is compressed to produce tablets of suitable shape and size.

D)

| Ampoule solution | |
|---|---|
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. Intermediate of formula B-20

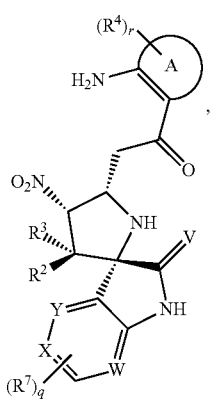

B-20

$R^2$ and $R^3$, each independently, is selected from among hydrogen, $C_{6-10}$aryl, 5-10 membered heteroaryl and 3-10 membered heterocyclyl, wherein said $C_{6-10}$aryl, 5-10 membered heteroaryl and 3-10 membered heterocyclyl is optionally substituted by one or more, identical or different $R^{b2}$ and/or $R^{c2}$;

each $R^{b2}$ is independently selected from among —$OR^{c2}$, —$NR^{c2}R^{c2}$, halogen, —CN, —C(O)$R^{c2}$, —C(O)O$R^{c2}$, —C(O)N$R^{c2}R^{c2}$, —S(O)$_2R^{c2}$, —S(O)$_2NR^{c2}R^{c2}$, —NHC(O)$R^{c2}$, —N($C_{1-4}$alkyl)C(O)$R^{c2}$ and the bivalent substituent =O, while =O may only be a substituent in non-aromatic ring systems;

each $R^{c2}$ independently of one another denotes hydrogen or a group, optionally substituted by one or more, identical or different $R^{d2}$ and/or $R^{e2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{d2}$ is independently selected from among —$OR^{e2}$, —$NR^{e2}R^{e2}$, halogen, —CN, —C(O)$R^{e2}$, —C(O)O$R^{e2}$, —C(O)N$R^{e2}R^{e2}$, —S(O)$_2R^{e2}$, —S(O)$_2NR^{e2}R^{e2}$, —NHC(O)$R^{e2}$, —N($C_{1-4}$alkyl)C(O)$R^{e2}$ and the bivalent substituent =O, while =O may only be a substituent in non-aromatic ring systems;

each $R^{e2}$ independently of one another denotes hydrogen or a group selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

A is selected from among phenyl and 5-6 membered heteroaryl;

each $R^4$ is independently selected from among $R^{a4}$ and $R^{b4}$;

each $R^{a4}$ independently of one another is a group, optionally substituted by one or more, identical or different $R^{b4}$ and/or $R^{c4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{b4}$ is independently selected from among —$OR^{c4}$, —$NR^{c4}R^{c4}$, halogen, —CN, —C(O)$R^{c4}$, —C(O)O$R^{c4}$, —C(O)N$R^{c4}R^{c4}$, —C(O)N$R^{g4}OR^{c4}$, —S(O)$_2R^{c4}$, —S(O)$_2NR^{c4}R^{c4}$, —NHSO$_2R^{c4}$, —N($C_{1-4}$alkyl)SO$_2R^{c4}$, —NHC(O)$R^{c4}$ and —N($C_{1-4}$alkyl)C(O)$R^{c4}$;

each $R^{c4}$ independently of one another denotes hydrogen or a group, optionally substituted by one or more, identical or different $R^{d4}$ and/or $R^{e4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{d4}$ is independently selected from among —$OR^{e4}$, —$NR^{e4}R^{e4}$, halogen, —CN, —C(O)$R^{e4}$, —C(O)O$R^{e4}$, —C(O)N$R^{e4}R^{e4}$, —C(O)N$R^{g4}OR^{e4}$, —S(O)$_2R^{e4}$, —S(O)$_2NR^{e4}R^{e4}$, —NHC(O)$R^{e4}$ and —N($C_{1-4}$alkyl)C(O)$R^{e4}$;

each $R^{e4}$ independently of one another denotes hydrogen or a group, optionally substituted by one or more, identical or different $R^{f4}$ and/or $R^{g4}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{f4}$ is independently selected from among —$OR^{g4}$, —$NR^{g4}R^{g4}$, halogen, —CN, —C(O)$R^{g4}$, —C(O)O$R^{g4}$, —C(O)N$R^{g4}R^{g4}$, —C(O)N$R^{g4}OR^{g4}$, —S(O)$_2R^{g4}$, —S(O)$_2NR^{g4}R^{g4}$, —NHC(O)$R^{g4}$ and —N($C_{1-4}$alkyl)C(O)$R^{g4}$;

each $R^{g4}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

r denotes the number 0, 1, 2 or 3;

each $R^7$ is independently selected from among halogen, $C_{1-4}$alkyl, —CN, $C_{1-4}$haloalkyl, —O$C_{1-4}$alkyl and —O$C_{1-4}$haloalkyl;

q denotes the number 0, 1, 2 or 3;

V is oxygen or sulfur; and wherein W, X and Y is each independently selected from —N= and —CH=, wherein the hydrogen in each —CH= may be replaced by a substituent $R^7$ if present and wherein a maximum of two of W, X and Y can be —N=, or a salt thereof.

2. A method for synthesizing an intermediate of formula B-20
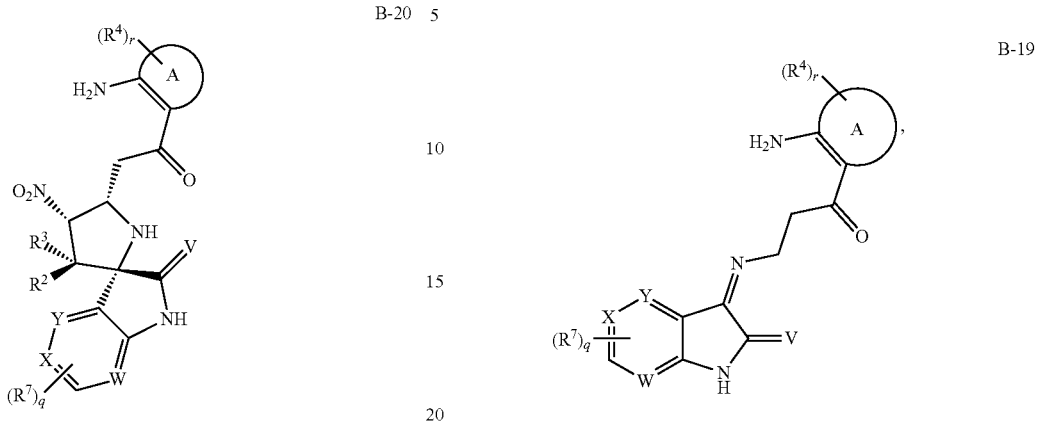
comprising reacting a compound B-2
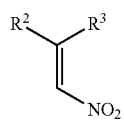
with an imine B-19
wherein $R^2$, $R^3$, $R^4$, $R^7$, A, V, r and q are as defined in claim 1, and wherein W, X and Y is each independently selected from —N= and —CH=, wherein the hydrogen in each —CH= may be replaced by a substituent $R^7$ if present and wherein a maximum of two of W, X and Y can be —N=.
* * * * *